(12) United States Patent
Coppola et al.

(10) Patent No.: US 8,263,629 B2
(45) Date of Patent: Sep. 11, 2012

(54) SUBSTITUTED AMINOBUTYRIC DERIVATIVES AS NEPRILYSIN INHIBITORS

(75) Inventors: Gary Mark Coppola, Budd Lake, NJ (US); Yuki Iwaki, Cambridge, MA (US); Rajeshri Ganesh Karki, Somerville, MA (US); Toshio Kawanami, Boston, MA (US); Gary Michael Ksander, Amherst, NH (US); Muneto Mogi, Waltham, MA (US); Robert Sun, Natick, MA (US)

(73) Assignee: Novartis AG, Basel (CH)

( * ) Notice: Subject to any disclaimer, the term of this patent is extended or adjusted under 35 U.S.C. 154(b) by 70 days.

(21) Appl. No.: 12/788,794

(22) Filed: May 27, 2010

(65) Prior Publication Data
US 2010/0305145 A1   Dec. 2, 2010

Related U.S. Application Data

(60) Provisional application No. 61/181,753, filed on May 28, 2009, provisional application No. 61/263,141, filed on Nov. 20, 2009, provisional application No. 61/324,938, filed on Apr. 16, 2010.

(51) Int. Cl.
| | |
|---|---|
| *A61K 31/42* | (2006.01) |
| *A61K 31/4245* | (2006.01) |
| *A61K 31/41* | (2006.01) |
| *C07D 271/04* | (2006.01) |
| *C07D 271/06* | (2006.01) |
| *C07D 271/08* | (2006.01) |
| *C07D 271/10* | (2006.01) |
| *C07D 263/30* | (2006.01) |
| *C07D 261/06* | (2006.01) |
| *C07D 257/02* | (2006.01) |

(52) U.S. Cl. ........ 514/364; 514/374; 514/378; 514/381; 548/131; 548/143; 548/215; 548/240; 548/250

(58) Field of Classification Search .................. 514/364, 514/374, 378, 381; 548/131, 143, 215, 240, 548/250
See application file for complete search history.

(56) References Cited

U.S. PATENT DOCUMENTS

| | | | |
|---|---|---|---|
| 4,281,180 A | | 7/1981 | Umezawa et al. |
| 4,610,816 A | | 9/1986 | Berger |
| 4,719,231 A | | 1/1988 | Umezawa et al. |
| 4,721,726 A | | 1/1988 | Berger |
| 4,738,803 A | | 4/1988 | Roques et al. |
| 5,200,426 A | | 4/1993 | Hersh et al. |
| 5,217,996 A | * | 6/1993 | Ksander ................. 514/533 |
| 5,250,522 A | | 10/1993 | De Lombaert |
| 5,273,990 A | | 12/1993 | De Lombaert |
| 5,294,632 A | | 3/1994 | Erion et al. |
| 5,414,017 A | | 5/1995 | Delaney et al. |
| 5,449,662 A | | 9/1995 | Scarborough |
| 5,517,996 A | | 5/1996 | Okada et al. |
| 5,550,119 A | | 8/1996 | De Lombaert et al. |
| 5,710,171 A | | 1/1998 | Dinsmore et al. |
| 5,891,912 A | | 4/1999 | Kawashima et al. |
| 5,968,980 A | | 10/1999 | Kawashima et al. |
| 6,169,103 B1 | | 1/2001 | Purchase, Jr. et al. |
| 2002/0193562 A1 | | 12/2002 | Robl |
| 2004/0063761 A1 | | 4/2004 | Kuduk et al. |
| 2008/0119557 A1 | | 5/2008 | Webb et al. |
| 2008/0188533 A1 | | 8/2008 | Choi et al. |
| 2008/0269305 A1 | | 10/2008 | Allegretti et al. |
| 2010/0305131 A1 | | 12/2010 | Coppola et al. |
| 2011/0124695 A1 | | 5/2011 | Iwaki et al. |

FOREIGN PATENT DOCUMENTS

| | | |
|---|---|---|
| EP | 0038046 | 10/1981 |
| EP | 0038046 A2 | 10/1981 |
| EP | 0077274 | 4/1983 |
| EP | 0077274 A1 | 4/1983 |
| EP | 0082088 | 6/1983 |
| EP | 0082088 A1 | 6/1983 |
| EP | 103077 | 3/1984 |
| EP | 0103077 A2 | 3/1984 |
| EP | 0117429 | 9/1984 |
| EP | 0117429 A1 | 9/1984 |
| EP | 0136883 | 4/1985 |

(Continued)

OTHER PUBLICATIONS

Golub et al. Science (1999), vol. 286 531-537.* Lala et al. Cancer and Metastasis Reviews (1998), 17(1), 91-106.*
Ksander, et al., "Dicarboxylic Acid Dipeptide Neutral Endopeptidase Inhibitors", Journal of Medicinal Chemistry (1995), 38(10), 1689-700.
Ksander, et al., "Enkephalinase inhibitors. 1. 2,4-Dibenzylglutaric acid derivatives", Journal of Medicinal Chemistry (1989), 32(12), 2519-26.
Fournie-Zaluski, et al., "Analgesic effects of kelatorphan, a new highly potent inhibitor of multiple enkephalin degrading enzymes", European Journal of Pharmacology (1984), 102(3-4), 525-8.
Bouboutou, et al., "Bidentate peptides: highly potent new inhibitors of enkephalin degrading enzymes", Life Sciences (1984), 35(9), 1023-30.

(Continued)

*Primary Examiner* — Rebecca Anderson
*Assistant Examiner* — Samantha Shterengarts
(74) *Attorney, Agent, or Firm* — Sophie Binet Cross

(57) ABSTRACT

The present invention provides a compound of formula I';

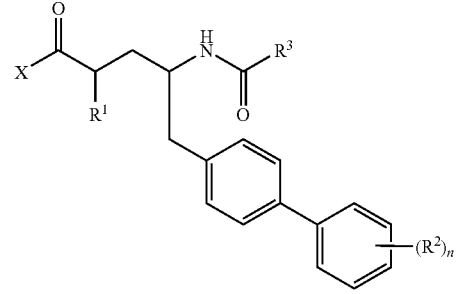

Formula I' or a pharmaceutically acceptable salt thereof, wherein $R^1$, $R^2$, $R^3$, X and n are defined herein. The invention also relates to a method for manufacturing the compounds of the invention, and its therapeutic uses. The present invention further provides a combination of pharmacologically active agents and a pharmaceutical composition.

15 Claims, No Drawings

FOREIGN PATENT DOCUMENTS

| | | |
|---|---|---|
| EP | 0136883 A2 | 4/1985 |
| EP | 0262053 | 3/1988 |
| EP | 0262053 A2 | 3/1988 |
| EP | 0356124 A2 | 2/1990 |
| EP | 0497192 | 8/1992 |
| EP | 0497192 A2 | 8/1992 |
| EP | 0533130 | 3/1993 |
| EP | 0533130 A1 | 3/1993 |
| EP | 0534492 | 3/1993 |
| EP | 0534492 A2 | 3/1993 |
| EP | 1903027 | 3/2008 |
| EP | 1903027 A1 | 3/2008 |
| EP | 2 070 928 A1 | 6/2009 |
| FR | 2597865 A1 | 10/1987 |
| GB | 2037754 | 7/1980 |
| GB | 2037754 A | 7/1980 |
| GB | 2207351 | 2/1989 |
| GB | 2207351 A | 2/1989 |
| GB | 2354440 | 3/2001 |
| GB | 2354440 A | 3/2001 |
| JP | 4149166 A | 5/1992 |
| JP | 5262709 | 10/1993 |
| JP | 5262709 A | 10/1993 |
| JP | 6234630 A | 8/1994 |
| JP | 7157459 A | 6/1995 |
| JP | 2000344614 A | 12/2000 |
| JP | 2003321358 | 11/2003 |
| JP | 2003321358 A | 11/2003 |
| WO | 91/02718 | 3/1991 |
| WO | 9102718 A1 | 3/1991 |
| WO | 91/09840 | 7/1991 |
| WO | 9109840 A1 | 7/1991 |
| WO | 94/20457 | 9/1994 |
| WO | 9420457 A1 | 9/1994 |
| WO | 95/35307 | 12/1995 |
| WO | 9535307 A1 | 12/1995 |
| WO | 97/47270 | 12/1997 |
| WO | 9747270 A3 | 12/1997 |
| WO | 98/09940 | 3/1998 |
| WO | 9809940 A1 | 3/1998 |
| WO | 98/18803 | 5/1998 |
| WO | 9818803 A1 | 5/1998 |
| WO | 98/53817 | 12/1998 |
| WO | 9853817 A1 | 12/1998 |
| WO | 99/26921 | 6/1999 |
| WO | 99/26922 | 6/1999 |
| WO | 99/26923 | 6/1999 |
| WO | 9926921 A1 | 6/1999 |
| WO | 9926922 A1 | 6/1999 |
| WO | 9926923 A1 | 6/1999 |
| WO | 99/36393 | 7/1999 |
| WO | 9936393 A1 | 7/1999 |
| WO | 02/26696 | 4/2002 |
| WO | 0226696 A1 | 4/2002 |
| WO | 03/059345 | 7/2003 |
| WO | 03059345 A1 | 7/2003 |
| WO | 2004062553 A2 | 7/2004 |
| WO | 2004/099171 | 11/2004 |
| WO | 2004099171 A2 | 11/2004 |
| WO | 2005/012270 | 2/2005 |
| WO | 2005/014534 | 2/2005 |
| WO | 2005012270 A2 | 2/2005 |
| WO | 2005014534 A1 | 2/2005 |
| WO | 2006/020358 | 2/2006 |
| WO | 2006020358 A2 | 2/2006 |
| WO | 2006/055725 | 5/2006 |
| WO | 2006055725 A2 | 5/2006 |
| WO | 2006/069096 | 6/2006 |
| WO | 2006069096 A1 | 6/2006 |
| WO | 2006/086456 | 8/2006 |
| WO | 2006086456 A2 | 8/2006 |
| WO | 2007/045663 | 4/2007 |
| WO | 2007045663 A2 | 4/2007 |
| WO | 2007/056324 | 5/2007 |
| WO | 2007/056546 | 5/2007 |
| WO | 2007056324 A2 | 5/2007 |
| WO | 2007056546 A1 | 5/2007 |
| WO | 2008/031567 | 3/2008 |
| WO | 2008031567 A1 | 3/2008 |
| WO | 2008/073138 | 6/2008 |
| WO | 2008073138 A2 | 6/2008 |
| WO | 2008/083967 | 7/2008 |
| WO | 2008083967 A2 | 7/2008 |
| WO | 2008/0138561 | 11/2008 |
| WO | 2008138561 A1 | 11/2008 |
| WO | 2008/153857 | 12/2008 |
| WO | 2008153857 A1 | 12/2008 |
| WO | 2009/061713 | 5/2009 |
| WO | 2009061713 A1 | 5/2009 |
| WO | 2009/076288 | 6/2009 |
| WO | 2009076288 A1 | 6/2009 |
| WO | 2009/090251 | 7/2009 |
| WO | 2009090251 A2 | 7/2009 |
| WO | 2010/011821 | 1/2010 |
| WO | 2010011821 A2 | 1/2010 |
| WO | 2010/136493 A1 | 12/2010 |
| WO | 2011/035569 A1 | 3/2011 |

OTHER PUBLICATIONS

Davies, et al., "First asymmetric synthesis of the Kelatorphan-like enkephalinase inhibitor (1S,2R,2'S )-2-[2'-(N-hydroxycarbamoylmethyl)-3'-phenylpropionylamino]cyclohexane-1-carboxylic acid", Journal of the Chemical Society, Perkin Transactions 1: Organic and Bio-Organic Chemistry (1998), (17), 2629-2634.

Bourdel, et al., New hydroxamate inhibitors of neurotensin-degrading enzymes: synthesis and enzyme active-site recognition, International Journal of Peptide & Protein Research (1996), 48(2), 148-155.

Doulut, et al., "Synthesis and analgesic effects of N-[3-[(hydroxyamino)carbonyl]-1-oxo-2(R)-benzylpropyl]-L-isoleucyl-L-leucine, a new potent inhibitor of multiple neurotensin/neuromedin N degrading enzymes", Journal of Medicinal Chemistry (1993), 36(10), 1369-79.

Fournie-Zaluski, et al., "Development of [125I]RB104, a potent inhibitor of neutral endopeptidase 24.11 , and its use in detecting nanogram quantities of the enzyme by inhibitor gel electrophoresis", Proceedings of the National Academy of Sciences of the United States of America (1992), 89(14), 6388-92.

Milhiet, et al., "Increase of neutral endopeptidase-24.11 with cellular density and enzyme modulation with an inhibitor on human Reh6 cell line", Biochemical Pharmacology (1992), 43(8), 1711-15.

Xie, et al., "Inhibitors of the enkephalin degrading enzymes. Modulation of activity of hydroxamate containing compounds by modifications of the C-terminal residue", International Journal of Peptide & Protein Research (1989), 34 (3), 246-55.

Tejedor-Real, et al., "Effect of mixed (RB 38A) and selective (RB 38B) inhibitors of enkephalin degrading enzymes on a model of depression in the rat", Biological Psychiatry (1993), 34(1-2), 100-7.

Xie, et al., "New inhibitors of enkephalin-degrading enzymes", Colloque INSERM (1989), 174 (Forum Pept., 2nd, 1988), 349-52.

Fournie-Zaluski, et al., "Enkephalin-degrading enzyme inhibitors. Crucial role of the C-terminal residue on the inhibitory potencies of retro-hydroxamate dipeptides", International Journal of Peptide & Protein Research (1989), 33 (2), 146-53.

Xie, et al., "New kelatorphan-related inhibitors of enkephalin metabolism: improved antinociceptive properties", Journal of Medicinal Chemistry (1989), 32(7), 1497-503.

Hernandez, et al., "Retro-inverso concept applied to the complete inhibitors of enkephalin-degrading enzymes", Journal of Medicinal Chemistry (1988), 31(9), 1825-31.

Fournie-Zaluski, et al., "Synthesis and biological properties of highly potent enkephalinase inhibitors", Pept., Proc. Eur. Pept. Symp., 16th (1981), Meeting Date 1980, 476-81.

Fournie-Zaluski, et al., "Differential recognition of enkephalinase and angiotensin-converting enzyme by new carboxyalkyl inhibitors", Life Sciences (1982), 31(26), 2947-54.

Roques, et al., "New enkephalinase inhibitors as probes to differentiate enkephalinase and angiotensin-converting enzyme active sites", Life Sciences (1982), 31(16-17), 1749-52.

Fournie-Zaluski, et al., "New carboxyalkyl inhibitors of brain enkephalinase : synthesis, biological activity and analgesic properties", Journal of Medicinal Chemistry (1983), 26(1), 60-5.

Matsuoka, et al., "2S,3R 3-Amino-2-hydroxy-4-phenylbutanoic acid derivatives, enkephalinase inhibitors, augment Met5-enkephalin-induced antinociception", Japanese Journal of Pharmacology (1988), 46(3), 205-10.
Hachisu, et al., "Relationship between enhancement of morphine analgesia and inhibition of enkephalinase by (2S,3R)-3-amino-2-hydroxy-4-phenylbutanoic acid derivatives", Life Sciences (1982), 30(20), 1739-46.
Bioorganic medicinal chemistry letters, 1996, vol. 6., No. 13, pp. 1487-1490.
Database WPI week 199227, Thomson Scientific, London, GB, AN 1992-223453 XP002591646 & JP 4149166 (nippon Kayaku) compound with RN: 144139-09-3.
Bioorganic & medicinal Chemistry letters, 2002, vol. 12, pp. 101-104 "Potent P1' biphenylmethyl substituted aggrecanase inhibitor".
Journal of medicinal chemistry (1998), 41, 1513-1523 Eli Wallace Novartis.
53601 (filed on same day) PCT/EP2010/057247.
53875 (not Foreign filed yet) cite provisonals.
Bouboutou et al.; "Bidentate Peptides : Highly Potent New Inhibitors of Enkephalin Degrading Enzymes"; Life Sciences; 35(9):1023-1030 (1984).
Bourdel et al.; "New hydroxamate inhibitors of neurotensin-degrading enzymes—Synthesis and enzyme active-site recognition"; International Journal of Peptide & Protein Research; 48(2):148-155 (1996).
De Lombaert et al.; "Dual Inhibition of Neutral Endopeptidase and Angiotensinconverting Enzyme by N-Phosphonomethyl and N-Carboxyalkyl Dipeptides"; Bioorganic & Medicinal Chemistry Letters; 4(22):2715-2720 (1994).
De Lombaert et al.; Non-Peptidic Inhibitors of Neutral Endopeptidase 24.11 1. Discovery and Optimization of Potency; Bioorganic & Medicinal Chemistry Letters; 5(2):145-150 (1995).
Doulut et al.; "Synthesis and Analgesic Effects of N-[3-[(Hydroxyamino)carbonyl]-1-oxo-2(R)-benzylpropyl]-L-isoleucyl-L-leucine, a New Potent Inhibitor of Multiple Neurotensin/Neuromedin N Degrading Enzymes"; Journal of Medicinal Chemistry; 36(10):1369-1379 (1993).
Fournie-Zaluski et al.; "Synthesis and Biological Properties of Highly Potent Enkephalinase Inhibitors"; Pept., Proc. Eur. Pept. Symp.; 16th; Meeting Date 1980, pp. 476-481 (1981).
Fournie-Zaluski et al.; "Differential Recognition of "Enkephalinase" and Angiotensin-Converting Enzyme by New Carboxyalkyl Inhibitors"; Life Sciences; 31(26):2947-2954 (1982).
Fournie-Zaluski et al.; "New Carboxyalkyl Inhibitors of Brain Enkephalinase: Synthesis, Biological Activity, and Analgesic Properties"; Journal of Medicinal Chemistry; 26(1):60-65 (1983).
Fournie-Zaluski et al.; "Analgesic Effects of Kelatorphan, a New Highly Potent Inhibitor of Multiple Enkephalin Degrading Enzymes"; European Journal of Pharmacology; 102(3-4):525-528 (1984).
Fournie-Zaluski et al.; "Enkephalin-degrading enzyme inhibitors: Crucial role of the C-terminal residue on the inhibitory potencies of retro-hydroxamate dipeptides"; International Journal of Peptide & Protein Research; 33 (2):146-153 (1989).
Hachisu et al.; "Relationship Between Enhancement of Morphine Analgesia and Inhibition of Enkephalinase by 2S, 3R 3-Amino-2-Hydroxy-4-Phenylbutanoic Acid Derivatives"; Life Sciences; 30 (20):1739-1746 (1982).
Hernandez et al.; "Retro-Inverso Concept Applied to the Complete Inhibitors of Enkephalin-Degrading Enzymes"; Journal of Medicinal Chemistry; 31(9):1825-1831 (1988).
Kanno et al.; "Synthesis and Evaluation of 2-(Biphenylmethyl)Glutaric Acid Amide Derivatives as Neutral Endopeptidase Inhibitors"; Bioorganic & Medicinal Chemistry Letters; 6 (13):1487-1490 (1996).
Ksander et al.; "Enkephalinase Inhibitors. 1. 2,4-Dibenzylglutaric Acid Derivatives"; Journal of Medicinal Chemistry; 32(12):2519-2526 (1989).
Ksander et al.; "Dicarboxylic Acid Dipeptide Neutral Endopeptidase Inhibitors"; Journal of Medicinal Chemistry; 38 (10):1689-1700 (1995).
Matsuoka et al.; "2S,3R 3-Amino-2-Hydroxy-4-Phenylbutanoic Acid Derivatives, Enkephalinase Inhibitors, Augment Met5-Enkephalin-Induced Antinociception"; Japanese Journal of Pharmacology; 46(3):205-210 (1988).
Milhiet et al.; "Increase of Neutral Endopeptidase-24.11 With Cellular Density and Enzyme Modulation With an Inhibitor on Human REH6 Cell Line"; Biochemical Pharmacology; 43(8):1711-1715 (1992).
Roques et al.; "New Enkephalinase Inhibitors as Probes to Differentiate. "Enkephalinase" and Angiotensin-Converting-Enzyme Active Sites"; Life Sciences; 31 (16-17):1749-1752 (1982).
Tejedor-Real et al.; "Effect of Mixed (RB 38A) and Selective (RB 38B) Inhibitors of Enkephalin Degrading Enzymes on a Model of Depression in the Rat"; Biological Psychiatry; 34(1-2):100-107 (1993).
Wallace et al.; "Design and Synthesis of Potent, Selective Inhibitors of Endothelin-Converting Enzyme"; Journal of Medicinal Chemistry; 41(9):1513-1523 (1998).
Xie et al.; "New inhibitors of enkephalin-degrading enzymes"; Colloque INSERM [2nd Forum Pept.]; 174:349-352 (1989).
Xie et al.; "Inhibitors of the enkephalin degrading enzymes: Modulation of activity of hydroxamate containing compounds by modifications of the C-terminal residue"; International Journal of Peptide & Protein Research; 34 (3):246-255 (1989).
Xie et al.; "New Kelatorphan-Related Inhibitors of Enkephalin Metabolism: Improved Antinociceptive Properties"; Journal of Medicinal Chemistry; 32(7):1497-1503 (1989).
Yao et al.; "Potent P1' Biphenylmethyl Substituted Aggrecanase Inhibitors"; Bioorganic & Medicinal Chemistry Letters; 12:101-104 (2002).
Library compound: RN:144139-09-3.
Bhagwat et al.; "Alpha-Mercaptoacyl Dipeptides That Inhibit Angiotensin Converting Enzyme and Neutral Endopeptidase 24.11."; Bioorganic & Medicinal Chemistry Letters; 5(7):735-738 (1995).
De Lombaert et al.; "N-Phosphonomethyl Dipeptides and Their Phosphonate Prodrugs, a New Generation of Neutral Endopeptidase (NEP, EC 3.4.24.11) Inhibitors1"; J. Med. Chem.; 37(4):498-511 (1994).
De Lombaert et al.; "Chemical and Plasma Hydrolyses of a Diphenyl Alpha-Aminomethyl Phosphonate Prodrug Inhibitor of Neutral Endopeptidase 24.11"; Bioorganic & Med. Chem. Ltrs.; 4(7):899-902 (1994).
De Lombaert et al.; "Non-Peptidic Inhibitors of Neutral Endopeptidase 24.11-2. Design and Pharmacology of Orally Active Phosphonate Prodrugs"; Bioorganic & Medicinal Chemistry Letters; 5(2):151-154 (1995).
Deaton et al.; "Thiol-based angiotensin-converting enzyme 2 inhibitors: P1 modifications for the exploration of the S1 subsite"; Bioorganic & Medicinal Chemistry Letters; 18:732-737 (2008).
Deaton et al.; "Thiol-based angiotensin-converting enzyme 2 inhibitors: P1' modifications for the exploration of the S1' subsite"; Bioorganic & Medicinal Chemistry Letters; 18:1681-1687 (2008).
Hanessian et al.; "Targeting ACE and ECE with dual acting inhibitors"; Bioorganic & Medicinal Chemistry Letters; 18:1058-1062 (2008).
Jeng et al.; "CGS 34226, a thiol-based dual inhibitor of endothelin converting enzyme-I and neutral endopeptidase 24.11"; Clinical Science; 103(Suppl. 48):98S-101S [Printed in Great Britain] (2002).
Park et al., "Therapeutic Potential of Atrial Natriuretic Peptide administration on Peripheral Arterial Diseases", Endocrinology 149(2):483-491 (2008).
Yamahara et al., "Significance and therapeutic potential of the natriuretic peptides/cGMP/cGMP-dependent protein kinase pathway in vascular regeneration", PNAS, 100(6):3404-3409 (2003).
Tokudome et al., "Impaired Recovery of Blood Flow After Hind-limb Ischemia in Mice Lacking Guanylyl Cyclase-A, a receptor for Atrial and Brain Natriuretic Peptides", Arterioscler Thromb Vasc Biol 29:1516-1521 (2009).

* cited by examiner

SUBSTITUTED AMINOBUTYRIC DERIVATIVES AS NEPRILYSIN INHIBITORS

This application claims benefit under 35 U.S.C. §119(e) of U.S. Provisional Application No. 61/181,753, filed May 28, 2009; U.S. Provisional Application No. 61/263,141, filed on Nov. 20, 2009 and U.S. Provisional Application No. 61/324,938 filed on Apr. 16, 2010; the contents of which are incorporated herein by reference in their entirety.

BACKGROUND OF THE INVENTION

Endogenous atrial natriuretic peptides (ANP), also called atrial natriuretic factors (ANF) have diuretic, natriuretic and vasorelaxant functions in mammals. The natural ANF peptides is metabolically inactivated, in particular by a degrading enzyme which has been recognized to correspond to the enzyme neutral endopeptidase (NEP) EC 3.4.24.11, also responsible for e.g. the metabolic inactivation of enkephalins.

Neutral endopeptidase (EC 3.4.24.11; enkephalinase; atriopeptidase; NEP) is a zinc-containing metalloprotease that cleaves a variety of peptide substrates on the amino side of hydrophobic residues [see *Pharmacol Rev*, Vol. 45, p. 87 (1993)]. Substrates for this enzyme include, but are not limited to, atrial natriuretic peptide (ANP, also known as ANF), brain natriuretic peptide (BNP), met- and leu-enkephalin, bradykinin, neurokinin A, endothelin-1 and substance P. ANP is a potent vasorelaxant and natriuretic agent [see *J Hypertens*, Vol. 19, p. 1923 (2001)]. Infusion of ANP in normal subjects resulted in a reproducible, marked enhancement of natriuresis and diuresis, including increases in fractional excretion of sodium, urinary flow rate and glomerular filtration rate [see *J Clin Pharmacol*, Vol. 27, p. 927 (1987)]. However, ANP has a short half-life in circulation, and NEP in kidney cortex membranes has been shown to be the major enzyme responsible for degrading this peptide [see *Peptides*, Vol. 9, p. 173 (1988)]. Thus, inhibitors of NEP (neutral endopeptidase inhibitors, NEPi) should increase plasma levels of ANP and, hence, are expected to induce natriuretic and diuretic effects.

This enzyme is involved in the breakdown of several bioactive oligopeptides, cleaving peptide bonds on the amino side of hydrophobic amino acid residues. The peptides metabolised include atrial natriuretic peptides (ANP), bombesin, bradykinin, calcitonin gene-related peptide, endothelins, enkephalins, neurotensin, substance P and vasoactive intestinal peptide. Some of these peptides have potent vasodilatory and neurohormone functions, diuretic and natriuretic activity or mediate behaviour effects.

SUMMARY OF THE INVENTION

The aim of the present invention is to provide novel compounds which are useful as neutral endopeptidase inhibitors, e.g. as inhibitors of the ANF-degrading enzyme in mammals, so as to prolong and potentiate the diuretic, natriuretic and vasodilator properties of ANF in mammals, by inhibiting the degradation thereof to less active metabolites.

The compounds of this invention are thus particularly useful for the treatment of conditions and disorders responsive to the inhibition of neutral endopeptidase (NEP) EC 3.4.24.11.

Thus, the compounds of the invention, by inhibiting the neutral endopeptidase EC.3.4.24.11, can potentiate the biological effects of bioactive peptides. Thus, in particular the compounds have utility in the treatment of a number of disorders, including hypertension, pulmonary hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retension), diabetic nephropathy, non-diabetic nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), Pulmonary Arterial hypertension, renal failure (including edema and salt retension), cyclical oedema, Menières disease, hyperaldosteroneism (primary and secondary) and hypercalciuria, ascites. In addition, because of their ability to potentiate the effects of ANF the compounds have utility in the treatment of glaucoma. As a further result of their ability to inhibit the neutral endopeptidase E.C.3.4.24.11 the compounds of the invention may have activity in other therapeutic areas including for example the treatment of menstrual disorders, preterm labour, pre-eclampsia, endometriosis, and reproductive disorders (especially male and female infertility, polycystic ovarian syndrome, implantation failure). Also the compounds of the invention should treat asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, the modulation of gastric acid secretion, the treatment of hyperreninaemia, cystic fibrosis, restenosis, type-2 diabetes, metabolic syndrome, diabetic complications and athereosclerosis, male and female sexual dysfunction. In a preferred embodiment the compounds of the invention are useful in the treatment of cardiovascular disorders.

The invention pertains to the compounds, methods for using them, and uses thereof as described herein. Examples of compounds of the invention include the compounds according to anyone of Formulae I' and I to VIC, or a pharmaceutically acceptable salt thereof, and the compounds of the examples.

The invention therefore provides a compound of the formula (I'):

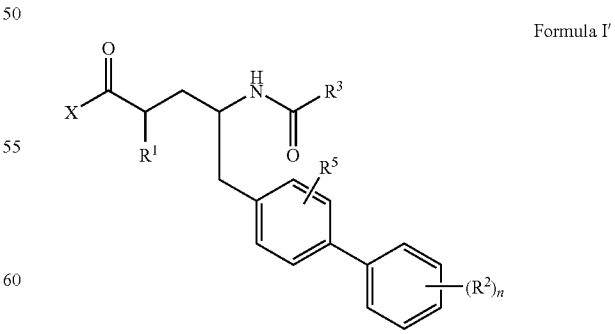

Formula I' or a pharmaceutically acceptable salt thereof, wherein:
$R^1$ is $C_{1-7}$alkyl;
for each occurrence, $R^2$ is independently $C_{1-7}$alkyl, $NO_2$, CN, halo, $C_{3-7}$cycloalkyl, hydroxy, $C_{1-7}$alkoxy, halo-$C_{1-7}$alkyl, $NR^bR^c$, $C_{6-10}$aryl, heteroaryl or heterocyclyl; wherein $R^b$ and $R^c$ for each occurrence, are independently H or $C_{1-7}$alkyl;

$R^3$ is $A^1C(O)X^1$ or $A^2$-$R^4$;

$R^4$ is $C_{6-10}$aryl or a heteroaryl, which can be monocyclic or bicyclic and which can be optionally substituted with one or more substituents independently selected from hydroxy, hydroxy-$C_{1-7}$alkyl, $NR^bR^c$, nitro, $C_{1-7}$alkoxy, halo, $C_{1-7}$alkyl, halo-$C_{1-7}$alkyl, $C_{2-7}$alkenyl, $C_{6-10}$aryl, heteroaryl, —C(O)$C_{1-7}$alkyl, —NHS(O)$_2$-$C_{1-7}$alkyl, —SO$_2$$C_{1-7}$alkyl and benzyl;

$R^5$ is H, halo, hydroxy, $C_{1-7}$alkoxy, halo, $C_{1-7}$alkyl or halo-$C_{1-7}$alkyl; and X and $X^1$ are independently OH, —O—$C_{1-7}$alkyl, —$NR^bR^c$, —NHS(O)$_2$—$C_{1-7}$alkyl, —NHS(O)$_2$-benzyl or —O—$C_{6-10}$ aryl; wherein alkyl is optionally substituted with one or more substituents independently selected from the group consisting of aryl, heteroaryl, heterocyclyl, —C(O)NH$_2$, —C(O)NH—$C_{1-6}$alkyl, and —C(O)N($C_{1-6}$alkyl)$_2$;

$A^1$ is a bond or a linear $C_{1-4}$alkylene substituted with one or more substituents independently selected from the group consisting of halo, O-acetate, $C_{1-7}$ alkyl and $C_{3-7}$cycloalkyl; in which two geminal alkyl can optionally combine to form a $C_{3-7}$cycloalkyl; or $A^1$ is a linear or branched $C_{2-6}$alkenylene; or $A^1$ is a linear $C_{1-4}$ alkylene wherein one or more carbon atom(s) is/are replaced with an heteroatom selected from O, $NR^a$; and $A^1$ is optionally substituted with one or more substituents independently selected from the group consisting of halo and $C_{1-7}$alkyl; in which $R^a$ for each occurrence, is independently H, $C_{1-7}$alkyl or CH$_2$C(O)OH; or $A^1$ is a $C_{3-7}$cycloalkyl, a heterocyclyl, a phenyl or a heteroaryl in which phenyl and heteroaryl are optionally substituted with one or more substituents independently selected from the group consisting of $C_{1-7}$alkyl, $C_{3-7}$cycloalkyl, halo-$C_{1-7}$ alkyl, hydroxy, $C_{1-7}$alkoxy, halo, $NR^bR^c$, OCH$_2$CO$_2$H, and OCH$_2$C(O)NH$_2$; or $A^1$ is —$C_{1-4}$alkylene-$C_{6-10}$-aryl-, —$C_{1-4}$alkylene-heteroaryl- or —$C_{1-4}$alkylene-heterocyclyl-, wherein $A^1$ may be in either direction; and $A^2$ is a bond or a linear or branched $C_{1-7}$alkylene which is optionally substituted with one or more substituents independently selected from the group consisting of halo, $C_{1-7}$alkoxy, hydroxy, O-Acetate and $C_{3-7}$cycloalkyl;

n is 0, 1, 2, 3, 4 or 5;

wherein each heteroaryl is a monocyclic or bicyclic aromatic ring comprising 5-10 ring atoms selected from carbon atoms and 1 to 5 heteroatoms, and each heterocyclyl is a monocyclic saturated or partially saturated but non-aromatic moiety comprising 4-7 ring atoms selected from carbon atoms and 1-5 heteroatoms, wherein each heteroatom of a heteroaryl or a heterocyclyl is independently selected from O, N and S.

The invention therefore provides a compound of the formula (I):

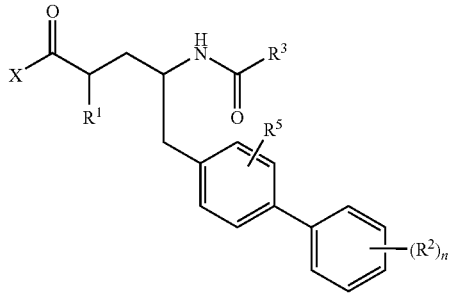

Formula I or a pharmaceutically acceptable salt thereof, wherein:

$R^1$ is $C_{1-7}$alkyl;

for each occurrence, $R^2$ is independently $C_{1-7}$alkyl, NO$_2$, CN, halo, $C_{3-7}$cycloalkyl, hydroxy, $C_{1-7}$alkoxy, halo-$C_{1-7}$alkyl, $NR^bR^c$, $C_{6-10}$aryl, heteroaryl or heterocyclyl; wherein $R^b$ and $R^c$ for each occurrence, are independently H or $C_{1-7}$alkyl;

$R^3$ is $A^1C(O)X^1$ or $A^2$-$R^4$;

$R^4$ is $C_{6-10}$aryl or a heteroaryl, which can be monocyclic or bicyclic and which can be optionally substituted with hydroxy, hydroxy-$C_{1-7}$alkyl, nitro, $C_{1-7}$alkoxy, halo, $C_{1-7}$alkyl, halo-$C_{1-7}$alkyl, $C_{6-10}$aryl, heteroaryl, —NHS(O)$_2$-$C_{1-7}$alkyl, —SO$_2$ $C_{1-7}$alkyl or benzyl;

$R^5$ is H, halo, hydroxy, $C_{1-7}$alkoxy, halo, $C_{1-7}$alkyl or halo-$C_{1-7}$akyl; and X and $X^1$ are independently OH, —O—$C_{1-7}$alkyl or $NR^bR^c$, —O—$C_{6-10}$aryl; wherein alkyl is optionally substituted with one or more substituents independently selected from the group consisting of aryl, heteroaryl, heterocyclyl, C(O)NH$_2$, C(O)NH—$C_{1-6}$alkyl, and C(O)N($C_{1-6}$alkyl)$_2$;

$A^1$ is a bond, or a linear $C_{1-4}$alkylene substituted with one or more substituents independently selected from the group consisting of halo, O-acetate, $C_{1-7}$ alkyl and $C_{3-7}$cycloalkyl; in which two geminal alkyl can optionally combine to form a $C_{3-7}$cycloalkyl; or $A^1$ is a linear $C_{1-4}$ alkylene wherein one or more carbon atom(s) is/are replaced with an heteroatom selected from O, $NR^a$; and $A^1$ is optionally substituted with one or more substituents independently selected from the group consisting of halo and $C_{1-7}$alkyl; in which $R^a$ for each occurrence, is independently H, $C_{1-7}$alkyl or CH$_2$C(O)OH; or $A^1$ is a $C_{3-7}$cycloalkyl, a heterocyclyl, a phenyl or a heteroaryl in which phenyl and heteroaryl are optionally substituted with one or more substituents independently selected from the group consisting of $C_{1-7}$alkyl, $C_{3-7}$cycloalkyl, halo-$C_{1-7}$ alkyl, hydroxy, $C_{1-7}$alkoxy, halo, $NR^bR^c$, OCH$_2$CO$_2$H, and OCH$_2$C(O)NH$_2$; or $A^1$ is —$C_{1-4}$alkylene-$C_{6-10}$-aryl-, —$C_{1-4}$alkylene-heteroaryl- or —$C_{1-4}$alkylene-heterocyclyl-, wherein $A^1$ may be in either direction; and $A^2$ is a bond or a linear or branched $C_{1-7}$alkylene which is optionally substituted with one or more substituents independently selected from the group consisting of halo, $C_{1-7}$alkoxy, hydroxy, O-Acetate and $C_{3-7}$cycloalkyl;

n is 0, 1, 2, 3, 4 or 5;

wherein each heteroaryl is a monocyclic or bicyclic aromatic ring comprising 5-10 ring atoms selected from carbon atoms and 1 to 5 heteroatoms, and each heterocyclyl is a monocyclic saturated or partially saturated but non-aromatic moiety comprising 4-7 ring atoms selected from carbon atoms and 1-5 heteroatoms, wherein each heteroatom of a heteroaryl or a heterocyclyl is independently selected from O, N and S.

In another embodiment, the invention pertains to a method for treating a disorders or diseases responsive to the inhibition of neutral endopeptidase EC 3.4.24.11 (NEP), in a subject in need of such treatment, comprising: administering to the subject an effective amount of a compound according to anyone of Formulae I-VIC, or a pharmaceutically acceptable salt thereof, such that the disorder or disease responsive to the inhibition of neutral endopeptidase EC 3.4.24.11 (NEP) in the subject is treated.

In yet another embodiment, the invention pertains to a method for treating hypertension, pulmonary hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retension), diabetic nephropathy, non-diabetic nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), Pulmonary Arterial hypertension, renal failure (including edema and salt retension), cyclical oedema, Meniéres disease, hyperaldosteroneism (primary and secondary) and hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, gastric acid secretion dysfunction, hyperreninaemia, cystic fibrosis, restenosis, type-2 diabetes, metabolic syndrome, diabetic complications and atherosclerosis, male and female sexual dysfunction; comprising administering to the subject a therapeutically effective amount of a compound according to anyone of Formulae I-VIC, or a pharmaceutically acceptable salt thereof such that the subject is treated.

In yet another embodiment, the invention pertains to pharmaceutical compositions, comprising a compound according to anyone of Formulae I-VIC, or a pharmaceutically acceptable salt thereof, and one or more pharmaceutically acceptable carriers.

In still another embodiment, the invention pertains to combinations including, a compound according to anyone of Formulae I-VIC, or a pharmaceutically acceptable salt thereof, and pharmaceutical combinations of one or more therapeutically active agents.

In another embodiment, the invention pertains to a method for inhibiting neutral endopeptidase EC 3.4.24.11 in a subject in need thereof, comprising: administering to the subject a therapeutically effective amount of a compound according to anyone of Formulae I-VIC, or a pharmaceutically acceptable salt thereof, such that neutral endopeptidase EC 3.4.24.11 is inhibited.

DETAILED DESCRIPTION OF THE INVENTION

Compounds of the Invention

References hereinafter to compounds of Formula I or I' apply equally to compounds according to anyone of Formulae IB to VIC.

References hereinafter to embodiments of the invention apply equally to compounds of Formula I or I' and compounds according to anyone of Formulae IB to VIC, insofar as the embodiments are present.

Various embodiments of the invention are described herein. It will be recognized that features specified in each embodiment may be combined with other specified features to provide further embodiments.

In one embodiment the invention provides a compound of the Formula I or I', or a pharmaceutically acceptable salt thereof wherein:
$R^1$ is $C_{1-7}$alkyl;
for each occurrence $R^2$ is independently $C_{1-7}$alkyl, halo, $C_{3-7}$cycloalkyl, hydroxy, $C_{1-7}$alkoxy, halo-$C_{1-7}$alkyl, $NR^bR^c$, $C_{6-10}$aryl, heteroaryl or heterocyclyl; wherein $R^b$ and $R^c$ for each occurrence, are independently H or $C_{1-7}$alkyl;
$R^3$ is $A^1C(O)X^1$ or $A^2$-$R^4$;
$R^4$ is aryl or a heteroaryl, which can be monocyclic or bicyclic and which can be optionally substituted with one or more substituents independently selected from the group consisting of hydroxy, $C_{1-7}$alkoxy, halo, $C_{1-7}$alkyl, halo-$C_{1-7}$alkyl, $C_{6-10}$aryl, heteroaryl, —NHS(O)$_2$-$C_{1-7}$alkyl, —SO$_2$ $C_{1-7}$alkyl and benzyl;
$R^5$ is H; and
X and $X^1$ are independently OH, —O—$C_{1-7}$alkyl or $NR^bR^c$;
$A^1$ is a linear $C_{1-4}$ alkylene substituted with one or more substituents independently selected from the group consisting of halo, O-acetate, $C_{1-7}$ alkyl and $C_{3-7}$cycloalkyl; in which two geminal alkyl can optionally combine to form a $C_{3-7}$cycloalkyl; or
$A^1$ is a linear $C_{1-4}$ alkylene wherein one or more carbon atom(s) is/are replaced with an heteroatom selected from O, $NR^a$; wherein $A^1$ is optionally substituted with one or more substituents independently selected from the group consisting of halo and $C_{1-7}$alkyl; in which $R^a$ for each occurrence, is independently H, $C_{1-7}$alkyl or $CH_2C(O)OH$; or
$A^1$ is a $C_{3-7}$cycloalkyl, a heterocyclyl, a phenyl or a heteroaryl in which phenyl and heteroaryl are optionally substituted with one or more substituents independently selected from the group consisting of $C_{1-7}$alkyl, $C_{3-7}$cycloalkyl, hydroxy, $C_{1-7}$alkoxy, halo, $NR^bR^c$, $OCH_2CO_2H$, and $OCH_2C(O)NH_2$; and
$A^2$ is a bond or a linear or branched $C_{1-7}$alkylene which is optionally substituted with one or more substituents independently selected from the group consisting of halo, $C_{1-7}$alkoxy, hydroxy, O-Acetate and $C_{3-7}$cycloalkyl;
n is 0, 1, 2, 3, 4 or 5;
wherein each heteroaryl is a monocyclic or bicyclic aromatic ring comprising 5-10 ring atoms selected from carbon atoms and 1 to 5 heteroatoms, and
each heterocyclyl is a monocyclic saturated or partially saturated but non-aromatic moiety comprising 4-7 ring atoms selected from carbon atoms and 1-5 heteroatoms, wherein each heteroatom of a heteroaryl or heterocyclyl is independently selected from O, N and S.

Certain compounds of Formula I or I' include compounds of Formula IA:

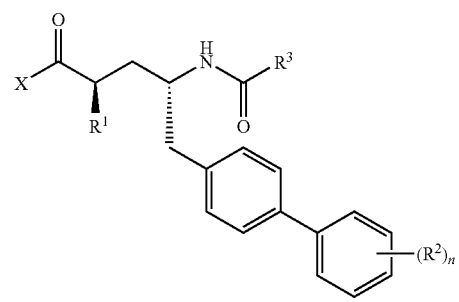

Formula IA or a pharmaceutically acceptable salt thereof, wherein X, $R^1$, $R^2$, $R^3$ and n have the definitions of Formula I, supra.

Certain compounds of Formulae I or I' wherein n is 1, 2, 3, 4 or 5; $R^2$ is halo and is attached to the meta position and the other optional $R^2$ groups are independently $C_{1-7}$alkyl, NO$_2$, CN, halo, $C_{3-7}$cycloalkyl, hydroxy, $C_{1-7}$alkoxy, halo-$C_{1-7}$ alkyl, $NR^bR^c$, $C_{6-10}$aryl, heteroaryl or heterocyclyl. This embodiment is illustrated by compounds of Formulae IB and IC:

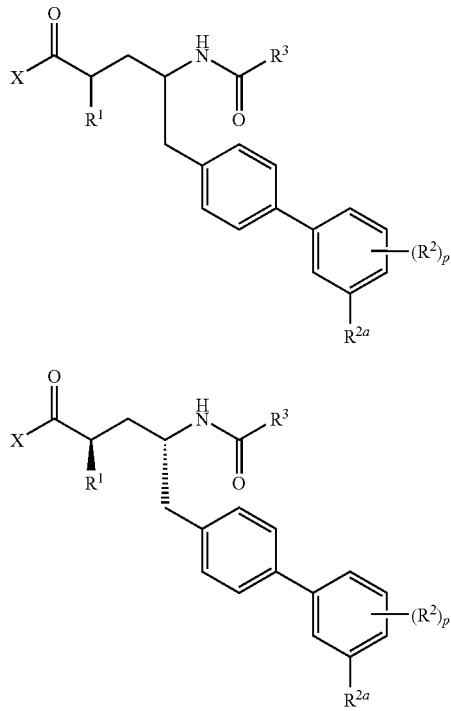

IB

IC or a pharmaceutically acceptable salt thereof, wherein X, $R^1$, $R^2$, $R^3$ have the definitions of Formula I or I', supra; p is 0, 1, 2, 3 or 4 and $R^{2a}$ is halo.

Certain compounds of Formula I or I' include compounds of Formula II:

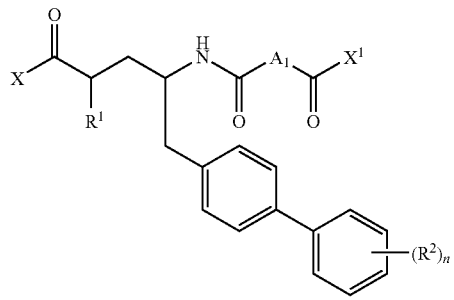

Formula II or a pharmaceutically acceptable salt thereof, wherein X, $X^1$, $A^1$, $R^1$, $R^2$ and n have the definitions of Formula I or I', supra.

Certain compounds of Formulae I, I' or II include compounds of Formula IIA:

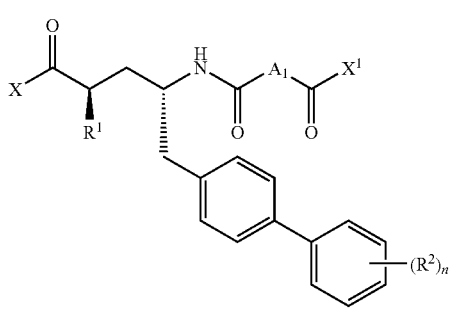

Formula IIA or a pharmaceutically acceptable salt thereof, wherein X, $X^1$, $A^1$, $R^1$, $R^2$ and n have the definitions of Formula I or I', supra.

Certain compounds of Formula I or I' include compounds of Formula IIB and IIC:

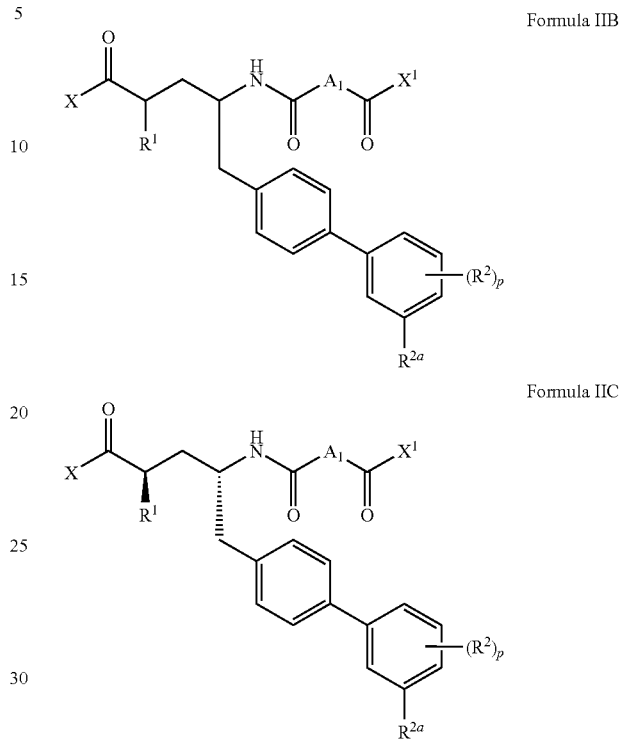

Formula IIB

Formula IIC or a pharmaceutically acceptable salt thereof, wherein X, $X^1$, $A^1$, $R^1$, $R^2$ have the definitions of Formula I or I', supra; p is 0, 1, 2, 3 or 4 and $R^{2a}$ is halo.

In another embodiment the invention provides a compound according to anyone of the formulae I', I to IC and II to IIC, or of any classes and subclasses described herein, or a pharmaceutically acceptable salt or solvate thereof, wherein $A^1$ is a linear $C_{1-4}$ alkylene substituted with one or more substituents independently selected from the group consisting of halo, O-acetate, $C_{1-7}$alkyl and $C_{3-7}$cycloalkyl; in which two geminal alkyl can optionally combine to form a $C_{3-7}$cycloalkyl.

A further embodiment includes compounds according to any one of Formulae I', I to IC and II to IIC, or of any classes and subclasses described herein, or a pharmaceutically acceptable salt thereof, wherein $A^1$ has the following formulae:

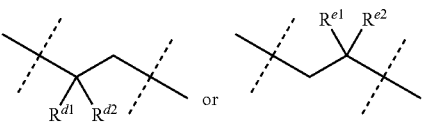

in which $R^{d1}$ and $R^{d2}$ are independently H, halo, $C_{3-7}$cycloalkyl, or $C_{1-7}$alkyl and at least one of $R^{d1}$ and $R^{d2}$ is other than H; and alternatively $R^{d1}$ and $R^{d2}$ can form together with the atoms to which they are attached a $C_{3-7}$cycloalkyl; and $R^{e1}$ and $R^{e2}$ are independently H, halo, $C_{3-7}$cycloalkyl, or $C_{1-7}$alkyl and at least one of $R^{e1}$ and $R^{e2}$ is other than H; and alternatively $R^{e1}$ and $R^{e2}$ can form together with the atoms to which they are attached a $C_{3-7}$cycloalkyl. In one aspect of this embodiment, $A^1$ is one of the following:

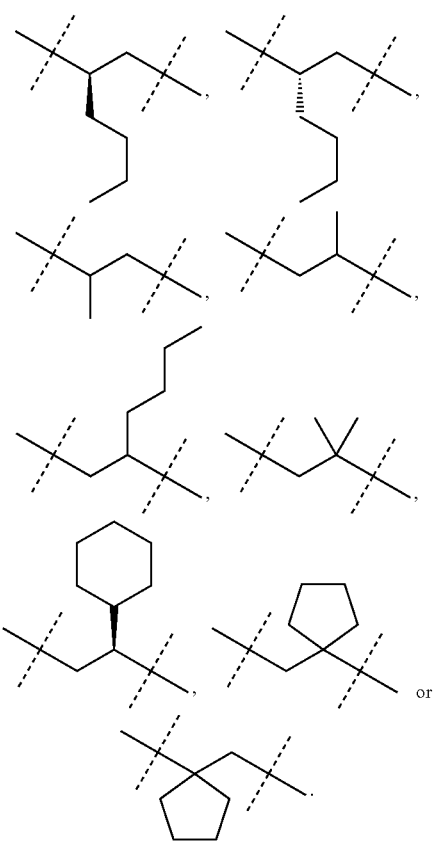

Yet another further embodiment include compounds according to any one of Formulae I', I to IC and II to IIC, or of any classes and subclasses described herein, or a pharmaceutically acceptable salt thereof, wherein $A^1$ has the following formulae:

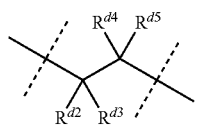

in which $R^{d3}$, $R^{d4}$, $R^{d5}$ and $R^{d6}$ are independently H, halo, O-acetate or $C_{1-7}$alkyl and at least one of $R^{d3}$, $R^{d4}$, $R^{d5}$ and $R^{d6}$ is other than H. In a further aspect of this embodiment, $A^1$ is one of the following:

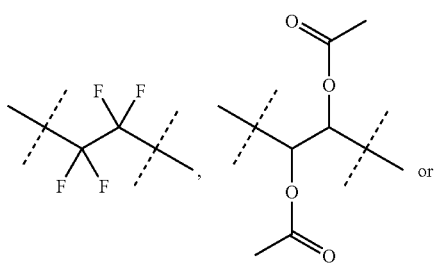

In another embodiment the invention provides a compound according to any one of the formulae I', I to IC and II to IIC, or of any classes and subclasses described herein, or a pharmaceutically acceptable salt or solvate thereof, wherein $A^1$ is a linear $C_{1-4}$ alkylene wherein one or more carbon atom(s) is/are replaced with an heteroatom selected from O, $NR^a$; and $A^1$ is optionally substituted with one or more substituents independently selected from the group consisting of halo and $C_{1-7}$alkyl; in which $R^a$ for each occurrence is independently H, $C_{1-7}$alkyl or $CH_2C(O)OH$. One further embodiment includes compounds according to anyone of Formulae I', I to IC and II to IIC wherein $A^1$ is one of the following:

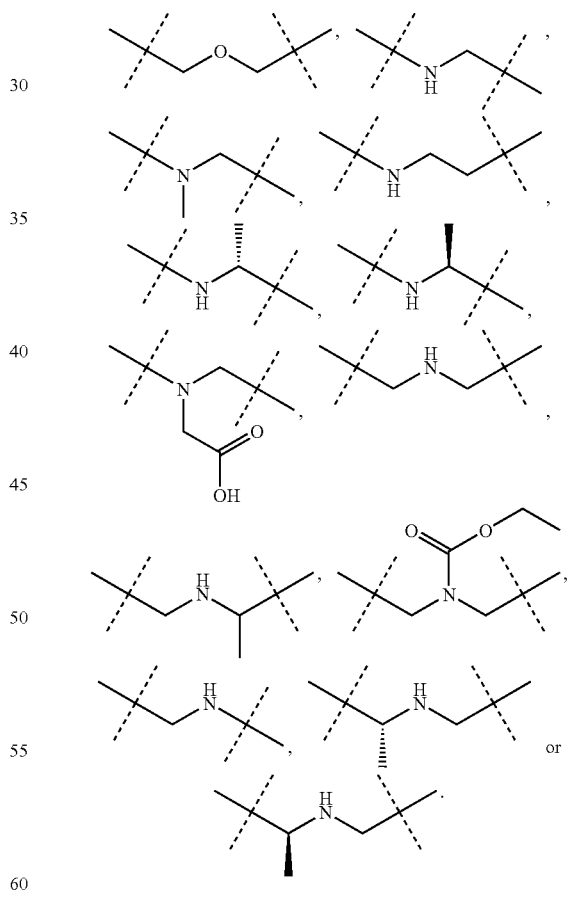

In yet another embodiment the invention provides a compound according to any one of Formulae I', I to IC and II to IIC or of any classes and subclasses described herein, or a pharmaceutically acceptable salt or solvate thereof, wherein $A^1$ is a $C_{3-7}$cycloalkyl, a heterocyclyl, a phenyl or a heteroaryl in which phenyl and heteroaryl are optionally substituted with one or more substituents independently selected from the group consisting of $C_{1-7}$alkyl, $C_{3-7}$cycloalkyl, halo-$C_{1-7}$alkyl, hydroxy, $C_{1-7}$alkoxy, halo, $NR^bR^c$, $OCH_2CO_2H$, and $OCH_2C(O)NH_2$. In one aspect of this embodiment the invention provides compounds according to any one of Formulae I', I to IC and II to IIC, or a pharmaceutically acceptable salt thereof, wherein $A^1$ is a optionally substituted $C_{3-7}$ cycloalkyl or a optionally substituted heterocyclyl. One further embodiment includes compounds according to any one of Formulae I', I to IC and II to IIC, or a pharmaceutically acceptable salt thereof, wherein $A^1$ is one of the following:

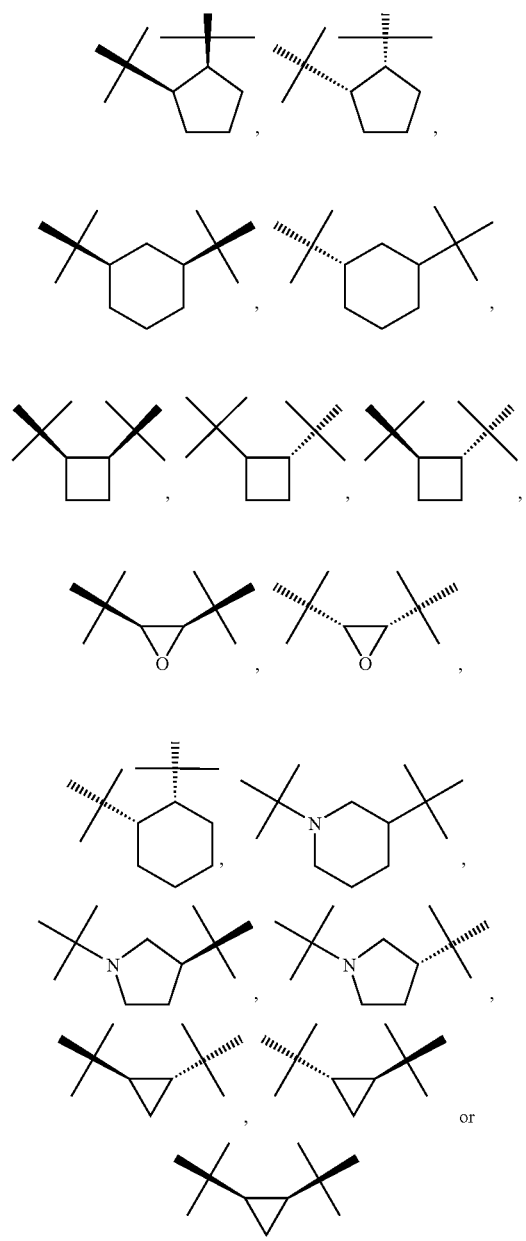

Certain compounds of the above embodiment include compounds according to any one of Formulae I', I to IC and II to IIC, or a pharmaceutically acceptable salt thereof, wherein $A^1$ is a 5-membered ring heteroaryl. This embodiment is illustrated by compounds of Formula III:

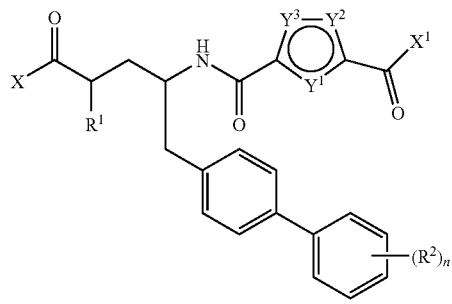

Formula III or a pharmaceutically acceptable salt thereof, wherein X, $X^1$, $R^1$, $R^2$ and n have the definitions of Formula I or I', supra and $Y^1$, $Y^2$ and $Y^3$ are independently N, NH, S, O or CH and form together with the ring atoms to which they are attached a 5-membered heteroaryl ring. In one aspect of this embodiment, the invention pertains to compounds of Formula IIIA:

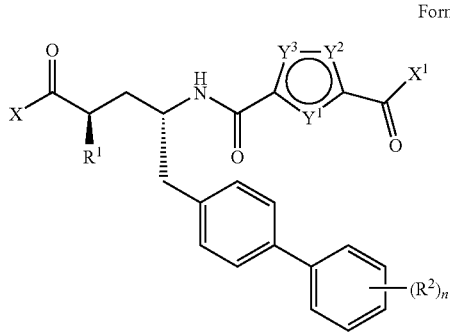

Formula IIIA or a pharmaceutically acceptable salt thereof, wherein X, $X^1$, $R^1$, $R^2$ and n have the definitions of Formula I or I', supra and $Y^1$, $Y^2$ and $Y^3$ are independently N, NH, S, O or CH and form together with the ring atoms to which they are attached a 5-membered heteroaryl ring.

In another aspect of this embodiment, the invention pertains to compounds of Formula IIIB or IIIC:

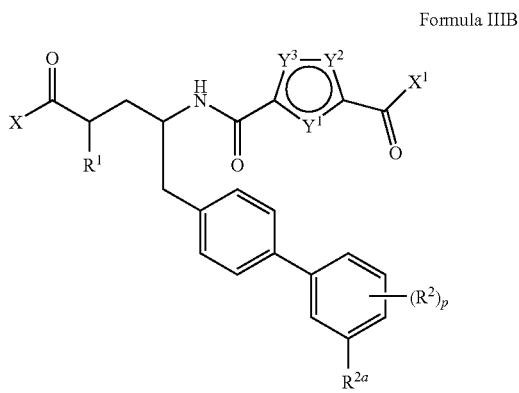

Formula IIIB

Formula IIIC

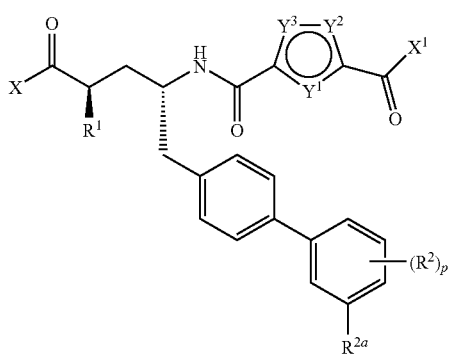

or a pharmaceutically acceptable salt thereof, wherein X, X$^1$, R$^1$, R$^2$ have the definitions of Formula I, supra and Y$^1$, Y$^2$ and Y$^3$ are independently N, NH, S, O or CH and form together with the ring atoms to which they are attached a 5-membered heteroaryl ring, p is 0, 1, 2, 3 or 4 and R$^{2a}$ is halo.

In a further embodiment, the invention pertains to compounds of Formula III to IIIC or a pharmaceutically acceptable salt thereof, wherein Y$^1$, Y$^2$ and Y$^3$ form together with the ring atoms to which they are attached a 5-membered heteroaryl ring selected from furan, thiophene, pyrrole, pyrazole, oxazole, thiazole, oxadiazole, thiadiazole, and triazole. One further embodiment includes compounds of Formula III wherein the 5-membered heteroaryl is one of the following:

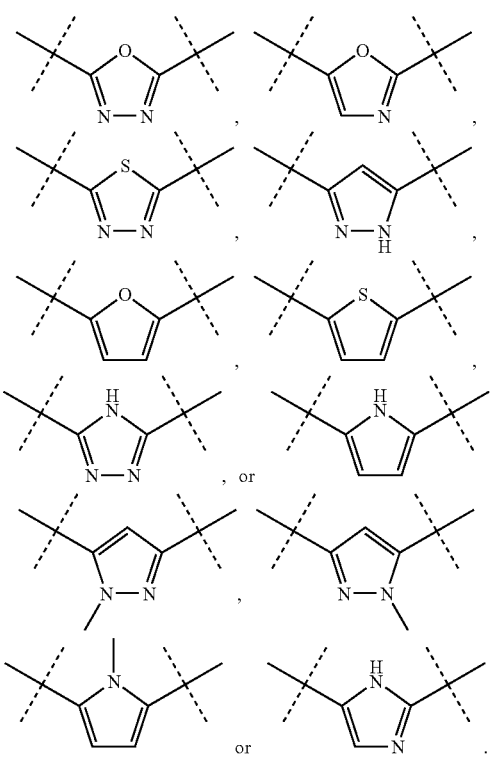

In yet another aspect of the above embodiment, the invention pertains to compounds according to any one of Formulae I', I to IC and II to IIC or a pharmaceutically acceptable salt thereof, wherein A$^1$ is a 5-membered heteroaryl attached at a nitrogen atom. This embodiment is illustrated by compounds of Formula IV or IVA:

Formula IV

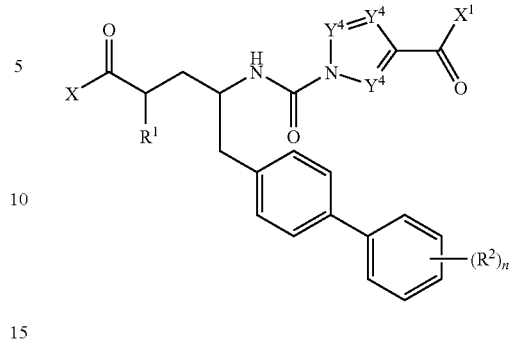

Formula IVA or a pharmaceutically acceptable salt thereof, wherein X, X$^1$, R$^1$, R$^2$ and n have the definitions of Formula I or I', supra and each Y$^4$ is independently N, S, O or CH.

In a further embodiment, the invention pertains to compounds of Formula IV or IVA wherein n is 1, 2, 3, 4 or 5; R$^2$ is halo in the meta position and the other optional R$^2$ groups are independently C$_{1-7}$alkyl, NO$_2$, CN, halo, C$_{3-7}$cycloalkyl, hydroxy, C$_{1-7}$alkoxy, NR$^b$R$^c$, C$_{6-10}$aryl, heteroaryl or heterocyclyl.

In yet another aspect of the above embodiment the invention provides a compound according to any one of Formulae I', I to IC and II to IIC or of any classes and subclasses described herein, or a pharmaceutically acceptable salt or solvate thereof, wherein A$^1$ is a phenyl or a 6-membered heteroaryl in which phenyl and heteroaryl are optionally substituted with one or more substituents independently selected from the group consisting of C$_{1-7}$alkyl, C$_{3-7}$cycloalkyl, hydroxy, C$_{1-7}$alkoxy, halo, NR$^b$R$^c$, OCH$_2$CO$_2$H, and OCH$_2$C(O)NH$_2$. One aspect of this embodiment include compounds according to anyone of Formulae I to IC and II to IIC, or a pharmaceutically salt thereof, wherein A$^1$ is connected to the amide C(O)NH moiety and to the C(O)X$^1$ moieties in a para arrangement. Another aspect of this embodiment include compounds according to any one of Formulae I', to IC, and II to IIC, or a pharmaceutically acceptable salt thereof, wherein A$^1$ is connected to the amide C(O)NH moiety and to the C(O)X$^1$ moieties in a meta arrangement. Compounds of this embodiment include compounds of Formula V:

Formula V

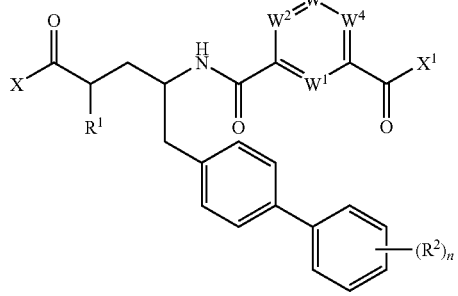

or a pharmaceutically acceptable salt thereof, wherein X, $X^1$, $R^1$, $R^2$ and n have the definitions of Formula I or I', supra and $W^1$, $W^2$, $W^3$ and $W^4$ are independently N or $CR^e$, in which each $R^e$ is independently selected from H, $C_{1-7}$alkyl, $C_{3-7}$cycloalkyl, halo-$C_{1-7}$alkyl, hydroxy, $C_{1-7}$alkoxy, halo, $NR^bR^c$, $OCH_2CO_2H$ and $OCH_2C(O)NH_2$.

In a further embodiment, the invention pertains to compounds of Formula VA:

Formula VA

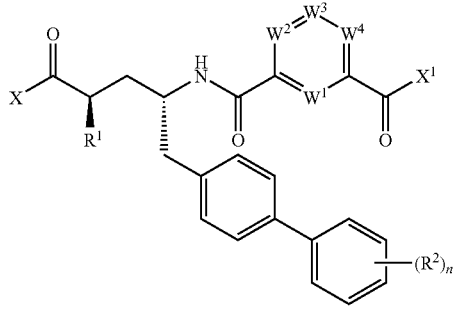

or a pharmaceutically acceptable salt thereof, wherein X, $X^1$, $R^1$, $R^2$, $W^1$, $W^2$, $W^3$ and $W^4$ and n have the definitions of Formulae I, I' or V, supra.

In one aspect of this embodiment, the invention pertains to compounds of Formula V or VA, or a pharmaceutically acceptable salt thereof, wherein $A^1$ is phenyl, pyridine or pyrimidine. One further embodiment includes compounds of Formula V or VA, or a pharmaceutically acceptable salt thereof, wherein $A^1$ is one of the following:

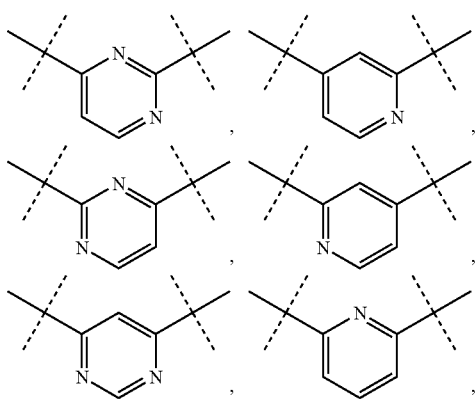

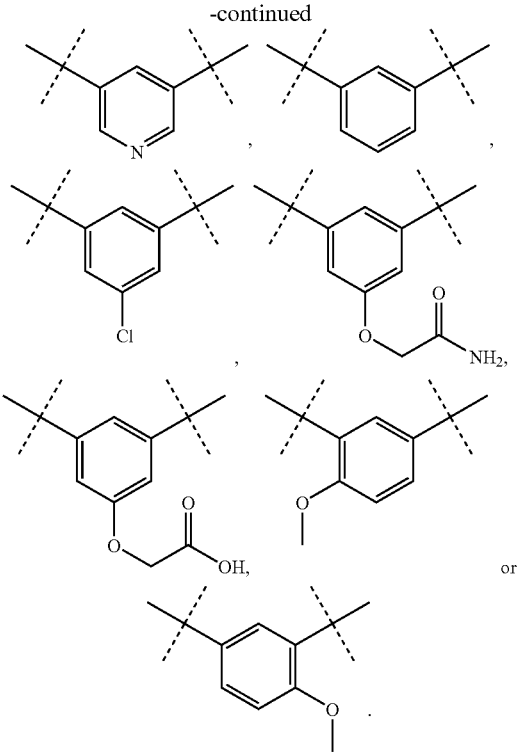

In a further aspect of the above embodiment, the invention pertains to compounds of Formula V or VA, or a pharmaceutically acceptable salt thereof, wherein n is 1, 2, 3, 4 or 5; $R^2$ is halo in the meta position and the other optional $R^2$ groups are independently $C_{1-7}$alkyl, $NO_2$, CN, halo, $C_{3-7}$cycloalkyl, hydroxy, $C_{1-7}$alkoxy, halo-$C_{1-7}$alkyl, $NR^bR^c$, $C_{6-10}$aryl, heteroaryl or heterocyclyl.

Certain compounds of the above embodiment include compounds according to any one of Formulae I', I to IC and II to IIC, or a pharmaceutically acceptable salt thereof, wherein $A^1$ is —$C_{1-4}$alkylene-$C_{6-10}$-aryl-, —$C_{1-4}$alkylene-heteroaryl- or —$C_{1-4}$alkylene-heterocyclyl-, —$C_{6-10}$aryl-$C_{1-4}$-alkylene-, -heteroaryl-$C_{1-4}$alkylene or -heterocyclyl-$C_{1-4}$alkylene-. In one aspect of this embodiment, $A^1$ is —$C_{1-4}$alkylene-$C_{6-10}$-aryl-, —$C_{1-4}$alkylene-heteroaryl- or —$C_{1-4}$alkylene-heterocyclyl-, wherein the alkylene portion is attached to C(O)NH group and the aryl, heteroaryl or heterocyclyl moities are attached to $C(O)X^1$. In another aspect of this embodiment, $A^1$ is —$CH_2$-phenyl- or -phenyl-$CH_2$—. In another aspect of this embodiment, $A^1$ is —$CH_2$-heteroaryl or - heteroaryl-$CH_2$—. In a further embodiment, $A^1$ is —$CH_2$-heterocyclyl or -heterocyclyl-$CH_2$—. Representative examples of $A^1$ are the following:

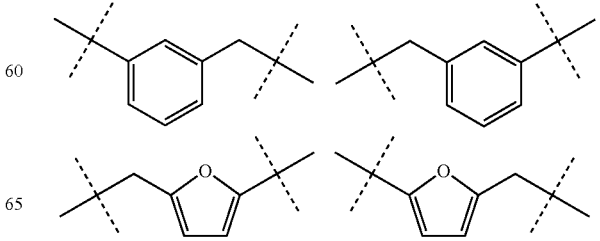

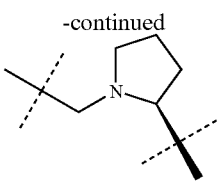

Certain compounds of Formula I or I' include compounds of Formula VI:

Formula VI

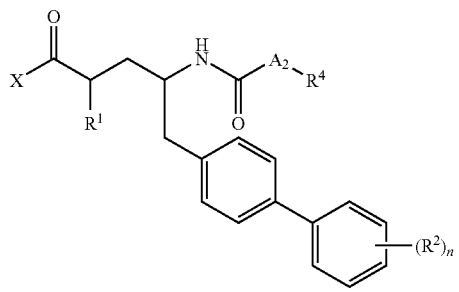

or a pharmaceutically acceptable salt thereof, wherein X, $A^2$, $R^1$, $R^2$, $R^4$ and n have the definitions of Formula I or I', supra.

A further embodiment includes compounds of Formula VIA:

Formula VIA

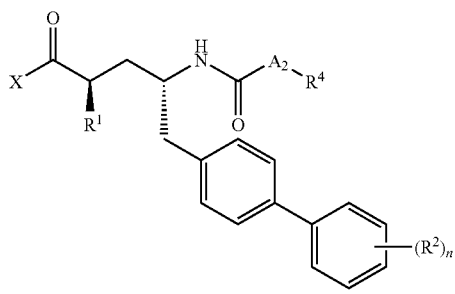

or a pharmaceutically acceptable salt thereof, wherein X, $A^2$, $R^1$, $R^2$, $R^4$ and n have the definitions of Formula I or I', supra.

Certain compounds of Formula VI or VIA include compounds of Formula VIB and VIC:

Formula VIB

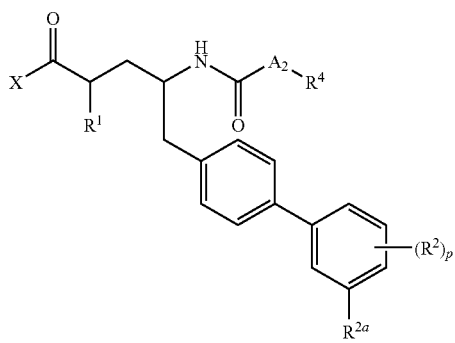

Formula VIC

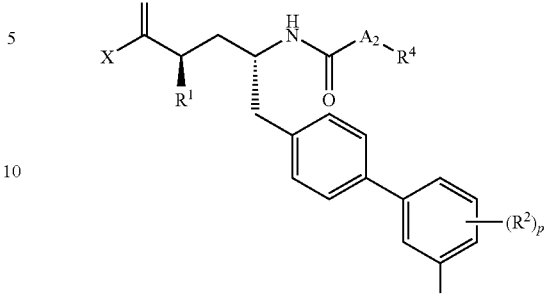

or a pharmaceutically acceptable salt thereof, wherein X, $A^2$, $R^1$, $R^2$, $R^4$ have the definitions of Formula I or I', supra; p is 0, 1, 2, 3 or 4 and $R^{2a}$ is halo.

A further aspect of this embodiment includes compounds according to anyone of Formulae VI to VIC, or a pharmaceutically acceptable salt thereof, wherein $A^2$ is $(CH_2)_p$ and p is 0, 1, 2 or 3. In one aspect of this embodiment, p is 0, therefore $A^2$ is a bond. In another aspect of this embodiment, $A^2$ is $CH_2$ or $CH_2$—$CH_2$.

In another aspect of this embodiment the invention provide compounds according to anyone of Formulae VI to VIC or a pharmaceutically acceptable salt thereof, wherein $R^4$ is an optionally substituted $C_{6-10}$aryl. Representative examples of aryl are benzoimidazolone, benzoisothiazolone or phenyl. In one further aspect of this embodiment, $R^4$ is phenyl. Substituents on the phenyl ring include for example, halo (e.g. F, Cl), hydroxy, halo-$C_{1-7}$alkyl (e.g. $CF_3$), $C_{1-7}$alkoxy or $C_{1-7}$alkyl.

In yet another aspect of this embodiment the invention provides compounds according to anyone of Formulae VI to VIC or a pharmaceutically acceptable salt thereof, wherein $R^4$ is an optionally substituted bicyclic heteroaryl.

In yet another aspect of this embodiment the invention provide compounds according to anyone of Formulae VI to VIC, or a pharmaceutically acceptable salt thereof, wherein $R^4$ is an optionally substituted 5- or 6-membered heteroaryl. In one aspect of this embodiment, $R^4$ is a 6-membered ring heteroaryl selected from the group consisting of pyrazinyl, pyridinyl, pyrimidinyl, oxo-pyranyl (e.g. pyranone, optionally substituted pyran-4-one, pyran-2-one such as 3-hydroxy-pyran-4-one, 3-hydroxy-pyran-2-one), and oxo-pyridinyl (e.g. pyridinone, optionally substituted pyridin-4-one or pyridin-2-one such as for example 3-hydroxy-1-methyl-pyridin-4-one or 1-benzyl-pyridin-2-one); or pyrimidinone (i.e. oxo-pyrimidinyl). In another aspect of this embodiment $R^4$ is a 5-membered ring heteroaryl selected from the group consisting of oxazole, pyrrole, pyrazole, isooxazole, triazole, tetrazole, oxadiazole (e.g. 1-oxa-3,4-diazole, 1-oxa-2,4-diazole), oxadiazolone (e.g. oxadiazol-2-one), thiazole, isothiazole, thiophene, imidazole and thiadiazole. Other representative examples of $R^4$ are oxazolone, thiazolone, oxadiazolone triazolone, oxazolone, imidazolone, pyrazolone. In a further embodiment, the optional substituents on $C_{6-10}$aryl and heteroaryl are selected from hydroxy, $C_{1-7}$alkyl, $C_{1-7}$alkoxy, halo, halo-$C_{1-7}$alkyl or benzyl.

In yet another aspect of the above embodiment the invention provide compounds according to anyone of Formulae VI to VIC or a pharmaceutically acceptable salt thereof, wherein $R^4$ is a bicyclic heteroaryl. A further embodiment includes compounds of Formula VI wherein $R^4$ is indolyl, benzothiazolyl or benzimidazolyl. Representative examples of $R^4$ are the following:

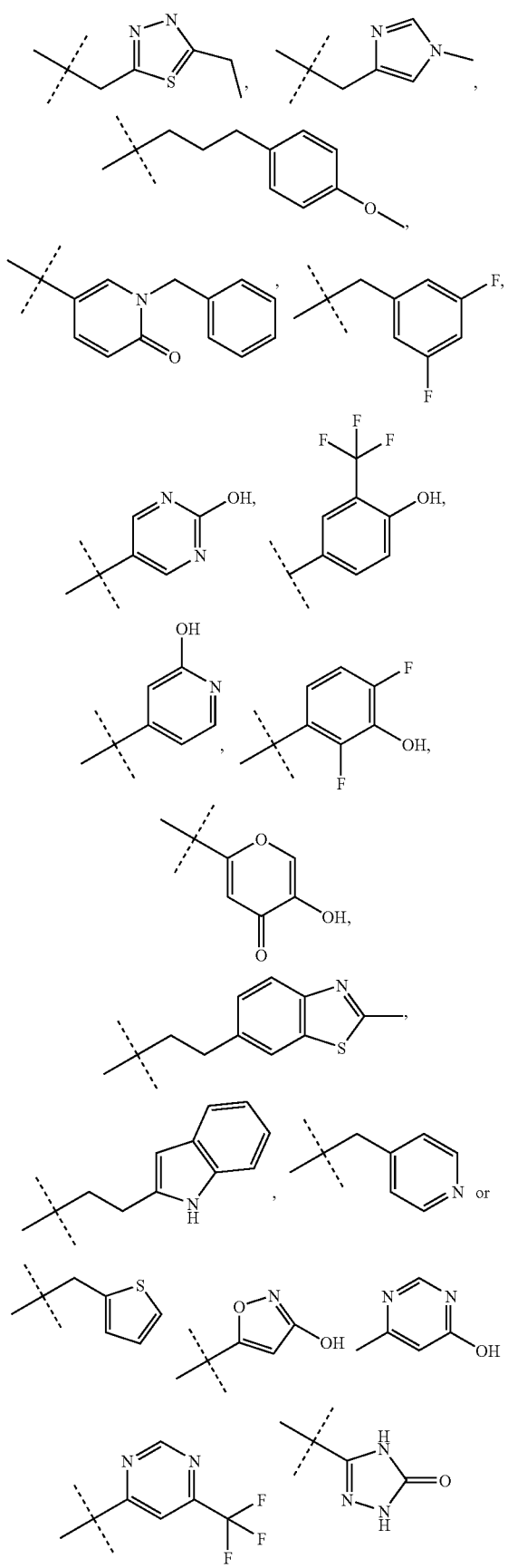

In one embodiment the invention provide compounds according to any one of Formulae I', I to IC, II to IIC, III to IIIC, IV, IVA, V, VA and VI to VIC or a pharmaceutically acceptable salt thereof, wherein $R^1$ is methyl.

In another embodiment the invention provide compounds according to any one of Formulae I', I, IA II, IIA, III, IIIA, IV, IVA, V, VA and VI to VIC or a pharmaceutically acceptable salt thereof, wherein each $R^2$ is independently halo, alkyl, alkoxy, hydroxy, haloalkyl and n is 0, 1 or 2. In a further embodiment of anyone of Formulae I', I, IA, II, IIA, III, IIIA, IV, IVA, V, VA and VI to VIC, or a pharmaceutically acceptable salt thereof, n is 1, 2, 3, 4 or 5, $R^2$ is halo in the meta position and the other optional $R^2$ groups are independently halo, $C_{1-7}$alkyl, $C_{1-7}$alkoxy, hydroxy, haloalkyl. In yet a further embodiment, the invention provide compounds according to any one of Formulae I', I, IA II, IIA, III, IIIA, IV, IVA, V, VA and VI to VIC, or a pharmaceutically acceptable salt thereof, wherein n is 1 or 2, $R^2$ is meta-chloro and the other optional $R^2$ group is halo, $C_{1-7}$alkyl, $C_{1-7}$alkoxy, hydroxy, haloalkyl.

In yet another embodiment the invention provide compounds according to any one of Formulae I', I to IC, II to IIC, III to IIIC, IV, IVA, V, VA and VI to VIC or a pharmaceutically acceptable salt thereof, wherein X and $X^1$ are independently OH or —O—$C_{1-7}$alkyl (e.g. O-ethyl or O-methyl). In one particular aspect of this embodiment X and $X^1$ are OH. In another aspect of this embodiment, X and $X^1$ are independently —O—$C_{1-7}$alkyl in which alkyl is substituted with $C_{6-10}$aryl, heteroaryl, heterocyclyl, C(O)$NH_2$, C(O)NH—$C_{1-6}$ alkyl, or C(O)N($C_{1-6}$alkyl)$_2$. Representative examples of X or $X^1$ are —O—$CH_2$—C(O)N($CH_3$)$_2$, —O—$CH_2$—$CH_2$-morpholine, —O—$CH_2$-dioxolone or —O-benzyl. In yet another aspect of this embodiment, X and X¹ are —O—C$_{6-10}$aryl. A representative examples of —O—C$_{6-10}$aryl is —O-(2,3-dihydro-1H-indene).

In another embodiment X, X¹, A¹, A², R², R¹ and R⁴ groups are those defined by the X, X¹, A¹, A², R², R¹ and R⁴ groups in the Examples section below.

In another embodiment individual compounds according to the invention are those listed in the Examples section below or a pharmaceutically acceptable salt thereof.

For purposes of interpreting this specification, the following definitions will apply unless specified otherwise and whenever appropriate, terms used in the singular will also include the plural and vice versa.

As used herein, the term "alkyl" refers to a fully saturated branched or unbranched (or straight chain or linear) hydrocarbon moiety, comprising 1 to 20 carbon atoms. Preferably the alkyl comprises 1 to 7 carbon atoms, and more preferably 1 to 4 carbon atoms. Representative examples of alkyl include methyl, ethyl, n-propyl, iso-propyl, n-butyl, sec-butyl, iso-butyl, tent-butyl, n-pentyl, isopentyl, neopentyl, n-hexyl, 3-methylhexyl, 2,2-dimethylpentyl, 2,3-dimethylpentyl, n-heptyl. The term "C$_{1-7}$alkyl" refers to a hydrocarbon having one to seven carbon atoms. The term "alkylene" refers to a divalent alkyl radical, wherein alkyl is as previously defined.

The term "alkenyl" refers to a branched or unbranched hydrocarbon having at least one carbon-carbon double bond. The term "C$_{2-7}$alkenyl" refers to a hydrocarbon having two to seven carbon atoms and comprising at least one carbon-carbon double bond. Representative examples of alkenyl are vinyl, prop-1-enyl, allyl, butenyl, isopropenyl or isobutenyl. The term "alkeylene" refers to a divalent alkenyl radical, wherein alkenyl is as previously defined.

As used herein, the term "haloalkyl" refers to an alkyl as defined herein, that is substituted by one or more halo groups as defined herein. Preferably the haloalkyl can be monohaloalkyl, dihaloalkyl or polyhaloalkyl including perhaloalkyl. A monohaloalkyl can have one iodo, bromo, chloro or fluoro within the alkyl group. Dihaloalky and polyhaloalkyl groups can have two or more of the same halo atoms or a combination of different halo groups within the alkyl. Preferably, the polyhaloalkyl contains up to 12, or 10, or 8, or 6, or 4, or 3, or 2 halo groups. Representative examples of haloalkyl are fluoromethyl, difluoromethyl, trifluoromethyl, chloromethyl, dichloromethyl, trichloromethyl, pentafluoroethyl, heptafluoropropyl, difluorochloromethyl, dichlorofluoromethyl, difluoroethyl, difluoropropyl, dichloroethyl and dichloropropyl. A perhaloalkyl refers to an alkyl having all hydrogen atoms replaced with halo atoms. The term "halo-C$_{1-7}$alkyl" refers to a hydrocarbon having one to seven carbon atoms and being substituted by one or more halo groups.

As used herein, the term "alkoxy" refers to alkyl-O—, wherein alkyl is defined herein above. Representative examples of alkoxy include, but are not limited to, methoxy, ethoxy, propoxy, 2-propoxy, butoxy, tent-butoxy, pentyloxy, hexyloxy, cyclopropyloxy-, cyclohexyloxy- and the like. Preferably, alkoxy groups have about 1-7, more preferably about 1-4 carbons.

As used herein, the term "cycloalkyl" refers to saturated or unsaturated but non-aromatic monocyclic, bicyclic or tricyclic hydrocarbon groups of 3-12 carbon atoms, preferably 3-8, or 3-7 carbon atoms. For bicyclic, and tricyclic cycloalkyl system, all rings are non-aromatic. Exemplary monocyclic hydrocarbon groups include cyclopropyl, cyclobutyl, cyclopentyl, cyclopentenyl, cyclohexyl and cyclohexenyl. Exemplary bicyclic hydrocarbon groups include bornyl, decahydronaphthyl, bicyclo[2.1.1]hexyl, bicyclo[2.2.1]heptyl, bicyclo[2.2.1]heptenyl, bicyclo[2.2.2] octyl. Exemplary tricyclic hydrocarbon groups include adamantyl. The term "C$_{3-7}$cycloakyl" refers to a cyclic hydrocarbon groups having 3 to 7 carbon atoms.

The term "aryl" refers to monocyclic or bicyclic aromatic hydrocarbon groups having 6-10 carbon atoms in the ring portion. The term "aryl" also refer to a group in which the aromatic ring is fused to a cycloalkyl ring, where the radical of attachment is on the aromatic ring or on the fused cycloalkyl ring. Representative examples of aryl are phenyl, naphthyl, hexahydroindyl, indanyl or tetrahydronaphthyl. The term "C$_{6-10}$aryl" refers to an aromatic hydrocarbon groups having 6 to 10 carbon atoms in the ring portion.

The term "Heteroaryl" includes monocyclic or bicyclic heteroaryl, containing from 5-10 ring members selected from carbon atoms and 1 to 5 heteroatoms, and each heteroatoms is independently selected from O, N or S, wherein S and N may be oxidized to various oxidation states. For bicyclic heteroaryl system, the system is fully aromatic (i.e. all rings are aromatic).

Typical monocyclic heteroaryl groups include thienyl, furyl, pyrrolyl, imidazolyl, pyrazolyl, thiazolyl, isothiazolyl, oxa-2,3-diazolyl, oxa-2,4-diazolyl, oxa-2,5-diazolyl, oxa-3,4-diazolyl, thia-2,3-diazolyl, thia-2,4-diazolyl, thia-2,5-diazolyl, thia-3,4-diazolyl, 3-, 4-, or 5-isothiazolyl, 2-, 4-, or 5-oxazolyl, 3-, 4-, or 5-isoxazolyl, 3- or 5-1,2,4-triazolyl, 4- or 5-1,2,3-triazolyl, tetrazolyl, 2-, 3-, or 4-pyridyl, 3- or 4-pyridazinyl, 3-, 4-, or 5-pyrazinyl, 2-pyrazinyl, 2-, 4-, or 5-pyrimidinyl.

The term "heteroaryl" also refers to a group in which a heteroaromatic ring is fused to one or more aryl, cycloaliphatic, or heterocyclyl rings, where the radical or point of attachment is on the heteroaromatic ring or on the fused aryl ring. Representative examples of bicyclic heteroaryl are indolyl, isoindolyl, indazolyl, indolizinyl, purinyl, quinolizinyl, quinolinyl, isoquinolinyl, cinnolinyl, phthalazinyl, naphthyridinyl, quinazolinyl, quinaxalinyl, thieno[2,3-b]furanyl, furo[3,2-b]-pyranyl, 5H-pyrido[2,3-d]-o-oxazinyl, 1H-pyrazolo[4,3-d]-oxazolyl, 4H-imidazo[4,5-d]thiazolyl, pyrazino[2,3-d]pyridazinyl, imidazo[2,1-b]thiazolyl, imidazo[1,2-b][1,2,4]triazinyl, 7-benzo[b]thienyl, benzoxazolyl, benzimidazolyl, benzothiazolyl, benzoxapinyl, benzoxazinyl, 1H-pyrrolo[1,2-b][2]benzazapinyl, benzofuryl, benzothiophenyl, benzotriazolyl, pyrrolo[2,3-b]pyridinyl, pyrrolo[3,2-c]pyridinyl, pyrrolo[3,2-c]pyridinyl, pyrrolo[3,2-b]pyridinyl, imidazo[4,5-b]pyridinyl, imidazo[4,5-c]pyridinyl, pyrazolo[4,3-d]pyridinyl, pyrazolo[4,3-c]pyridinyl, pyrazolo[3,4-c]pyridinyl, pyrazolo[3,4-d]pyridinyl, pyrazolo[3,4-b]pyridinyl, imidazo[1,2-a]pyridinyl, pyrazolo[1,5-a]pyridinyl, pyrrolo[1,2-b]pyridazinyl, imidazo[1,2-c]pyrimidinyl, pyrido[3,2-d]pyrimidinyl, pyrido[4,3-d]pyrimidinyl, pyrido[3,4-d]pyrimidinyl, pyrido[2,3-d]pyrimidinyl, pyrido[2,3-b]pyrazinyl, pyrido[3,4-b]pyrazinyl, pyrimido[5,4-d]pyrimidinyl, pyrazino[2,3-b]pyrazinyl, or pyrimido[4,5-d]pyrimidinyl.

When a heteroaryl moiety is substituted with hydroxy, the invention also pertains to its oxo tautomeric. For example, an oxadiazole substituted with hydroxy also includes oxo-oxadiazole or also known as oxadiazolone. The tautomerisation is represented as follow:

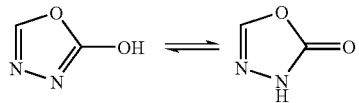

As used herein, the term "heterocyclyl" refers to an optionally substituted, saturated or unsaturated non-aromatic (partially unsaturated) ring or ring system, e.g., which is a 3-, 4-, 5-, 6-, or 7-membered monocyclic, 7-, 8-, 9-, 10-, 11-, or 12-membered bicyclic or 10-, 11-, 12-, 13-, 14- or 15-membered tricyclic ring system and contains at least one heteroatom selected from O, S and N, where the N and S can also optionally be oxidized to various oxidation states. For bicyclic and tricyclic heterocyclyl ring system, a non-aromatic ring system is defined as being a non-fully or partially unsaturated ring system. Therefore bicyclic and tricyclic heterocyclyl ring systems includes heterocyclyl ring systems wherein one of the fused rings is aromatic but the other(s) is (are) non-aromatic. In one embodiment, heterocyclyl moiety represents a saturated monocyclic ring containing from 5-7 ring atoms and optionally containing a further heteroatom, selected from O, S or N. The heterocyclic group can be attached at a heteroatom or a carbon atom. The heterocyclyl can include fused or bridged rings as well as spirocyclic rings. Examples of heterocycles include dihydrofuranyl, dioxolanyl, dioxanyl, dithianyl, piperazinyl, pyrrolidine, dihydropyranyl, oxathiolanyl, dithiolanyl, oxathianyl, thiomorpholino, oxiranyl, aziridinyl, oxetanyl, oxepanyl, azetidinyl, tetrahydrofuranyl, tetrahydrothiophenyl, pyrrolidinyl, tetrahydropyranyl, piperidinyl, morpholino, piperazinyl, azepinyl, oxapinyl, oxaazepanyl, oxathianyl, thiepanyl, azepanyl, dioxepanyl, and diazepanyl.

The term "hydroxyalkyl" refers to alkyl groups, as described above, in which the alkyl group is substituted with one or more hydroxy.

The term "hydroxy" includes groups with an —OH.

The term "halogen" includes fluorine, bromine, chlorine and iodine. The term "perhalogenated" generally refers to a moiety wherein all hydrogens are replaced by halogen atoms.

The term "heteroatom" includes atoms of any element other than carbon or hydrogen. Preferred heteroatoms are nitrogen, oxygen, sulfur and phosphorus. In another embodiment, the heteroatom is nitrogen, oxygen or sulfur.

It will be noted that the structure of some of the compounds of this invention includes asymmetric carbon atoms. It is to be understood accordingly that the isomers arising from such asymmetry (e.g., all enantiomers and diastereomers) are included within the scope of this invention, unless indicated otherwise. Such isomers can be obtained in substantially pure form by classical separation techniques and by stereochemically controlled synthesis. Furthermore, the structures and other compounds and moieties discussed in this application also include all tautomers thereof.

As used herein, the term "isomers" refers to different compounds that have the same molecular formula but differ in arrangement and configuration of the atoms. Also as used herein, the term "an optical isomer" or "a stereoisomer" refers to any of the various stereo isomeric configurations which may exist for a given compound of the present invention and includes geometric isomers. It is understood that a substituent may be attached at a chiral center of a carbon atom. Therefore, the invention includes enantiomers, diastereomers or racemates of the compound. "Enantiomers" are a pair of stereoisomers that are non-superimposable mirror images of each other. A 1:1 mixture of a pair of enantiomers is a "racemic" mixture. The term is used to designate a racemic mixture where appropriate. "Diastereoisomers" are stereoisomers that have at least two asymmetric atoms, but which are not mirror-images of each other. The absolute stereochemistry is specified according to the Cahn-Ingold-Prelog R-S system. When a compound is a pure enantiomer the stereochemistry at each chiral carbon may be specified by either R or S. Resolved compounds whose absolute configuration is unknown can be designated (+) or (−) depending on the direction (dextro- or levorotatory) which they rotate plane polarized light at the wavelength of the sodium D line. Certain of the compounds described herein contain one or more asymmetric centers or axes and may thus give rise to enantiomers, diastereomers, and other stereoisomeric forms that may be defined, in terms of absolute stereochemistry, as (R)- or (S)-. The present invention is meant to include all such possible isomers, including racemic mixtures, optically pure forms and intermediate mixtures. Optically active (R)- and (S)-isomers may be prepared using chiral synthons or chiral reagents, or resolved using conventional techniques. If the compound contains a double bond, the substituent may be E or Z configuration. If the compound contains a disubstituted cycloalkyl, the cycloalkyl substituent may have a cis- or trans-configuration. All tautomeric forms are also intended to be included.

Any asymmetric atom (e.g., carbon or the like) of the compound(s) of the present invention can be present in racemic or enantiomerically enriched, for example the (R)-, (S)- or (R,S)-configuration. In certain embodiments, each asymmetric atom has at least 50% enantiomeric excess, at least 60% enantiomeric excess, at least 70% enantiomeric excess, at least 80% enantiomeric excess, at least 90% enantiomeric excess, at least 95% enantiomeric excess, or at least 99% enantiomeric excess in the (R)- or (S)-configuration. Substituents at atoms with unsaturated bonds may, if possible, be present in cis-(Z)- or trans-(E)-form.

Accordingly, as used herein a compound of the present invention can be in the form of one of the possible isomers, rotamers, atropisomers, tautomers or mixtures thereof, for example, as substantially pure geometric (cis or trans) isomers, diastereomers, optical isomers (antipodes), racemates or mixtures thereof.

Any resulting mixtures of isomers can be separated on the basis of the physicochemical differences of the constituents, into the pure or substantially pure geometric or optical isomers, diastereomers, racemates, for example, by chromatography and/or fractional crystallization.

Any resulting racemates of final products or intermediates can be resolved into the optical antipodes by known methods, e.g., by separation of the diastereomeric salts thereof, obtained with an optically active acid or base, and liberating the optically active acidic or basic compound. In particular, a basic moiety may thus be employed to resolve the compounds of the present invention into their optical antipodes, e.g., by fractional crystallization of a salt formed with an optically active acid, e.g., tartaric acid, dibenzoyl tartaric acid, diacetyl tartaric acid, di-O,O'-p-toluoyl tartaric acid, mandelic acid, malic acid or camphor-10-sulfonic acid. Racemic products can also be resolved by chiral chromatography, e.g., high pressure liquid chromatography (HPLC) using a chiral adsorbent.

As used herein, the term "pharmaceutically acceptable salts" refers to salts that retain the biological effectiveness and properties of the compounds of this invention and, which are not biologically or otherwise undesirable. In many cases, the compounds of the present invention are capable of forming acid and/or base salts by virtue of the presence of amino and/or carboxyl groups or groups similar thereto. Pharmaceutically acceptable acid addition salts can be formed with inorganic acids and organic acids, e.g., acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. The pharmaceutically acceptable salts of the present invention can be synthesized from a parent compound, a basic or acidic moiety, by conventional chemical methods. Generally, such salts can be prepared by reacting free acid forms of these compounds with a stoichiometric amount of the appropriate base (such as Na, Ca, Mg, or K hydroxide, carbonate, bicarbonate, or the like), or by reacting free base forms of these compounds with a stoichiometric amount of the appropriate acid. Such reactions are typically carried out in water or in an organic solvent, or in a mixture of the two. Generally, non-aqueous media like ether, ethyl acetate, ethanol, isopropanol, or acetonitrile are preferred, where practicable. Lists of additional suitable salts can be found, e.g., in "Remington's Pharmaceutical Sciences", 20th ed., Mack Publishing Company, Easton, Pa., (1985); and in "Handbook of Pharmaceutical Salts: Properties, Selection, and Use" by Stahl and Wermuth (Wiley-VCH, Weinheim, Germany, 2002).

Any formula given herein is also intended to represent unlabeled forms as well as isotopically labeled forms of the compounds. For example, any hydrogen represented by "H" in any of the formulae herein is intended to represent all isotopic forms of hydrogen (e.g. $^1H$, $^2H$ or D, $^3H$); any carbon represented by "C" in any of the formulae herein is intended to represent all isotopic forms of carbon (e.g. $^{11}C$; $^{13}C$; $^{14}C$); any nitrogen represented by "N" is intended to represent all isotopic forms of nitrogen (e.g. $^{14}N$, $^{15}N$). Other examples of isotopes that are included in the invention include isotopes of oxygen, sulfur, phosphorous, fluorine, iodine and chlorine, such as $^{18}F$ $^{31}P$, $^{32}P$, $^{35}S$, $^{36}Cl$, $^{125}I$. The invention includes various isotopically labeled compounds as defined herein, for example those into which radioactive isotopes, such as $^3H$, $^{13}C$, and $^{14}C$ are present. In one embodiment, the atoms in the formulae herein occur in their natural abundance. In another embodiment, one or more hydrogen atom may be enriched in $^2H$; or/and one or more carbon atom may be enriched in $^{11}C$, $^{13}C$ or $^{14}C$; or/and one or more nitrogen may be enriched in $^{14}N$. Such isotopically labelled compounds are useful in metabolic studies (with $^{14}C$), reaction kinetic studies (with, for example $^2H$ or $^3H$), detection or imaging techniques, such as positron emission tomography (PET) or single-photon emission computed tomography (SPECT) including drug or substrate tissue distribution assays, or in radioactive treatment of patients. In particular, an $^{18}F$ or labeled compound may be particularly desirable for PET or SPECT studies. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

Further, enrichment with heavier isotopes, particularly deuterium (i.e., $^2H$ or D) may afford certain therapeutic advantages resulting from greater metabolic stability, for example increased in vivo half-life or reduced dosage requirements or an improvement in therapeutic index. It is understood that deuterium in this context is regarded as a substituent of a compound according to anyone of the formulae I', I to VIC. The concentration of such a heavier isotope, specifically deuterium, may be defined by the isotopic enrichment factor. The term "isotopic enrichment factor" as used herein means the ratio between the isotopic abundance and the natural abundance of a specified isotope. If a substituent in a compound of this invention is denoted deuterium, such compound has an isotopic enrichment factor for each designated deuterium atom of at least 3500 (52.5% deuterium incorporation at each designated deuterium atom), at least 4000 (60% deuterium incorporation), at least 4500 (67.5% deuterium incorporation), at least 5000 (75% deuterium incorporation), at least 5500 (82.5% deuterium incorporation), at least 6000 (90% deuterium incorporation), at least 6333.3 (95% deuterium incorporation), at least 6466.7 (97% deuterium incorporation), at least 6600 (99% deuterium incorporation), or at least 6633.3 (99.5% deuterium incorporation).

Isotopically-enriched compounds according to anyone of formulae I', I to VIC can generally be prepared by conventional techniques known to those skilled in the art or by processes analogous to those described in the accompanying Examples and Preparations using an appropriate isotopically-enriched reagent in place of the non-enriched reagent previously employed.

Pharmaceutically acceptable solvates in accordance with the invention include those wherein the solvent of crystallization may be isotopically substituted, e.g. $D_2O$, $d_6$-acetone, $d_6$-DMSO.

Compounds of the invention, i.e. compounds according to anyone of formulae I', I to VIC that contain groups capable of acting as donors and/or acceptors for hydrogen bonds may be capable of forming co-crystals with suitable co-crystal formers. These co-crystals may be prepared from compounds according to anyone of formulae I', I to VIC by known co-crystal forming procedures. Such procedures include grinding, heating, co-subliming, co-melting, or contacting in solution compounds according to anyone of formulae I', I to VIC with the co-crystal former under crystallization conditions and isolating co-crystals thereby formed. Suitable co-crystal formers include those described in WO 2004/078163. Hence the invention further provides co-crystals comprising a compound according to anyone of formulae I' and I to VIC.

As used herein, the term "pharmaceutically acceptable carrier" includes any and all solvents, dispersion media, coatings, surfactants, antioxidants, preservatives (e.g., antibacterial agents, antifungal agents), isotonic agents, absorption delaying agents, salts, preservatives, drugs, drug stabilizers, binders, excipients, disintegration agents, lubricants, sweetening agents, flavoring agents, dyes, such like materials and combinations thereof, as would be known to one of ordinary skill in the art (see, for example, Remington's Pharmaceutical Sciences, 18th Ed. Mack Printing Company, 1990, pp. 1289-1329). Except insofar as any conventional carrier is incompatible with the active ingredient, its use in the therapeutic or pharmaceutical compositions is contemplated.

The term "a therapeutically effective amount" of a compound of the present invention refers to an amount of the compound of the present invention that will elicit the biological or medical response of a subject, for example, reduction or inhibition of an enzyme or a protein activity, or amelioration of a symptom, alleviation of a condition, slow or delay disease progression, or prevention of a disease, etc. In one non-limiting embodiment, the term "a therapeutically effective amount" refers to the amount of the compound of the present invention that, when administered to a subject, is effective to (1) at least partially alleviate, inhibit, prevent and/or ameliorate a condition, a disorder or a disease, or a symptom thereof (i) ameliorated by the inhibition of neutral endopeptidase EC 3.4.24.11 or (ii) associated with neutral endopeptidase EC 3.4.24.11 activity, or (iii) characterized by abnormal activity of neutral endopeptidase EC 3.4.24.11; or (2) reduce or inhibit the activity of neutral endopeptidase EC 3.4.24.11; or (3) reduce or inhibit the expression of neutral endopeptidase EC 3.4.24.11. In another non-limiting embodiment, the term "a therapeutically effective amount" refers to the amount of the compound of the present invention that, when administered to a cell, or a tissue, or a non-cellular biological material, or a medium, is effective to at least partially reduce or inhibit the activity of neutral endopeptidase EC 3.4.24.11; or at least partially reduce or inhibit the expression of neutral endopeptidase EC 3.4.24.11

As used herein, the term "subject" refers to an animal. Preferably, the animal is a mammal. A subject also refers to for example, primates (e.g., humans), cows, sheep, goats, horses, dogs, cats, rabbits, rats, mice, fish, birds and the like. In a preferred embodiment, the subject is a human.

As used herein, the term "inhibition" or "inhibiting" refers to the reduction or suppression of a given condition, symptom, or disorder, or disease, or a significant decrease in the baseline activity of a biological activity or process.

As used herein, the term "treating" or "treatment" of any disease or disorder refers in one embodiment, to ameliorating the disease or disorder (i.e., slowing or arresting or reducing the development of the disease or at least one of the clinical symptoms thereof). In another embodiment "treating" or "treatment" refers to alleviating or ameliorating at least one physical parameter including those which may not be discernible by the patient. In yet another embodiment, "treating" or "treatment" refers to modulating the disease or disorder, either physically, (e.g., stabilization of a discernible symptom), physiologically, (e.g., stabilization of a physical parameter), or both. In yet another embodiment, "treating" or "treatment" refers to preventing or delaying the onset or development or progression of the disease or disorder.

As used herein, the term "a," "an," "the" and similar terms used in the context of the present invention (especially in the context of the claims) are to be construed to cover both the singular and plural unless otherwise indicated herein or clearly contradicted by the context.

The term "hypertension" refers to a condition where the pressure of blood within the blood vessels is higher than normal as it circulates through the body. When the systolic pressure exceeds 150 mmHg or the diastolic pressure exceeds 90 mmHg for a sustained period of time, damage is done to the body. For example, excessive systolic pressure can rupture blood vessels anywhere, and when it occurs within the brain, a stroke results. Hypertension may also cause thickening and narrowing of the blood vessels which ultimately could lead to atherosclerosis.

The term "type 2 diabetes" including type 2 diabetes associated with hypertension refers to a disease in which the pancreas does not secrete sufficient insulin due to an impairment of pancreatic beta-cell function and/or in which there is to insensitivity to produced insulin (insulin resistance). Typically, the fasting plasma glucose is less than 126 mg/dL, while pre-diabetes is, e.g., a condition which is characterized by one of following conditions: impaired fasting glucose (110-125 mg/dL) and impaired glucose tolerance (fasting glucose levels less than 126 mg/dL and post-prandial glucose level between 140 mg/dL and 199 mg/dL). Type 2 diabetes mellitus can be associated with or without hypertension. Diabetes mellitus occurs frequently, e.g., in African American, Latino/Hispanic American, Native American, Native American, Asian American and Pacific Islanders. Markers of insulin resistance include HbA1C, HOMA IR, measuring collagen fragments, TGF-$\beta$ in urine, PAI-1 and prorenin.

All methods described herein can be performed in any suitable order unless otherwise indicated herein or otherwise clearly contradicted by context. The use of any and all examples, or exemplary language (e.g. "such as") provided herein is intended merely to better illuminate the invention and does not pose a limitation on the scope of the invention otherwise claimed.

Compounds of the present invention are either obtained in the free form, as a salt thereof, or as prodrug derivatives thereof.

When both a basic group and an acid group are present in the same molecule, the compounds of the present invention may also form internal salts, e.g., zwitterionic molecules.

The present invention also provides pro-drugs of the compounds of the present invention that converts in vivo to the compounds of the present invention. A pro-drug is an active or inactive compound that is modified chemically through in vivo physiological action, such as hydrolysis, metabolism and the like, into a compound of this invention following administration of the prodrug to a subject. The suitability and techniques involved in making and using pro-drugs are well known by those skilled in the art. Prodrugs can be conceptually divided into two non-exclusive categories, bioprecursor prodrugs and carrier prodrugs. See *The Practice of Medicinal Chemistry*, Ch. 31-32 (Ed. Wermuth, Academic Press, San Diego, Calif., 2001). Generally, bioprecursor prodrugs are compounds, which are inactive or have low activity compared to the corresponding active drug compound that contain one or more protective groups and are converted to an active form by metabolism or solvolysis. Both the active drug form and any released metabolic products should have acceptably low toxicity. Carrier prodrugs are drug compounds that contain a transport moiety, e.g., that improve uptake and/or localized delivery to a site(s) of action. Desirably for such a carrier prodrug, the linkage between the drug moiety and the transport moiety is a covalent bond, the prodrug is inactive or less active than the drug compound, and any released transport moiety is acceptably non-toxic. For prodrugs where the transport moiety is intended to enhance uptake, typically the release of the transport moiety should be rapid. In other cases, it is desirable to utilize a moiety that provides slow release, e.g., certain polymers or other moieties, such as cyclodextrins. Carrier prodrugs can, for example, be used to improve one or more of the following properties: increased lipophilicity, increased duration of pharmacological effects, increased site-specificity, decreased toxicity and adverse reactions, and/or improvement in drug formulation (e.g., stability, water solubility, suppression of an undesirable organoleptic or physiochemical property). For example, lipophilicity can be increased by esterification of (a) hydroxyl groups with lipophilic carboxylic acids (e.g., a carboxylic acid having at least one lipophilic moiety), or (b) carboxylic acid groups with lipophilic alcohols (e.g., an alcohol having at least one lipophilic moiety, for example aliphatic alcohols).

Exemplary prodrugs are, e.g., esters of free carboxylic acids and S-acyl derivatives of thiols and O-acyl derivatives of alcohols or phenols, wherein acyl has a meaning as defined herein. Preferred are pharmaceutically acceptable ester derivatives convertible by solvolysis under physiological conditions to the parent carboxylic acid, e.g., lower alkyl esters, cycloalkyl esters, lower alkenyl esters, benzyl esters, mono- or di-substituted lower alkyl esters, such as the ω-(amino, mono- or di-lower alkylamino, carboxy, lower alkoxycarbonyl)-lower alkyl esters, the α-(lower alkanoyloxy, lower alkoxycarbonyl or di-lower alkylaminocarbonyl)-lower alkyl esters, such as the pivaloyloxymethyl ester and the like conventionally used in the art. In addition, amines have been masked as arylcarbonyloxymethyl substituted derivatives which are cleaved by esterases in vivo releasing the free drug and formaldehyde (Bundgaard, *J. Med. Chem.* 2503 (1989)). Moreover, drugs containing an acidic NH group, such as imidazole, imide, indole and the like, have been masked with N-acyloxymethyl groups (Bundgaard, *Design of Prodrugs*, Elsevier (1985)). Hydroxy groups have been masked as esters and ethers. EP 039,051 (Sloan and Little) discloses Mannich-base hydroxamic acid prodrugs, their preparation and use.

Furthermore, the compounds of the present invention, including their salts, can also be obtained in the form of their hydrates, or include other solvents used for their crystallization.

General Synthetic Aspects

The compounds of the invention can be synthesized using the methods described in the following schemes, examples, and by using art recognized techniques. All compounds described herein are included in the invention as compounds. Compounds of the invention may be synthesized according to at least one of the methods described in schemes 1-3.

Within the scope of this text, only a readily removable group that is not a constituent of the particular desired end product of the compounds of the present invention is designated a "protecting group", unless the context indicates otherwise. The protection of functional groups by such protecting groups, the protecting groups themselves, and their cleavage reactions are described for example in standard reference works, such as J. F. W. McOmie, "Protective Groups in Organic Chemistry", Plenum Press, London and New York 1973, in T. W. Greene and P. G. M. Wuts, "Protective Groups in Organic Synthesis", Third edition, Wiley, New York 1999.

Salts of compounds of the present invention having at least one salt-forming group may be prepared in a manner known per se. For example, salts of compounds of the present invention having acid groups may be formed, for example, by treating the compounds with metal compounds, such as alkali metal salts of suitable organic carboxylic acids, e.g. the sodium salt of 2-ethylhexanoic acid, with organic alkali metal or alkaline earth metal compounds, such as the corresponding hydroxides, carbonates or hydrogen carbonates, such as sodium or potassium hydroxide, carbonate or hydrogen carbonate, with corresponding calcium compounds or with ammonia or a suitable organic amine, stoichiometric amounts or only a small excess of the salt-forming agent preferably being used. Acid addition salts of compounds of the present invention are obtained in customary manner, e.g. by treating the compounds with an acid or a suitable anion exchange reagent. Internal salts of compounds of the present invention containing acid and basic salt-forming groups, e.g. a free carboxy group and a free amino group, may be formed, e.g. by the neutralisation of salts, such as acid addition salts, to the isoelectric point, e.g. with weak bases, or by treatment with ion exchangers.

Salts can be converted in customary manner into the free compounds; metal and ammonium salts can be converted, for example, by treatment with suitable acids, and acid addition salts, for example, by treatment with a suitable basic agent.

Mixtures of isomers obtainable according to the invention can be separated in a manner known per se into the individual isomers; diastereoisomers can be separated, for example, by partitioning between polyphasic solvent mixtures, recrystallisation and/or chromatographic separation, for example over silica gel or by e.g. medium pressure liquid chromatography over a reversed phase column, and racemates can be separated, for example, by the formation of salts with optically pure salt-forming reagents and separation of the mixture of diastereoisomers so obtainable, for example by means of fractional crystallisation, or by chromatography over optically active column materials.

Intermediates and final products can be worked up and/or purified according to standard methods, e.g. using chromatographic methods, distribution methods, (re-) crystallization, and the like.

The following applies in general to all processes mentioned herein before and hereinafter.

All the above-mentioned process steps can be carried out under reaction conditions that are known per se, including those mentioned specifically, in the absence or, customarily, in the presence of solvents or diluents, including, for example, solvents or diluents that are inert towards the reagents used and dissolve them, in the absence or presence of catalysts, condensation or neutralizing agents, for example ion exchangers, such as cation exchangers, e.g. in the H+ form, depending on the nature of the reaction and/or of the reactants at reduced, normal or elevated temperature, for example in a temperature range of from about −100° C. to about 190° C., including, for example, from approximately −80° C. to approximately 150° C., for example at from −80 to −60° C., at room temperature, at from −20 to 40° C. or at reflux temperature, under atmospheric pressure or in a closed vessel, where appropriate under pressure, and/or in an inert atmosphere, for example under an argon or nitrogen atmosphere.

At all stages of the reactions, mixtures of isomers that are formed can be separated into the individual isomers, for example diastereoisomers or enantiomers, or into any desired mixtures of isomers, for example racemates or mixtures of diastereoisomers, for example analogously to the methods described under "Additional process steps".

The solvents from which those solvents that are suitable for any particular reaction may be selected include those mentioned specifically or, for example, water, esters, such as lower alkyl-lower alkanoates, for example ethyl acetate, ethers, such as aliphatic ethers, for example diethyl ether, or cyclic ethers, for example tetrahydrofuran or dioxane, liquid aromatic hydrocarbons, such as benzene or toluene, alcohols, such as methanol, ethanol or 1- or 2-propanol, nitriles, such as acetonitrile, halogenated hydrocarbons, such as methylene chloride or chloroform, acid amides, such as dimethylformamide or dimethyl acetamide, bases, such as heterocyclic nitrogen bases, for example pyridine or N-methylpyrrolidin-2-one, carboxylic acid anhydrides, such as lower alkanoic acid anhydrides, for example acetic anhydride, cyclic, linear or branched hydrocarbons, such as cyclohexane, hexane or isopentane, methycyclohexane, or mixtures of those solvents, for example aqueous solutions, unless otherwise indicated in Typically, the compounds according to anyone of formulae I' and I to VIC can be prepared according to the Schemes 1 to 3 provided infra.

The general methods of preparation and synthesis of the described compounds herein are illustrated in Schemes 1, 2, 3 and 4.

Scheme 1

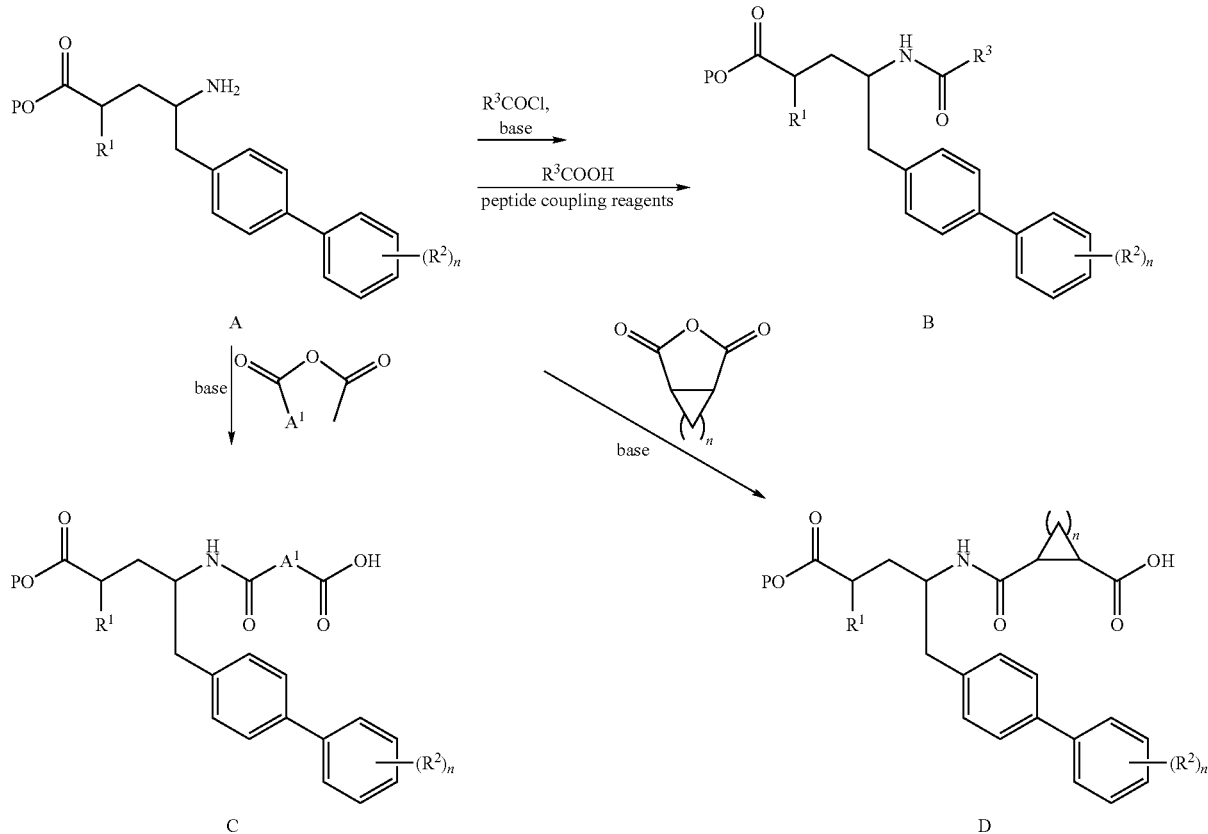

the description of the processes. Such solvent mixtures may also be used in working up, for example by chromatography or partitioning.

The compounds, including their salts, may also be obtained in the form of hydrates, or their crystals may, for example, include the solvent used for crystallization. Different crystalline forms may be present.

The invention relates also to those forms of the process in which a compound obtainable as an intermediate at any stage of the process is used as starting material and the remaining process steps are carried out, or in which a starting material is formed under the reaction conditions or is used in the form of a derivative, for example in a protected form or in the form of a salt, or a compound obtainable by the process according to the invention is produced under the process conditions and processed further in situ.

All starting materials, building blocks, reagents, acids, bases, dehydrating agents, solvents and catalysts utilized to synthesize the compounds of the present invention are either commercially available or can be produced by organic synthesis methods known to one of ordinary skill in the art (Houben-Weyl 4$^{th}$ Ed. 1952, Methods of Organic Synthesis, Thieme, Volume 21).

Intermediate A, or salts thereof, was prepared according to the route described in U.S. Pat. No. 5,217,996 or in WO2008083967 wherein P is alkyl or benzyl and R$^1$ is defined as in Formula I or I' supra. Amide B, wherein R$^3$ is defined above, is prepared by the condensation of intermediate A with an alkyl or aryl acid chloride in the presence of a base such as, but not limited to, pyridine, triethylamine and diisopropylethylamine. Intermediate A can also be converted to compounds of Formula B by amidation reactions with a variety of alkyl or aryl carboxylic acids using coupling reagents such as, but not limited to, EDCI or HATU. Compounds of formula C are obtained from intermediate A by reaction with an appropriate anhydride, wherein A$^1$ is defined above, in the presence of a base such as, but not limited to, pyridine, triethylamine and diisopropylethylamine. Similarly, compounds or Formula D wherein A$^1$ is a cycloalkyl, can be obtained using a bicyclic anhydride wherein n=1-4.

Scheme 2 illustrates the synthesis of compounds according to anyone of Formula I; I to IC and II to IIC wherein A$^1$ is a linear C$_{1-4}$alkylene wherein one carbon is replaced by a nitrogen atom or A$^1$ is a heterocyclyl or heteroaryl.

Scheme 2

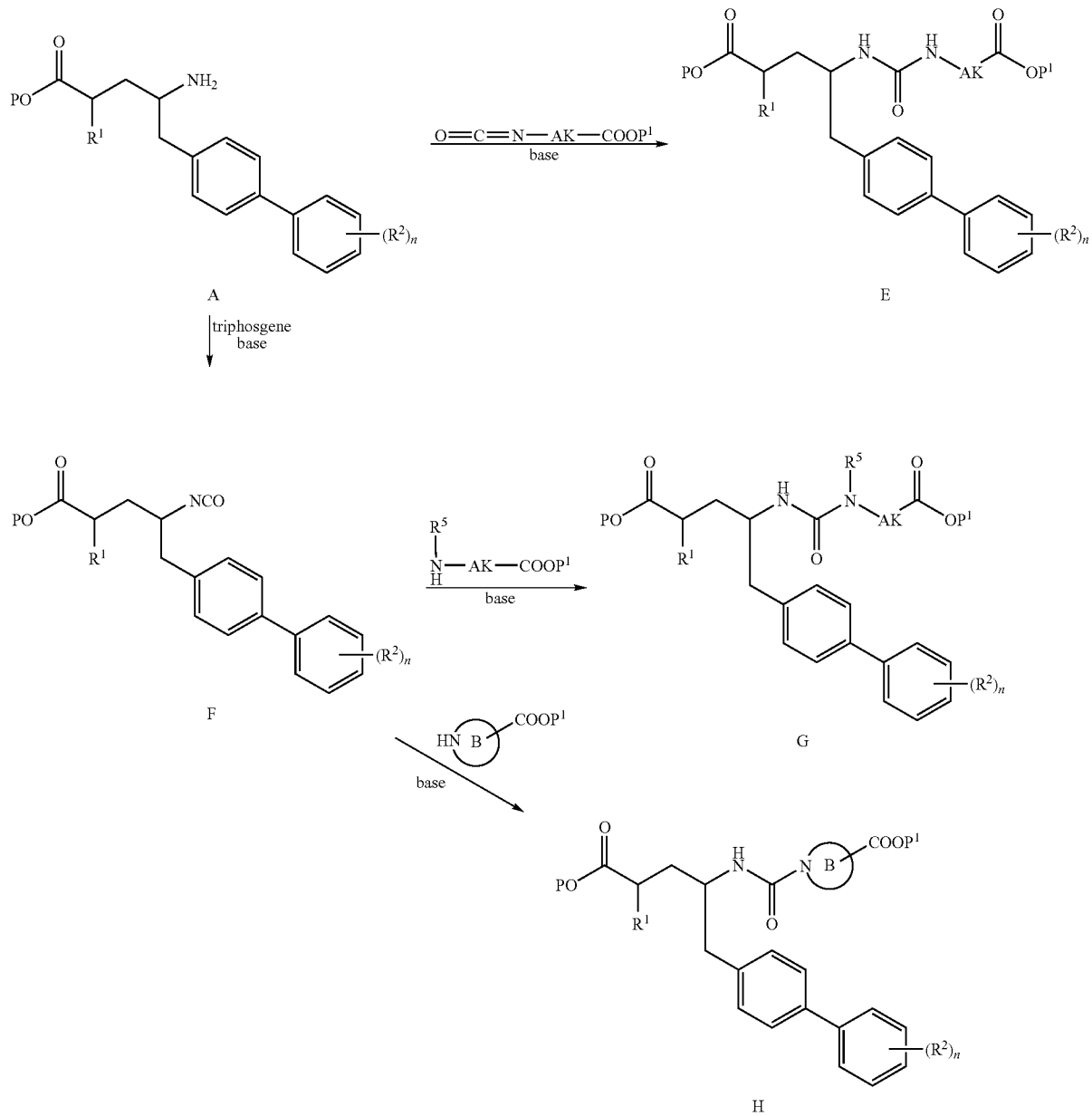

Compounds according to anyone of Formulae II to IIC wherein $A^1$ is a linear $C_{1-4}$alkylene wherein one carbon is replaced by a nitrogen atom, represented by compounds E, are prepared from intermediate A by reaction with an alkyl isocyanate, wherein $P^1$ is alkyl or benzyl and AK is an alkyl, in the presence of a base such as, but not limited to, pyridine, triethylamine and diisopropylethylamine. Alternatively, intermediate A is converted to isocyanate F with reagents such as, but not limited to, triphosgene in the presence of a base such as, but not limited to NaHCO$_3$. Substituted analogs, represented by compounds G, are prepared by reacting compound F with an appropriate protected amino acid in the presence of a base such as, but not limited to NaHCO$_3$. Similarly, compounds according to anyone of Formulae II to IIC wherein $A^1$ is a heterocyclyl or a heteroaryl containing a Nitrogen atom which is linked to C(O)NH amide bond, and represented by compounds H, are prepared from the reaction of compound F with protected cyclic amino acids wherein B is heterocyclyl or heteroaryl and the carboxylate group can be attached at any position not occupied by a heteroatom. Compounds B to H are converted to their corresponding carboxylic acids (P, $P^1$=H) by standard hydrolytic methods using a base such as, but not limited to, NaOH or LiOH. The hydrolysis reactions are performed at either ambient or elevated temperatures. When P or $P^1$ is benzyl, the preferable method of deprotection is hydrogenation in the presence of a catalyst such as, but not limited to, palladium-on-carbon at atmospheric or elevated pressure.

Scheme 3 illustrates the synthesis of compounds of Formula V wherein $R^4$ is a tetrazole.

Scheme 3

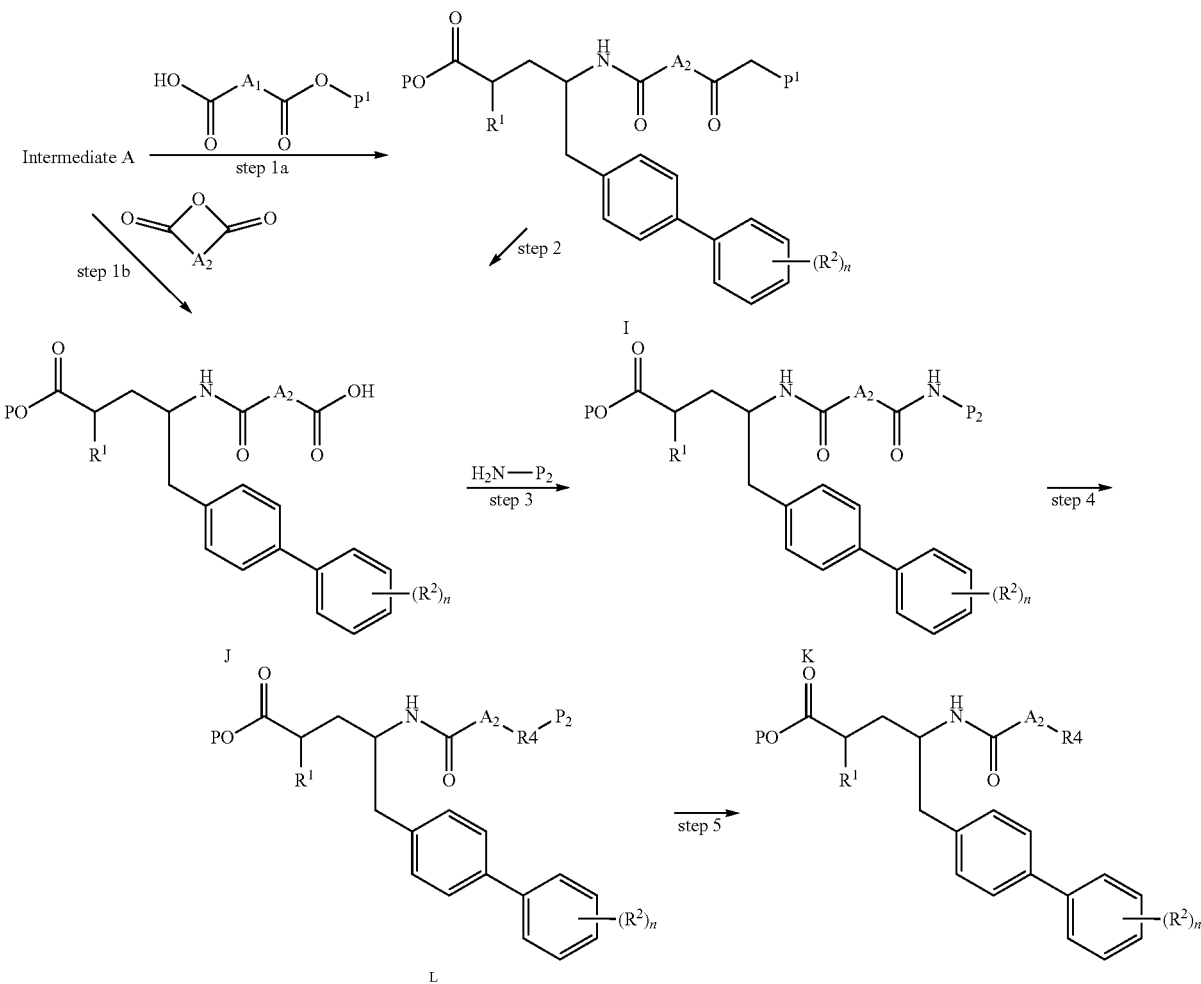

Intermediate A is reacted with an appropriate carboxylic acid as described in step 1a, using standard coupling reagents selected from, but not limited to, DCC, EDCl, PyBOP or BOP in presence or absence of a reagent such as 1-hydroxybenazotriazole, 1-hydroxy-7-azabenzotriazole or pentafluorophenol to generate intermediate I, in which protecting group P1 can be removed using a base selected from, but not limited to, NaOH, KOH or LiOH, or an acid selected from, but not limited to, TFA or HCl, or hydrogenation with a catalyst such as, but not limited to, palladium-on-carbon under hydrogen to generate intermediate J; alternatively, intermediate A is reacted with an appropriate anhydride as described in step 1b, in the presence of a base selected from, but not limited to, pyridine, triethylamine or diisopropylethylamine to generate intermediate J. Intermediate J is then coupled with $P_2$ protected amine wherein $P_2$ is selected from, but not limited to, methyl, ethyl, benzyl or propionitrile using standard coupling reagents selected from, but not limited to, DCC, EDCl, PyBOP or BOP in presence or absence of a reagent such as 1-hydroxybenazotriazole, 1-hydroxy-7-azabenzotriazole or pentafluorophenol to generate intermediate K. Finally K is converted into a compound of Formula V wherein $R^4$ is a tetrazole using reagents such as, but not limited to, trimethylsilyl azide, triphenylphosphine and diisopropyl azodicarboxylate, to generate intermediate L, in which protecting group P2 can be removed using, for example if P2 protected amine used in step 3 is 3-aminopropionitrile, base such as 1,8-diazabicyclo[5.4.0]undec-7-ene.

Scheme 4 illustrates the synthesis of intermediate A which is useful for the preparation of compounds of Formula I' or I.

Scheme 4

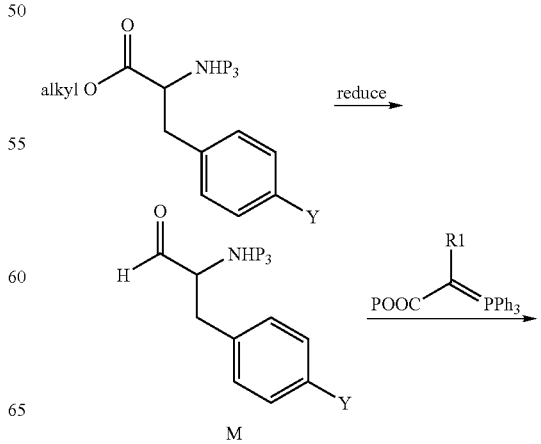

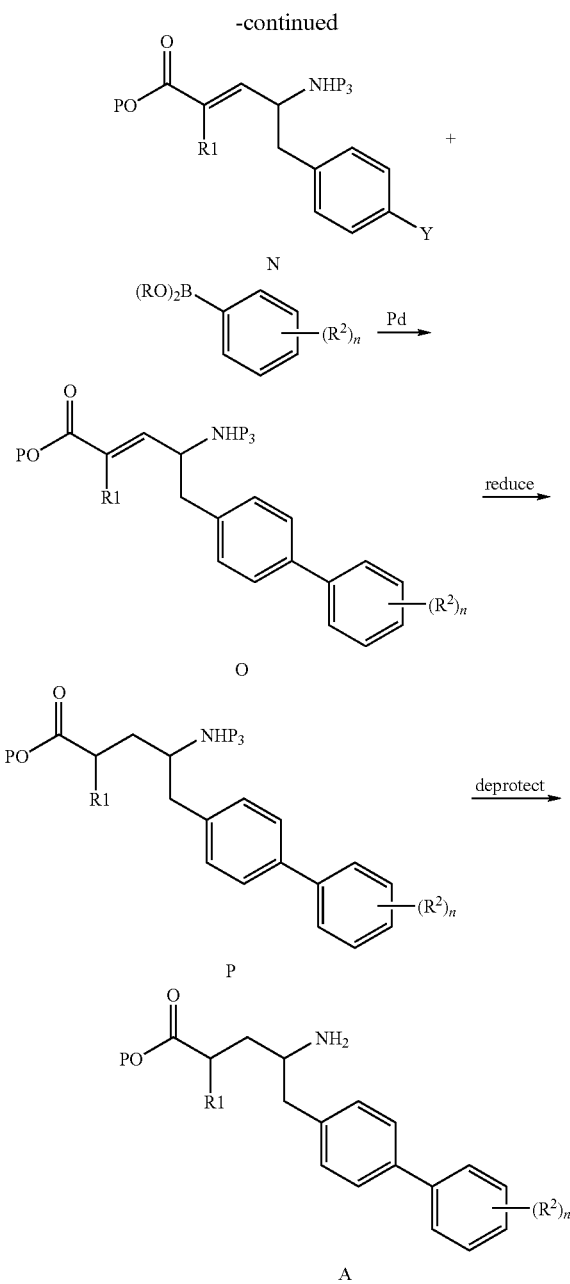

Aldehyde M is prepared by reduction of a protected amino acid ester with a reducing agent such as, but not limited to, diisobutyl aluminum hydride. The protecting group $P_3$ can be chosen from, but not limited to, Boc or Cbz and group Y can be chosen from, but not limited to, halogen or triflate. Intermediate N is prepared from intermediate M by methodology such as, but not limited to, a Wittig reaction employing an appropriate phosphorus reagent such as, but not limited to, a triphenyl phosphonium ylide. The substituted biphenyl intermediate O is prepared from Intermediate N by methodology such as, but not limited to, a Suzuki reaction employing reactants such as, but not limited to, arylboronic acids or arylboronic esters catalyzed by a palladium(0) complex such as, but not limited to, tetrakis(triphenylphosphine)palladium or dichloro[1,1'-bis(diphenylphosphino)ferrocene]palladium (II) dichloromethane adduct. The olefin of Intermediate O is reduced to furnish Intermediate P by hydrogenation in the presence of a catalyst such as, but not limited to, platinum-on-carbon or platinum oxide at atmospheric or elevated pressure. Alternatively, the reduction can be performed using chiral catalysts and ligands such as, but not limited to, those described in patent application WO2008031567. The protecting group $P_3$ can be removed with an acid selected from, but not limited to, TFA or HCl, or hydrogenation with a catalyst such as, but not limited to, palladium-on-carbon under hydrogen to generate intermediate A.

The invention further includes any variant of the present processes, in which an intermediate product obtainable at any stage thereof is used as starting material and the remaining steps are carried out, or in which the starting materials are formed in situ under the reaction conditions, or in which the reaction components are used in the form of their salts or optically pure antipodes.

Compounds of the invention and intermediates can also be converted into each other according to methods generally known perse. U.S. patent application No. 61/324,943 filed on Apr. 16, 2010, also describes the synthesis of various intermediates for incorporation of the $R^3$ moiety as described in Formula I; and is therefore incorporated by reference.

In another aspect, the present invention provides a pharmaceutical composition comprising a compound of the present invention or a pharmaceutically acceptable salt thereof and one or more pharmaceutically acceptable carriers. The pharmaceutical composition can be formulated for particular routes of administration such as oral administration, parenteral administration, and rectal administration, etc. In addition, the pharmaceutical compositions of the present invention can be made up in a solid form including capsules, tablets, pills, granules, powders or suppositories, or in a liquid form including solutions, suspensions or emulsions. The pharmaceutical compositions can be subjected to conventional pharmaceutical operations such as sterilization and/or can contain conventional inert diluents, lubricating agents, or buffering agents, as well as adjuvants, such as preservatives, stabilizers, wetting agents, emulsifers and buffers etc.

Typically, the pharmaceutical compositions are tablets and gelatin capsules comprising the active ingredient together with a) diluents, e.g., lactose, dextrose, sucrose, mannitol, sorbitol, cellulose and/or glycine;

b) lubricants, e.g., silica, talcum, stearic acid, its magnesium or calcium salt and/or polyethyleneglycol; for tablets also c) binders, e.g., magnesium aluminum silicate, starch paste, gelatin, tragacanth, methylcellulose, sodium carboxymethylcellulose and/or polyvinylpyrrolidone; if desired d) disintegrants, e.g., starches, agar, alginic acid or its sodium salt, or effervescent mixtures; and/or e) absorbents, colorants, flavors and sweeteners.

Tablets may be either film coated or enteric coated according to methods known in the art.

Suitable compositions for oral administration include an effective amount of a compound of the invention in the form of tablets, lozenges, aqueous or oily suspensions, dispersible powders or granules, emulsion, hard or soft capsules, or syrups or elixirs. Compositions intended for oral use are prepared according to any method known in the art for the manufacture of pharmaceutical compositions and such compositions can contain one or more agents selected from the group consisting of sweetening agents, flavoring agents, coloring agents and preserving agents in order to provide pharmaceutically elegant and palatable preparations. Tablets contain the active ingredient in admixture with nontoxic pharmaceutically acceptable excipients which are suitable for the manufacture of tablets. These excipients are, for example, inert diluents, such as calcium carbonate, sodium carbonate, lactose, calcium phosphate or sodium phosphate; granulating and disintegrating agents, for example, corn starch, or alginic acid; binding agents, for example, starch, gelatin or acacia; and lubricating agents, for example magnesium stearate, stearic acid or talc. The tablets are uncoated or coated by known techniques to delay disintegration and absorption in the gastrointestinal tract and thereby provide a sustained action over a longer period. For example, a time delay material such as glyceryl monostearate or glyceryl distearate can be employed. Formulations for oral use can be presented as hard gelatin capsules wherein the active ingredient is mixed with an inert solid diluent, for example, calcium carbonate, calcium phosphate or kaolin, or as soft gelatin capsules wherein the active ingredient is mixed with water or an oil medium, for example, peanut oil, liquid paraffin or olive oil.

Certain injectable compositions are aqueous isotonic solutions or suspensions, and suppositories are advantageously prepared from fatty emulsions or suspensions. Said compositions may be sterilized and/or contain adjuvants, such as preserving, stabilizing, wetting or emulsifying agents, solution promoters, salts for regulating the osmotic pressure and/or buffers. In addition, they may also contain other therapeutically valuable substances. Said compositions are prepared according to conventional mixing, granulating or coating methods, respectively, and contain about 0.1-75%, or contain about 1-50%, of the active ingredient.

Suitable compositions for transdermal application include an effective amount of a compound of the invention with carrier. Carriers include absorbable pharmacologically acceptable solvents to assist passage through the skin of the host. For example, transdermal devices are in the form of a bandage comprising a backing member, a reservoir containing the compound optionally with carriers, optionally a rate controlling barrier to deliver the compound of the skin of the host at a controlled and predetermined rate over a prolonged period of time, and means to secure the device to the skin.

Suitable compositions for topical application, e.g., to the skin and eyes, include aqueous solutions, suspensions, ointments, creams, gels or sprayable formulations, e.g., for delivery by aerosol or the like. Such topical delivery systems will in particular be appropriate for dermal application. They are thus particularly suited for use in topical, including cosmetic, formulations well-known in the art. Such may contain solubilizers, stabilizers, tonicity enhancing agents, buffers and preservatives.

As used herein a topical application may also pertain to an inhalation or to an intranasal application. They are conveniently delivered in the form of a dry powder (either alone, as a mixture, for example a dry blend with lactose, or a mixed component particle, for example with phospholipids) from a dry powder inhaler or an aerosol spray presentation from a pressurised container, pump, spray, atomizer or nebuliser, with or without the use of a suitable propellant.

The present invention further provides anhydrous pharmaceutical compositions and dosage forms comprising the compounds of the present invention as active ingredients, since water may facilitate the degradation of certain compounds.

Anhydrous pharmaceutical compositions and dosage forms of the invention can be prepared using anhydrous or low moisture containing ingredients and low moisture or low humidity conditions. An anhydrous pharmaceutical composition may be prepared and stored such that its anhydrous nature is maintained. Accordingly, anhydrous compositions are preferably packaged using materials known to prevent exposure to water such that they can be included in suitable formulary kits. Examples of suitable packaging include, but are not limited to, hermetically sealed foils, plastics, unit dose containers (e.g., vials), blister packs, and strip packs.

The invention further provides pharmaceutical compositions and dosage forms that comprise one or more agents that reduce the rate by which the compound of the present invention as an active ingredient will decompose. Such agents, which are referred to herein as "stabilizers," include, but are not limited to, antioxidants such as ascorbic acid, pH buffers, or salt buffers, etc.

The compounds according to anyone of formulae I', I to VIC, II to IIC, III to IIIC, IV, IVA, V, VA and VI to VIC in free form or in pharmaceutically acceptable salt form, exhibit valuable pharmacological properties, e.g. neutral endopeptidase EC 3.4.24.11 modulating properties, e.g. as indicated in in vitro and in vivo tests as provided in the next sections and are therefore indicated for therapy.

Compounds of the invention may be useful in the treatment of an indication selected from hypertension, pulmonary hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retension), diabetic nephropathy, non-diabetic nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), Pulmonary Arterial hypertension, renal failure (including edema and salt retention), cyclical oedema, Menières disease, hyperaldosteroneism (primary and secondary) and hypercalciuria, ascites, glaucoma, menstrual disorders, preterm labour, pre-eclampsia, endometriosis, and reproductive disorders (especially male and female infertility, polycystic ovarian syndrome, implantation failure), asthma, obstructive sleep apnea, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, the modulation of gastric acid secretion, the treatment of hyperreninaemia, cystic fibrosis, restenosis, type-2 diabetes, metabolic syndrome, diabetic complications and atherosclerosis, male and female sexual dysfunction. Thus, as a further embodiment, the present invention provides the use of a compound according to anyone of formulae I', I to VIC, II to IIC, III to IIIC, IV, IVA, V, VA and VI to VIC, or a pharmaceutically acceptable salt thereof. In a further embodiment, the therapy is selected from a disease which is associated with neutral endopeptidase EC 3.4.24.11 activity. In another embodiment, the disease is selected from the afore-mentioned list, suitably hypertension, pulmonary hypertension, isolated systolic hypertension, resistant hypertension, peripheral vascular disease, heart failure, congestive heart failure, left ventricular hypertrophy, angina, renal insufficiency, renal failure (including edema and salt retension), diabetic nephropathy, non-diabetic nephropathy, type-2 diabetes, and diabetic complications and most suitably cardiovascular disorders, such as hypertension, renal insufficiency including edema and congestive heart failure.

In another embodiment, the invention provides a method of treating a disease which is associated with neutral endopeptidase EC 3.4.24.11 activity comprising administration of a therapeutically acceptable amount of a compound according to anyone of formulae I', I to VIC, II to IIC, III to IIIC, IV, IVA, V, VA and VI to VIC, or a pharmaceutically acceptable salt thereof. In a further embodiment, the disease is selected from the afore-mentioned list, suitably hypertension, pulmonary hypertension, isolated systolic hypertension, resistant hypertension, peripheral vascular disease, heart failure, congestive heart failure, left ventricular hypertrophy, angina, renal insufficiency, renal failure (including edema and salt retention), diabetic nephropathy, non-diabetic nephropathy, type-2 diabetes, and diabetic complications and most suitably cardiovascular disorders, such as hypertension, renal insufficiency including edema and congestive heart failure.

The pharmaceutical composition or combination of the present invention can be in unit dosage of about 1-1000 mg of active ingredient(s) for a subject of about 50-70 kg, or about 1-500 mg or about 1-250 mg or about 1-150 mg or about 0.5-100 mg, or about 1-50 mg of active ingredients. The therapeutically effective dosage of a compound, the pharmaceutical composition, or the combinations thereof, is dependent on the species of the subject, the body weight, age and individual condition, the disorder or disease or the severity thereof being treated. A physician, clinician or veterinarian of ordinary skill can readily determine the effective amount of each of the active ingredients necessary to prevent, treat or inhibit the progress of the disorder or disease.

The above-cited dosage properties are demonstrable in vitro and in vivo tests using advantageously mammals, e.g., mice, rats, dogs, monkeys or isolated organs, tissues and preparations thereof. The compounds of the present invention can be applied in vitro in the form of solutions, e.g., preferably aqueous solutions, and in vivo either enterally, parenterally, advantageously intravenously, e.g., as a suspension or in aqueous solution. The dosage in vitro may range between about $10^{-3}$ molar and $10^{-9}$ molar concentrations. A therapeutically effective amount in vivo may range depending on the route of administration, between about 0.1-500 mg/kg, or between about 1-100 mg/kg.

The activity of a compound according to the present invention can be assessed by the following in vitro & in vivo methods and/or by the following in vitro & in vivo methods well-described in the art. See A fluorescence lifetime-based assay for protease inhibitor profiling on human kallikrein 7 Doering K, Meder G, Hinnenberger M, Woelcke J, Mayr L M, Hassiepen U Biomol Screen. 2009 January; 14(1):1-9.

In particular, the in vitro inhibition of recombinant human neutral endopeptidase (NEP, EC 3.4.24.11) can be determined as follows:

Recombinant human neutral endopeptidase (expressed in insect cells and purified using standard methods, final concentration 7 pM) is pre-incubated with test compounds at various concentrations for 1 hour at room temperature in 10 mM sodium phosphate buffer at pH 7.4, containing 150 mM NaCl and 0.05% (w/v) CHAPS. The enzymatic reaction is started by the addition of a synthetic peptide substrate Cys (PT14)-Arg-Arg-Leu-Trp-OH to a final concentration of 0.7 µM. Substrate hydrolysis leads to an increase fluorescence lifetime (FLT) of PT14 measured by the means of a FLT reader as described by Doering et al. (2009). The effect of the compound on the enzymatic activity was determined after 1 hour (t=60 min) incubation at room temperature. The IC50 values, corresponding to the inhibitor concentration showing 50% reduction of the FLT values measured in absence of inhibitor, are calculated from the plot of percentage of inhibition vs. inhibitor concentration using non-linear regression analysis software.

Using the test assay (as described above) compounds of the invention exhibited inhibitory efficacy in accordance to Table 1, provided infra.

TABLE 1

Inhibitory Activity of Compounds

| Compounds: Example # | Human NEP $IC_{50}$ (nM) |
|---|---|
| Example 1-1 | 283 |
| Example 2-1 | 267 |
| Example 3-6 | 250 |
| Example 3-32 | 1 |
| Example 3-60 | 7.3 |
| Example 5-1 | 350 |
| Example 6-1 | 450 |
| Example 7-1 | 93 |
| Example 9-1 | 142 |
| Example 13-1 | 14 |
| Example 49-1 | 0.04 |
| Example 49-2 | 0.03 |
| Example 49-3 | 0.3 |

The compound of the present invention may be administered either simultaneously with, or before or after, at least one other therapeutic agent. The compound of the present invention may be administered separately, by the same or different route of administration, or together in the same pharmaceutical composition.

In one embodiment, the invention provides a product comprising a compound according to anyone of formulae I', I to VIC, II to IIC, III to IIIC, IV, IVA, V, VA and VI to VIC and at least one other therapeutic agent as a combined preparation for simultaneous, separate or sequential use in therapy. In one embodiment, the therapy is the treatment of a disease or condition associated with neutral endopeptidase EC 3.4.24.11 activity.

Products provided as a combined preparation include a composition comprising the compound according to anyone of formulae I', I to VIC, II to IIC, III to IIIC, IV, IVA, V, VA and VI to VIC, or a pharmaceutically acceptable salt thereof, and the other therapeutic agent(s) together in the same pharmaceutical composition, or the compound according to anyone of formulae I' and I to VIC, or a pharmaceutically acceptable salt thereof, and the other therapeutic agent(s) in separate form, e.g. in the form of a kit.

In one embodiment, the invention provides a pharmaceutical composition comprising a compound according to anyone of formulae I' and I to VIC, or a pharmaceutically acceptable salt thereof, and another therapeutic agent(s). Optionally, the pharmaceutical composition may comprise a pharmaceutically acceptable excipient, as described above.

In one embodiment, the invention provides a kit comprising two or more separate pharmaceutical compositions, at least one of which contains a compound according to anyone of formulae I' and I to VIC, or a pharmaceutically acceptable salt thereof. In one embodiment, the kit comprises means for separately retaining said compositions, such as a container, divided bottle, or divided foil packet. An example of such a kit is a blister pack, as typically used for the packaging of tablets, capsules and the like.

The kit of the invention may be used for administering different dosage forms, for example, oral and parenteral, for administering the separate compositions at different dosage intervals, or for titrating the separate compositions against one another. To assist compliance, the kit of the invention typically comprises directions for administration.

In the combination therapies of the invention, the compound of the invention and the other therapeutic agent may be manufactured and/or formulated by the same or different manufacturers. Moreover, the compound of the invention and the other therapeutic may be brought together into a combination therapy: (i) prior to release of the combination product to physicians (e.g. in the case of a kit comprising the compound of the invention and the other therapeutic agent); (ii) by the physician themselves (or under the guidance of the physician) shortly before administration; (iii) in the patient themselves, e.g. during sequential administration of the compound of the invention and the other therapeutic agent. Accordingly, the invention provides the use of a compound according to anyone of formulae i to VIC, or a pharmaceutically acceptable salt thereof, in the manufacture of a medicament for treating a disease or condition associated with neutral endopeptidase EC 3.4.24.11 activity, wherein the medicament is prepared for administration with another therapeutic agent. The invention also provides the use of another therapeutic agent in the manufacture of medicament for treating a disease or condition associated with neutral endopeptidase EC 3.4.24.11 activity, wherein the medicament is prepared for administration with a compound according to anyone of formulae I' and I to VIC, or a pharmaceutically acceptable salt thereof.

The invention also provides a compound according to anyone of Formulae I' and I to VIC, or a pharmaceutically acceptable salt thereof, for use in a method of treating a disease or condition associated with neutral endopeptidase EC 3.4.24.11 activity, wherein the compound according to anyone of formulae I' and I to VIC, or a pharmaceutically acceptable salt thereof, is prepared for administration with another therapeutic agent. The invention also provides another therapeutic agent for use in a method of treating a disease or condition associated with neutral endopeptidase EC 3.4.24.11, wherein the other therapeutic agent is prepared for administration with a compound according to anyone of formulae I' and I to VIC, or a pharmaceutically acceptable salt thereof. The invention also provides a compound according to anyone of formulae I' and I to VIC, or a pharmaceutically acceptable salt thereof, for use in a method of treating a disease or condition associated with neutral endopeptidase EC 3.4.24.11, wherein the compound according to anyone of formulae I' and I to VIC, or a pharmaceutically acceptable salt thereof, is administered with another therapeutic agent. The invention also provides another therapeutic agent for use in a method of treating a disease or condition associated with neutral endopeptidase EC 3.4.24.11 activity, wherein the other therapeutic agent is administered with a compound according to anyone of formulae I' and I to VIC, or a pharmaceutically acceptable salt thereof.

The invention also provides the use of a compound according to anyone of formulae I' and I to VIC, or a pharmaceutically acceptable salt thereof, in the manufacture of a medicament for treating a disease or condition associated with neutral endopeptidase EC 3.4.24.11 activity, wherein the patient has previously (e.g. within 24 hours) been treated with another therapeutic agent. The invention also provides the use of another therapeutic agent in the manufacture of a medicament for treating a disease or condition associated with neutral endopeptidase EC 3.4.24.11 activity, wherein the patient has previously (e.g. within 24 hours) been treated with a compound according to anyone of formulae I' and I to VIC, or a pharmaceutically acceptable salt thereof.

In one embodiment, the other therapeutic agent is selected from: HMG-Co-A reductase inhibitor, an anigiotensin receptor blocker (ARBs, angiotensin II receptor antagonist), angiotensin converting enzyme (ACE) Inhibitor, a calcium channel blocker (CCB), an endothelin antagonist, a renin inhibitor, a diuretic, an ApoA-I mimic, an anti-diabetic agent, an obesity-reducing agent, an aldosterone receptor blocker, an endothelin receptor blocker, an aldosterone synthase inhibitors (ASI), a CETP inhibitor or a phophodiesterase type 5 (PDE5) inhibitor.

The term "in combination with" a second agent or treatment includes co-administration of the compound of the invention (e.g., a compound according to anyone of Formulae I' and I to VIC or a compound otherwise described herein) with the second agent or treatment, administration of the compound of the invention first, followed by the second agent or treatment and administration of the second agent or treatment first, followed by the compound of the invention.

The term "second agent" includes any agent which is known in the art to treat, prevent, or reduce the symptoms of a disease or disorder described herein, e.g. a disorder or disease responsive to the inhibition of neutral endopeptidase, such as for example, hypertension, pulmonary hypertension, isolated systolic hypertension, resistant hypertension, peripheral vascular disease, heart failure, congestive heart failure, left ventricular hypertrophy, angina, renal insufficiency (diabetic or non-diabetic), renal failure (including edema and salt retension), diabetic nephropathy, non-diabetic nephropathy, nephroic syndrome, glomerulonephritis, scleroderma, glomerular sclerosis, proteinurea of primary renal disease, renal vascular hypertention, diabetic retinopathy and end-stage renal disease (ESRD), endothelial dysfunction, diastolic dysfunction, hypertrophic cardiomyopathy, diabetic cardiac myopathy, supraventricular and ventricular arrhythmias, atrial fibrillation (AF), cardiac fibrosis, atrial flutter, detrimental vascular remodeling, plaque stabilization, myocardial infarction (MI), renal fibrosis, polycystic kidney disease (PKD), Pulmonary Arterial hypertension, renal failure (including edema and salt retension), cyclical oedema, Menières disease, hyperaldosteroneism (primary and secondary) and hypercalciuria, ascites, glaucoma, menstrual disorders, preterm labour, pre-eclampsia, endometriosis, and reproductive disorders (especially male and female infertility, polycystic ovarian syndrome, implantation failure), obstructive sleep apnea, asthma, inflammation, leukemia, pain, epilepsy, affective disorders such as depression and psychotic condition such as dementia and geriatric confusion, obesity and gastrointestinal disorders (especially diarrhea and irritable bowel syndrome), wound healing (especially diabetic and venous ulcers and pressure sores), septic shock, the modulation of gastric acid secretion, the treatment of hyperreninaemia, cystic fibrosis, restenosis, type-2 diabetes, metabolic syndrome, diabetic complications and atherosclerosis, male and female sexual dysfunction.

Examples of second agents include HMG-Co-A reductase inhibitors, angiotensin II receptor antagonists, angiotensin converting enzyme (ACE) Inhibitors, calcium channel blockers (CCB), endothelin antagonists, renin inhibitors, diuretics, ApoA-I mimics, anti-diabetic agents, obesity-reducing agents, aldosterone receptor blockers, endothelin receptor blockers, aldosterone synthase inhibitors (ASI) and CETP inhibitors.

The term "HMG-Co-A reductase inhibitor" (also called beta-hydroxy-beta-methylglutaryl-co-enzyme-A reductase inhibitors) includes active agents that may be used to lower the lipid levels including cholesterol in blood. Examples include atorvastatin, cerivastatin, compactin, dalvastatin, dihydrocompactin, fluindostatin, fluvastatin, lovastatin, pitavastatin, mevastatin, pravastatin, rivastatin, simvastatin, and velostatin, or, pharmaceutically acceptable salts thereof.

The term "ACE-inhibitor" (also called angiotensin converting enzyme inhibitors) includes molecules that interrupt the enzymatic degradation of angiotensin I to angiotensin II. Such compounds may be used for the regulation of blood pressure and for the treatment of congestive heart failure. Examples include alacepril, benazepril, benazeprilat, captopril, ceronapril, cilazapril, delapril, enalapril, enaprilat, fosinopril, imidapril, lisinopril, moveltopril, perindopril, quinapril, ramipril, spirapril, temocapril, and trandolapril, or, pharmaceutically acceptables salt thereof.

The term "endothelin antagonist" includes bosentan (cf. EP 526708 A), tezosentan (cf. WO 96/19459), or, pharmaceutically acceptable salts thereof.

The term "renin inhibitor" includes ditekiren (chemical name: [1S-[1R*,2R*,4R*(1R*,2R*)]]-1-[(1,1-dimethylethoxy)carbonyl]-L-proly I-L-phenylalanyl-N-[2-hydroxy-5-methyl-1-(2-methylpropyl)-4-[[[2-methyl-1-[[(2-pyridinylmrthyl)amino]carbonyl]butyl]amino]carbonyl]hexyl]-N-alfa-methyl-L-histidinamide); terlakiren (chemical name: [R-(R*,S*)]-N-(4-morpholinylcarbonyl)-L-phenylalanyl-N-[1-(cyclohexylmethyl)-2-hydroxy-3-(1-methylethoxy)-3-oxopropyl]-S-methyl-L-cysteineamide); Aliskiren (chemical name: (2S,4S,5S,7S)-5-amino-N-(2-carbamoyl-2,2-dimethylethyl)-4-hydroxy-7-{[4-methoxy-3-(3-methoxypropoxy)phenyl]methyl}-8-methyl-2-(propan-2-yl)nonanamide) and zankiren (chemical name: [1S-[1R*[R*(R*)],2S*,3R*]]-N-[1-(cyclohexylmethyl)-2,3-dihydroxy-5-methylhexyl]alfa-[[2-[[(4-methyl-1-piperazinyl)sulfonyl]methyl]-1-oxo-3-phenylpropyl]-amino]-4-thiazolepropanamide), or, hydrochloride salts thereof, or, SPP630, SPP635 and SPP800 as developed by Speedel, or RO 66-1132 and RO 66-1168 of Formula (A) and (B):

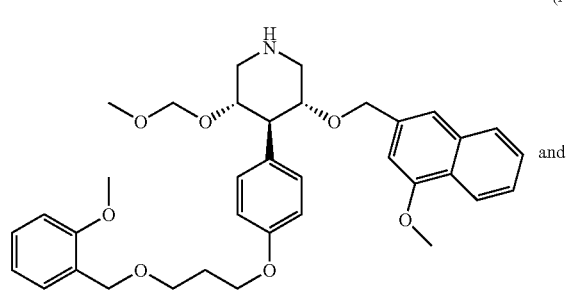

(A)

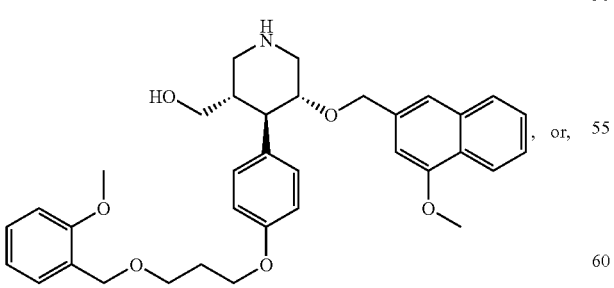

(B)

, or, pharmaceutically acceptable salts thereof.

The term "aliskiren", if not defined specifically, is to be understood both as the free base and as a salt thereof, especially a pharmaceutically acceptable salt thereof, most preferably a hemi-fumarate salt thereof.

An angiotensin II receptor antagonist or a pharmaceutically acceptable salt thereof is understood to be an active ingredient which bind to the $AT_1$-receptor subtype of angiotensin II receptor but do not result in activation of the receptor. As a consequence of the inhibition of the $AT_1$ receptor, these antagonists can, for example, be employed as antihypertensives or for treating congestive heart failure.

The class of $AT_1$ receptor antagonists comprises compounds having differing structural features, essentially preferred are the non-peptidic ones. For example, mention may be made of the compounds which are selected from the group consisting of valsartan, losartan, candesartan, eprosartan, irbesartan, saprisartan, tasosartan, telmisartan, the compound with the designation E-1477 of the following formula

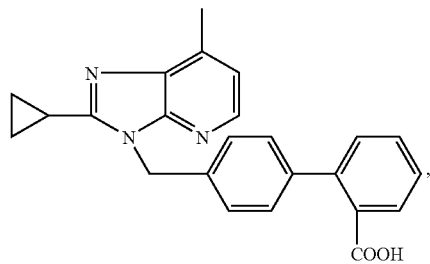

the compound with the designation SC-52458 of the following formula

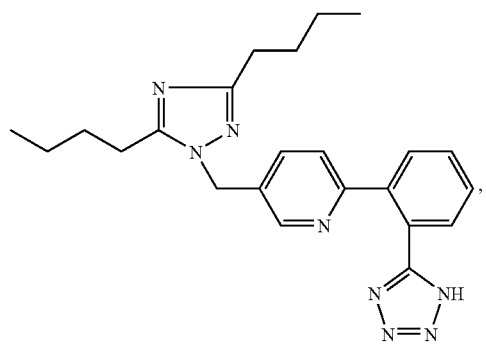

and the compound with the designation ZD-8731 of the following formula

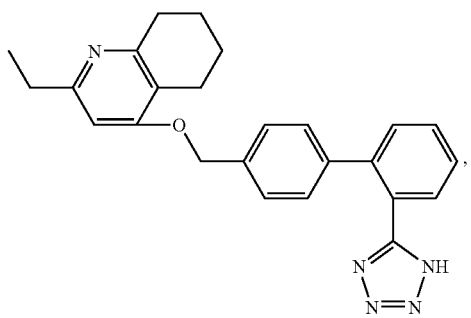

or, in each case, a pharmaceutically acceptable salt thereof.

Preferred $AT_1$-receptor antagonist are those agents which have been marketed, most preferred is valsartan or a pharmaceutically acceptable salt thereof.

The term "calcium channel blocker (CCB)" includes dihydropyridines (DHPs) and non-DHPs (e.g., diltiazem-type and verapamil-type CCBs). Examples include amlodipine, felodipine, ryosidine, isradipine, lacidipine, nicardipine, nifedipine, niguldipine, niludipine, nimodipine, nisoldipine, nitrendipine, and nivaldipine, and is preferably a non-DHP representative selected from the group consisting of flunarizine, prenylamine, diltiazem, fendiline, gallopamil, mibefradil, anipamil, tiapamil and verapamil, or, pharmaceutically acceptable salts thereof. CCBs may be used as anti-hypertensive, anti-angina pectoris, or anti-arrhythmic drugs.

The term "diuretic" includes thiazide derivatives (e.g., chlorothiazide, hydrochlorothiazide, methylclothiazide, and chlorothalidon).

The term "ApoA-I mimic" includes D4F peptides (e.g., formula D-W-F-K-A-F-Y-D-K-V-A-E-K-F-K-E-A-F)

The term "anti-diabetic agent" includes insulin secretion enhancers that promote the secretion of insulin from pancreatic β-cells. Examples include biguanide derivatives (e.g., metformin), sulfonylureas (SU) (e.g., tolbutamide, chlorpropamide, tolazamide, acetohexamide, 4-chloro-N-[(1-pyrrolidinylamino)carbonyl]-benzensulfonamide (glycopyramide), glibenclamide (glyburide), gliclazide, 1-butyl-3-metanilylurea, carbutamide, glibonuride, glipizide, gliquidone, glisoxepid, glybuthiazole, glibuzole, glyhexamide, glymidine, glypinamide, phenbutamide, and tolylcyclamide), or pharmaceutically acceptable salts thereof. Further examples include phenylalanine derivatives (e.g., nateglinide [N-(trans-4-isopropylcyclohexylcarbonyl)-D-phenylalanine] (cf. EP 196222 and EP 526171) of the formula

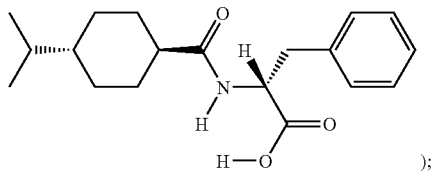

repaglinide [(S)-2-ethoxy-4-{2-[[3-methyl-1-[2-(1-piperidinyl)phenyl]butyl]amino]-2-oxoethyl}benzoic acid] (cf. EP 589874, EP 147850 A2, in particular Example 11 on page 61, and EP 207331 A1); calcium (2S)-2-benzyl-3-(cis-hexahydro-2-isoindolinlycarbonyl)-propionate dihydrate (e.g., mitiglinide (cf. EP 507534)); and glimepiride (cf. EP 31058). Further examples include DPP-IV inhibitors, GLP-1 and GLP-1 agonists.

DPP-IV is responsible for inactivating GLP-1. More particularly, DPP-IV generates a GLP-1 receptor antagonist and thereby shortens the physiological response to GLP-1. GLP-1 is a major stimulator of pancreatic insulin secretion and has direct beneficial effects on glucose disposal.

The DPP-IV inhibitor can be peptidic or, preferably, non-peptidic. DPP-IV inhibitors are in each case generically and specifically disclosed e.g. in WO 98/19998, DE 196 16 486 A1, WO 00/34241 and WO 95/15309, in each case in particular in the compound claims and the final products of the working examples, the subject-matter of the final products, the pharmaceutical preparations and the claims are hereby incorporated into the present application by reference to these publications. Preferred are those compounds that are specifically disclosed in Example 3 of WO 98/19998 and Example 1 of WO 00/34241, respectively.

GLP-1 is an insulinotropic protein which is described, e.g., by W. E. Schmidt et al. in *Diabetologia*, 28, 1985, 704-707 and in U.S. Pat. No. 5,705,483.

The term "GLP-1 agonists" includes variants and analogs of GLP-1(7-36)NH$_2$ which are disclosed in particular in U.S. Pat. Nos. 5,120,712, 5,118,666, 5,512,549, WO 91/11457 and by C. Orskov et al in J. Biol. Chem. 264 (1989) 12826. Further examples include GLP-1(7-37), in which compound the carboxy-terminal amide functionality of Arg$^{36}$ is displaced with Gly at the 37$^{th}$ position of the GLP-1(7-36)NH$_2$ molecule and variants and analogs thereof including GLN$^9$-GLP-1(7-37), D-GLN$^9$-GLP-1(7-37), acetyl LYS$^9$-GLP-1(7-37), LYS$^{18}$-GLP-1(7-37) and, in particular, GLP-1(7-37)OH, VAL$^8$-GLP-1(7-37), GLY$^8$-GLP-1(7-37), THR$^8$-GLP-1(7-37), MET$^8$-GLP-1(7-37) and 4-imidazopropionyl-GLP-1. Special preference is also given to the GLP agonist analog exendin-4, described by Greig et al. in *Diabetologia* 1999, 42, 45-50.

Also included in the definition "anti-diabetic agent" are insulin sensitivity enhancers which restore impaired insulin receptor function to reduce insulin resistance and consequently enhance the insulin sensitivity. Examples include hypoglycemic thiazolidinedione derivatives (e.g., glitazone, (S)-((3,4-dihydro-2-(phenyl-methyl)-2H-1-benzopyran-6-yl)methyl-thiazolidine-2,4-dione (englitazone), 5-{[4-(3-(5-methyl-2-phenyl-4-oxazolyl)-1-oxopropyl)-phenyl]-methyl}-thiazolidine-2,4-dione (darglitazone), 5-{[4-(1-methyl-cyclohexyl)methoxy)-phenyl]methyl}-thiazolidine-2,4-dione (ciglitazone), 5-{[4-(2-(1-indolyl)ethoxy)phenyl]methyl}-thiazolidine-2,4-dione (DRF2189), 5-{4-[2-(5-methyl-2-phenyl-4-oxazolyl)-ethoxy)]benzyl}-thiazolidine-2,4-dione (BM-13.1246), 5-(2-naphthylsulfonyl)-thiazolidine-2,4-dione (AY-31637), bis{4-[(2,4-dioxo-5-thiazolidinyl)methyl]phenyl}methane (YM268), 5-{4-[2-(5-methyl-2-phenyl-4-oxazolyl)-2-hydroxyethoxy]benzyl}-thiazolidine-2,4-dione (AD-5075), 5-[4-(1-phenyl-1-cyclopropanecarbonylamino)-benzyl]-thiazolidine-2,4-dione (DN-108) 5-{[4-(2-(2,3-dihydroindol-1-yl)ethoxy)phenyl]methyl}-thiazolidine-2,4-dione, 5-[3-(4-chlorophenyl])-2-propynyl]-5-phenylsulfonyl)thiazolidine-2,4-dione, 5-[3-(4-chlorophenyl])-2-propynyl]-5-(4-fluorophenyl-sulfonyl)thiazolidine-2,4-dione, 5-{[4-(2-(methyl-2-pyridinyl-amino)-ethoxy)phenyl]methyl}-thiazolidine-2,4-dione (rosiglitazone), 5-{[4-(2-(5-ethyl-2-pyridyl)ethoxy)phenyl]-methyl}thiazolidine-2,4-dione (pioglitazone), 5-{[4-((3,4-dihydro-6-hydroxy-2,5,7,8-tetramethyl-2H-1-benzopyran-2-yl)methoxy)-phenyl]-methyl}-thiazolidine-2,4-dione (troglitazone), 5-[6-(2-fluorobenzyloxy)naphthalen-2-ylmethyl]-thiazolidine-2,4-dione (MCC555), 5-{[2-(2-naphthyl)-benzoxazol-5-yl]-methyl}thiazolidine-2,4-dione (T-174) and 5-(2,4-dioxothiazolidin-5-ylmethyl)-2-methoxy-N-(4-trifluoromethyl-benzyl)benzamide (KRP297)).

Further anti-diabetic agents include, insulin signalling pathway modulators, like inhibitors of protein tyrosine phosphatases (PTPases), antidiabetic non-small molecule mimetic compounds and inhibitors of glutamine-fructose-6-phosphate amidotransferase (GFAT); compounds influencing a dysregulated hepatic glucose production, like inhibitors of glucose-6-phosphatase (G6Pase), inhibitors of fructose-1,6-bisphosphatase (F-1,6-Bpase), inhibitors of glycogen phosphorylase (GP), glucagon receptor antagonists and inhibitors of phosphoenolpyruvate carboxykinase (PEPCK); pyruvate dehydrogenase kinase (PDHK) inhibitors; inhibitors of gastric emptying; insulin; inhibitors of GSK-3; retinoid X receptor (RXR) agonists; agonists of Beta-3 AR; agonists of uncoupling proteins (UCPs); non-glitazone type PPARγ agonists; dual PPARα/PPARγ agonists; antidiabetic vanadium containing compounds; incretin hormones, like glucagon-like peptide-1 (GLP-1) and GLP-1 agonists; beta-cell imidazoline receptor antagonists; miglitol; α₂-adrenergic antagonists; and pharmaceutically acceptable salts thereof.

The term "obesity-reducing agent" includes lipase inhibitors (e.g., orlistat) and appetite suppressants (e.g., sibutramine and phentermine).

An aldosterone synthase inhibitor or a pharmaceutically acceptable salt thereof is understood to be an active ingredient that has the property to inhibit the production of aldosterone. Aldosterone synthase (CYP11B2) is a mitochondrial cytochrome P450 enzyme catalyzing the last step of aldosterone production in the adrenal cortex, i.e., the conversion of 11-deoxycorticosterone to aldosterone. The inhibition of the aldosterone production with so-called aldosterone synthase inhibitors is known to be a successful variant to treatment of hypokalemia, hypertension, congestive heart failure, atrial fibrillation or renal failure. Such aldosterone synthase inhibition activity is readily determined by those skilled in the art according to standard assays (e.g., US 2007/0049616).

The class of aldosterone synthase inhibitors comprises both steroidal and non-steroidal aldosterone synthase inhibitors, the later being most preferred.

Preference is given to commercially available aldosterone synthase inhibitors or those aldosterone synthase inhibitors that have been approved by the health authorities.

The class of aldosterone synthase inhibitors comprises compounds having differing structural features. For example, mention may be made of the compounds which are selected from the group consisting of the non-steroidal aromatase inhibitors anastrozole, fadrozole (including the (+)-enantiomer thereof), as well as the steroidal aromatase inhibitor exemestane, or, in each case where applicable, a pharmaceutically acceptable salt thereof.

The most preferred non-steroidal aldosterone synthase inhibitor is the (+)-enantiomer of the hydrochloride of fadrozole (U.S. Pat. Nos. 4,617,307 and 4,889,861) of formula

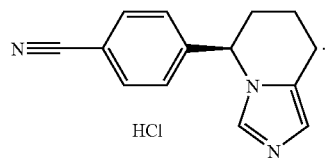

or, if appropriable, a pharmaceutically acceptable salt thereof.

A preferred steroidal aldosterone antagonist is eplerenone (cf. EP 122232 A) of the formula

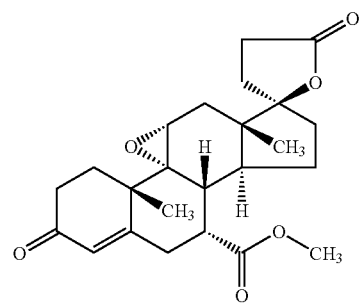

or Spironolactone; or, in each case, if appropriable, a pharmaceutically acceptable salt thereof.

Aldosterone synthase inhibitors useful in said combination are compounds and analogs generically and specifically disclosed e.g. in US2007/0049616, in particular in the compound claims and the final products of the working examples, the subject-matter of the final products, the pharmaceutical preparations and the claims are hereby incorporated into the present application by reference to this publication. Preferred aldosterone synthase inhibitors suitable for use in the present invention include, without limitation 4-(6,7-dihydro-5H-pyrrolo[1,2-c]imidazol-5-yl)-3-methylbenzonitrile; 5-(2-chloro-4-cyanophenyl)-6,7-dihydro-5H-pyrrolo[1,2-c]imidazole-5-carboxylic acid (4-methoxybenzyl)methylamide; 4'-fluoro-6-(6,7,8,9-tetrahydro-5H-imidazo[1,5-a]azepin-5-yl)biphenyl-3-carbonitrile; 5-(4-Cyano-2-methoxyphenyl)-6,7-dihydro-5H-pyrrolo[1,2-c]imidazole-5-carboxylic acid butyl ester; 4-(6,7-Dihydro-5H-pyrrolo[1,2-c]imidazol-5-yl)-2-methoxybenzonitrile; 5-(2-Chloro-4-cyanophenyl)-6,7-dihydro-5H-pyrrolo[1,2-c]imidazole-5-carboxylic acid 4-fluorobenzyl ester; 5-(4-Cyano-2-trifluoromethoxyphenyl)-6,7-dihydro-5H-pyrrolo[1,2-c]imidazole-5-carboxylic acid methyl ester; 5-(4-Cyano-2-methoxyphenyl)-6,7-dihydro-5H-pyrrolo[1,2-c]imidazole-5-carboxylic acid 2-isopropoxyethyl ester; 4-(6,7-Dihydro-5H-pyrrolo[1,2-c]imidazol-5-yl)-2-methylbenzonitrile; 4-(6,7-dihydro-5H-pyrrolo[1,2-c]imidazol-5-yl)-3-fluorobenzonitrile; 4-(6,7-Dihydro-5H-pyrrolo[1,2-c]imidazol-5-yl)-2-methoxybenzonitrile; 3-Fluoro-4-(7-methylene-6,7-dihydro-5H-pyrrolo[1,2-c]imidazol-5-yl)benzonitrile; cis-3-Fluoro-4-[7-(4-fluoro-benzyl)-5,6,7,8-tetrahydro-imidazo[1,5-a]pyridin-5-yl]benzonitrile; 4'-Fluoro-6-(9-methyl-6,7,8,9-tetrahydro-5H-imidazo[1,5-a]azepin-5-yl)biphenyl-3-carbonitrile; 4'-Fluoro-6-(9-methyl-6,7,8,9-tetrahydro-5H-imidazo[1,5-a]azepin-5-yl)biphenyl-3-carbonitrile or in each case, the (R) or (S) enantiomer thereof; or if appropriable, a pharmaceutically acceptable salt thereof.

The term aldosterone synthase inhibitors also include compounds and analogs disclosed in WO2008/076860, WO2008/076336, WO2008/076862, WO2008/027284, WO2004/046145, WO2004/014914, WO2001/076574.

Furthermore Aldosterone synthase inhibitors also include compounds and analogs disclosed in U.S. patent applications US2007/0225232, US2007/0208035, US2008/0318978, US2008/0076794, US2009/0012068, US20090048241 and in PCT applications WO2006/005726, WO2006/128853, WO2006128851, WO2006/128852, WO2007065942, WO2007/116099, WO2007/116908, WO2008/119744 and in European patent application EP 1886695. Preferred aldosterone synthase inhibitors suitable for use in the present invention include, without limitation 8-(4-Fluorophenyl)-5,6-dihydro-8H-imidazo[5,1-c][1,4]oxazine; 4-(5,6-Dihydro-8H-imidazo[5,1-c][1,4]oxazin-8-yl)-2-fluorobenzonitrile; 4-(5,6-Dihydro-8H-imidazo[5,1-c][1,4]oxazin-8-yl)-2,6-difluorobenzonitrile; 4-(5,6-Dihydro-8H-imidazo[5,1-c][1,4]oxazin-8-yl)-2-methoxybenzonitrile; 3-(5,6-Dihydro-8H-imidazo[5,1-c][1,4]oxazin-8-yl)benzonitrile; 4-(5,6-Dihydro-8H-imidazo[5,1-c][1,4]oxazin-8-yl)phthalonitrile; 4-(8-(4-Cyanophenyl)-5,6-dihydro-8H-imidazo[5,1-c][1,4]oxazin-8-yl)benzonitrile; 4-(5,6-Dihydro-8H-imidazo[5,1-c][1,4]oxazin-8-yl)benzonitrile; 4-(5,6-Dihydro-8H-imidazo[5,1-c][1,4]oxazin-8-yl)naphthalene-1-carbonitrile; 8-[4-(1H-Tetrazol-5-yl)phenyl1-5,6-dihydro-8H-imidazo[5,1-c][1,4]oxazine as developed by Speedel or in each case, the (R) or (S) enantiomer thereof; or if appropriable, a pharmaceutically acceptable salt thereof.

The term "endothelin receptor blocker" includes bosentan.

The term "CETP inhibitor" refers to a compound that inhibits the cholesteryl ester transfer protein (CETP) mediated transport of various cholesteryl esters and triglycerides from HDL to LDL and VLDL. Such CETP inhibition activity is readily determined by those skilled in the art according to standard assays (e.g., U.S. Pat. No. 6,140,343). Examples include compounds disclosed in U.S. Pat. Nos. 6,140,343 and 6,197,786 (e.g., [2R,4S]-4-[(3,5-bis-trifluoromethyl-benzyl)-methoxycarbonyl-amino]-2-ethyl-6-trifluoromethyl-3,4-dihydro-2H-quinoline-1-carboxylic acid ethyl ester (torcetrapib); compounds disclosed in U.S. Pat. No. 6,723,752 (e.g., (2R)-3-{[3-(4-Chloro-3-ethyl-phenoxy)-phenyl]-[[3-(1,1,2,2-tetrafluoro-ethoxy)-phenyl]-methyl]-amino}-1,1,1-trifluoro-2-propanol); compounds disclosed in U.S. patent application Ser. No. 10/807,838; polypeptide derivatives disclosed in U.S. Pat. No. 5,512,548; rosenonolactone derivatives and phosphate-containing analogs of cholesteryl ester disclosed in *J. Antibiot.*, 49(8): 815-816 (1996), and *Bioorg. Med. Chem. Lett.;* 6:1951-1954 (1996), respectively. Furthermore, the CETP inhibitors also include those disclosed in WO2000/017165, WO2005/095409 and WO2005/097806.

Second agent of particular interest include Endothelin antagonists, renin inhibitors, angiotensin II receptor antagonists, calcium channel blockers, diuretics, antidiabetic agents such as DPPIV inhibitors, and aldosterone synthase inhibitors.

Exemplification of the Invention:

Abbreviations:

| | |
|---|---|
| ATP: adenosine 5'-triphosphate | AS: Aldosterone Synthase |
| BINAP: racemic 2,2'-bis(diphenylphosphino)-1,1'-binaphthyl | BOC: tertiary butyl carboxy |
| br: broad | bs: broad singlet |
| Ac: Acetyl | Atm: atmosphere |
| Aq: aqueous | calcd: calculated |
| Bn: benzyl | Boc: tert-butoxycarbonyl |
| BOP-Cl: Bis(2-oxo-3-oxazolidinyl)-phosphonic Chloride | CDI: carbonyldiimidazole |
| d: doublet | DAST: (diethylamino)sulfur trifluoride |
| dd: doublet of doublets | DCM: dichloromethane |
| DIEA: diisopropylethylamine | DME: 1,4-dimethoxyethane |
| DMF: N,N-dimethylformamide | DMSO: dimethylsulfoxide |
| DIPEA: N,N-diisopropylethylamine | DMAP: N,N-dimethylaminopyridine |
| DAD: diode array detector | DTT: dithiothreitol |
| DPPA: diphenylphosphorylazide | EDCl, EDIC: N-Ethyl-N'-(3-dimethylaminopropyl)carbodiimide hydrochloride |
| EDTA: ethylenediamine tetraacetic acid | ESI: electrospray ionization |
| Et and EtOAc: ethyl and ethyl acetate | EDC: N-Ethyl-N'-(3-dimethylaminopropyl)carbodiimide hydrochloride |
| HATU: O-(7-azobenzotriazol-1-yl)-1,1,3,3-tetramethyluroniumhexafluorophosphate | HOBt: 1-hydroxy-7-azabenzotriazole |
| HBTU: 2-(1H-benzotriazole-1-yl)-1,1,3,3-tetramethyluronium-hexafluorophosphate | hrs: hours |
| HPLC: high pressure liquid chromatography | LC and LCMS: liquid chromatography and liquid chromatography and mass spectrometry |
| HPLC-RT (retention time) | |
| H: Hour(s) | HOAt: 1-hydroxy-7-azabezotriazole |
| IR: infrared | LDA: lithium diisopropylamide |
| MeOD: methanol-d4 | MeOH: methanol |
| MS: mass spectrometry | m: multiplet |
| min: minutes | m/z: mass to charge ratio |
| Ms: mesyl | Me: methyl |
| M and mM: Molar and millimole(s) | Mg: milligram |
| n.d.: not determined | NMR: nuclear magnetic resonance |
| ppm: parts per million | Pr and iPr: propyl and isopropyl |
| Ph: Phenyl | Pd/C: Palladium on Carbom |
| PyBOP: benzotriazol-1-yloxy Tripyrrolidinophosphoniumhexafluorophosphate | RT: room temperature |
| PS: polymer supported | RP: reverse phase |
| q: quartet | |
| s: singlet | t: triplet |
| TFA: trifluoroacetic acid | THF: tetrahydrofuran |
| TMSCI: trimethylsilyl chloride | TEA: triethylamine |
| Tf: triflate | tBu: tert-butyl |
| TLC: thin layer chromatography | Tris•HCl: aminotris(hydroxymethyl) methane hydrochloride |
| µL, mL and L: microlitre, millilitre and litre | UV: ultraviolet |

The following examples are intended to illustrate the invention and are not to be construed as being limitations thereon. Temperatures are given in degrees centrigrade. If not mentioned otherwise, all evaporations are performed under reduced pressure, preferably between about 15 mm Hg and 100 mm Hg (=20-133 mbar). The structure of final products, intermediates and starting materials is confirmed by standard analytical methods, e.g., microanalysis and spectroscopic characteristics, e.g., MS, IR, NMR. Abbreviations used are those conventional in the art.

All starting materials, building blocks, reagents, acids, bases, dehydrating agents, solvents, and catalysts utilized to synthesis the compounds of the present invention are either commercially available or can be produced by organic synthesis methods known to one of ordinary skill in the art (Houben-Weyl 4th Ed. 1952, Methods of Organic Synthesis, Thieme, Volume 21). Further, the compounds of the present invention can be produced by organic synthesis methods known to one of ordinary skill in the art as shown in the following examples.

The compounds in the examples 1-1 to 59-1 have been found to have $IC_{50}$ values in the range of about 0.01 nM to about 10,000 nM for NEP.

The conditions for measuring the retention times are as follows:

HPLC condition A:
Column: INERTSIL C8-3, 3 μm×33 mm×3.0 mm at 40° C.
Flow rate: 2 mL/min
Mobile phase: $H_2O$ (5 mM NH4+HCOO—)
Gradient: linear gradient from 5% to 95% MeCN in 2 min
Detection: DAD-UV at 200-400 nm
HPLC condition B:
Column: INERTSIL C8-3, 3 μm×33 mm×3.0 mm at 40° C.
Flow rate: 2 mL/min
Mobile phase: 0.1% Formic acid
Gradient: linear gradient from 5% to 95% MeCN/MeOH in 2 min
Detection: UV at 215 nm
HPLC condition C:
Column: INERTSIL C8-3, 3 μm×33 mm×3.0 mm at 40° C.
Flow rate: 2 ml/min
Mobile phase: A) $H_2O$ (5 mM NH4+HCOO—), B) 50% MeOH/50% MeCN
Gradient: linear gradient from 5% B to 95% B in 2 min
Detection: DAD-UV at 200-400 nm
HPLC condition D:
Column: Inertsil C8-3, 3 μm×33 mm×3.0 mm at 40° C.
Flow rate: 2 ml/min
Mobile phase: A) $H_2O$ (5 mM NH4+HCOO—), B) 50% MeOH/50% MeCN
Gradient: linear gradient from 40% B to 95% B in 2 min
Detection: UV at 214 nm
HPLC condition E
Column: Inertsil C8-3, 3 μm×33 mm×3.0 mm at 40° C.
Flow rate: 2 ml/min
Mobile phase: A) $H_2O$ (5 mM NH4+HCOO—), B) 50% MeOH/50% MeCN
Gradient: linear gradient from 60% B to 95% B in 2 min
Detection: UV at 214 nm The relative stereochemistry was determined using two dimensional NMR. Under the reaction condition, it would be unexpected that the stereocenter bearing the bisphenyl-methyl group racemize. Therefore, the absolute stereochemistry was determined based on the relative stereochemistry and the absolute stereochemistry of the stereocenter bearing the bisphenyl-methyl group.

EXAMPLE 1-1

Synthesis of N-((1S,3R)-1-biphenyl-4-ylmethyl-3-carboxy-butyl)-isophthalamic acid

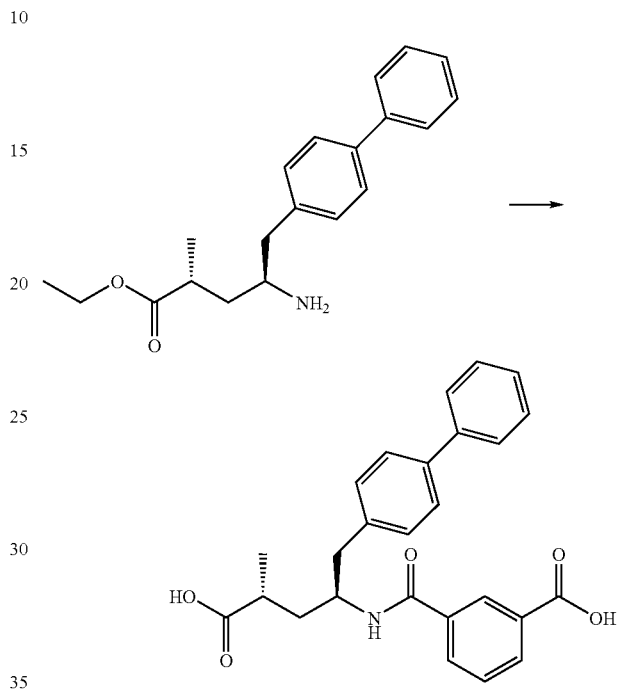

To a mixture of (2R,4S)-4-amino-5-biphenyl-4-yl-2-methyl-pentanoic acid ethyl ester hydrochloride (70 mg, 0.201 mmol) and 3-chlorocarbonylbenzoic acid methyl ester (0.302 mmol) in methylene chloride (0.5 mL) is added pyridine (0.5 mL) and the mixture is stirred at room temperature for 24 hours. The solvents are removed under reduced pressure and ethyl acetate is added. The solution is washed with aqueous 1M HCl and brine and the organic phase is dried over sodium sulfate. The solvent is removed under reduced pressure and the residue is purified by column chromatography using methylene chloride to furnish N-((1S,3R)-1-biphenyl-4-ylmethyl-3-ethoxycarbonyl-butyl)-isophthalamic acid. Next, to a solution of N-((1S,3R)-1-biphenyl-4-ylmethyl-3-ethoxycarbonyl-butyl)-isophthalamic acid (0.287 mmol) in ethanol (10 mL) is added aqueous 1M NaOH (1.2 mL, 1.12 mmol) and the mixture is stirred at 50-60° C. for 5 hours. The ethanol is removed under reduced pressure and water is added. The solution is acidified with 1M HCl and the mixture is extracted with ethyl acetate. The organic phase is dried over sodium sulfate and the solvent is removed under reduced pressure. The residue is purified by preparative HPLC using a gradient of MeCN/water (0.1% TFA). The proper fractions are lyophilized to furnish N-((1S,3R)-1-biphenyl-4-ylmethyl-3-carboxy-butyl)-isophthalamic acid. HPLC Retention time 1.05 minutes (condition A); MS 432.3 (M+1); 1H NMR (400 MHz, DMSO-d6) δ ppm 1.09 (d, J=7.07 Hz, 3H), 1.60 (m, 1H), 1.89 (m, 1H), 2.47 (m, 1H), 2.86 (m, 2H), 4.27 (m, 1H), 7.27-7.35 (m, 3H), 7.34 (t, 1H), 7.43 (t, 2H), 7.55-7.66 (m, 5H), 8.01-8.07 (m, 2H), 8.39 (s, 1H), 8.47 (d, J=8.46 Hz, 1H).

Following compounds are prepared using similar procedure as example 1-1 with appropriate reagents and conditions:

| Example # | Product | Reagent | Hydrolysis Condition | HPLC-RT (condition) | MS (M + 1) |
|---|---|---|---|---|---|
| Example 1-2 | (2R,4S)-5-biphenyl-4-yl-4-[2-(3-methoxy-phenyl)-acetylamino]-2-methyl-pentanoic acid | 3-methoxyphenylacetyl chloride | Aq. NaOH, EtOH, RT | 1.31 min. (A) | 432.4 |
| Example 1-3 | N-((1S,3R)-1-biphenyl-4-ylmethyl-3-carboxy-butyl)-terephthalamic acid | methyl 4-(chlorocarbonyl)benzoate | Aq. NaOH, EtOH, 60° C. | 1.09 min. (A) | 432.3 |

EXAMPLE 1-2

1H NMR (400 MHz, MeOD-d4) δ ppm 1.15 (d, J=7.07 Hz, 3H), 1.50 (m, 1H), 1.95 (m, 1H), 2.50 (m, 1H), 2.71 (dd, J=7.83 Hz, 7.71 Hz, 1H), 2.83 (dd, J=5.56 Hz, 5.70 Hz, 1H), 3.40 (s, 2H), 3.70 (s, 3H), 4.18 (m, 1H), 6.75 (m, 3H), 7.14 (t, J=8.34 Hz, 3H), 7.31 (t, J=7.33 Hz, 1H), 7.42 (m, 4H), 7.56 (d, J=7.33 Hz, 2H), 7.85 (d, J=8.97 Hz, 1H).

EXAMPLE 1-3

1H NMR (400 MHz, DMSO-d6) δ ppm 0.96 (d, J=7.20 Hz, 3H), 1.49 (m, 1H), 1.68 (m, 1H), 2.33 (m, 1H), 2.77 (m, 1H), 3.06 (dd, 1H), 4.11 (m, 1H), 7.30-7.35 (m, 3H), 7.44 (t, 1H), 7.59 (td, J=8.21 Hz, 2H), 7.65 (d, J=7.20 Hz, 2H), 7.85 (q, 4H), 10.46 (m, 1H).

EXAMPLE 2-1

Synthesis of (2R,4S)-5-biphenyl-4-yl-4-(3-carboxy-3-methyl-butyrylamino)-2-methyl-pentanoic acid

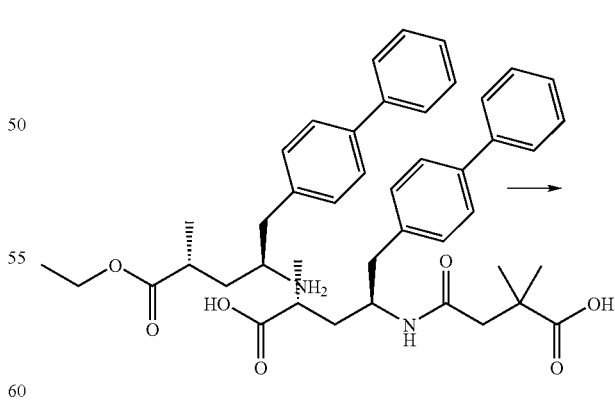

A solution of (2R,4S)-4-amino-5-biphenyl-4-yl-2-methyl-pentanoic acid ethyl ester hydrochloride (100 mg, 0.287 mmol) and 3,3-dimethyl-dihydro-furan-2,5-dione (0.431 mmol) in 1:1 methylene chloride/pyridine (1.4 mL) is stirred at room temperature for 24 hours. The solvents are removed under reduced pressure and obtained residue is used directly in the subsequent hydrolysis reaction.

Next, to a solution of the obtained residue (0.287 mmol) in ethanol (10 mL) is added aqueous 1M NaOH (2 mL, 6.97 mmol) and the mixture is stirred at room temperature for 18 hours. The mixture is poured into ethyl acetate and is washed with aqueous 1M HCl, the organic phase is dried over magnesium sulfate and the solvent is removed under reduced pressure. The residue is purified by preparative HPLC using a gradient of MeCN/water (0.1% TFA). The proper fractions are lyophilized to furnish (2R,4S)-5-biphenyl-4-yl-4-(3-carboxy-3-methyl-butyrylamino)-2-methyl-pentanoic acid. HPLC Retention time 1.03 minutes (condition A); MS 412.4 (M+1); 1H NMR (400 MHz, DMSO-d6) δ ppm 0.97-1.07 (m, 9H), 1.32 (m, 1H), 1.72 (m, 1H), 2.25 (q, 2H), 2.45 (m, 1H), 2.64-2.74 (m, 2H), 3.91 (s, 1H), 7.25 (d, J=8.08 Hz, 2H), 7.34 (t, 1H), 7.45 (t, 2H), 7.56 (d, J=8.08 Hz, 2H), 7.64 (d, J=7.58 Hz, 2H), 7.88 (s, broad, 1H).

Following compounds are prepared using similar procedure as example 2-1 with appropriate reagents and conditions:

| Example # | Product | Reagent | Hydrolysis Condition | HPLC-RT (condition) | MS (M + 1) |
|---|---|---|---|---|---|
| Example 2-2 | 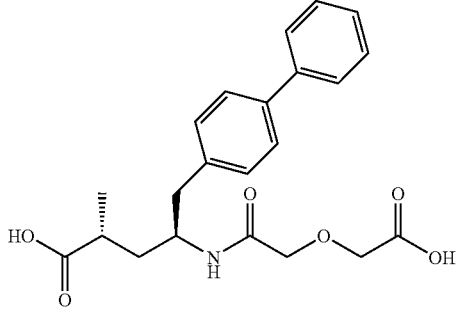<br>(2R,4S)-5-biphenyl-4-yl-4-(2-carboxymethoxy-acetylamino)-2-methyl-pentanoic acid | 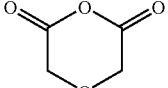 | Aq. NaOH, EtOH, RT | 0.91 min. (A) | 400.3 |
| Example 2-3 | 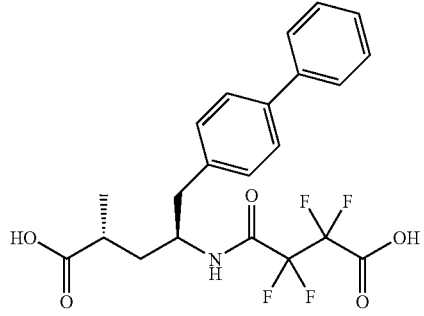<br>(2R,4S)-5-(biphenyl-4-yl)-4-(3-carboxy-2,2,3,3-tetrafluoropropanamido)-2-methylpentanoic acid | 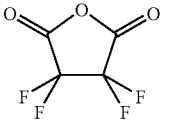 | Aq. NaOH, EtOH, RT | 1.06 min. (A) | 456.3 |
| Example 2-4 | 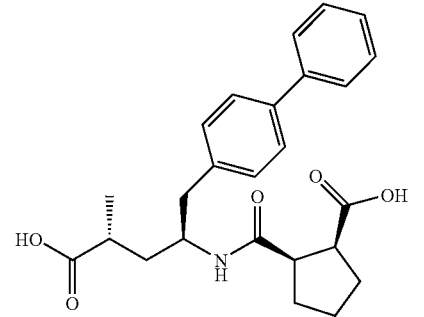<br>(1S,2R)-2-((1S,3R)-1-biphenyl-4-ylmethyl-3-carboxy-butylcarbamoyl)-cyclopentanecarboxylic acid | 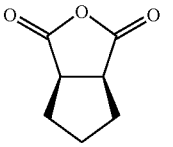 | Aq. NaOH, EtOH, RT | 1.09 min. (A) | 424.4 |

| Example # | Product | Reagent | Hydrolysis Condition | HPLC-RT (condition) | MS (M + 1) |
|---|---|---|---|---|---|
| Example 2-5 | (1R,2S)-2-((1S,3R)-1-biphenyl-4-ylmethyl-3-carboxy-butylcarbamoyl)-cyclopentanecarboxylic acid | | Aq. NaOH, EtOH, RT | 1.12 min. (A) | 424.4 |
| Example 2-6 | (1R,2S)-2-((1S,3R)-1-biphenyl-4-ylmethyl-3-carboxy-butylcarbamoyl)-cyclopropanecarboxylic acid | | Aq. NaOH, EtOH, 60° C. | 0.99 min. (A) | 396.3 |
| Example 2-7 | (1S,2R)-2-((1S,3R)-1-biphenyl-4-yl-methyl-3-carboxy-butylcarbamoyl)-cyclobutanecarboxylic acid | | Aq. NaOH, EtOH, 60° C. | 1.01 min. (A) | 410.3 |
| Example 2-8 | (1R,2S)-2-((1S,3R)-1-biphenyl-4-yl-methyl-3-carboxy-butylcarbamoyl)-cyclobutanecarboxylic acid | | Aq. NaOH, EtOH, 60° C. | 1.04 min. (A) | 410.3 |

| Example # | Product | Reagent | Hydrolysis Condition | HPLC-RT (condition) | MS (M + 1) |
|---|---|---|---|---|---|
| Example 2-9 | (2R,3S)-3-((1S,3R)-1-biphenyl-4-yl-methyl-3-carboxy-butylcarbamoyl)-oxirane-2-carboxylic acid | | Aq. NaOH, EtOH, 60° C. | 0.87 min. (A) | 398.3 |
| Example 2-10 | (2S,3R)-3-((1S,3R)-1-biphenyl-4-yl-methyl-3-carboxy-butylcarbamoyl)-oxirane-2-carboxylic acid | | Aq. NaOH, EtOH, 60° C. | 0.93 min. (A) | 398.3 |
| Example 2-11 | (1R*,2S*)-2-((1S,3R)-1-biphenyl-4-ylmethyl-3-carboxy-butylcarbamoyl)-cyclohexanecarboxylic acid | | Aq. NaOH, EtOH, RT | 1.25 min. (A) | 438.3 |

-continued

| Example # | Product | Reagent | Hydrolysis Condition | HPLC-RT (condition) | MS (M + 1) |
|---|---|---|---|---|---|
| Example 2-12 | 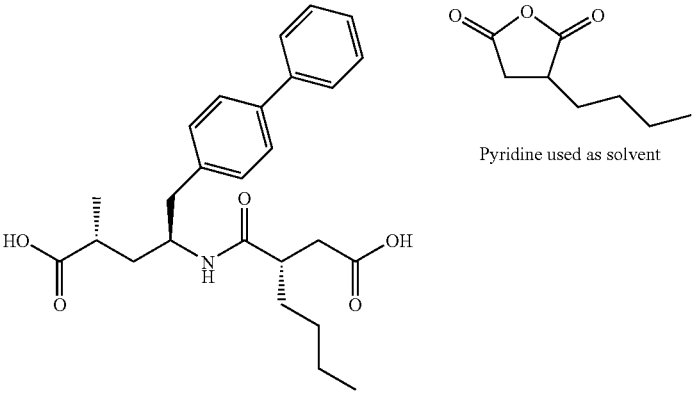<br>(S)-3-((1S,3R)-1-biphenyl-4-ylmethyl-3-carboxy-butylcarbamoyl)-heptanoic acid | 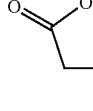<br>Pyridine used as solvent | Aq. NaOH, EtOH, RT | 1.28 min. (A) | 440.3 |
| Example 2-13 | 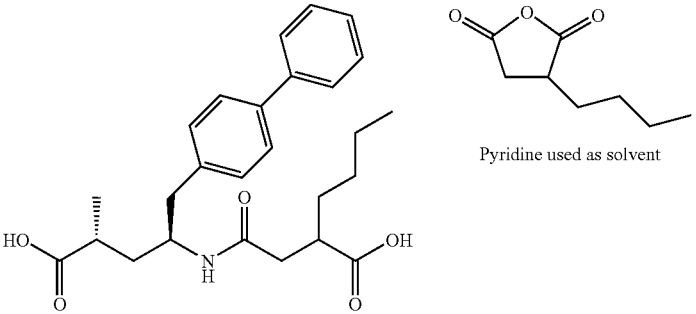<br>2-[((1S,3R)-1-biphenyl-4-ylmethyl-3-carboxy-butylcarbamoyl)-methyl]-hexanoic acid | 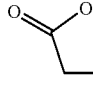<br>Pyridine used as solvent | Aq. NaOH, EtOH, RT | 1.21 min. (A) | 440.4 |
| Example 2-14 | 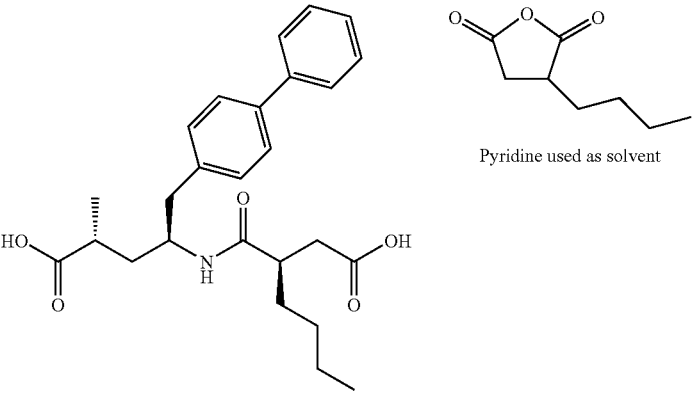<br>(R)-3-((2S,4R)-1-(biphenyl-4-yl)-4-carboxypentan-2-ylcarbamoyl)heptanoic acid | 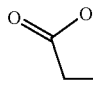<br>Pyridine used as solvent | Aq. NaOH, EtOH, RT | 1.24 min. (A) | 440.3 |

| Example # | Product | Reagent | Hydrolysis Condition | HPLC-RT (condition) | MS (M + 1) |
|---|---|---|---|---|---|
| Example 2-15 | 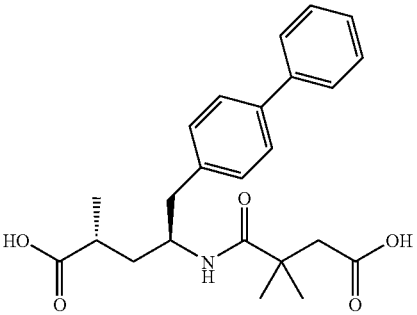<br>(2R,4S)-5-(biphenyl-4-yl)-4-(3-carboxy-2,2-dimethylpropanamido)-2-methylpentanoic acid | 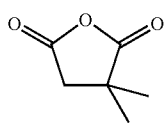<br>Pyridine used as solvent | Aq. NaOH, EtOH, RT | 1.13 min. (A) | 412.3 |
| Example 2-16 | 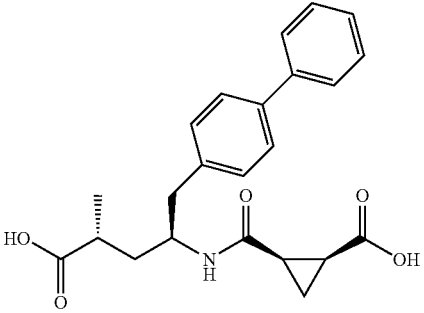<br>(1S,2R)-2-((1S,3R)-1-biphenyl-4-ylmethyl-3-carboxy-butylcarbamoyl)-cyclopropanecarboxylic acid | 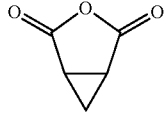<br>Pyridine used as solvent | Aq. NaOH, EtOH, 60° C. | 0.99 min. (A) | 396.3 |

EXAMPLE 2-2

1H NMR (400 MHz, MeCN-d3) δ ppm 1.11 (d, J=6.95 Hz, 3H), 1.56 (m, 1H), 1.88 (m, 1H), 2.51 (m, 1H), 2.78-2.90 (m, 2H), 4.20 (m, 1H), 7.09 (d, J=8.97 Hz, 1H), 7.29 (d, J=8.08 Hz, 2H), 7.35 (t, 1H), 7.45 (t, 2H), 7.57 (d, J=8.08 Hz, 2H), 7.6 (d, J=7.58 Hz, 2H).

EXAMPLE 2-3

1H NMR (400 MHz, MeOD-d4) δ ppm 1.16 (d, J=7.20 Hz, 3H), 1.62 (m, 1H), 1.97 (m, 1H), 2.52 (m, 1H), 2.87 (m, 2H), 4.25 (m, 1H), 7.32 (m, 3H), 7.43 (t, 1H), 7.54 (d, J=8.21 Hz, 2H), 7.59 (d, J=7.83 Hz, 1H), 7.60 (d, J=8.34 Hz, 1H), 8.99 (d, J=8.58 Hz, 1H).

EXAMPLE 2-4

1H NMR (400 MHz, MeCN-d3) δ ppm 1.07 (d, J=6.82 Hz, 3H), 1.47 (m, 1H), 1.61 (m, 2H), 1.73-1.95 (m, 4H), 2.45 (m, 1H), 2.73-2.96 (m, 5H), 4.0.6 (m, 1H), 6.64 (d, J=8.72 Hz, 1H), 7.29 (d, J=8.08 Hz, 2H), 7.35 (t, 1H), 7.45 (t, 2H), 7.57 (d, J=8.21 Hz, 2H), 7.64 (d, J=7.33 Hz, 2H).

EXAMPLE 2-5

1H NMR (400 MHz, MeCN-d3) δ ppm 1.09 (d, J=6.69 Hz, 3H), 1.37 (m, 1H), 1.46 (m, 2H), 1.61 (m, 2H), 1.73-1.86 (m, 4H), 2.51 (m, 1H), 2.72 (m, 1H), 2.84-2.96 (m, 3H), 4.0.6 (m, 1H), 6.77 (d, J=8.72 Hz, 1H), 7.30 (d, J=8.08 Hz, 2H), 7.35 (t, 1H), 7.45 (t, 2H), 7.56 (d, J=7.96 Hz, 2H), 7.62 (d, J=7.71 Hz, 2H).

EXAMPLE 2-6

1H NMR (400 MHz, DMSO-d6) δ ppm 1.05 (d, J=6.95 Hz, 3H), 1.10 (m, 1H), 1.27 (m, 1H), 1.38 (m, 1H), 1.77 (m, 1H), 1.85-1.96 (m, 2H), 2.43 (m, 1H), 2.67-2.77 (m, 2H), 3.94 (m, 1H), 7.27 (d, J=8.21 Hz, 2H), 7.34 (t, 1H), 7.45 (1, 2H), 7.58 (d, J=8.21 Hz, 2H), 7.65 (d, J=7.20 Hz, 2H), 8.18 (d, J=8.34 Hz, 1H).

EXAMPLE 2-7

1H NMR (400 MHz, DMSO-d6) δ ppm 1.01 (d, J=7.20 Hz, 3H), 1.30 (m, 1H), 1.70 (m, 1H), 2.38-2.44 (m, 2H), 1.93-2.05 (m, 3H), 2.31-2.42 (m, 2H), 2.59 (m, 1H), 2.84 (m, 1H), 3.18-3.30 (m, 2H), 3.92 (m, 1H), 7.28 (d, J=8.21 Hz, 2H), 7.34 (t, 1H), 7.45 (t, 2H), 7.58 (d, J=8.21 Hz, 2H), 7.66 (d, J=7.20 Hz, 3H).

EXAMPLE 2-8

1H NMR (400 MHz, DMSO-d6) δ ppm 1.06 (d, J=6.95 Hz, 3H), 1.36 (m, 1H), 1.76 (m, 2H), 1.94 (m, 2H), 2.25 (m, 1H), 2.45 (m, 1H), 2.71 (m, 2H), 3.18 (m, 2H), 3.95 (m, 1H), 7.25 (d, J=8.34 Hz, 2H), 7.34 (t, 1H), 7.44 (t, 2H), 7.56 (d, J=8.21 Hz, 2H), 7.64 (d, J=7.07 Hz, 3H).

EXAMPLE 2-9

1H NMR (400 MHz, DMSO-d6) δ ppm 1.02 (d, J=7.20 Hz, 3H), 1.45 (m, 1H), 1.70 (m, 1H), 2.40 (m, 1H), 2.59 (m, 1H), 2.76 (m, 1H), 3.69 (d, J=5.05 Hz, 1H), 3.75 (d, J=5.05 Hz, 1H), 3.98 (m, 1H), 7.27 (d, J=8.08 Hz, 2H), 7.34 (t, 1H), 7.45 (1, 2H), 7.59 (d, J=8.21 Hz, 2H), 7.66 (d, J=7.20 Hz, 2H), 7.95 (d, J=8.59 Hz, 1H).

EXAMPLE 2-10

1H NMR (400 MHz, DMSO-d6) δ ppm 1.04 (d, J=7.07 Hz, 3H), 1.37 (m, 1H), 1.76 (m, 1H), 2.43 (m, 1H), 2.66-2.81 (m, 2H), 3.59 (d, J=5.18 Hz, 1H), 3.72 (d, J=4.93 Hz, 1H), 4.02 (m, 1H), 7.26 (d, J=8.21 Hz, 2H), 7.34 (t, 1H), 7.45 (t, 2H), 7.58 (d, J=8.21 Hz, 2H), 7.66 (d, J=7.20 Hz, 2H), 7.83 (d, J=8.84 Hz, 1H).

EXAMPLE 2-11

1H NMR (400 MHz, DMSO-d6) δ ppm 1.06 (d, J=7.07 Hz, 3H), 1.15 (m, 1H), 1.30-2.08 (m, 11H), 2.40 (m, 1H), 2.66 (m, 2H), 2.76 (m, 1H), 3.99 (m, 1H), 7.26 (t, 2H), 7.34 (t, 1H), 7.45 (t, 2H), 7.53-7.66 (m, 4H).

EXAMPLE 2-12

1H NMR (400 MHz, MeOD-d4) δ ppm 0.88 (t, J=7.07 Hz, 3H), 1.15 (d, J=7.07 Hz, 3H), 1.43 (m, 7H), 1.90 (m, 1H), 2.24 (dd, J=6.69 Hz, 6.57 Hz, 1H), 2.39 (dd, J=7.58 Hz, 7.58 Hz, 1H), 2.57 (m, 2H), 2.81 (m, 2H), 4.15 (m, 1H), 7.30 (d, J=8.21 Hz, 2H), 7.41 (m, 2H), 7.51 (m, 2H), 7.57 (m, 2H).

EXAMPLE 2-13

1H NMR (400 MHz, MeOD-d4) δ ppm 0.85 (t, J=7.07 Hz, 3H), 1.16 (d, J=7.07 Hz, 3H), 1.43 (m, 7H), 1.92 (m, 1H), 2.21 (dd, J=7.71 Hz, 7.71 Hz, 1H), 2.47 (m, 2H), 2.59 (m, 1H), 2.81 (m, 2H), 4.13 (m, 1H), 7.30 (m, 3H), 7.41 (m, 2H), 7.52 (m, 2H), 7.59 (m, 2H).

EXAMPLE 2-14

1H NMR (400 MHz, MeOD-d4) δ ppm 0.73 (t, J=7.33 Hz, 3H), 0.97 (m, 2H), 1.13 (m, 2H), 1.16 (d, J=7.07 Hz, 3H), 1.29 (m, 1H), 1.39 (m, 1H), 1.50 (m, 1H), 1.94 (m, 1H), 2.24 (m, 1H), 2.51 (m, 2H), 2.61 (m, 1H), 2.74 (dd, J=9.09 Hz, 8.97 Hz, 1H), 2.88 (dd, J=5.18 Hz, 4.67 Hz, 1H), 4.25 (m, 1H), 7.30 (m, 3H), 7.41 (m, 2H), 7.52 (d, J=8.34 Hz, 2H), 7.57 (dd, J=0.63 Hz, 1.26 hz, 2H).

EXAMPLE 2-15

1H NMR (400 MHz, DMSO-d6) δ ppm 1.02 (m, 9H), 1.31 (m, 1H), 1.72 (m, 1H), 2.20 (m, 2H), 2.45 (m, 1H), 2.68 (m, 2H), 3.91 (m, 1H), 7.23 (d, J=8.08 Hz, 2H), 7.33 (d, J=7.20 Hz, 1H), 7.44 (d, J=7.83 Hz, 2H), 7.55 (d, J=8.08 Hz, 2H), 7.63 (dd, J=0.76 Hz, 1.14 Hz, 2H), 7.88 (s, 1H).

EXAMPLE 2-16

1H NMR (400 MHz, DMSO-d6) δ ppm 1.05 (d, J=7.06 Hz, 3H), 1.10 (m, 1H), 1.27 (m, 1H), 1.39 (m, 1H), 1.78 (m, 1H), 1.86-1.95 (m, 2H), 2.44 (m, 1H), 2.69-2.77 (m, 2H), 3.95 (m, 1H), 7.28 (d, J=8.25 Hz, 2H), 7.35 (t, 1H), 7.46 (t, 2H), 7.59 (d, J=8.25 Hz, 2H), 7.66 (d, J=7.15 Hz, 2H), 8.19 (d, J=8.25 Hz, 1H).

EXAMPLE 3-1

Synthesis of (2R,4S)-5-biphenyl-4-yl-2-methyl-4-(2-thiophen-2-yl-acetylamino)-pentanoic acid

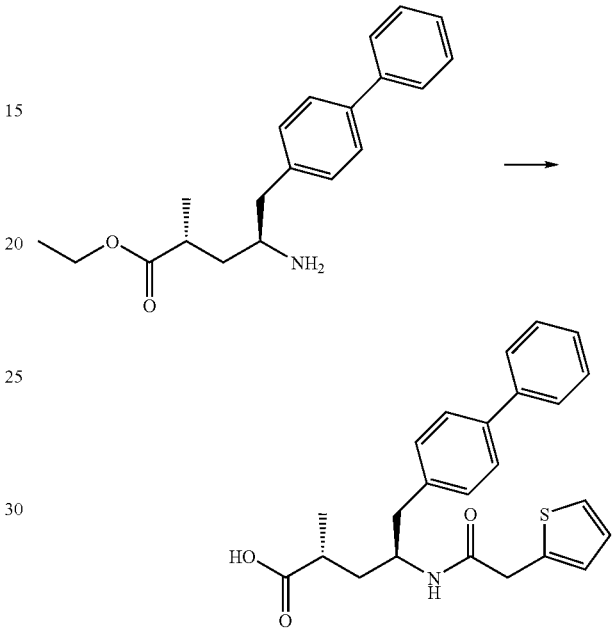

To a solution of thiophen-2-yl-acetic acid (0.144 mmol) in DMF (5 mL) is added HATU (0.216 mmol). After stirring the mixture at room temperature for 10 minutes, (2R,4S)-4-amino-5-biphenyl-4-yl-2-methyl-pentanoic acid ethyl ester hydrochloride (0.144 mmol) and triethylamine (0.359 mmol) is added and the mixture is stirred at room temperature for 18 hours. The mixture is poured into ethyl acetate and the mixture is washed with aqueous 1M HCl and brine. The organic phase is dried over magnesium sulfate and the solvent is removed under reduced pressure to give (2R,4S)-5-biphenyl-4-yl-2-methyl-4-(2-thiophen-2-yl-acetylamino)-pentanoic acid ethyl ester which is used directly in the subsequent hydrolysis reaction.

Next, to a solution of (2R,4S)-5-biphenyl-4-yl-2-methyl-4-(2-thiophen-2-yl-acetylamino)-pentanoic acid ethyl ester (0.287 mmol) in ethanol (10 mL) is added aqueous 1M NaOH (2 mL, 6.97 mmol) and the mixture is stirred at room temperature for 18 hours. The mixture is poured into ethyl acetate and is washed with aqueous 1M HCl, the organic phase is dried over magnesium sulfate and the solvent is removed under reduced pressure. The residue is purified by preparative HPLC using a gradient of MeCN/water (0.1% TFA). The proper fractions are lyophilized to furnish (2R,4S)-5-biphenyl-4-yl-2-methyl-4-(2-thiophen-2-yl-acetylamino)-pentanoic acid. HPLC Retention time 1.23 minutes (condition A); MS 408.3 (M+1); 1H NMR (400 MHz, MeOD-d4) δ ppm 1.16 (d, J=7.07 Hz, 3H), 1.50 (m, 1H), 1.96 (m, 1H), 2.52 (m, 1H), 2.72 (dd, J=7.71 Hz, 7.58 Hz, 1H), 2.84 (dd, J=5.81 Hz, 5.66 Hz, 1H), 3.64 (d, J=1.26 Hz, 2H), 4.20 (m, 1H), 6.82 (m, 1H), 6.89 (m, 1H), 7.21 (m, 3H), 7.32 (m, 1H), 7.42 (m, 2H), 7.46 (m, 2H), 7.57 (m, 2H), 7.95 (d, J=8.59 Hz, 1H).

Following compounds are prepared using similar procedure as example 3-1 with appropriate reagents and conditions:

| Example # | Product | Reagent | Hydrolysis Condition | HPLC-RT (condition) | MS (M + 1) |
|---|---|---|---|---|---|
| Example 3-2 | 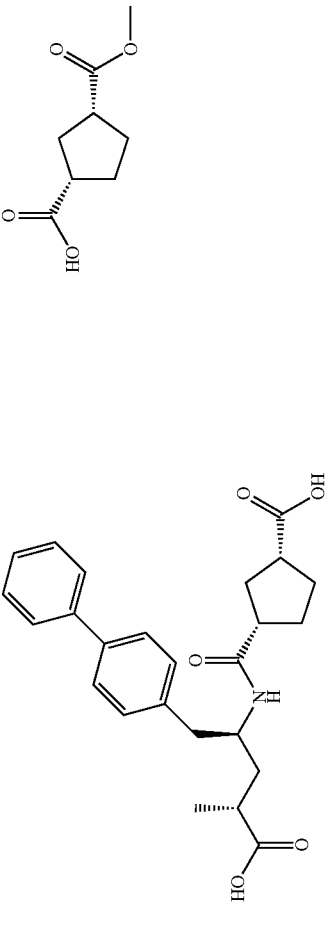 (2R,4S)-5-biphenyl-4-yl-4-(3-1H-indol-3-yl-propionylamino)-2-methyl-pentanoic acid | 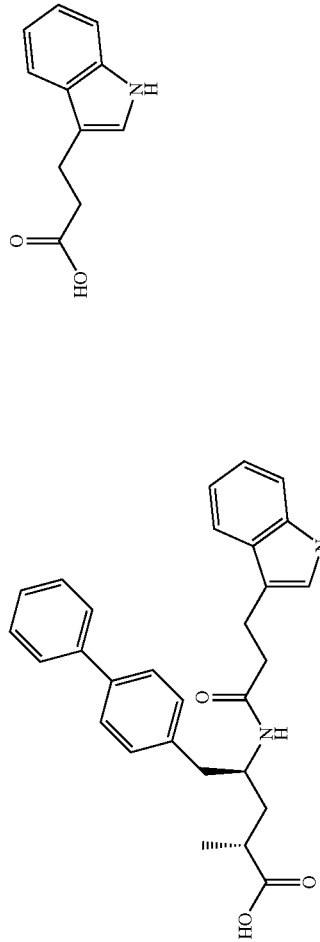 | Aq. NaOH, EtOH, RT | 1.31 min. (A) | 455.4 |
| Example 3-3 | 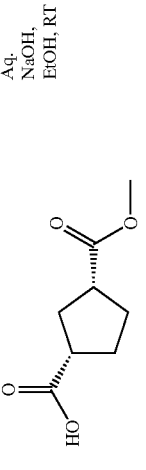 (1R,3S)-3-(((1S,3R)-1-biphenyl-4-ylmethyl-3-carboxy-butylcarbamoyl)-cyclopentanecarboxylic acid | 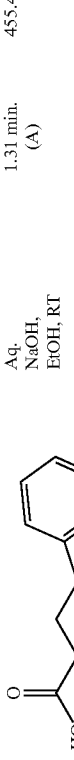 | Aq. NaOH, EtOH, RT | 1.09 min. (A) | 424.4 |

-continued
| Example # | Product | Reagent | Hydrolysis Condition | HPLC-RT (condition) | MS (M + 1) |
|---|---|---|---|---|---|
| Example 3-4 | 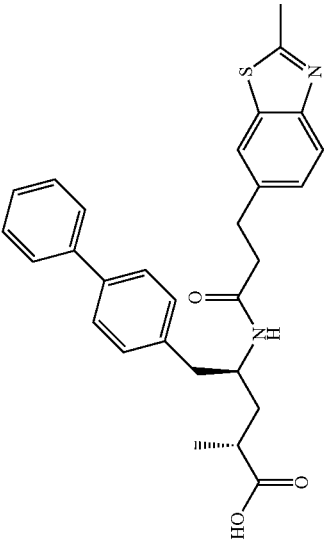<br>(2R,4S)-5-biphenyl-4-yl-2-methyl-4-(2-pyridin-4-yl-acetylamino)-pentanoic acid | 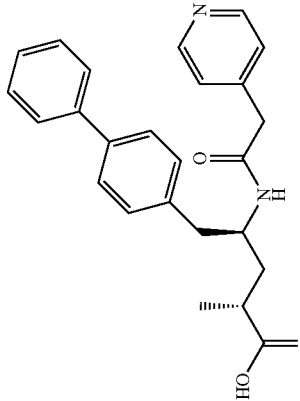 | Aq. NaOH, EtOH, RT | 1.08 min. (A) | 403.4 |
| Example 3-5 | 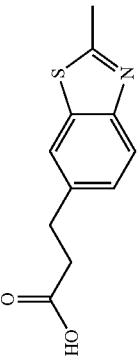<br>(2R,4S)-5-biphenyl-4-yl-2-methyl-4-[3-(2-methyl-benzothiazol-6-yl)-propionylamino]-pentanoic acid |  | Aq. NaOH, EtOH, RT | 1.25 min. (A) | 487.3 |

-continued
| Example # | Product | Reagent | Hydrolysis Condition | HPLC-RT (condition) | MS (M + 1) |
|---|---|---|---|---|---|
| Example 3-6 | 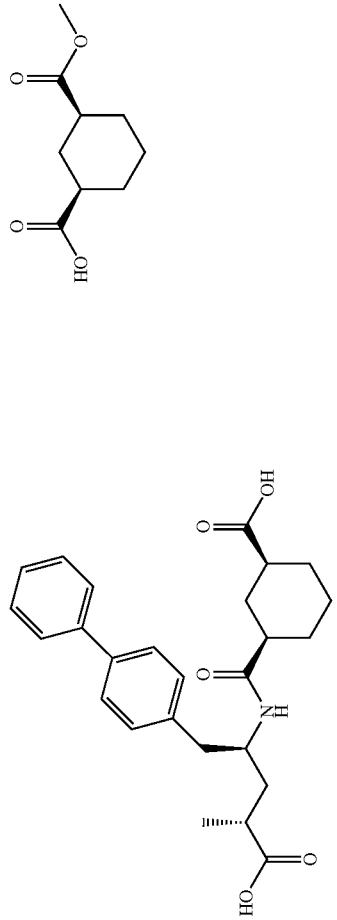<br>(2R,4S)-5-biphenyl-4-yl-2-methyl-4-[4-(2-methyl-benzothiazol-6-yl)-butyrylamino]-pentanoic acid | 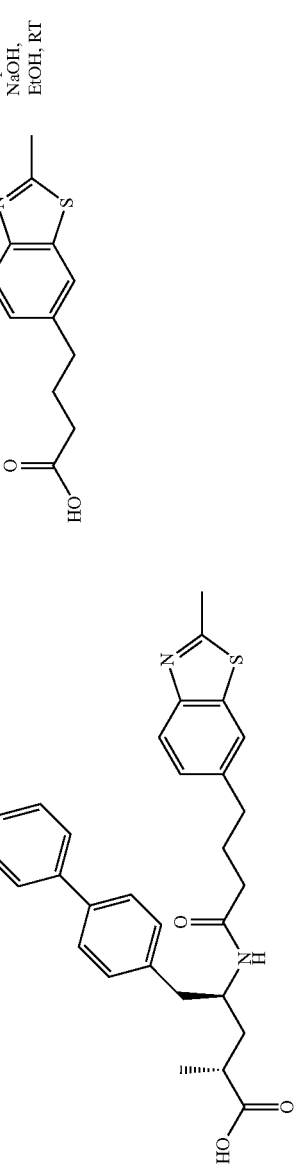 | Aq. NaOH, EtOH, RT | 1.26 min. (A) | 501.3 |
| Example 3-7 | <br>(1S,3R)-3-(((1S,3R)-1-biphenyl-4-ylmethyl-3-carboxy-butylcarbamoyl)-cyclohexanecarboxylic acid |  | Aq. NaOH, EtOH, RT | 1.08 min. (A) | 438.4 |

-continued
| Example # | Product | Reagent | Hydrolysis Condition | HPLC-RT (condition) | MS (M + 1) |
|---|---|---|---|---|---|
| Example 3-8 | 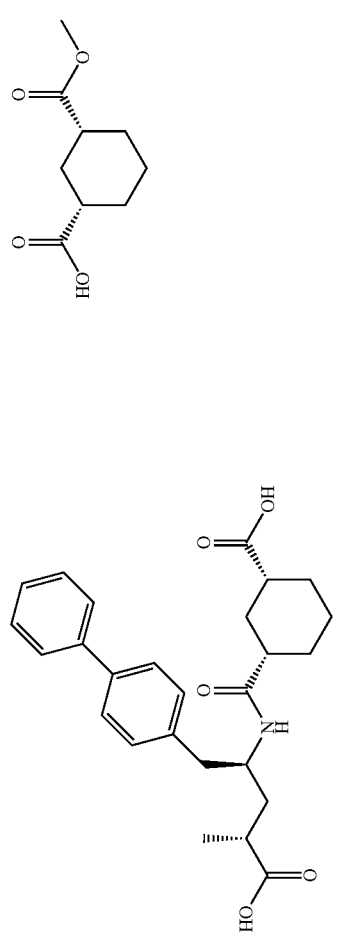<br>(1R,3S)-3-((1S,3R)-1-biphenyl-4-ylmethyl-3-carboxy-butylcarbamoyl)-cyclohexanecarboxylic acid | 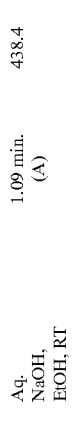 | Aq. NaOH, EtOH, RT | 1.09 min. (A) | 438.4 |
| Example 3-9 | 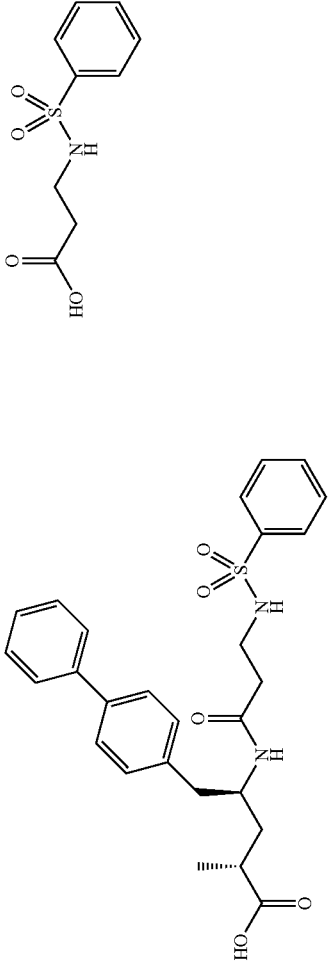<br>(2R,4S)-4-(3-benzenesulfonylamino-propionylamino)-5-biphenyl-4-yl-2-methyl-pentanoic acid | 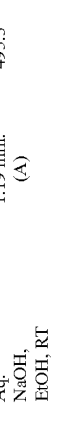 | Aq. NaOH, EtOH, RT | 1.19 min. (A) | 495.3 |

| Example # | Product | Reagent | Hydrolysis Condition | HPLC-RT (condition) | MS (M + 1) |
|---|---|---|---|---|---|
| Example 3-10 | 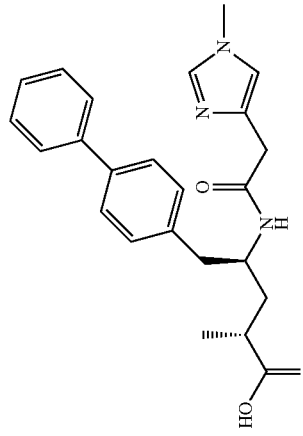 (2R,4S)-5-biphenyl-4-yl-4-[2-(3,5-difluoro-phenyl)-acetylamino]-2-methyl-pentanoic acid | 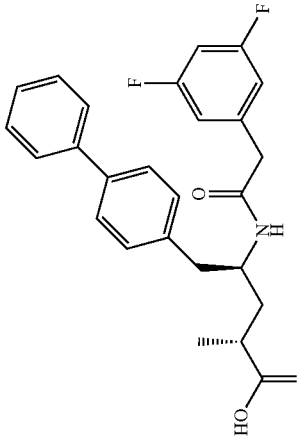 | Aq. NaOH, EtOH, RT | 1.21 min. (A) | 438.4 |
| Example 3-11 | 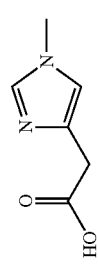 (2R,4S)-5-biphenyl-4-yl-2-methyl-4-[2-(1-methyl-1H-imidazol-4-yl)-acetylamino]-pentanoic acid | 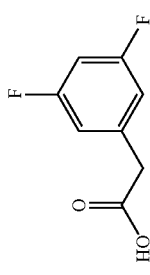 | Aq. NaOH, EtOH, RT | 0.99 min. (A) | 406.4 |

| Example # | Product | Reagent | Hydrolysis Condition | HPLC-RT (condition) | MS (M + 1) |
|---|---|---|---|---|---|
| Example 3-12 | 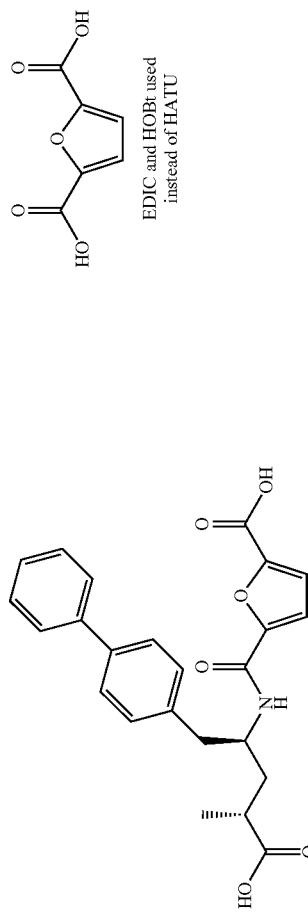<br>(2R,4S)-5-biphenyl-4-yl-4-[2-(5-ethyl-[1,3,4]thiadiazol-2-yl)-acetylamino]-2-methyl-pentanoic acid | 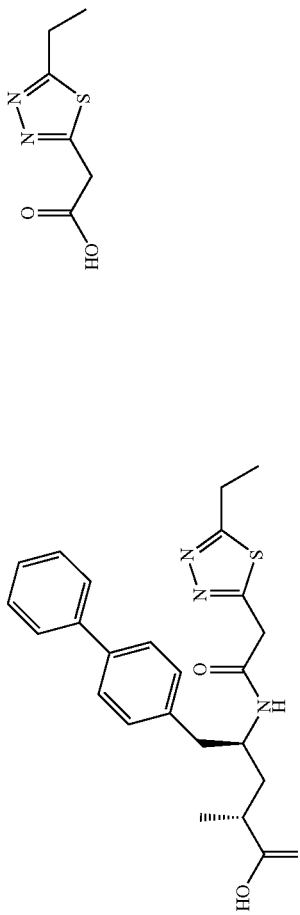 | Aq. NaOH, EtOH, RT | 1.15 min. (A) | 438.3 |
| Example 3-13 | <br>5-((1S,3R)-1-biphenyl-4-ylmethyl-3-carboxy-butylcarbamoyl)-furan-2-carboxylic acid | <br>EDIC and HOBt used instead of HATU | Aq. NaOH, EtOH, 60° C. | 1.18 min. (A) | 422.3 |

-continued

| Example # | Product | Reagent | Hydrolysis Condition | HPLC-RT (condition) | MS (M + 1) |
|---|---|---|---|---|---|
| Example 3-14 | 5-((1S,3R)-1-biphenyl-4-ylmethyl-3-carboxy-butylcarbamoyl)-thiophene-2-carboxylic acid | EDIC and HOBt used instead of HATU | Aq. NaOH, EtOH, 60° C. | 1.17 min. (A) | 438.3 |
| Example 3-15 | (2R,4S)-5-biphenyl-4-yl-4-[4-(4-methoxy-phenyl)-butyrylamino]-2-methyl-pentanoic acid | EDIC and HOBt used instead of HATU | Aq. NaOH, EtOH, 60° C. | 1.44 min. (A) | 460.3 |

-continued
| Example # | Product | Reagent | Hydrolysis Condition | HPLC-RT (condition) | MS (M + 1) |
|---|---|---|---|---|---|
| Example 3-16 | 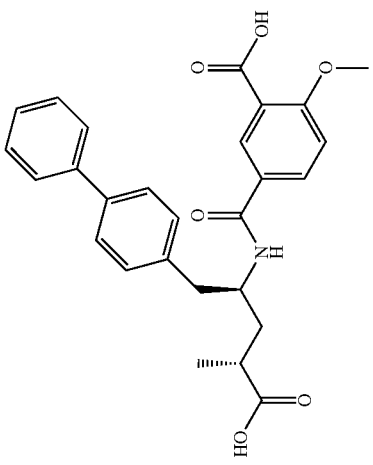<br>(2R,4S)-4-[(1-benzyl-6-oxo-1,6-dihydro-pyridine-3-carbonyl)-amino]-5-biphenyl-4-yl-2-methyl-pentanoic acid | 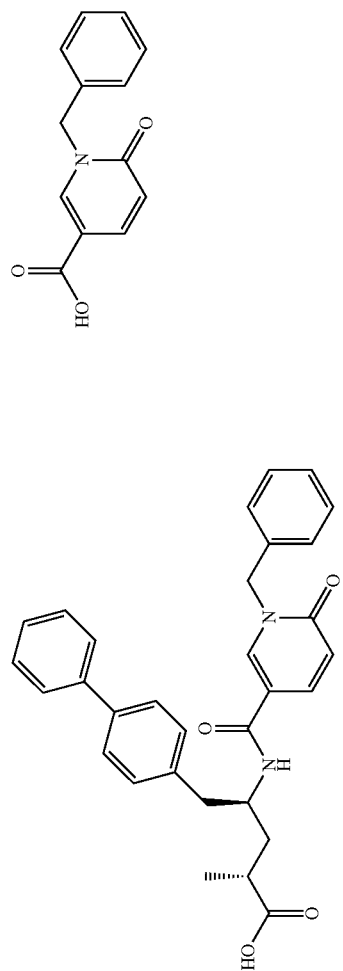 | Aq. NaOH, EtOH, RT | 1.28 min. (A) | 495.3 |
| Example 3-17 | 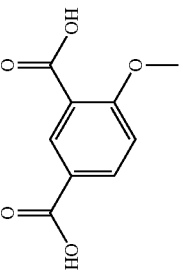<br>N-((1S,3R)-1-biphenyl-4-ylmethyl-3-carboxy-butyl)-6-methoxy-isophthalamic acid | 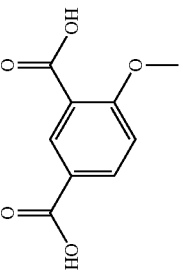<br>EDIC and HOBt used instead of HATU | Aq. NaOH, EtOH, 60° C. | 1.31 min. (A) | 462.3 |

| Example # | Product | Reagent | Hydrolysis Condition | HPLC-RT (condition) | MS (M + 1) |
|---|---|---|---|---|---|
| Example 3-18 | 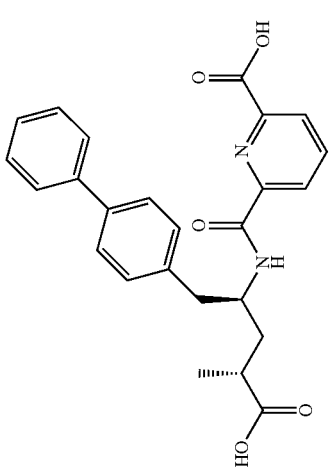<br>N-((1S,3R)-1-biphenyl-4-ylmethyl-3-carboxy-butyl)-4-methoxy-isophthalamic acid | 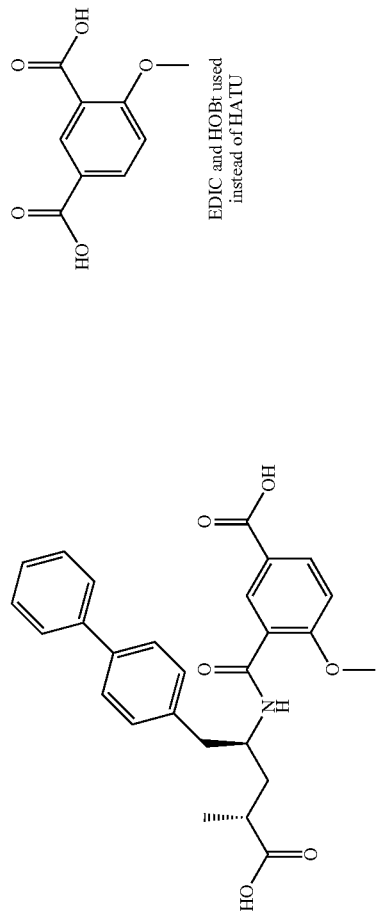<br>EDIC and HOBt used instead of HATU | Aq. NaOH, EtOH, 60° C. | 1.24 min. (A) | 462.3 |
| Example 3-19 | 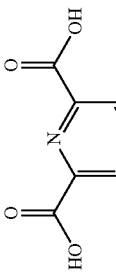<br>6-((1S,3R)-1-biphenyl-4-ylmethyl-3-carboxy-butylcarbamoyl)-pyridine-2-carboxylic acid | 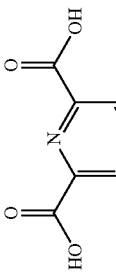<br>EDIC and HOBt used instead of HATU | Aq. NaOH, EtOH, 60° C. | 0.95 min. (A) | 433.3 |

| Example # | Product | Reagent | Hydrolysis Condition | HPLC-RT (condition) | MS (M + 1) |
|---|---|---|---|---|---|
| Example 3-20 | 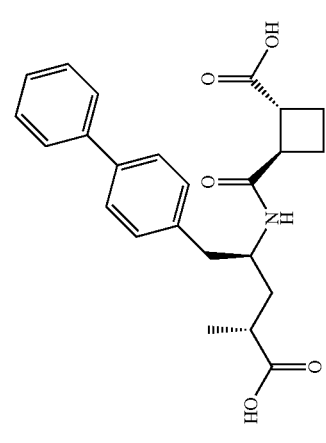 N-((1S,3R)-1-biphenyl-4-ylmethyl-3-carboxy-butyl)-5-chloro-isophthalamic acid | 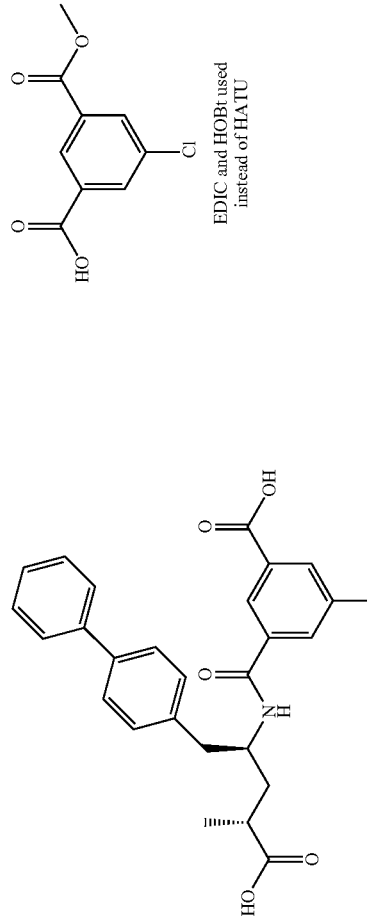 EDIC and HOBt used instead of HATU | Aq. NaOH, EtOH, 60° C. | 1.02 min. (A) | 466.2 |
| Example 3-21 | 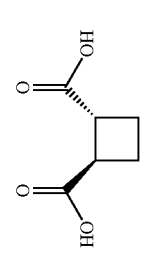 (1R*,2R*)-2-((1S,3R)-1-biphenyl-4-ylmethyl-3-carboxy-butylcarbamoyl)-cyclobutanecarboxylic acid | 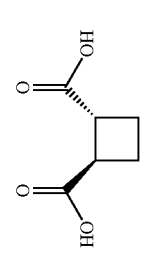 EDIC and HOBt used instead of HATU | Aq. NaOH, EtOH, 60° C. | 0.97 min. (A) | 410.3 |

-continued
| Example # | Product | Reagent | Hydrolysis Condition | HPLC-RT (condition) | MS (M + 1) |
|---|---|---|---|---|---|
| Example 3-22 | 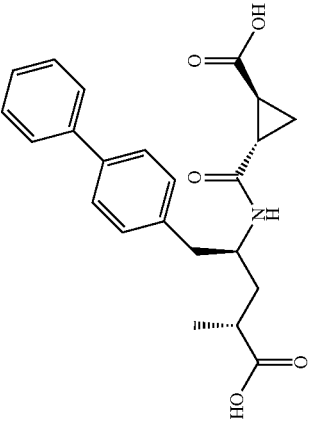<br>(1R,2R)-2-((1S,3R)-1-biphenyl-4-yl-methyl-3-carboxy-butylcarbamoyl)-cyclopropanecarboxylic acid | 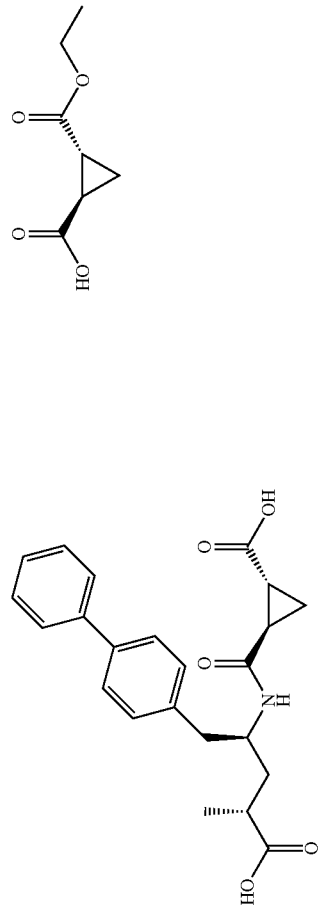 | Aq. NaOH, EtOH, RT | 1.01 min. (A) | 396.3 |
| Example 3-23 | <br>(1S,2S)-2-((1S,3R)-1-biphenyl-4-yl-methyl-3-carboxy-butylcarbamoyl)-cyclopropanecarboxylic acid |  | Aq. NaOH, EtOH, RT | 1.04 min. (A) | 396.3 |

| Example # | Product | Reagent | Hydrolysis Condition | HPLC-RT (condition) | MS (M + 1) |
|---|---|---|---|---|---|
| Example 3-24 | 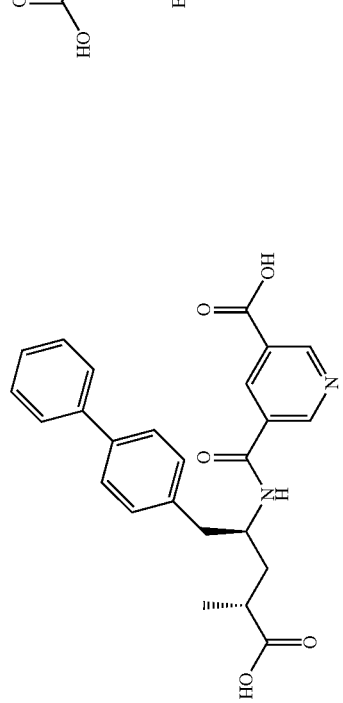<br>5-((1S,3R)-1-biphenyl-4-ylmethyl-3-carboxy-butylcarbamoyl)-nicotinic acid | 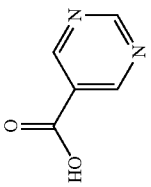<br>EDIC and HOBt used instead of HATU | Aq. NaOH, EtOH, 60° C. | 1.04 min. (A) | 433.2 |
| Example 3-25 | 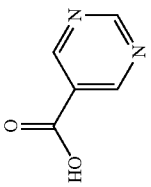<br>(2R,4S)-5-(biphenyl-4-yl)-2-methyl-4-(pyrimidine-5-carboxamido)pentanoic acid | 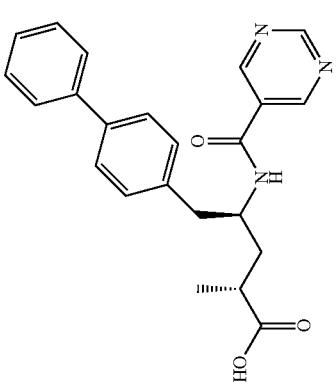 | Aq. NaOH, EtOH, RT | 1.40 min. (A) | 390.3 |

-continued
| Example # | Product | Reagent | Hydrolysis Condition | HPLC-RT (condition) | MS (M + 1) |
|---|---|---|---|---|---|
| Example 3-26 | 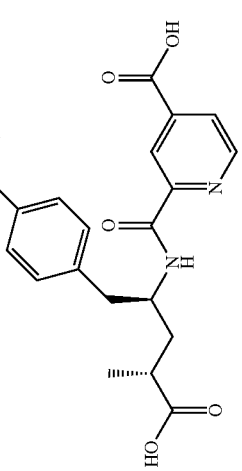 4-((1S,3R)-1-biphenyl-4-ylmethyl-3-carboxy-butylcarbamoyl)-pyridine-2-carboxylic acid | 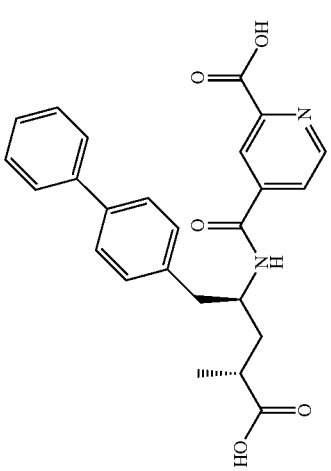 EDIC and HOBt used instead of HATU | Aq. NaOH, EtOH, 50° C. | 1.07 min. (A) | 433.3 |
| Example 3-27 | 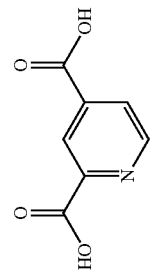 2-((1S,3R)-1-biphenyl-4-ylmethyl-3-carboxy-butylcarbamoyl)-isonicotinic acid | 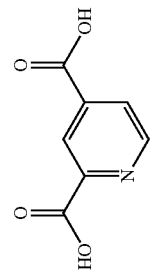 EDIC and HOBt used instead of HATU | Aq. NaOH, EtOH, 50° C. | 1.14 min. (A) | 433.3 |

-continued

| Example # | Product | Reagent | Hydrolysis Condition | HPLC-RT (condition) | MS (M + 1) |
|---|---|---|---|---|---|
| Example 3-28 | 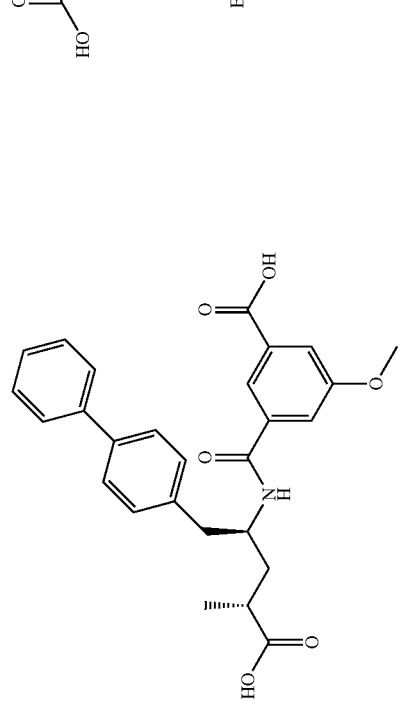<br>N-((1S,3R)-1-biphenyl-4-ylmethyl-3-carboxy-butyl)-5-methoxy-isophthalamic acid | 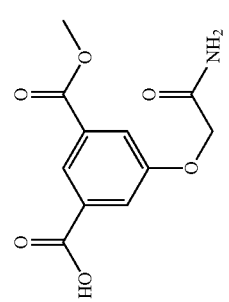<br>EDIC and HOBt used instead of HATU | Aq. NaOH, EtOH, 50° C. | 1.00 min. (A) | 462.0 |
| Example 3-29 | 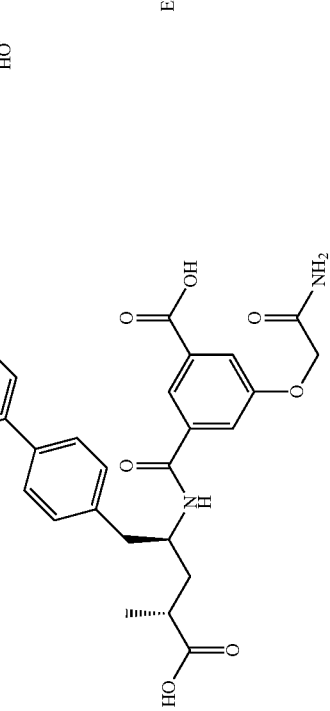<br>N-((1S,3R)-1-biphenyl-4-ylmethyl-3-carboxy-butyl)-5-carbamoylmethoxy-isophthalamic acid | 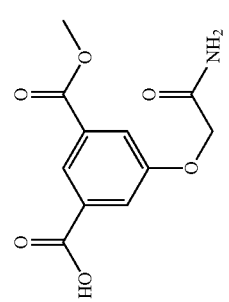<br>EDIC and HOBt used instead of HATU | Aq. NaOH, EtOH, 50° C. | 0.98 min. (A) | 505.2 |

-continued
| Example # | Product | Reagent | Hydrolysis Condition | HPLC-RT (condition) | MS (M + 1) |
|---|---|---|---|---|---|
| Example 3-30 | 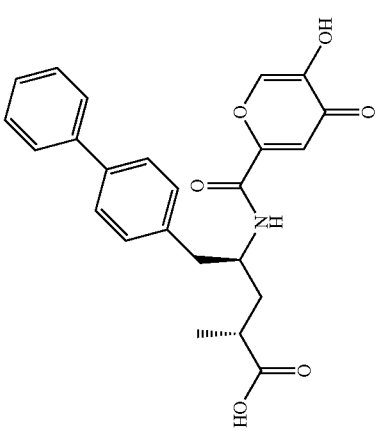 N-((1S,3R)-1-biphenyl-4-ylmethyl-3-carboxy-butyl)-5-carboxymethoxy-isophthalamic acid | 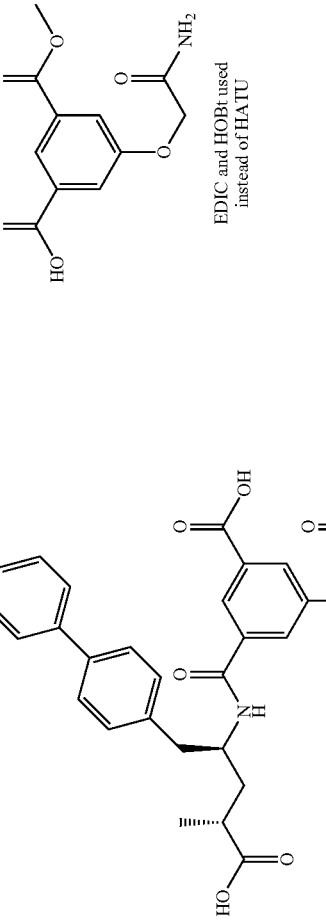 EDIC and HOBt used instead of HATU | Aq. NaOH, EtOH, 50° C. | 0.99 min. (A) | 506.2 |
| Example 3-31 | 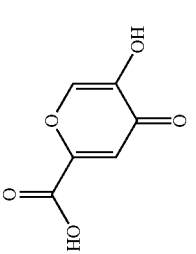 (2R,4S)-5-biphenyl-4-yl-4-[(5-hydroxy-4-oxo-4H-pyran-2-carbonyl)-amino]-2-methyl-pentanoic acid | 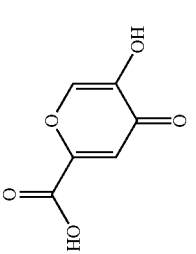 EDIC and HOBt used instead of HATU | Aq. NaOH, EtOH, 50° C. | 1.32 min. (A) | 422.2 |

-continued
| Example # | Product | Reagent | Hydrolysis Condition | HPLC-RT (condition) | MS (M + 1) |
|---|---|---|---|---|---|
| Example 3-32 | 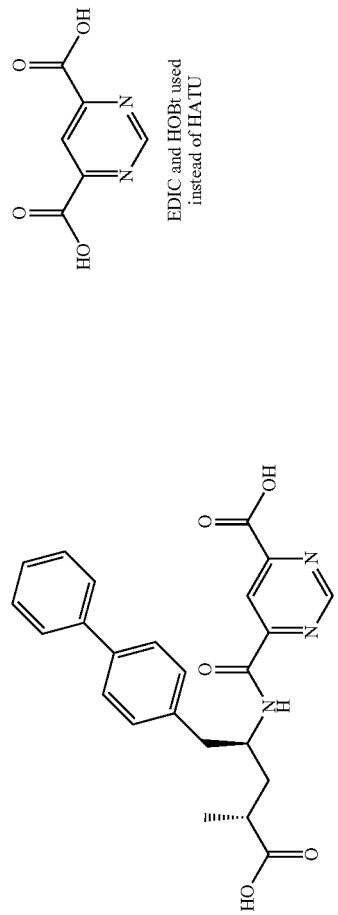<br>6-((2S,4R)-1-(biphenyl-4-yl)-4-carboxypentan-2-yl)carbamoyl)pyrimidine-4-carboxylic acid | 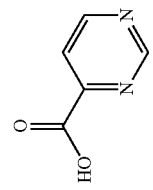<br>EDIC and HOBt used instead of HATU | Aq. NaOH, EtOH, RT | 1.24 min. (A) | 434.2 |
| Example 3-33 | 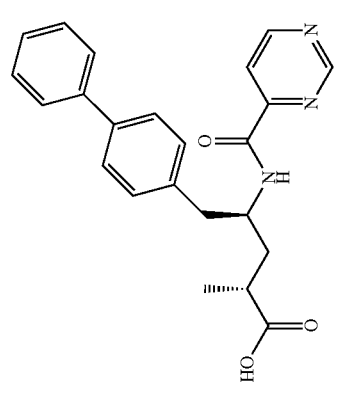<br>(2R,4S)-5-(biphenyl-4-yl)-2-methyl-4-(pyrimidine-4-carboxamido)pentanoic acid | 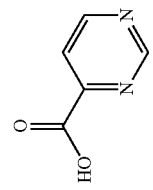<br>EDIC and HOBt used instead of HATU | Aq. NaOH, EtOH, RT | 1.41 min. (A) | 390.2 |

-continued
| Example # | Product | Reagent | Hydrolysis Condition | HPLC-RT (condition) | MS (M + 1) |
|---|---|---|---|---|---|
| Example 3-34 | 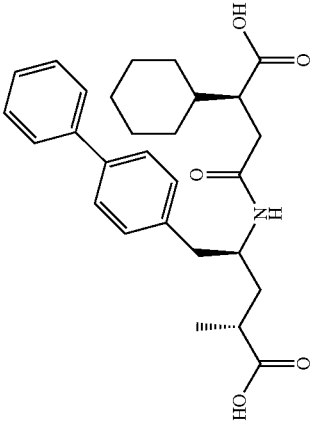<br>6-((1S,3R)-1-biphenyl-4-ylmethyl-3-carboxy-butylcarbamoyl)-nicotinic acid | 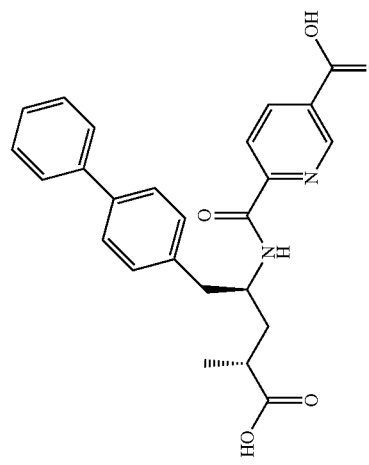<br>EDIC and HOBt used instead of HATU | Aq. NaOH, EtOH, 50° C. | 1.24 min. (A) | 433.2 |
| Example 3-35 | 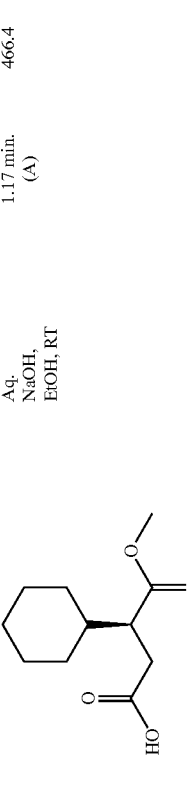<br>(2R,4S)-5-biphenyl-4-yl-4-((S)-3-carboxy-3-cyclohexyl-propionylamino)-2-methyl-pentanoic acid | 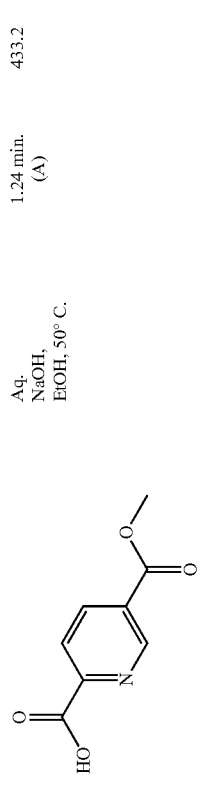 | Aq. NaOH, EtOH, RT | 1.17 min. (A) | 466.4 |

| Example # | Product | Reagent | Hydrolysis Condition | HPLC-RT (condition) | MS (M + 1) |
|---|---|---|---|---|---|
| Example 3-36 | 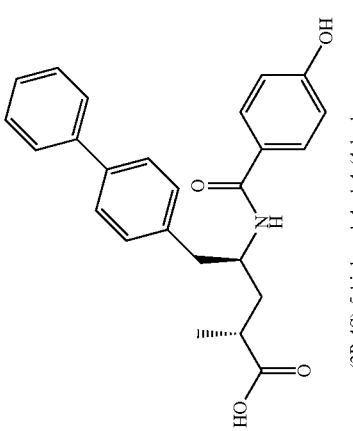<br>N-((1S,3R)-1-biphenyl-4-ylmethyl-3-carboxybutyl)-2,3,5,6-tetrafluoro-terephthalamic acid | 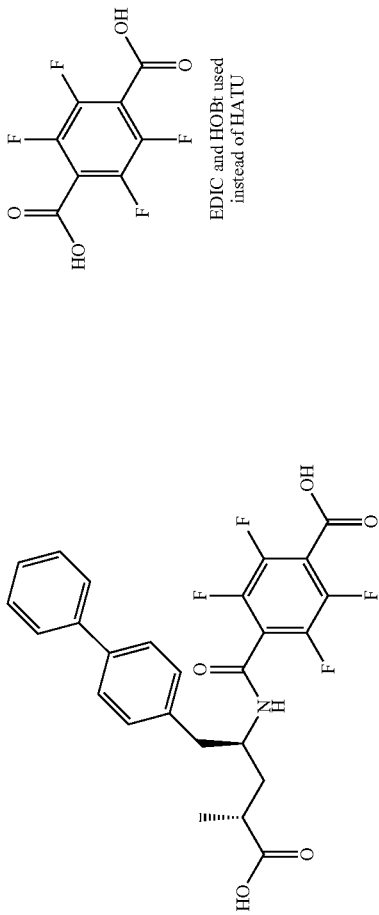<br>EDIC and HOBt used instead of HATU | Aq. NaOH, EtOH, 50° C. | 1.22 min. (A) | 504.1 |
| Example 3-37 | 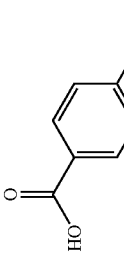<br>(2R,4S)-5-biphenyl-4-yl-4-(4-hydroxy-benzoylamino)-2-methyl-pentanoic acid | 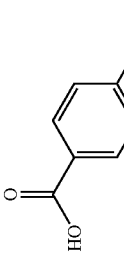<br>EDIC and HOBt used instead of HATU | Aq. NaOH, EtOH, 50° C. | 1.26 min. (A) | 404.2 |

| Example # | Product | Reagent | Hydrolysis Condition | HPLC-RT (condition) | MS (M + 1) |
|---|---|---|---|---|---|
| Example 3-38 | 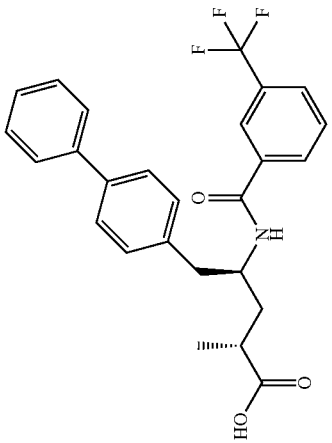 (2R,4S)-5-biphenyl-4-yl-4-(4-hydroxy-3-trifluoromethyl-benzoylamino)-2-methyl-pentanoic acid | 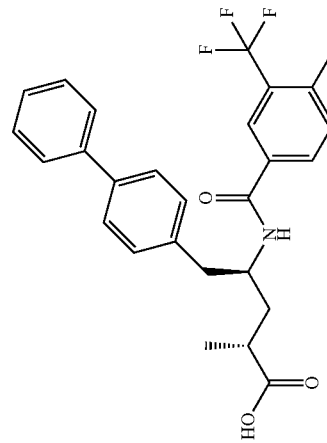 EDIC and HOBt used instead of HATU | Aq. NaOH, EtOH, 50° C. | 1.48 min. (A) | 472.1 |
| Example 3-39 | 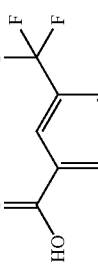 (2R,4S)-5-biphenyl-4-yl-2-methyl-4-(3-trifluoromethyl-benzoylamino)-pentanoic acid | 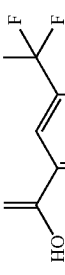 EDIC and HOBt used instead of HATU | Aq. NaOH, EtOH, 50° C. | 1.53 min. (A) | 456.2 |

| Example # | Product | | Reagent | Hydrolysis Condition | HPLC-RT (condition) | MS (M + 1) |
|---|---|---|---|---|---|---|
| Example 3-40 | 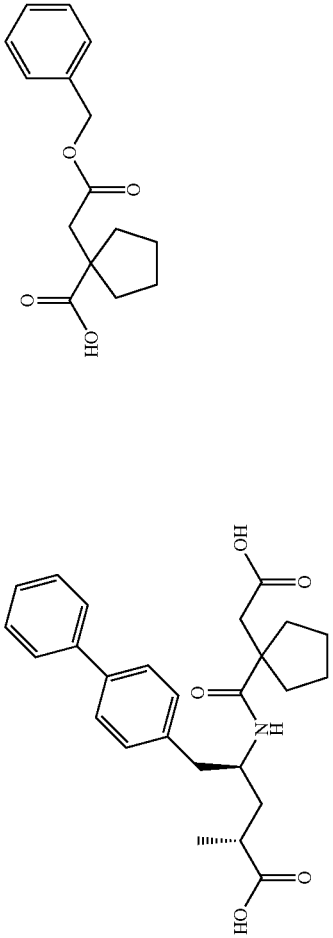 | (2R,4S)-5-(biphenyl-4-yl)-4-(1-(carboxymethyl)cyclopentanecarboxamido)-2-methylpentanoic acid | 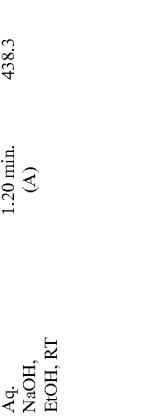 | Aq. NaOH, EtOH, RT | 1.20 min. (A) | 438.3 |
| Example 3-41 | 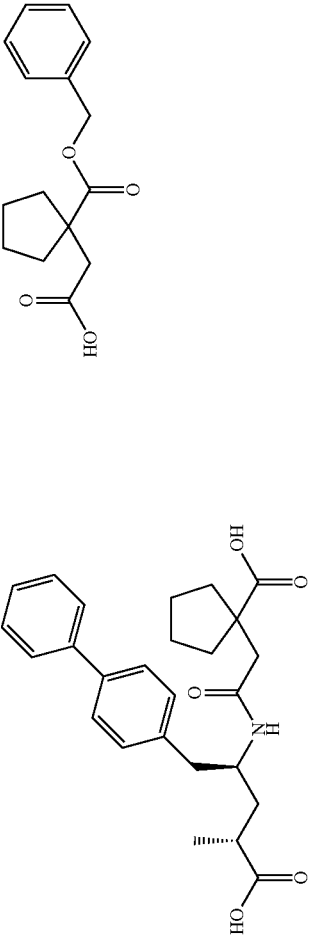 | 1-(2-((2S,4R)-1-(biphenyl-4-yl)-4-carboxypentan-2-yl)amino)-2-oxoethyl)cyclopentanecarboxylic acid |  | Aq. NaOH, EtOH, RT | 1.25 min. (A) | 438.3 |

-continued
| Example # | Product | Reagent | Hydrolysis Condition | HPLC-RT (condition) | MS (M + 1) |
|---|---|---|---|---|---|
| Example 3-42 | 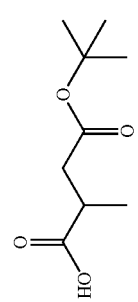 (2R,4S)-5-biphenyl-4-yl-4-(3-carboxy-butyrylamino)-2-methyl-pentanoic acid | 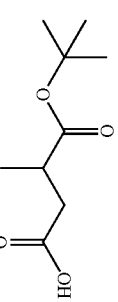 | Aq. NaOH, EtOH, RT | 0.98 min. (A) | 398.4 |
| Example 3-43 |  (2R,4S)-5-(biphenyl-4-yl)-4-(3-carboxy-2-methylpropanamido)-2-methylpentanoic acid |  | Aq. NaOH, EtOH, RT | 0.99 min. (A) | 398.4 |

-continued
| Example # | Product | Reagent | Hydrolysis Condition | HPLC-RT (condition) | MS (M + 1) |
|---|---|---|---|---|---|
| Example 3-44 | 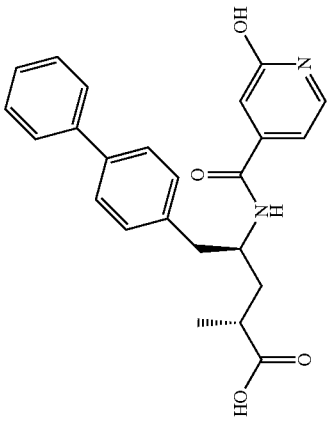 (2R,4S)-5-biphenyl-4-yl-4-(2,4-difluoro-3-hydroxy-benzoylamino)-2-methyl-pentanoic acid | 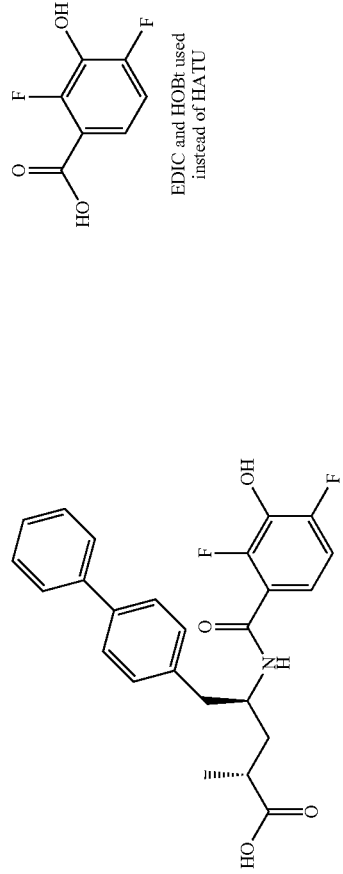 EDIC and HOBt used instead of HATU | Aq. NaOH, EtOH, RT | 1.55 min. (B) | 440.0 |
| Example 3-45 | 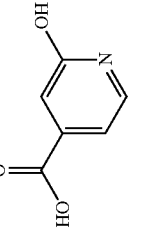 (2R,4S)-5-biphenyl-4-yl-4-[(2-hydroxy-pyridine-4-carbonyl)-amino]-2-methyl-pentanoic acid |  EDIC and HOBt used instead of HATU | Aq. NaOH, EtOH, RT | 1.33 min. (B) | 405.0 |

-continued
| Example # | Product | Reagent | Hydrolysis Condition | HPLC-RT (condition) | MS (M + 1) |
|---|---|---|---|---|---|
| Example 3-46 | 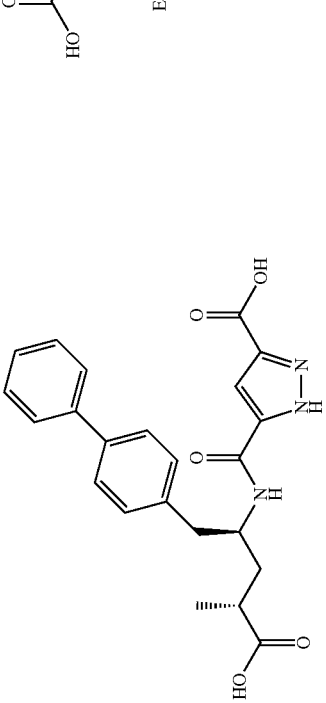 (2R,4S)-5-biphenyl-4-yl-4-(3-methanesulfonyl-benzoylamino)-2-methyl-pentanoic acid | 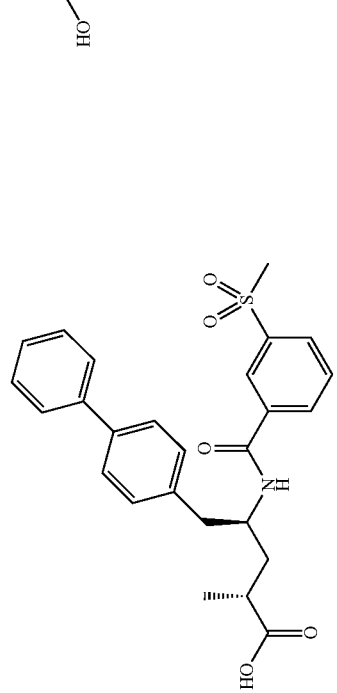 | Aq. NaOH, EtOH, RT | 1.33 min. (A) | 466.2 |
| Example 3-47 | 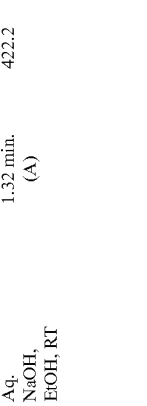 5-((1S,3R)-1-biphenyl-4-ylmethyl-3-carboxy-butylcarbamoyl)-1H-pyrazole-3-carboxylic acid |  EDIC and HOBt used instead of HATU | Aq. NaOH, EtOH, RT | 1.32 min. (A) | 422.2 |

-continued
| Example # | Product | Reagent | Hydrolysis Condition | HPLC-RT (condition) | MS (M + 1) |
|---|---|---|---|---|---|
| Example 3-48 | 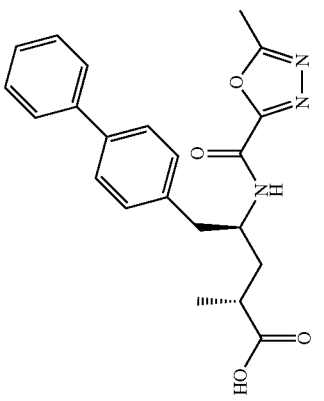 (2R,4S)-5-biphenyl-4-yl-2-methyl-4-[(1H-pyrazole-3-carbonyl)-amino]-pentanoic acid | 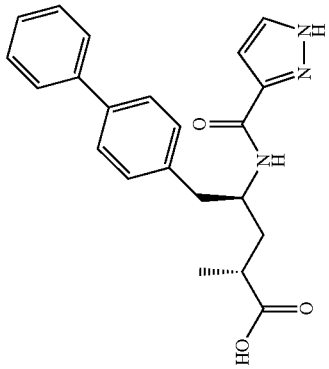 EDIC and HOBt used instead of HATU | Aq. NaOH, EtOH, RT | 1.13 min. (A) | 378.0 |
| Example 3-49 | 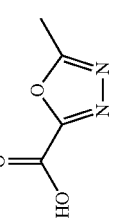 (2R,4S)-5-biphenyl-4-yl-2-methyl-4-[(5-methyl-[1,3,4]oxadiazole-2-carbonyl)-amino]-pentanoic acid | 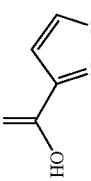 | Aq. NaOH, EtOH, 50° C. | 0.95 min. (D) | 394.0 |

| Example # | Product | Reagent | Hydrolysis Condition | HPLC-RT (condition) | MS (M + 1) |
|---|---|---|---|---|---|
| Example 3-50 | 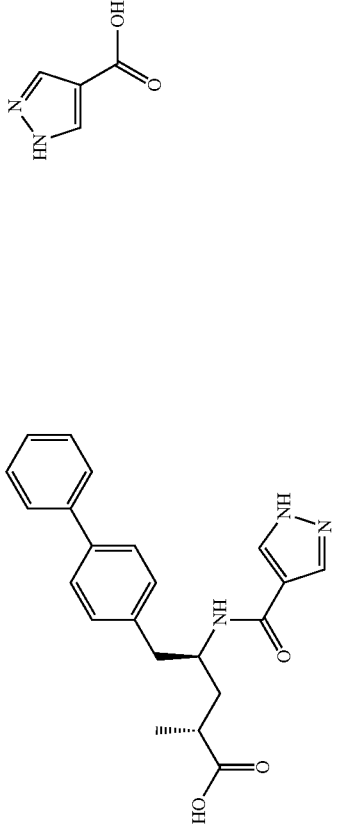 (2R,4S)-5-Biphenyl-4-yl-2-methyl-4-[(1H-pyrazole-4-carbonyl)-amino]-pentanoic acid | 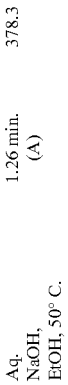 | Aq. NaOH, EtOH, 50° C. | 1.26 min. (A) | 378.3 |
| Example 3-51 | 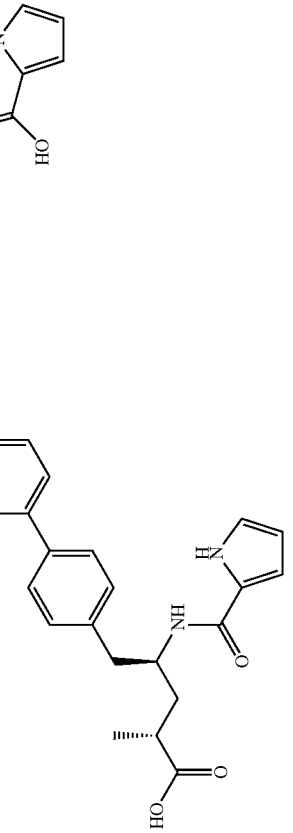 (2R,4S)-5-Biphenyl-4-yl-2-methyl-4-[(1H-pyrrole-2-carbonyl)-amino]-pentanoic acid | 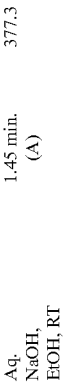 | Aq. NaOH, EtOH, RT | 1.45 min. (A) | 377.3 |

| Example # | Product | Reagent | Hydrolysis Condition | HPLC-RT (condition) | MS (M + 1) |
|---|---|---|---|---|---|
| Example 3-52 | 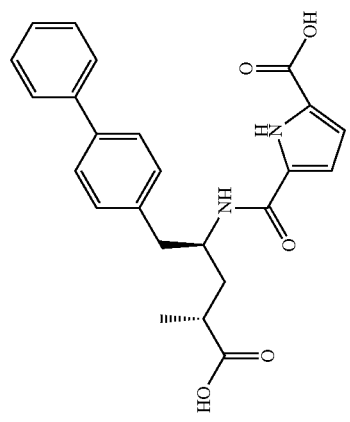 5-((1S,3R)-1-Biphenyl-4-ylmethyl-3-carboxy-butylcarbamoyl)-1H-pyrrole-2-carboxylic acid | 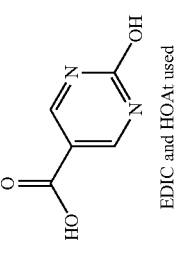 | Aq. NaOH, EtOH, RT | 1.28 min. (A) | 421.2 |
| Example 3-53 | 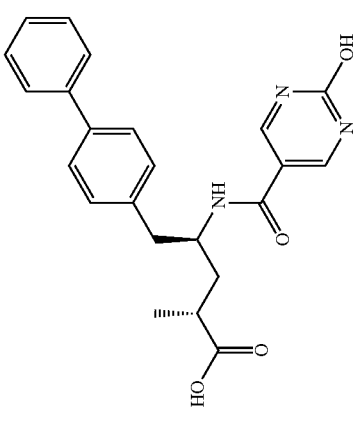 (2R,4S)-5-(biphenyl-4-yl)-4-(2-hydroxypyrimidine-5-carboxamido)-2-methylpentanoic acid | 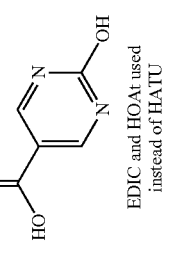 EDIC and HOAt used instead of HATU | Aq. NaOH, THF, MeOH, 50° C. | 1.42 min. (C) | 406.3 |

-continued
| Example # | Product | Reagent | Hydrolysis Condition | HPLC-RT (condition) | MS (M + 1) |
|---|---|---|---|---|---|
| Example 3-54 | 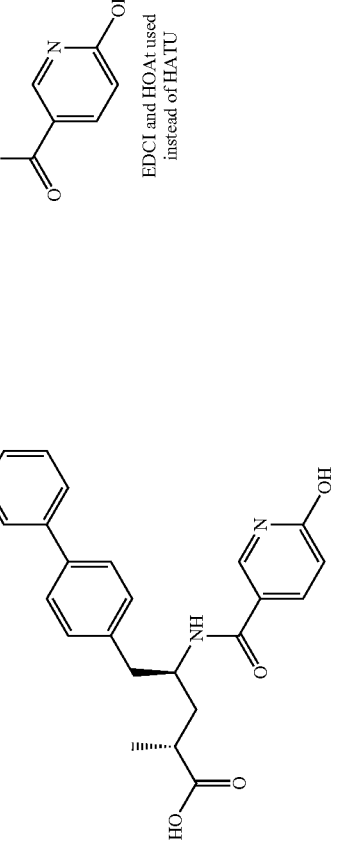 (2R,4S)-5-biphenyl-4-yl-4-[(1H-[1,2,4]triazole-3-carbonyl)-amino]-pentanoic acid | 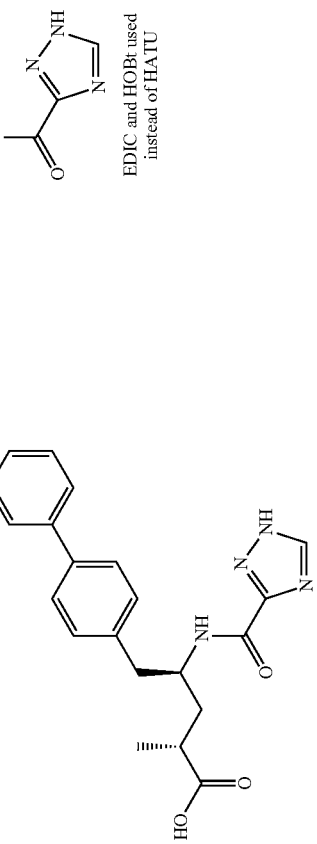 EDIC and HOBt used instead of HATU | Aq. NaOH, THF, EtOH, RT | 1.12 min. (A) | 379.3 |
| Example 3-55 |  (2R,4S)-5-biphenyl-4-yl-4-[((6-hydroxy-pyridine-3-carbonyl)-amino]-2-methyl-pentanoic acid |  EDCI and HOAt used instead of HATU | Aq. NaOH, MeOH, RT | 1.43 min. (B) | 405 |

| Example # | Product | Reagent | Hydrolysis Condition | HPLC-RT (condition) | MS (M + 1) |
|---|---|---|---|---|---|
| Example 3-56 | 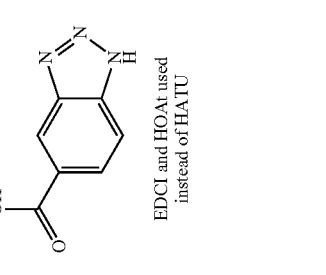<br>(2R,4S)-4-[(1H-benzotriazole-5-carbonyl)-amino]-5-biphenyl-4-yl-2-methyl-pentanoic acid | 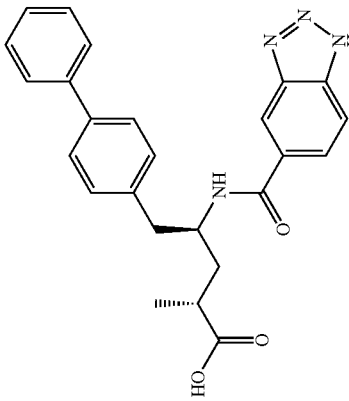<br>EDCI and HOAt used instead of HATU | Aq. NaOH, MeOH, RT | 1.61 min. (B) | 429 |
| Example 3-57 | 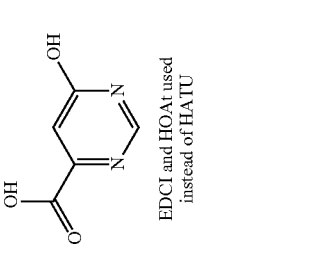<br>(2R,4S)-5-biphenyl-4-yl-4-[(6-hydroxy-pyrimidine-4-carbonyl)-amino]-2-methyl-pentanoic acid | 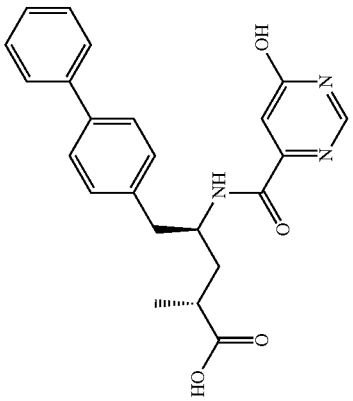<br>EDCI and HOAt used instead of HATU | Aq. NaOH, MeOH, RT | 1.57 min. (B) | 406 |

-continued
| Example # | Product | Reagent | Hydrolysis Condition | HPLC-RT (condition) | MS (M + 1) |
|---|---|---|---|---|---|
| Example 3-58 | 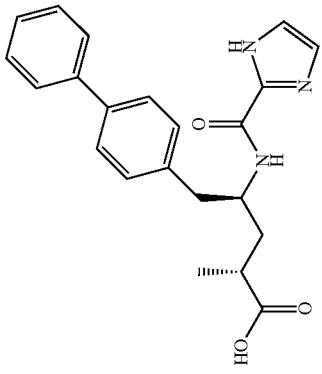 (2R,4S)-5-Biphenyl-4-yl-4-[(1H-imidazole-2-carbonyl)-amino]-2-methyl-pentanoic acid | 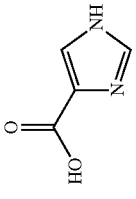 EDCI and HOBt used instead of HATU | Aq. NaOH, EtOH, 50° C. | 1.19 min. (C) | 378.3 |
| Example 3-59 | 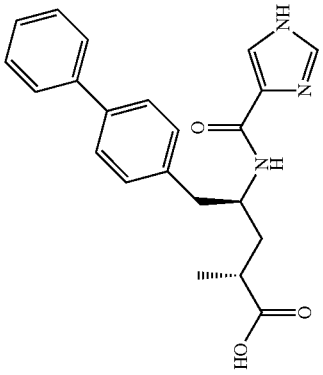 (2R,4S)-5-Biphenyl-4-yl-4-[(1H-imidazole-4-carbonyl)-amino]-2-methyl-pentanoic acid | 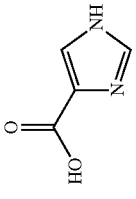 EDCI and HOBt used instead of HATU | Aq. NaOH, EtOH, 50° C. | 1.16 min. (C) | 378.3 |

| Example # | Product | Reagent | Hydrolysis Condition | HPLC-RT (condition) | MS (M + 1) |
|---|---|---|---|---|---|
| Example 3-60 | 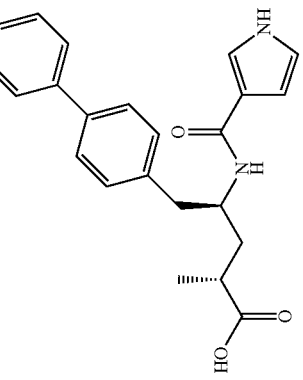<br>4-((1S,3R)-1-Biphenyl-4-ylmethyl-3-carboxy-butylcarbamoyl)-1H-imidazole-2-carboxylic acid | 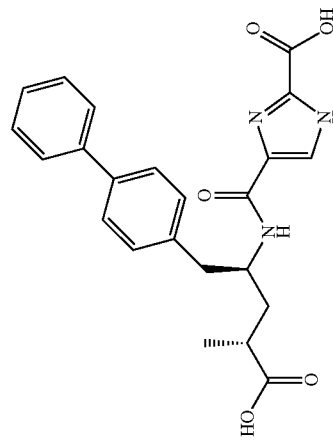<br>Intermediate 27 | Aq. NaOH, EtOH, RT | 0.98 min. (C) | 422.3 |
| Example 3-61 | 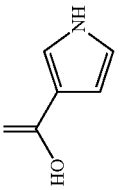<br>(2R,4S)-5-Biphenyl-4-yl-2-methyl-4-[(1H-pyrrole-3-carbonyl)-amino]-pentanoic acid | 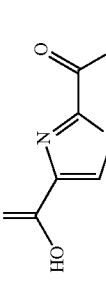 | Aq. NaOH, EtOH, RT | 1.29 min. (C) | 377.1 |

-continued
| Example # | Product | Reagent | Hydrolysis Condition | HPLC-RT (condition) | MS (M + 1) |
|---|---|---|---|---|---|
| Example 3-62 | 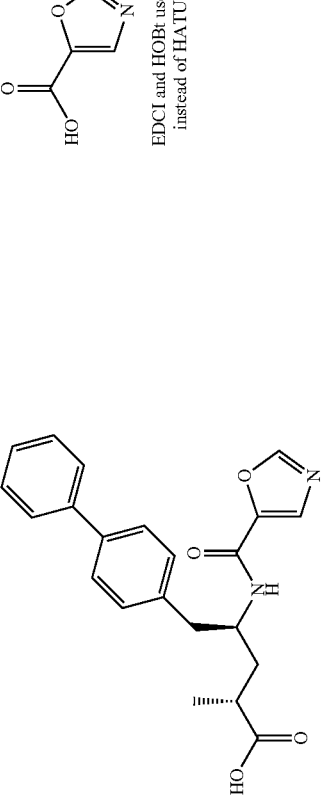<br>(2R,4S)-5-Biphenyl-4-yl-2-methyl-4-[(oxazole-4-carbonyl)-amino]-pentanoic acid | 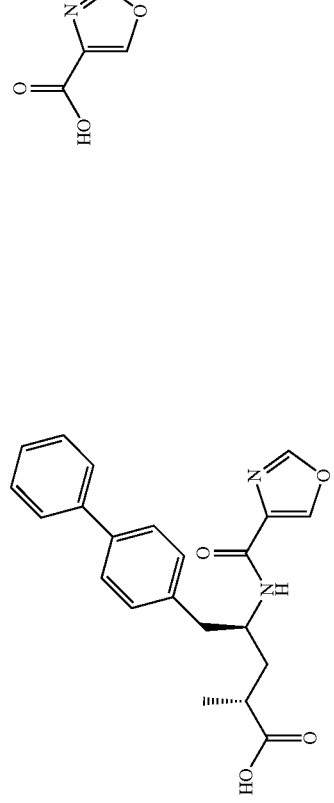 | Aq. NaOH, EtOH, RT | 1.14 min. (C) | 379.1 |
| Example 3-63 | <br>(2R,4S)-5-Biphenyl-4-yl-2-methyl-4-[(oxazole-5-carbonyl)-amino]-pentanoic acid | <br>EDCI and HOBt used instead of HATU | Aq. NaOH, EtOH, 50° C. | 1.10 min. (C) | 379.2 |

-continued
| Example # | Product | Reagent | Hydrolysis Condition | HPLC-RT (condition) | MS (M + 1) |
|---|---|---|---|---|---|
| Example 3-64 | 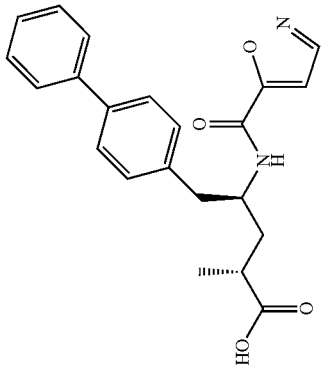<br>(2R,4S)-5-Biphenyl-4-yl-4-[(isoxazole-5-carbonyl)-amino]-2-methyl-pentanoic acid | 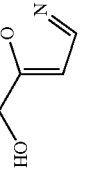<br>plus Intermediate 2 | BCl₃, DCM, RT | 1.18 min. (C) | 379.3 |
| Example 3-65 | 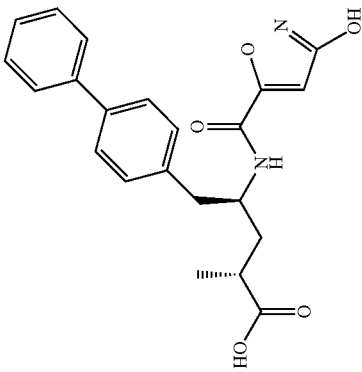<br>(2R,4S)-5-Biphenyl-4-yl-4-[((3-hydroxy-isoxazole-5-carbonyl)-amino]-2-methyl-pentanoic acid | 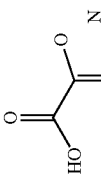<br>EDCI and HOBt used instead of HATU | Aq. NaOH, EtOH, 50° C. | 1.22 min. (C) | 395.2 |

-continued

| Example # | Product | Reagent | Hydrolysis Condition | HPLC-RT (condition) | MS (M + 1) |
|---|---|---|---|---|---|
| Example 3-66 | (2R,4S)-5-Biphenyl-4-yl-2-methyl-4-[(1-methyl-1H-pyrazole-3-carbonyl)-amino]-pentanoic acid | 1-methyl-1H-pyrrole-3-carboxylic acid | Aq. NaOH, EtOH, RT | 1.32 min. (C) | 392.1 |
| Example 3-67 | 5-((1S,3R)-1-Biphenyl-4-ylmethyl-3-carboxy-butylcarbamoyl)-1-methyl-1H-pyrazole-3-carboxylic acid | 1-methyl-1H-pyrrole-2,4-dicarboxylic acid; EDCI and HOBt used instead of HATU | Aq. NaOH, EtOH, 50° C. | 0.93 min. (C) | 436.3 |

| Example # | Product | Reagent | Hydrolysis Condition | HPLC-RT (condition) | MS (M + 1) |
|---|---|---|---|---|---|
| Example 3-68 | 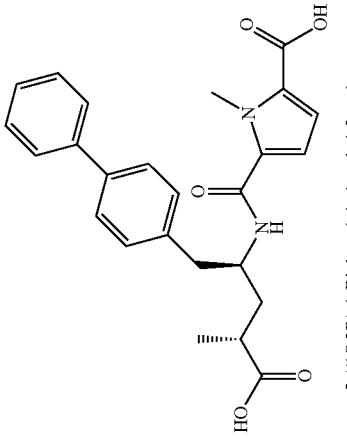<br>5-((1S,3R)-1-Biphenyl-4-ylmethyl-3-carboxy-butylcarbamoyl)-2-methyl-2H-pyrazole-3-carboxylic acid | 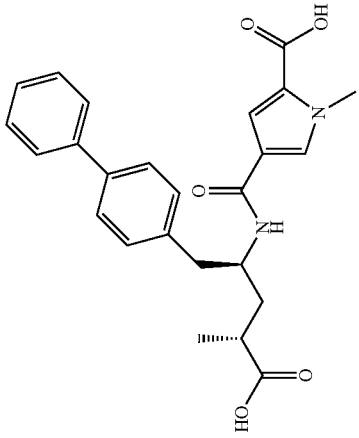<br>EDCI and HOBt used instead of HATU | Aq. NaOH, EtOH, 50° C. | 0.97 min. (C) | 436.3 |
| Example 3-69 | 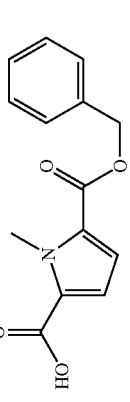<br>5-((1S,3R)-1-Biphenyl-4-ylmethyl-3-carboxy-butylcarbamoyl)-1-methyl-1H-pyrrole-2-carboxylic acid |  | Aq. NaOH, EtOH, RT | 1.05 min. (C) | 435.3 |

| Example # | Product | Reagent | Hydrolysis Condition | HPLC-RT (condition) | MS (M + 1) |
|---|---|---|---|---|---|
| Example 3-70 | 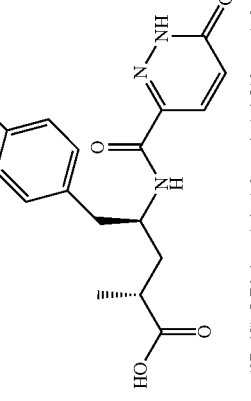 (2R,4S)-5-Biphenyl-4-yl-2-methyl-4-[(5-oxo-4,5-dihydro-1H-pyrazole-3-carbonyl)-amino]-pentanoic acid | 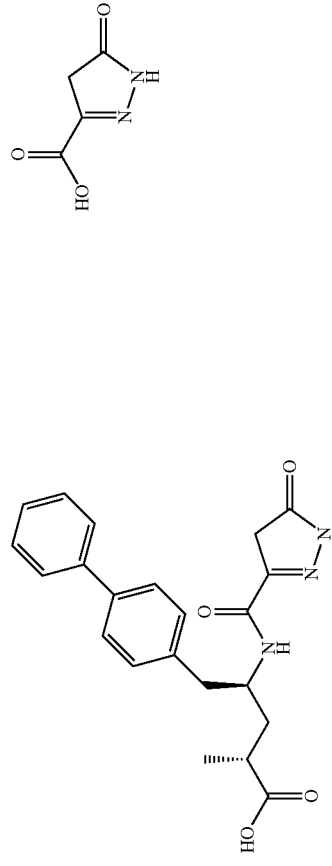 | Aq. NaOH, EtOH, RT | 1.10 min. (C) | 394.2 |
| Example 3-71 | 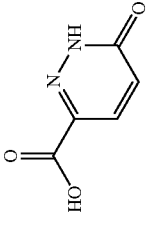 (2R,4S)-5-Biphenyl-4-yl-2-methyl-4-[(6-oxo-1,6-dihydro-pyridazine-3-carbonyl)-amino]-pentanoic acid | 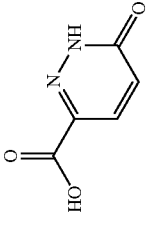 | Aq. NaOH, EtOH, RT | 1.10 min. (C) | 406.1 |

-continued
| Example # | Product | Reagent | Hydrolysis Condition | HPLC-RT (condition) | MS (M + 1) |
|---|---|---|---|---|---|
| Example 3-72 | 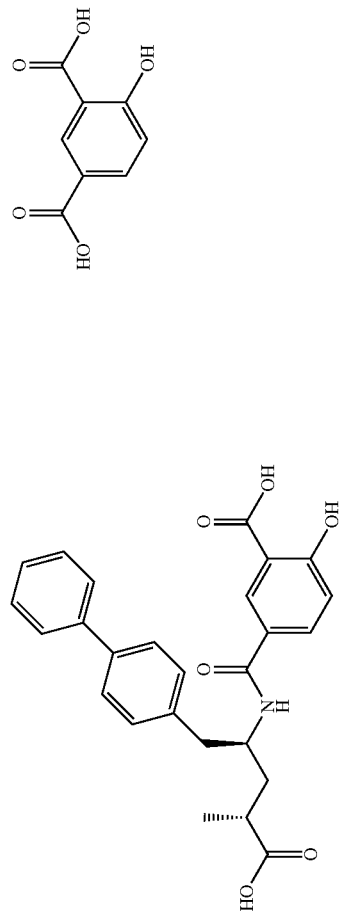 N-((1S,3R)-1-Biphenyl-4-ylmethyl-3-carboxy-butyl)-6-hydroxy-isophthalamic acid | 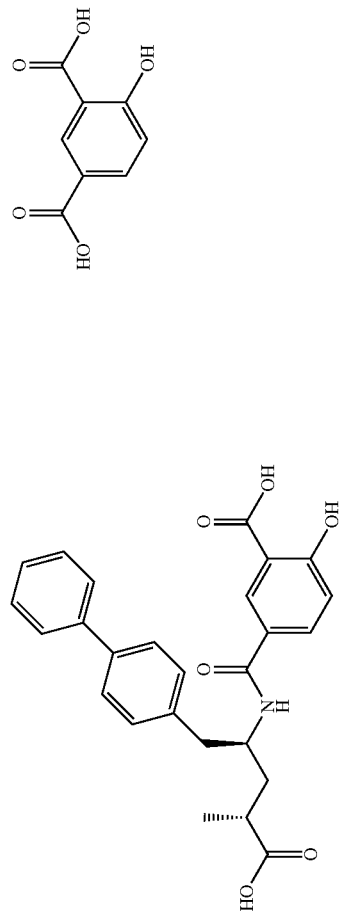 | Aq. NaOH, EtOH, RT | 1.10 min. (C) | 448.3 |
| Example 3-73 | 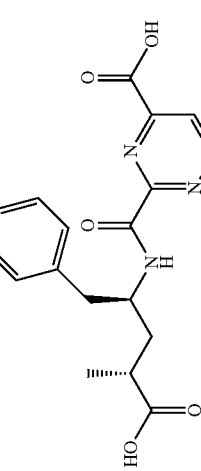 2-((1S,3R)-1-Biphenyl-4-ylmethyl-3-carboxy-butylcarbamoyl)-pyrimidine-4-carboxylic acid | 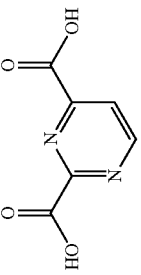 | Aq. NaOH, EtOH, RT | 1.19 min. (C) | 434.1 |

| Example # | Product | Reagent | Hydrolysis Condition | HPLC-RT (condition) | MS (M + 1) |
|---|---|---|---|---|---|
| Example 3-74 | 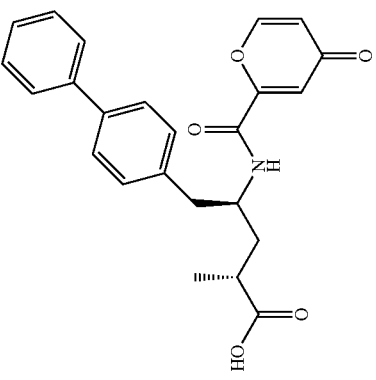<br>4-((1S,3R)-1-Biphenyl-4-ylmethyl-3-carboxy-butylcarbamoyl)-pyrimidine-2-carboxylic acid | 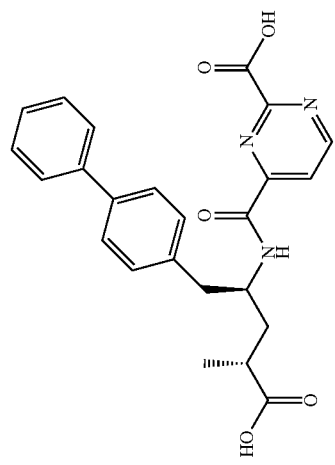 | Aq. NaOH, EtOH, RT | 0.96 min. (C) | 434.3 |
| Example 3-75 | <br>(2R,4S)-5-Biphenyl-4-yl-2-methyl-4-[(4-oxo-4H-pyran-2-carbonyl)-amino]-pentanoic acid | 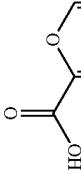<br>plus Intermediate 2 | BCl$_3$, DCM. RT | 1.21 min. (C) | 406.1 |

-continued
| Example # | Product | Reagent | Hydrolysis Condition | HPLC-RT (condition) | MS (M + 1) |
|---|---|---|---|---|---|
| Example 3-76 | 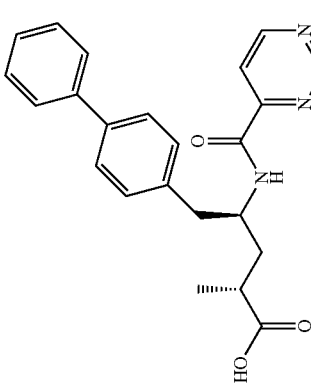<br>(2R,4S)-5-Biphenyl-4-yl-4-[(5-hydroxy-6-oxo-6H-pyran-2-carbonyl)-amino]-2-methyl-pentanoic acid | 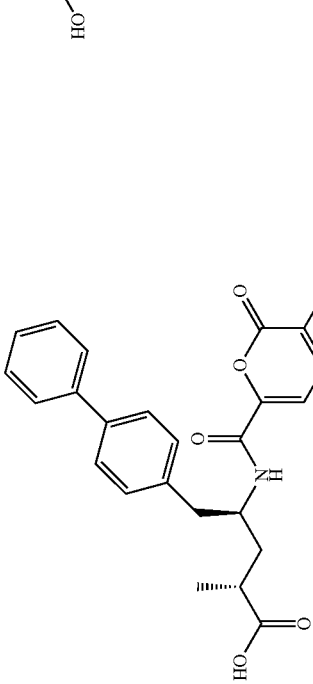<br>plus Intermediate 2 | BCl$_3$, DCM, RT | 1.13 min. (C) | 422.1 |
| Example 3-77 | 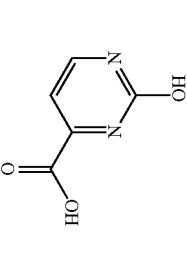<br>(2R,4S)-5-Biphenyl-4-yl-4-[(2-hydroxy-pyrimidine-4-carbonyl)-amino]-2-methyl-pentanoic acid | 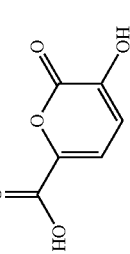 | Aq. NaOH, EtOH, RT | 1.20 min. (C) | 406.2 |

-continued

| Example # | Product | Reagent | Hydrolysis Condition | HPLC-RT (condition) | MS (M + 1) |
|---|---|---|---|---|---|
| Example 3-78 | (2R,4S)-5-Biphenyl-4-yl-2-methyl-4-[(1,1,3-trioxo-2,3-dihydro-1H-1-benzo[d]isothiazole-6-carbonyl)-amino]-pentanoic acid | | Aq. NaOH, EtOH, RT | 1.10 min. (C) | 493.1 |
| Example 3-79 | 6-((1S,3R)-1-Biphenyl-4-ylmethyl-3-carboxy-butylcarbamoyl)-2-hydroxy-pyrimidine-4-carboxylic acid | | Aq. NaOH, EtOH, RT | 1.04 min. (C) | 450.3 |

| Example # | Product | Reagent | Hydrolysis Condition | HPLC-RT (condition) | MS (M + 1) |
|---|---|---|---|---|---|
| Example 3-80 | 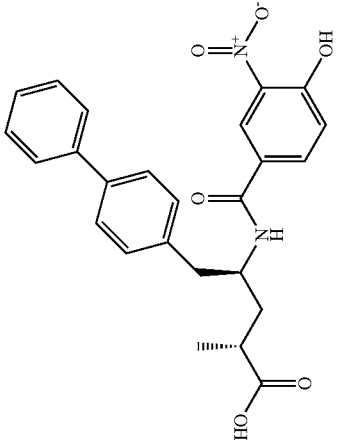 (2R,4S)-5-Biphenyl-4-yl-4-[(2-hydroxymethyl-oxazole-5-carbonyl)-amino]-2-methyl-pentanoic acid | 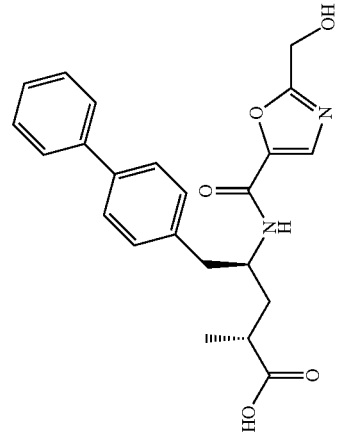 | Aq. NaOH, THF, RT | 1.30 min. (C) | 409.4 |
| Example 3-81 | 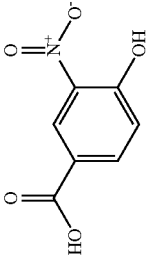 (2R,4S)-5-Biphenyl-4-yl-4-(4-hydroxy-3-nitro-benzoylamino)-2-methyl-pentanoic acid | 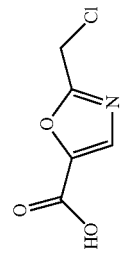 | Aq. NaOH, EtOH, 50° C. | 1.28 min. (C) | 449.0 |

-continued
| Example # | Product | Reagent | Hydrolysis Condition | HPLC-RT (condition) | MS (M + 1) |
|---|---|---|---|---|---|
| Example 3-83 | 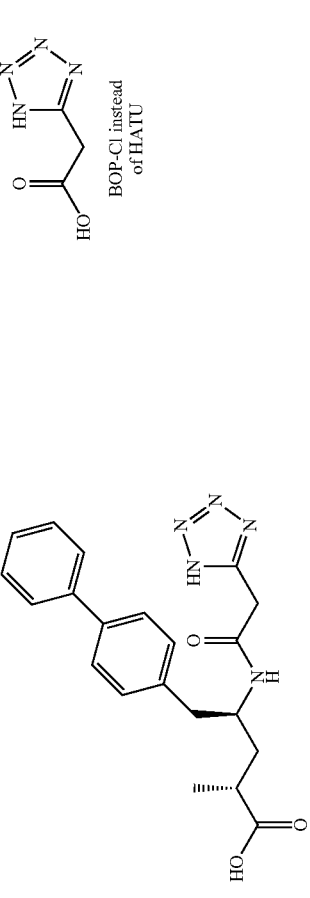<br>(S)-1-[((1S,3R)-1-Biphenyl-4-ylmethyl-3-carboxy-butylcarbamoyl)-methyl]-pyrrolidine-2-carboxylic acid | 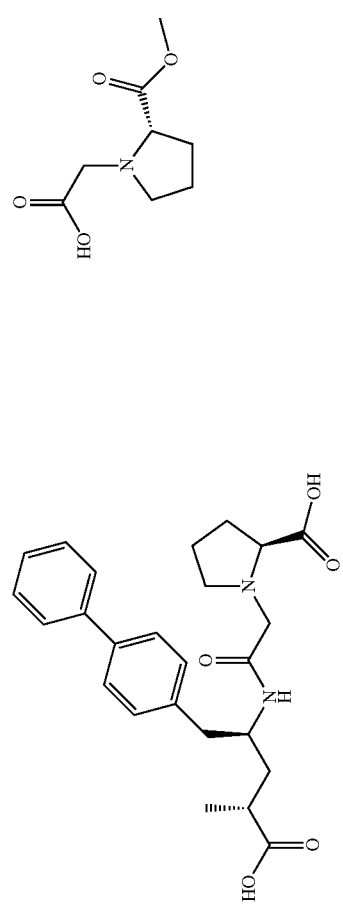 | Aq. NaOH, THF, RT | 1.05 min. (C) | 439.2 |
| Example 3-84 | 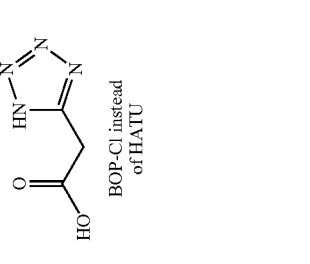<br>(2R,4S)-5-Biphenyl-4-yl-2-methyl-4-(2-1H-tetrazol-5-yl-acetylamino)-pentanoic acid | 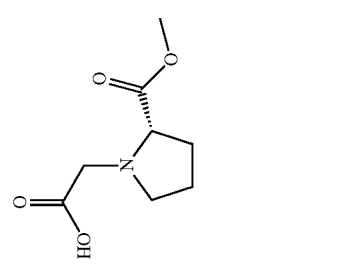<br>BOP-Cl instead of HATU | Aq. NaOH, MeOH, RT | 0.70 min. (D) | 394.0 |

| Example # | Product | Reagent | Hydrolysis Condition | HPLC-RT (condition) | MS (M + 1) |
|---|---|---|---|---|---|
| Example 3-85 | 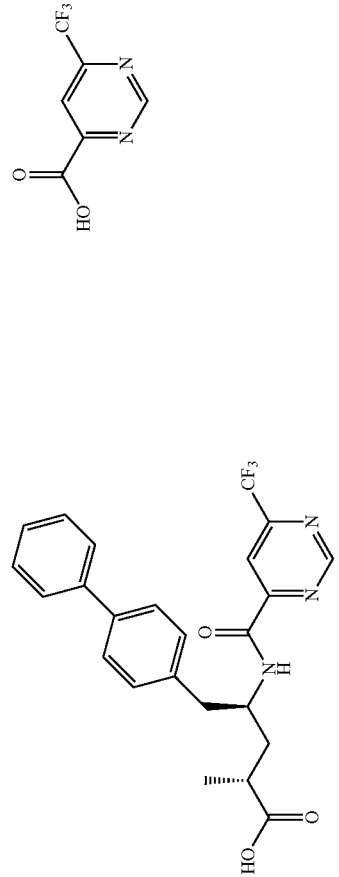<br>(2R,4S)-5-Biphenyl-4-yl-2-methyl-4-[(6-trifluoromethyl-pyrimidine-4-carbonyl)-amino]-pentanoic acid |  | Aq. NaOH, MeOH, RT | 1.38 min. (D) | 458.1 |
| Example 3-86 | 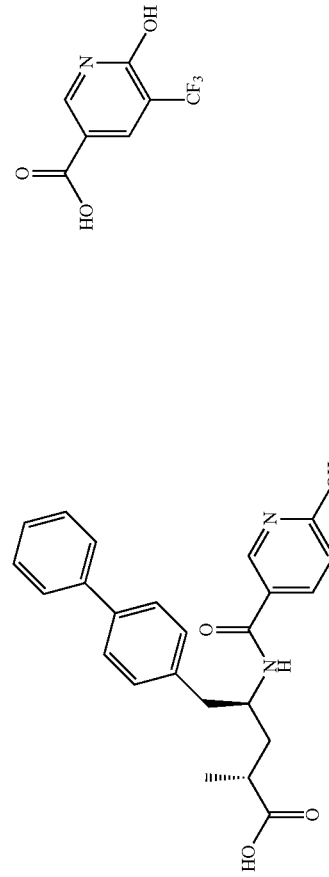<br>(2R,4S)-5-(biphenyl-4-yl)-4-(6-hydroxy-5-(trifluoromethyl)nicotinamido)-2-methylpentanoic acid | 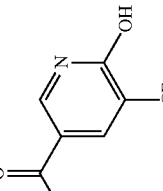 | Aq. NaOH, MeOH, RT | 1.62 min. (B) | 473.1 |

-continued
| Example # | Product | Reagent | Hydrolysis Condition | HPLC-RT (condition) | MS (M + 1) |
|---|---|---|---|---|---|
| Example 3-87 | 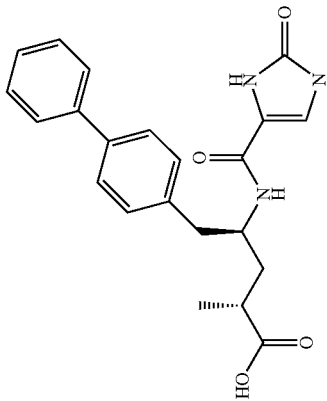 (2R,4S)-5-(biphenyl-4-yl)-2-methyl-4-(2-oxo-2,3-dihydro-1H-imidazole-4-carboxamido)pentanoic acid | 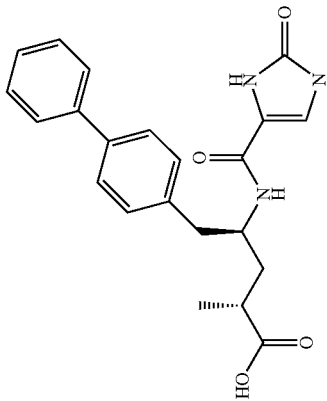 EDCI and HOAt Used instead of HATU | Aq. NaOH, MeOH, RT | 1.50 min. (B) | 394.2 |
| Example 3-89 | 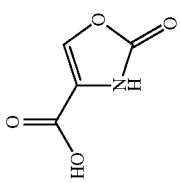 (2R,4S)-5-(biphenyl-4-yl)-2-methyl-4-(2-oxo-2,3-dihydrooxazole-4-carboxamido)pentanoic acid | 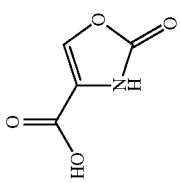 | Aq. NaOH, MeOH, RT | 1.62 min. (B) | 395.3 |

-continued

| Example # | Product | Reagent | Hydrolysis Condition | HPLC-RT (condition) | MS (M + 1) |
|---|---|---|---|---|---|
| Example 3-90 | (2R,4S)-5-(biphenyl-4-yl)-2-methyl-4-(2-oxo-2,3-dihydrothiazole-5-carboxamido)pentanoic acid | Hydrolysis of Example 56-1 | Aq. NaOH, MeOH, RT | 1.65 min. (B) | 411.2 |
| Example 3-91 | (2R,4S)-5-(biphenyl-4-yl)-2-methyl-4-(5-oxo-4,5-dihydro-1,3,4-oxadiazole-2-carboxamido)pentanoic acid | Hydrolysis of Example 57-1 | Aq. NaOH, MeOH, RT | 1.63 min. (B) | 396.2 |

| Example # | Product | Reagent | Hydrolysis Condition | HPLC-RT (condition) | MS (M + 1) |
|---|---|---|---|---|---|
| Example 3-92 | 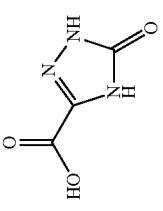 (2R,4S)-5-(biphenyl-4-yl)-2-methyl-4-(2,4,5-trifluoro-3-hydroxybenzamido)pentanoic acid | 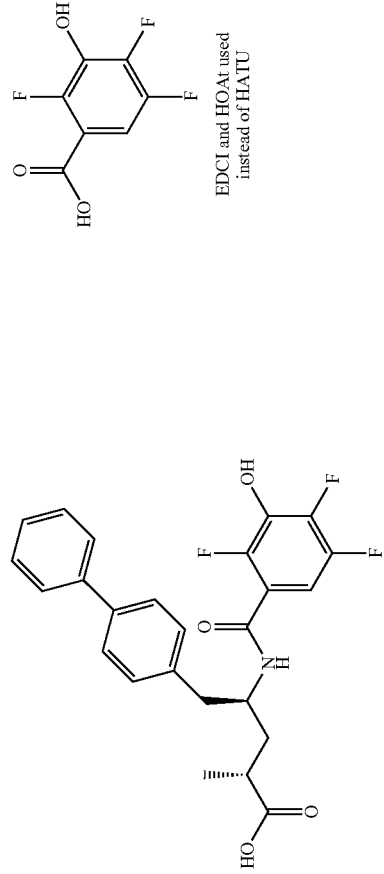 EDCI and HOAt used instead of HATU | Aq. NaOH, MeOH, RT | 1.60 min. (B) | 458.1 |
| Example 3-93 | 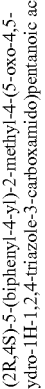 (2R,4S)-5-(biphenyl-4-yl)-2-methyl-4-(5-oxo-4,5-dihydro-1H-1,2,4-triazole-3-carboxamido)pentanoic acid |  EDCI and HOAt used instead of HATU | Aq. NaOH, MeOH, RT | 1.48 min. (B) | 395.3 |

-continued
| Example # | Product | Reagent | Hydrolysis Condition | HPLC-RT (condition) | MS (M + 1) |
|---|---|---|---|---|---|
| Example 3-94 | 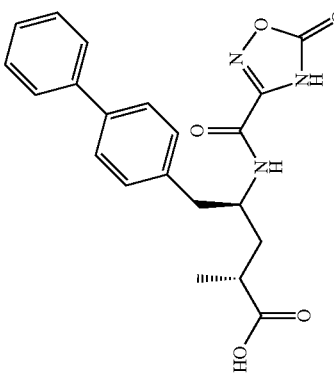<br>(2R,4S)-5-(biphenyl-4-yl)-4-(3-hydroxy-1H-pyrazole-5-carboxamido)-2-methylpentanoic acid | 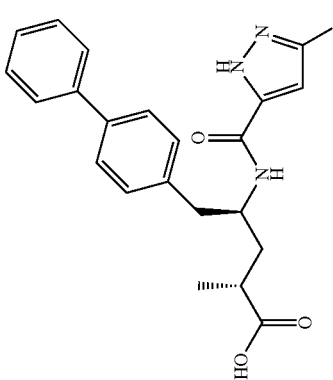<br>EDCI and HOAt used instead of HATU | Aq. NaOH, MeOH, RT | 1.66 min. (B) | 394.3 |
| Example 3-95 | 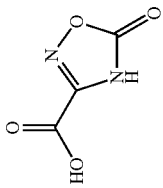<br>(2R,4S)-5-(biphenyl-4-yl)-2-methyl-4-(5-oxo-4,5-dihydro-1,2,4-oxadiazole-3-carboxamido)pentanoic acid | <br>Intermediate 35 | Aq. NaOH, MeOH, RT | 1.83 min. (B) | 396.2 |

| Example # | Product | Reagent | Hydrolysis Condition | HPLC-RT (condition) | MS (M + 1) |
|---|---|---|---|---|---|
| Example 3-96 | (2R,4S)-5-(biphenyl-4-yl)-2-methyl-4-(2-oxo-2,3-dihydrooxazole-5-carboxamido)pentanoic acid | Hydrolysis of Example 58-1 | Aq. NaOH, MeOH, RT | 1.72 min. (B) | 395.2 |
| Example 3-97 | (2R,4S)-5-(3'-chlorobiphenyl-4-yl)-2-methyl-4-(5-oxo-4,5-dihydro-1,2,4-oxadiazole-3-carboxamido)pentanoic acid | Intermediate 35 | Aq. NaOH, MeOH, RT | 1.64 min. (B) | 430.2 |

-continued
| Example # | Product | Reagent | Hydrolysis Condition | HPLC-RT (condition) | MS (M + 1) |
|---|---|---|---|---|---|
| Example 3-98 | 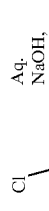<br>(2R,4S)-5-(3'-chlorobiphenyl-4-yl)-2-methyl-4-(5-oxo-4,5-dihydro-1,3,4-oxadiazole-2-carboxamido)pentanoic acid | 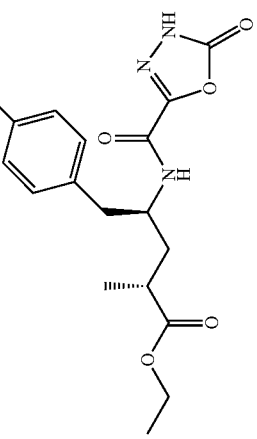<br>Hydrolysis of Example 59-1 | Aq. NaOH, MeOH, RT | 1.60 min. (B) | 430.1 |

EXAMPLE 3-2

1H NMR (400 MHz, Acetone-d6) δ ppm 1.28 (d, J=6.95 Hz, 3H), 1.54-1.70 (m, 2H), 2.09 (m, 1H), 2.67 (m, 1H), 2.81 (m, 1H), 3.06 (m, 2H), 3.26 (m, 2H), 4.47 (M, 1H), 7.25 (t, 1H), 7.34 (t, 1H), 7.36 (s, 1H), 7.49 (d, J=8.08 Hz, 2H), 7.60 (t, 2H), 7.69 (t, 2H), 7.7 (d, J=8.08 Hz, 2H), 7.80 (d, J=7.83 Hz, 1H), 7.88 (d, J=7.33 Hz, 2H).

EXAMPLE 3-3

1H NMR (400 MHz, Acetone-d6) δ ppm 1.36 (d, J=6.95 Hz, 3H), 1.79 (m, 1H), 2.07-2.19 (m, 5H), 2.26-2.33 (m, 2H), 2.80 (m, 1H), 2.98-3.06 (m, 2H), 3.11 (t, 1H), 4.48 (M, 1H), 7.53-7.57 (m, 3H), 7.67 (t, 2H), 7.80 (d, J=8.21 Hz, 2H), 7.87 (d, J=7.33 Hz, 2H).

EXAMPLE 3-4

1H NMR (400 MHz, MeOD-d4) δ ppm 1.19 (d, J=7.07 Hz, 3H), 1.58 (m, 1H), 2.01 (m, 1H), 2.55 (m, 1H), 2.71 (dd, J=8.84 Hz, 8.72 Hz, 1H), 2.91 (dd, J=5.43 Hz, 5.32 Hz, 1H), 3.72 (d, J=5.81 Hz, 2H), 4.28 (m, 1H), 7.24 (d, J=8.08 Hz, 2H), 7.33 (m, 1H), 7.44 (t, J=7.83 Hz, 2H), 7.48 (d, J=8.08 Hz, 2H), 7.58 (d, J=7.96 Hz, 2H), 7.65 (d, J=6.32 Hz, 2H), 8.22 (d, J=9.09 Hz, 1H), 8.53 (d, J=6.32 Hz, 2H).

EXAMPLE 3-5

1H NMR (400 MHz, MeOD-d4) δ ppm 1.01 (d, J=7.07 Hz, 3H), 1.32 (m, 1H), 1.84 (m, 1H), 2.27 (m, 1H), 2.50 (m, 1H), 2.66 (dd, J=7.33 Hz, 7.20 Hz, 1H), 2.73 (dd, J=5.81 Hz, 5.61 Hz, 1H), 2.99 (1, J=7.20 Hz, 2H), 4.13 (m, 1H), 7.09 (d, J=8.21 Hz, 2H), 7.32 (m, 2H), 7.41 (m, 4H), 7.53 (m, 2H), 7.72 (d, J=1.26 Hz, 1H), 7.78 (d, J=8.34 Hz, 1H).

EXAMPLE 3-6

1H NMR (400 MHz, MeOD-d4) δ ppm 1.18 (d, J=7.07 Hz, 3H), 1.50 (m, 1H), 1.80 (m, 1H), 1.97 (m, 1H), 2.14 (m, 2H), 2.54 (m, 3H), 2.70 (m, 1H), 2.79 (s, 3H), 2.87 (dd, J=5.43 Hz, 1H), 4.28 (m, 1H), 7.21 (m, 2H), 7.29 (m, 4H), 7.41 (m, 2H), 7.46 (d, J=8.21 Hz, 2H), 7.57 (d, J=1.01 Hz, 1H), 7.67 (d, J=8.34 Hz, 1H), 7.81 (d, J=9.22 Hz, 1H).

EXAMPLE 3-9

1H NMR (400 MHz, CDCl3) δ ppm 1.09 (d, J=6.95 Hz, 3H), 1.45 (m, 1H), 1.81 (m, 1H), 2.19-2.33 (m, 2H), 2.47 (m, 1H), 2.69-2.80 (m, 2H), 2.99 (t, 2H), 3.82 (m, 2H), 4.08 (m, 1H), 6.61 (d, J=8.97 Hz, 1H), 7.26 (d, J=8.21 Hz, 2H), 7.35 (1, 1H), 7.45 (t, 2H), 7.55 (d, J=8.21 Hz, 2H), 7.62 d, J=7.45 Hz, 2H), 7.79 (d, J=7.58 Hz, 1H).

EXAMPLE 3-10

1H NMR (400 MHz, DMSO-d6) δ ppm 1.06 (d, J=7.07 Hz, 3H), 1.38 (m, 1H), 1.82 (m, 1H), 2.41 (m, 1H), 2.63-2.77 (m, 2H), 3.41 (s, 2H), 3.97 (m, 1H), 6.88 (d, J=6.32 Hz, 2H), 7.05 (m, 1H), 7.19 (d, J=8.21 Hz, 2H), 7.34 (t, 1H), 7.45 (1, 2H), 7.51 (d, J=8.21 Hz, 2H), 7.62 (d, J=8.08 Hz, 2H), 7.99 (d, J=8.46 Hz, 1H).

EXAMPLE 3-11

1H NMR (400 MHz, MeOD-d4) δ ppm 1.15 (d, J=7.07 Hz, 3H), 1.51 (m, 1H), 1.95 (m, 1H), 2.51 (m, 1H), 2.74 (dd, J=7.83 Hz, 7.71 Hz, 1H), 2.85 (dd, J=5.68 Hz, 5.81 Hz, 1H), 3.38 (s, 2H), 3.56 (s, 3H), 4.22 (m, 1H), 6.72 (s, 1H), 7.23 (d, J=8.08 Hz, 2H), 7.31 (t, J=7.33 Hz, 1H), 7.42 (t, J=7.83 Hz, 2H), 7.52 (t, J=8.08 Hz, 3H), 7.59 (d, J=7.33 Hz, 2H).

EXAMPLE 3-12

1H NMR (400 MHz, DMSO-d6) δ ppm 1.07 (d, J=7.07 Hz, 3H), 1.22 (t, 3H), 1.39 (m, 1H), 1.83 (m, 1H), 2.43 (m, 1H), 2.65-2.79 (m, 2H), 2.95 (q, 2H), 3.92 (s, 2H), 3.99 (m, 1H), 7.22 (d, J=8.21 Hz, 2H), 7.34 (t, 1H), 7.45 (t, 2H), 7.52 (d, J=8.21 Hz, 2H), 7.63 (d, J=7.20 Hz, 2H), 8.26 (d, J=8.59 Hz, 1H).

EXAMPLE 3-13

1H NMR (400 MHz, DMSO-d6) δ ppm 1.07 (d, J=7.07 Hz, 3H), 1.60 (m, 1H), 1.88 (m, 1H), 2.42 (m, 1H), 2.84 (m, 2H), 4.23 (m, 1H), 7.19 (d, J=3.66 Hz, 1H), 7.28 (m, 3H), 7.33 (t, 1H), 7.44 (t, 1H), 7.57 (d, J=8.34 Hz, 2H), 7.63 (d, J=8.08, 2H), 8.43 (d, J=8.84 Hz, 1H).

EXAMPLE 3-14

1H NMR (400 MHz, DMSO-d6) δ ppm 1.08 (d, J=7.07 Hz, 3H), 1.57 (m, 1H), 1.88 (m, 1H), 2.42 (m, 1H), 2.84 (m, 2H), 4.18 (m, 1H), 7.28 (d, J=8.21 Hz, 2H), 7.33 (t, 1H), 7.44 (t, 1H), 7.57 (d, J=8.21 Hz, 2H), 7.63 (d, J=8.08 Hz, 2H), 7.71 (d, J=3.92 Hz, 1H), 7.76 (d, J=3.92 Hz, 1H).

EXAMPLE 3-15

1H NMR (400 MHz, DMSO-d6) δ ppm 1.06 (d, J=7.07 Hz, 3H), 1.35 (m, 1H), 1.66 (m, 2H), 1.79 (m, 1H), 2.00 (m, 2H), 2.39 (m, 3H), 2.69 (m, 2H), 3.69 (s, 3H), 4.01 (m, 1H), 6.78 (d, J=8.59 Hz, 2H), 7.02 (d, J=8.46 Hz, 2H), 7.25 (d, J=8.08 Hz, 2H), 7.33 (t, 1H), 7.43 (t, 1H), 7.55 (d, J=8.08 Hz, 2H), 7.60 (d, J=7.83 Hz, 2H), 7.67 (d, J=8.59 Hz, 1H).

EXAMPLE 3-16

1H NMR (400 MHz, DMSO-d6) δ ppm 1.07 (d, J=7.07 Hz, 3H), 1.52 (m, 1H), 1.86 (m, 1H), 2.44 (m, 1H), 2.80 (d, J=6.57 Hz, 2H), 4.18 (m, 1H), 5.15 (q, 2H), 6.47 (d, J=9.47 Hz, 1H), 7.23-7.38 (m, 8H), 7.44 (t, 2H), 7.53 (d, J=8.21 Hz, 2H), 7.61 (d, J=7.20 Hz, 2H), 7.87 (m, 1H), 8.01 (d, J=8.46 Hz, 1H).

EXAMPLE 3-17

1H NMR (400 MHz, DMSO-d6) δ ppm 1.08 (d, J=7.07 Hz, 3H), 1.57 (m, 1H), 1.87 (m, 1H), 2.45 (m, 1H), 2.84 (m, 2H), 3.86 (s, 3H), 4.24 (m, 1H), 7.18 (d, J=8.97 Hz, 1H), 7.28 (d, J=8.21 Hz, 2H), 7.33 (t, 1H), 7.43 (t, 2H), 7.56 (d, J=8.21 Hz, 2H), 7.63 (d, J=7.96 Hz, 2H), 7.96 (m, 1H), 8.14 (m, 1H), 8.26 (d, J=8.46 Hz, 1H), 12.04 (s, broad, 1H), 12.84 (s, broad, 1H).

EXAMPLE 3-18

1H NMR (400 MHz, DMSO-d6) δ ppm 1.10 (d, J=7.07 Hz, 3H), 1.51 (m, 1H), 1.88 (m, 1H), 2.54 (m, 1H), 2.84 (d, J=6.57 Hz, 2H), 3.90 (s, 3H), 4.24 (m, 1H), 7.20 (d, J=8.72 Hz, 1H), 7.32 (d, J=8.21 Hz, 2H), 7.34 (t, 1H), 7.45 (t, 2H), 7.60 (d, J=8.21 Hz, 2H), 7.66 (d, J=7.20 Hz, 2H), 7.98-8.07 (m, 3H).

EXAMPLE 3-19

1H NMR (400 MHz, DMSO-d6) δ ppm 1.10 (d, J=7.07 Hz, 3H), 1.64 (m, 1H), 1.97 (m, 1H), 2.45 (m, 1H), 2.92 (m, 2H), 4.34 (m, 1H), 7.31 (d, J=8.08 Hz, 2H), 7.33 (t, 1H), 7.43 (t, 2H), 7.56 (d, J=8.21 Hz, 2H), 7.63 (d, J=7.20 Hz, 2H), 8.18-8.26 (m, 3H), 9.02 (d, J=9.22 Hz, 1H).

EXAMPLE 3-20

1H NMR (400 MHz, DMSO-d6) δ ppm 1.09 (d, J=7.07 Hz, 3H), 1.60 (m, 1H), 1.89 (m, 1H), 2.45 (m, 1H), 2.87 (d, J=6.82 Hz, 2H), 4.26 (m, 1H), 7.29 (d, J=8.21 Hz, 2H), 7.33 (t, 1H), 7.44 (t, 2H), 7.57 (d, J=8.34 Hz, 2H), 7.63 (d, J=7.83 Hz, 2H), 8.02 (m, 1H), 8.06 (m, 1H), 8.32 (m, 1H), 8.57 (d, J=8.46 Hz, 1H).

EXAMPLE 3-21

1H NMR (400 MHz, DMSO-d6) δ ppm 1.04 (t, 3H), 1.34 (m, 1H), 1.77 (m, 1H), 1.88-2.01 (m, 4H), 2.37 (m, 1H), 2.64-2.77 (m, 2H), 3.13 (m, 2H), 3.94 (m, 1H), 7.23 (d, J=7.71 Hz, 2H), 7.34 (t, 1H), 7.45 (t, 2H), 7.55 (m, 2H), 7.64 (m, 3H).

EXAMPLE 3-22

1H NMR (400 MHz, DMSO-d6) δ ppm 1.06 (d, J=7.07 Hz, 3H), 1.11 (m, 1H), 1.16 (m, 1H), 1.36 (m, 1H), 1.65 (m, 1H), 1.80 (m, 1H), 2.04 (m, 1H), 2.40 (m, 1H), 2.72 (m, 2H), 3.95 (m, 1H), 7.24 (d, J=8.21 Hz, 2H), 7.34 (t, 1H), 7.45 (t, 2H), 7.57 (d, J=8.21 Hz, 2H), 7.65 (d, J=7.20 Hz, 2H), 8.15 (d, J=8.34 Hz, 1H).

EXAMPLE 3-23

1H NMR (400 MHz, DMSO-d6) δ ppm 1.06 (d, J=7.20 Hz, 3H), 1.09 (m, 2H), 1.37 (m, 1H), 1.73-1.83 (m, 2H), 2.03 (m, 1H), 2.41 (m, 1H), 2.71 (d, J=6.57 Hz, 2H), 3.96 (m, 1H), 7.24 (d, J=8.21 Hz, 2H), 7.35 (t, 1H), 7.45 (t, 2H), 7.58 (d, J=8.21 Hz, 2H), 7.65 (d, J=7.20 Hz, 2H), 8.16 (d, J=8.34 Hz, 1H).

EXAMPLE 3-24

1H NMR (400 MHz, DMSO-d6) δ ppm 1.09 (d, J=7.07 Hz, 3H), 1.62 (m, 1H), 1.91 (m, 1H), 2.45 (m, 1H), 2.88 (d, J=6.57 Hz, 2H), 4.29 (m, 1H), 7.31 (d, J=8.08 Hz, 2H), 7.34 (t, 1H), 7.45 (1, 2H), 7.58 (d, J=8.08 Hz, 2H), 7.64 (d, J=7.58 Hz, 2H), 8.63 (s, 1H), 8.67 (d, J=8.46 Hz, 1H), 9.14 (dd, J=14.02 Hz, 2H).

EXAMPLE 3-25

1H NMR (400 MHz, MeOD-d4) δ ppm 1.20 (d, J=7.07 Hz, 3H), 1.75 (m, 1H), 2.05 (m, 1H), 2.61 (m, 1H), 2.93 (m, 2H), 4.46 (m, 1H), 7.31 (m, 3H), 7.40 (t, J=7.83 Hz, 2H), 7.54 (dd, J=8.21 Hz, 8.34 Hz, 2H), 8.60 (d, J=8.46 Hz, 1H), 9.02 (m, 2H), 9.24 (m, 1H).

EXAMPLE 3-26

1H NMR (400 MHz, DMSO-d6) δ ppm 1.09 (d, J=7.07 Hz, 3H), 1.61 (m, 1H), 1.90 (m, 1H), 2.45 (m, 1H), 2.86 (d, J=6.69 Hz, 2H), 4.27 (m, 1H), 7.29 (d, J=8.21 Hz, 2H), 7.33 (t, 1H), 7.43 (1, 2H), 7.57 (d, J=8.21 Hz, 2H), 7.63 (d, J=7.20 Hz, 2H), (7.90 m, 1H), 8.38 (s, 1H), 8.74 (d, J=8.59 Hz, 1H), 8.83 (d, J=4.42 Hz, 1H).

EXAMPLE 3-27

1H NMR (400 MHz, DMSO-d6) δ ppm 1.08 (d, J=7.07 Hz, 3H), 1.71 (m, 1H), 1.91 (m, 1H), 2.43 (m, 1H), 2.83-2.99 (m, 2H), 4.33 (m, 1H), 7.29 (d, J=8.21 Hz, 2H), 7.33 (t, 1H), 7.43 (t, 2H), 7.55 (d, J=8.21 Hz, 2H), 7.62 (d, J=7.20 Hz, 2H), 8.00 (m, 1H), 8.35 (s, 1H), 8.78 (d, J=9.35 Hz, 1H), 8.86 (d, J=4.93 Hz, 1H).

EXAMPLE 3-28

1H NMR (400 MHz, DMSO-d6) δ ppm 1.09 (d, J=7.07 Hz, 3H), 1.60 (m, 1H), 1.89 (m, 1H), 2.45 (m, 1H), 2.86 (m, 2H), 4.25 (m, 1H), 7.29 (d, J=8.21 Hz, 2H), 7.33 (t, 1H), 7.43 (t, 2H), 7.56 (m, 4H), 7.64 (d, J=7.20 Hz, 2H), 7.99 (s, 1H), 8.43 (d, J=8.46 Hz, 1H).

EXAMPLE 3-29

1H NMR (400 MHz, DMSO-d6) δ ppm 1.09 (d, J=7.07 Hz, 3H), 1.59 (m, 1H), 1.89 (m, 1H), 2.45 (m, 1H), 2.85 (m, 2H), 4.26 (m, 1H), 4.55 (s, 2H), 7.29 (d, J=8.21 Hz, 2H), 7.33 (t, 1H), 7.45 (m, 3H), 7.56-7.64 (m, 7H), 8.03 (s, 1H), 8.46 (d, J=8.59 Hz, 1H).

EXAMPLE 3-30

1H NMR (400 MHz, DMSO-d6) δ ppm 1.09 (d, J=7.07 Hz, 3H), 1.59 (m, 1H), 1.88 (m, 1H), 2.45 (m, 1H), 2.85 (m, 2H), 4.25 (m, 1H), 4.82 (s, 2H), 7.29 (d, J=8.21 Hz, 2H), 7.33 (t, 1H), 7.43 (m, 3H), 7.51 (m, 1H), 7.57 (d, J=8.08 Hz, 2H), 7.58 (s, 1H), 7.63 (d, J=7.20 Hz, 2H), 8.01 (s, 1H), 8.45 (d, J=8.46 Hz, 1H).

EXAMPLE 3-31

1H NMR (400 MHz, DMSO-d6) δ ppm 1.07 (d, J=7.07 Hz, 3H), 1.60 (m, 1H), 1.86 (m, 1H), 2.41 (m, 1H), 2.77-2.88 (m, 2H), 4.19 (m, 1H), 6.82 (s, 1H), 7.27 (d, J=7.96 Hz, 2H), 7.33 (t, 1H), 7.44 (t, 2H), 7.57 (d, J=8.08 Hz, 2H), 7.65 (d, J=7.20, 2H), 8.12 (s, 1H), 8.75 (d, J=8.72, 1H).

EXAMPLE 3-32

1H NMR (400 MHz, DMSO-d6) δ ppm 1.07 (d, J=7.20 Hz, 3H), 1.72 (m, 1H), 1.91 (m, 1H), 2.42 (m, 1H), 2.85 (dd, J=7.45 Hz, 6.19 Hz, 1H), 2.96 (dd, J=7.96 Hz, 8.08 Hz, 1H), 4.32 (m, 1H), 7.30 (m, 3H), 7.43 (m, 2H), 7.54 (m, 2H), 7.62 (m, 2H), 8.33 (s, 1H), 9.03 (d, J=9.22 Hz, 1H), 9.51 (s, 1H), 12.04 (s, 1H), 14.16 (s, 1H).

EXAMPLE 3-33

1H NMR (400 MHz, DMSO-d6) δ ppm 1.06 (d, J=7.07 Hz, 3H), 1.71 (m, 1H), 1.90 (m, 1H), 2.42 (m, 1H), 2.83 (dd, J=6.06 Hz, 6.06 Hz, 1H), 2.94 (dd, J=7.83 Hz, 7.96 Hz, 1H), 4.30 (m, 1H), 7.29 (m, 3H), 7.43 (t, J=7.83 Hz, 2H), 7.54 (d, J=8.08 Hz, 2H), 7.61 (d, J=7.58 Hz, 2H), 7.94 (d, J=1.26 Hz, 1.26 Hz, 1H), 8.91 (d, J=9.35 Hz, 1H), 9.03 (d, J=5.05 Hz, 1H), 9.34 (d, J=1.14 Hz, 1H), 12.03 (s, 1H).

EXAMPLE 3-34

1H NMR (400 MHz, DMSO-d6) δ ppm 1.07 (d, J=7.07 Hz, 3H), 1.69 (m, 1H), 1.89 (m, 1H), 2.42 (m, 1H), 2.81-2.98 (m, 2H), 4.31 (m, 1H), 7.28 (d, J=8.21 Hz, 2H), 7.32 (t, 1H), 7.43 (t, 2H), 7.55 (d, J=8.34 Hz, 2H), 7.62 (d, J=7.83 Hz, 2H), 8.07 (d, J=7.45 Hz, 1H), 8.42 (m, 1H), 8.83 (d, J=9.22 Hz, 1H), 9.10 (m, 1H).

EXAMPLE 3-36

1H NMR (400 MHz, DMSO-d6) δ ppm 1.10 (d, J=7.07 Hz, 3H), 1.43 (m, 1H), 1.91 (m, 1H), 2.47 (m, 1H), 2.76-2.90 (m, 2H), 4.19 (m, 1H), 7.30 (d, J=8.08 Hz, 2H), 7.35 (t, 1H), 7.46 (t, 2H), 7.60 (d, J=8.21 Hz, 2H), 7.66 (d, J=7.20 Hz, 2H), 8.87 (d, J=8.49 Hz, 1H).

EXAMPLE 3-37

1H NMR (400 MHz, DMSO-d6) δ ppm 1.07 (d, J=7.07 Hz, 3H), 1.55 (m, 1H), 1.85 (m, 1H), 2.45 (m, 1H), 2.76-2.89 (m, 2H), 4.21 (m, 1H), 6.77 (d, J=8.72 Hz, 2H), 7.28 (d, J=8.21 Hz, 2H), 7.33 (t, 1H), 7.43 (t, 2H), 7.56 (d, J=8.34 Hz, 2H), 7.65 (d, J=7.83 Hz, 2H), 7.68 (d, J=8.84 Hz, 2H), 7.99 (d, J=8.46 Hz, 1H), 9.92 (s, broad, 1H).

EXAMPLE 3-38

1H NMR (400 MHz, DMSO-d6) δ ppm 1.08 (d, J=7.07 Hz, 3H), 1.56 (m, 1H), 1.87 (m, 1H), 2.45 (m, 1H), 2.79-2.88 (m, 2H), 4.23 (m, 1H), 7.05 (d, J=8.59 Hz, 1H), 7.28 (d, J=8.21 Hz, 2H), 7.33 (t, 1H), 7.43 (t, 2H), 7.56 (d, J=8.21 Hz, 2H), 7.63 (d, J=7.20 Hz, 2H), 7.92 (dd, 1H), 7.99 (s, 1H), 8.24 (d, J=8.46 Hz, 1H).

EXAMPLE 3-39

1H NMR (400 MHz, DMSO-d6) δ ppm 1.10 (d, J=7.07 Hz, 3H), 1.61 (m, 1H), 1.91 (m, 1H), 2.48 (m, 1H), 2.87 (d, J=6.82 Hz, 2H), 4.28 (m, 1H), 7.30 (d, J=8.21 Hz, 2H), 7.33 (t, 1H), 7.44 (t, 2H), 7.57 (d, J=8.21 Hz, 2H), 7.63 (d, J=7.20 Hz, 2H), 7.71 (t, 1H), 7.89 (d, J=8.08 Hz, 1H), 8.09 (s, 1H), 8.11 (s, 1H), 8.52 (d, J=8.46 Hz, 1H).

EXAMPLE 3-40

1H NMR (400 MHz, MeOD-d4) δ ppm 1.14 (d, J=7.07 Hz, 3H), 1.54 (m, 7H), 1.93 (m, 3H), 2.57 (m, 3H), 2.82 (d, J=7.83 Hz, 2H), 4.23 (m, 1H), 7.30 (m, 3H), 7.41 (t, J=7.83 Hz, 2H), 7.49 (m, 2H), 7.56 (m, 2H).

EXAMPLE 3-41

1H NMR (400 MHz, MeOD-d4) δ ppm 1.16 (d, J=7.07 Hz, 3H), 1.53 (m, 7H), 1.96 (m, 3H), 2.55 (m, 3H), 2.74 (dd, J=7.83 Hz, 7.71 Hz, 1H), 2.84 (dd, J=6.95 Hz, 6.06 Hz, 1H), 4.17 (m, 1H), 7.30 (m, 3H), 7.42 (t, J=7.83 Hz, 2H), 7.51 (d, J=8.21 Hz, 2H), 7.56 (m, 2H).

EXAMPLE 3-42

1H NMR (400 MHz, MeOD-d4) δ ppm 1.08 (d, J=7.07 Hz, 3H), 1.15 (d, J=7.07 Hz, 3H), 1.19 (1, J=7.07 Hz, 1H), 1.47 (m, 1H), 1.92 (m, 1H), 2.16 (dd, J=8.21 Hz, 8.21 Hz, 1H), 2.52 (dd, J=6.19 Hz, 6.32 Hz, 1H), 2.69 (dd, J=6.95 Hz, 7.83 Hz, 1H), 2.81 (m, 2H), 4.16 (m, 1H), 7.30 (m, 3H), 7.41 (m, 2H), 7.52 (m, 2H), 7.58 (m, 2H).

EXAMPLE 3-43

1H NMR (400 MHz, MeOD-d4) δ ppm 1.09 (d, J=6.95 Hz, 3H), 1.14 (d, J=7.07 Hz, 3H), 1.50 (m, 1H), 1.93 (m, 1H), 2.15 (dd, J=7.96 Hz, 7.96 Hz, 1H), 2.38 (dd, J=6.44 Hz, 6.32 Hz, 1H), 2.49 (m, 1H), 2.69 (m, 1H), 2.82 (m, 2H), 4.12 (m, 1H), 7.30 (m, 3H), 7.41 (m, 2H), 7.51 (m, 2H), 7.58 (m, 2H).

EXAMPLE 3-44

1H NMR (400 MHz, CHLOROFORM-d) δ ppm 1.19 (d, J=6.82 Hz, 3H) 1.62 (ddd, J=14.27, 11.12, 3.16 Hz, 1H) 2.05 (ddd, J=14.27, 11.12, 3.16 Hz, 1H) 2.51-2.63 (m, 1H) 2.96 (dd, J=14.20, 5.90 Hz, 2H) 4.49-4.61 (m, 1H) 6.63 (dd, J=8.10, 4.50 Hz, 1H) 6.88 (dd, J=8.20, 1.80 Hz, 1H) 7.28 (d, J=8.08 Hz, 2H) 7.43 (t, J=7.58 Hz, 2H) 7.56 (t, J=8.10 Hz, 4H) 7.75 (dt, J=8.53, 2.15 Hz, 1H).

EXAMPLE 3-45

1H NMR (400 MHz, CHLOROFORM-d) δ ppm 1.17 (d, J=6.82 Hz, 3H) 1.61-1.79 (m, 1H) 1.88-2.04 (m, 1H) 2.46-2.64 (m, 1H) 2.80-2.96 (m, 2H) 4.27-4.40 (m, 1H) 6.53-6.60 (m, 1H) 6.73 (br. s., 1H) 7.19-7.38 (m, 6H) 7.43-7.55 (m, 4H).

EXAMPLE 3-46

1H NMR (400 MHz, DMSO-d6) δ ppm 1.09 (d, J=7.07 Hz, 3H), 1.60 (m, 1H), 1.91 (m, 1H), 2.47 (m, 1H), 2.87 (d, J=6.69 Hz, 2H), 4.28 (m, 1H), 7.30 (d, J=8.08 Hz, 2H), 7.33 (t, 1H), 7.43 (t, 2H), 7.57 (d, J=8.08 Hz, 2H), 7.63 (d, J=7.83 Hz, 2H), 7.75 (t, 1H), 8.07 (d, J=8.08 Hz, 1H), 8.13 (d, J=7.83 Hz, 1H), 8.31 (s, 1H), 8.56 (d, J=8.59 Hz, 1H).

EXAMPLE 3-47

1H NMR (400 MHz, DMSO-d6) δ ppm 1.0.8 (d, J=7.07 Hz, 3H), 1.58 (m, 1H), 1.88 (m, 1H), 2.43 (m, 1H), 2.83 (m, 2H), 4.23 (m, 1H), 7.28 (d, J=8.34 Hz, 2H), 7.33 (t, 1H), 7.43 (t, 2H), 7.56 (d, J=8.08 Hz, 2H), 7.63 (d, J=8.34 Hz, 2H), 8.05-8.45 (m, broad, 1H).

EXAMPLE 3-48

1H NMR (400 MHz, DMSO-d6) δ ppm 1.08 (d, J=7.07 Hz, 3H), 1.58 (m, 1H), 1.86 (m, 1H), 2.42 (m, 1H), 2.79 (m, 1H), 2.88 (m, 1H), 4.23 (m, 1H), 6.63 (s, 1H), 7.28 (d, J=8.08 Hz, 2H), 7.33 (t, 1H), 7.43 (t, 2H), 7.56 (d, J=8.34 Hz, 2H), 7.63 (d, J=8.08 Hz, 2H), 7.73 (s, 1H), 8.01 (d, J=8.84 Hz, 1H).

EXAMPLE 3-49

1H NMR (400 MHz, MeOD) δ ppm 1.19 (d, J=7.3 Hz, 3 H), 1.67-1.77 (m, 1 H), 1.98-2.09 (m, 1 H), 2.51-2.63 (m, 4 H), 2.85-2.99 (m, 2 H), 4.35-4.49 (m, 1 H), 7.26-7.34 (m, 3 H), 7.36-7.43 (m, 2 H), 7.49-7.54 (m, 2 H), 7.54-7.59 (m, 2 H), 8.94 (d, J=9.1 Hz, 1 H).

EXAMPLE 3-50

1H NMR (400 MHz, DMSO-d6) δ ppm 1.07 (d, J=7.07 Hz, 3H), 1.49 (m, 1H), 1.86 (m, 1H), 2.45 (m, 1H), 2.80 (m, 2H), 4.18 (m, 1H), 7.27 (d, J=8.34 Hz, 2H), 7.33 (t, 1H), 7.43 (t, 2H), 7.56 (d, J=8.34 Hz, 2H), 7.63 (d, J=8.08 Hz, 2H), 7.81 (d, J=8.59 Hz, 1H), 8.00 (s, broad, 2H).

EXAMPLE 3-51

1H NMR (400 MHz, MeOD-d4): δ ppm 1.17-1.19 (d, J=7.07 Hz, 3H), 1.59-1.66 (m, 1H), 1.96-2.03 (m, 1H), 2.54-2.60 (m, 1H), 2.86-2.95 (m, 2H), 4.32-4.37 (m, 1H), 6.14-6.16 (m, 1H), 6.79-6.81 (dd, J=1.26 Hz, 1.52 Hz, 1H), 6.88-6.89 (m, 1H), 7.25-7.32 (m, 3H), 7.38-7.42 (m, 2H), 7.50-7.52 (m, 2H), 7.55-7.58 (m, 2H).

EXAMPLE 3-52

1H NMR (400 MHz, MeOD-d4): δ ppm 1.17-1.19 (d, J=7.07 Hz, 3H), 1.61-1.68 (m, 1H), 1.97-2.04 (m, 1H), 2.51-

2.60 (m, 1H), 2.91-2.93 (d, J=6.82 Hz, 2H), 4.32-4.39 (m, 1H), 6.68-6.69 (d, J=3.79 Hz, 1H), 6.77-6.78 (d, J=3.79 Hz, 1H), 7.27-7.32 (m, 3H), 7.38-7.42 (m, 2H), 7.51-7.53 (m, 2H), 7.57-7.59 (m, 2H).

EXAMPLE 3-53

1H NMR (400 MHz, DMSO-d6) δ ppm 1.07 (d, J=7.07 Hz, 3H), 1.49-1.56 (m, 1H), 1.83-1.90 (m, 1H), 2.41-2.51 (m, 1H), 2.80 (A of AB, J=14.5 Hz, 1H), 2.81 (B of AB, J=14.5 Hz, 1H) 4.14-4.23 (m, 1H), 7.27 (d, J=8.3 Hz, 2H), 7.31-7.35 (m, 1H) 7.42-7.46 (m, 2H), 7.57 (d, J=8.3 Hz, 2H), 7.63-7.65 (m, 2H) 8.08 (d, J=8.59 Hz, 1H) 8.65 (br s, 2H) 12.04 (br s, 1H).

EXAMPLE 3-54

1H NMR (400 MHz, DMSO-d6) δ ppm 1.08 (d, J=7.07 Hz, 3H), 1.65 (m, 1H), 1.87 (m, 1H), 2.41 (m, 1H), 2.78-2.94 (m, 2H), 4.26 (m, 1H), 7.28 (d, J=8.34 Hz, 2H), 7.33 (t, 1H), 7.43 (t, 2H), 7.56 (d, J=8.34 Hz, 2H), 7.63 (d, J=7.07 Hz, 2H), 8.09 (s, broad, 0.35H), 8.33 (s, broad, 0.5H), 8.61-8.81 (m, 2H), 12.04 (s, broad, 1h), 14.42 (s, broad, 0.45H), 14.88 (s, broad, 0.35H).

EXAMPLE 3-55

1H NMR (400 MHz, MeOD) δ ppm 1.19 (d, J=6.32 Hz, 3H) 1.63-1.76 (m, 1H) 1.95-2.08 (m, 1H) 2.50-2.65 (m, 1H) 2.83-2.97 (m, 2H) 4.31-4.46 (m, 1H) 6.51 (d, J=9.09 Hz, 1H) 7.27-7.33 (m, 3H) 7.40 (t, J=7.71 Hz, 2H) 7.52 (d, J=7.58 Hz, 2H) 7.57 (d, J=7.58 Hz, 2H) 7.88-7.96 (m, 2H).

EXAMPLE 3-56

1H NMR (400 MHz, ACETONITRILE-d3) δ ppm 1.17 (d, J=6.95 Hz, 3H) 1.74 (ddd, J=14.24, 10.77, 3.66 Hz, 1H) 2.13-2.23 (m, 1H) 2.58-2.69 (m, 1H) 2.97-3.02 (m, 2H) 4.40-4.51 (m, 1H) 7.22 (d, J=9.09 Hz, 1H) 7.33-7.48 (m, 5H) 7.56-7.64 (m, 4H) 7.85 (br. s., 1H).

EXAMPLE 3-57

1H NMR (400 MHz, ACETONITRILE-d3) δ ppm 1.09 (d, J=7.07 Hz, 3H) 1.64-1.69 (m, 2H) 2.43-2.50 (m, 1H) 2.86-2.93 (m, 2H) 4.20-4.35 (m, 1H) 6.88 (d, J=1.01 Hz, 1H) 7.25-7.34 (m, 4H) 7.38-7.44 (m, 2H) 7.50-7.54 (m, 2H) 7.56-7.61 (m, 2H) 8.04 (d, J=1.01 Hz, 1H).

EXAMPLE 3-58

1H NMR (400 MHz, DMSO-d6) δ ppm 1.08 (d, J=7.07 Hz, 3H), 1.61 (m, 1H), 1.89 (m, 1H), 2.44 (m, 1H), 2.79-2.93 (m, 2H), 4.24 (m, 1H), 7.27 (d, J=8.34 Hz, 2H), 7.30 (s, 2H), 7.33 (t, 1H), 7.44 (t, 2H), 7.55 (d, J=8.08 Hz, 2H), 7.63 (d, J=7.33 Hz, 2H), 8.37 (d, J=9.35 Hz, 1H).

EXAMPLE 3-59

1H NMR (400 MHz, DMSO-d6) δ ppm 1.09 (d, J=7.07 Hz, 3H), 1.56 (m, 1H), 1.92 (m, 1H), 2.08 (s, 1H), 2.45 (m, 1H), 2.84 (d, J=6.82 Hz, 2H), 4.24 (m, 1H), 7.29 (d, J=8.34 Hz, 2H), 7.34 (1, 1H), 7.44 (t, 2H), 7.56 (d, J=8.34 Hz, 2H), 7.63 (d, J=8.34 Hz, 2H), 8.01 (s, 1H), 8.42 (d, J=8.59 Hz, 1H), 8.79 (s, broad, 1H).

EXAMPLE 3-60

1H NMR (400 MHz, DMSO-d6): 1H NMR (400 MHz, DMSO-d6): δ ppm 1.06-1.08 (d, J=7.07 Hz, 3H), 1.58-1.65 (m, 1H), 1.82-1.89 (m, 1H), 2.38-2.45 (m, 1H), 2.77-2.82 (m, 1H), 2.89-2.94 (m, 1H), 4.21-4.30 (m, 1H), 7.26-7.28 (m, 2H), 7.30-7.35 (m, 1H), 7.41-7.45 (m, 2H), 7.54-7.56 (m, 2H), 7.62-7.64 (m, 2H), 7.67 (s, 1H), 7.89-7.91 (d, J=9.09 Hz, 1H), 12.01 (s, 1H).

EXAMPLE 3-61

1H NMR (400 MHz, DMSO-d6): δ ppm 1.06-1.07 (d, J=7.07 Hz, 3H), 1.45-1.52 (m, 1H), 1.79-1.86 (m, 1H), 2.41-2.47 (m, 1H), 2.73-2.86 (m, 2H), 4.12-4.21 (m, 1H), 6.45-6.46 (q, J=2.53 Hz, 4.29 Hz, 1H), 6.71-6.73 (q, J=2.27 Hz, 4.45 Hz, 1H), 7.27-7.34 (m, 4H), 7.41-7.45 (m, 2H), 7.52-7.57 (m, 3H), 7.62-7.64 (m, 2H), 11.09 (s, 1H), 12.07 (s, 1H).

EXAMPLE 3-62

1H NMR (400 MHz, DMSO-d6) δ ppm 1.07 (d, 3H) 1.62 (ddd, J=13.89, 9.85, 4.55 Hz, 1H) 1.86 (ddd, J=13.77, 9.47, 4.04 Hz, 1H) 2.41 (ddd, J=9.35, 7.07, 4.55 Hz, 1H) 2.73-2.96 (m, 2H) 4.16-4.31 (m, 1H) 7.27 (d, J=8.08 Hz, 2H) 7.30-7.37 (m, 1H) 7.44 (t, J=7.71 Hz, 2H) 7.56 (d, J=8.34 Hz, 2H) 7.60-7.69 (m, 2H) 8.15 (d, J=9.09 Hz, 1H) 8.51 (d, J=1.01 Hz, 1H) 8.54 (d, J=1.01 Hz, 1H).

EXAMPLE 3-63

1H NMR (400 MHz, DMSO-d6) δ ppm 1.08 (d, J=7.07 Hz, 3H), 1.57 (m, 1H), 1.87 (m, 1H), 2.43 (m, 1H), 2.76-2.87 (m, 2H), 4.21 (m, 1H), 7.27 (d, J=8.34 Hz, 2H), 7.33 (t, 1H), 7.44 (t, 2H), 7.57 (d, J=8.34 Hz, 2H), 7.65 (d, J=7.07 Hz, 2H), 7.72 (s, 1H), 8.45 (d, J=8.59 Hz, 1H), 8.54 (s, 1H).

EXAMPLE 3-64

1H NMR (400 MHz, DMSO-d6) δ ppm 1.05 (d, J=7.33 Hz, 3H) 1.58 (ddd, J=13.89, 9.73, 4.17 Hz, 1H) 1.84 (ddd, J=13.71, 9.66, 3.92 Hz, 1H) 2.29-2.47 (m, 1H) 2.67 (dt, J=3.73, 1.80 Hz, 0H) 2.77-2.94 (m, 2H) 4.19 (d, J=6.06 Hz, 1H) 7.02 (d, J=1.77 Hz, 1H) 7.28 (d, J=8.08 Hz, 2H) 7.30-7.37 (m, 1H) 7.40-7.47 (m, 2H) 7.57 (d, J=8.08 Hz, 2H) 7.61-7.67 (m, 1H) 8.71 (d, J=2.02 Hz, 1H).

EXAMPLE 3-65

1H NMR (400 MHz, DMSO-d6) δ ppm 1.07 (d, J=7.07 Hz, 3H), 1.58 (m, 1H), 1.87 (m, 1H), 2.41 (m, 1H), 2.77-2.87 (m, 2H), 4.17 (m, 1H), 6.50 (s, 1H), 7.27 (d, J=8.34 Hz, 2H), 7.33 (s, 2H), 7.33 (t, 1H), 7.44 (t, 2H), 7.57 (d, J=8.34 Hz, 2H), 7.64 (d, J=8.08 Hz, 2H), 8.66 (d, J=8.84 Hz, 1H), 11.66 (s, broad, 1H).

EXAMPLE 3-66

1H NMR (400 MHz, DMSO-d6) δ ppm 1.06 (d, J=7.07 Hz, 3H) 1.59 (ddd, J=14.02, 9.98, 4.55 Hz, 1H) 1.84 (ddd, J=13.64, 9.60, 4.04 Hz, 1H) 2.30-2.47 (m, 1H) 2.67-2.82 (m, 1H) 2.89 (dd, J=13.64, 7.58 Hz, 1H) 3.89 (s, 3H) 4.23 (dd, J=9.60, 7.07 Hz, 1H) 6.55 (d, J=2.27 Hz, 1H) 7.21-7.39 (m, 3H) 7.37-7.48 (m, 2H) 7.56 (d, J=8.34 Hz, 2H) 7.60-7.68 (m, 2H) 7.74 (d, J=2.27 Hz, 1H) 7.92 (d, J=8.84 Hz, 1H).

EXAMPLE 3-67

1H NMR (400 MHz, DMSO-d6) δ ppm 1.09 (d, J=7.07 Hz, 3H), 1.57 (m, 1H), 1.87 (m, 1H), 2.46 (m, 1H), 2.81 (d, J=6.82 Hz, 2H), 4.00 (s, 3H), 4.20 (m, 1H), 7.29 (d, J=8.34 Hz, 2H), 7.30 (s, 1H), 7.34 (t, 1H), 7.44 (t, 2H), 7.58 (d, J=8.08 Hz, 2H), 7.64 (d, J=7.07 Hz, 2H), 8.38 (d, J=8.59 Hz, 1H).

EXAMPLE 3-68

1H NMR (400 MHz, DMSO-d6) δ ppm 1.07 (d, J=7.07 Hz, 3H), 1.60 (m, 1H), 1.85 (m, 1H), 2.41 (m, 1H), 2.75-2.91 (m, 2H), 4.13 (s, 3H), 4.24 (m, 1H), 7.10 (s, 1H), 7.27 (d, J=8.08 Hz, 2H), 7.33 (t, 1H), 7.44 (t, 2H), 7.56 (d, J=8.34 Hz, 2H), 7.64 (d, J=7.07 Hz, 2H), 8.14 (d, J=9.09 Hz, 1H).

EXAMPLE 3-69

1H NMR (400 MHz, DMSO-d6): δ ppm 1.08-1.10 (d, J=7.07 Hz, 3H), 1.53-1.60 (m, 1H), 1.83-1.90 (m, 1H), 2.43-2.47 (m, 1H), 2.80-2.81 (d, J=7.07 Hz, 2H), 3.94 (s, 3H), 4.16-4.24 (m, 1H), 6.59-6.60 (d, J=4.04 Hz, 1H), 6.77-6.78 (d, J=4.04 Hz, 1H), 7.28-7.30 (d, J=8.08 Hz, 2H), 7.31-7.35 (m, 1H), 7.42-7.46 (m, 2H), 7.56-7.58 (d, J=8.34 Hz, 2H), 7.61-7.64 (m, 4H), 8.12-8.14 (d, J=8.84 Hz, 1H), 12.05 (s, 1H), 12.52 (s, 1H)

EXAMPLE 3-70

1H NMR (400 MHz, DMSO-d6) δ ppm 1.08 (d, 3H) 1.42-1.61 (m, 1H) 1.86 (ddd, J=13.64, 9.47, 4.17 Hz, 1H) 2.35-2.46 (m, 2H) 2.75-2.86 (m, 2H) 4.18 (d, J=9.09 Hz, 1H) 5.95 (br. s., 1H) 7.27 (d, J=8.34 Hz, 2H) 7.30-7.37 (m, 1H) 7.40-7.48 (m, 2H) 7.56 (d, J=8.08 Hz, 2H) 7.60-7.67 (m, 2H) 7.97 (d, J=8.59 Hz, 1H).

EXAMPLE 3-71

1H NMR (400 MHz, DMSO-d6) δ ppm 1.07 (d, J=7.07 Hz, 3H) 1.56-1.70 (m, 1H) 1.79-1.92 (m, 1H) 2.36-2.45 (m, 1H) 2.74-2.96 (m, 2H) 4.15-4.29 (m, 1H) 6.90-6.97 (m, 1H) 7.27 (d, J=8.34 Hz, 2H) 7.30-7.37 (m, 1H) 7.44 (s, 2H) 7.56 (d, J=8.34 Hz, 2H) 7.63 (s, 2H) 7.75 (d, J=9.85 Hz, 1H) 8.24-8.34 (m, 1H) 12.03 (br. s., 1H).

EXAMPLE 3-72

1H NMR (400 MHz, DMSO-d6): 1H NMR (400 MHz, DMSO-d6): δ ppm 1.06-1.08 (d, J=7.07 Hz, 3H), 1.53-1.60 (m, 1H), 1.83-1.89 (m, 1H), 2.41-2.46 (m, 1H), 2.78-2.88 (m, 2H), 4.20-4.27 (m, 1H), 6.99-7.01 (d, J=8.84 Hz, 1H), 7.27-7.29 (d, J=8.08 Hz, 2H), 7.30-7.34 (m, 1H), 7.41-7.46 (m, 2H), 7.54-7.56 (m, 2H), 7.61-7.63 (m, 2H), 7.94-7.97 (dd, J=2.27 Hz, 1H), 8.25-8.27 (d, J=8.34 Hz, 1H), 8.31-8.32 (d, J=2.27 Hz, 1H), 11.66 (s, 1H), 12.02 (s, 1H).

EXAMPLE 3-73

1H NMR (400 MHz, MeOD-d4) δ ppm 1.19-1.21 (d, J=7.33 Hz, 3H), 1.73-1.81 (m, 1H), 2.04-2.13 (m, 1H), 2.59-2.63 (m, 1H), 2.98-3.00 (d, J=6.82 Hz, 2H), 4.49-4.53 (m, 1H), 7.27-7.41 (m, 6H), 7.49-7.51 (m, 2H), 7.55-7.57 (m, 2H), 8.18-8.19 (d, J=4.80 Hz, 1H), 9.17-9.18 (d, J=4.80 Hz, 1H).

EXAMPLE 3-74

1H NMR (400 MHz, DMSO-d6): 1H NMR (400 MHz, DMSO-d6): δ ppm 1.07-1.09 (d, J=7.07 Hz, 3H), 1.65-1.72 (m, 1H), 1.90-1.97 (m, 1H), 2.41-2.47 (m, 1H), 2.86-2.95 (m, 2H), 4.28-4.37 (m, 1H), 7.29-7.34 (m, 3H), 7.41-7.45 (t, J=7.83 Hz, 2H), 7.55-7.57 (m, 2H), 7.61-7.64 (m, 2H), 8.07-8.08 (d, J=5.05 Hz, 1H), 8.94-8.96 (d, J=9.09 Hz, 1H), 9.18-9.19 (d, J=5.05 Hz, 1H), 12.06 (s, 1H), 13.58 (s, 1H).

EXAMPLE 3-75

1H NMR (400 MHz, DMSO-d6) δ ppm 1.07 (d, 4H) 1.51-1.69 (m, 1H) 1.87 (ddd, J=13.83, 9.66, 4.04 Hz, 1H) 2.43 (ddd, J=9.54, 7.14, 4.55 Hz, 2H) 2.74-2.92 (m, 2H) 4.12-4.29 (m, 1H) 6.42 (dd, J=5.81, 2.53 Hz, 1H) 6.73 (d, J=2.78 Hz, 1H) 7.27 (d, J=8.34 Hz, 2H) 7.30-7.39 (m, 1H) 7.39-7.49 (m, 2H) 7.58 (d, J=8.34 Hz, 2H) 7.61-7.70 (m, 2H) 8.22 (d, J=5.81 Hz, 1H) 8.78 (d, J=8.84 Hz, 1H) 12.07 (br. s., 1H).

EXAMPLE 3-76

1H NMR (600 MHz, DMSO-$d_6$) δ ppm 1.07 (d, J=7.06 Hz, 3H) 1.62 (s, 1H) 1.84 (s, 1H) 2.74-2.81 (m, 1H) 2.89 (s, 1H) 4.20 (br. s., 1H) 6.71 (d, J=7.43 Hz, 1H) 6.91 (d, J=7.52 Hz, 1H) 7.26 (d, J=8.16 Hz, 2H) 7.30-7.36 (m, 1H) 7.44 (s, 2H) 7.57 (d, J=7.98 Hz, 2H) 7.64 (s, 2H) 8.38 (s, 1H) 10.77 (s, 1H).

EXAMPLE 3-77

1H NMR (400 MHz, DMSO-d6): δ ppm 1.06-1.07 (d, J=7.07 Hz, 3H), 1.63-1.70 (m, 1H), 1.82-1.89 (m, 1H), 2.32-2.40 (m, 1H), 2.77-2.82 (m, 1H), 2.88-2.94 (m, 1H), 4.16-4.25 (m, 1H), 6.76 (s, 1H), 7.25-7.27 (d, J=8.08 Hz, 2H), 7.31-7.35 (m, 1H), 7.41-7.45 (t, J=7.83 Hz, 2H), 7.55-7.57 (d, J=8.34 Hz, 2H), 7.62-7.65 (m, 2H), 8.10 (s, 1H), 8.63-8.65 (d, J=9.35 Hz, 1H), 12.03 (s, 1H), 12.34 (s, 1H).

EXAMPLE 3-78

1H NMR (400 MHz, DMSO-d6) δ ppm 1.09 (d, J=7.07 Hz, 3H) 1.61 (ddd, J=14.02, 10.11, 4.42 Hz, 1H) 1.90 (ddd, J=13.71, 9.66, 3.92 Hz, 1H) 2.86 (d, J=6.32 Hz, 2H) 4.23-4.32 (m, 2H) 7.30 (d, J=8.34 Hz, 2H) 7.32-7.36 (m, 1H) 7.40-7.47 (m, 2H) 7.57 (d, J=8.08 Hz, 2H) 7.60-7.67 (m, 2H) 7.96 (d, J=8.08 Hz, 1H) 8.18 (dd, J=7.96, 1.39 Hz, 1H) 8.33 (s, 1H) 8.64 (d, J=8.59 Hz, 1H).

EXAMPLE 3-79

1H NMR (400 MHz, MeOD-d4): δ ppm 1.16-1.18 (d, J=7.07 Hz, 3H), 1.71-1.78 (m, 1H), 2.00-2.07 (m, 1H), 2.52-2.59 (m, 1H), 2.92-2.94 (m, 2H), 4.36-4.44 (m, 1H), 7.27-7.32 (m, 3H), 7.37-7.41 (m, 2H), 7.50-7.58 (m, 5H), 8.61-8.63 (d, J=9.53, 1H).

EXAMPLE 3-80

1H NMR (400 MHz, DMSO-d6): δ ppm 1.05-1.07 (d, J=7.07 Hz, 3H), 1.51-1.59 (m, 1H), 1.81-1.89 (m, 1H), 2.38-2.45 (m, 1H), 2.77-2.89 (m, 2H), 4.16-4.22 (m, 1H), 4.53 (s, 2H), 5.77 (s, 1H), 7.26-7.28 (m, 2H), 7.31-7.35 (m, 1H), 7.42-7.46 (m, 2H), 7.56-7.58 (m, 2H), 7.63-7.66 (m, 3H).

EXAMPLE 3-81

1H NMR (400 MHz, DMSO-d6) δ ppm 1.08 (d, J=7.07 Hz, 3H), 1.57 (m, 1H), 1.88 (m, 1H), 2.45 (m, 1H), 2.79-2.89 (m, 2H), 4.23 (m, 1H), 7.17 (d, J=8.59 Hz, 1H), 7.28 (d, J=8.08 Hz, 2H), 7.33 (t, 1H), 7.44 (t, 2H), 7.57 (d, J=8.34 Hz, 2H), 7.63 (d, J=7.33 Hz, 2H), 7.98 (dd, J=8.59 and 2.27, 1H), 8.34 (d, J=8.59 Hz, 1H), 8.38 (d, J=2.27 Hz, 1H), 11.57 (s, broad, 1H).

EXAMPLE 3-83

1H NMR (400 MHz, DMSO-d6) δ ppm 1.08 (d, J=7.07 Hz, 3H) 1.34-1.46 (m, 1H) 1.86 (ddd, J=13.64, 9.60, 4.04 Hz, 2H) 1.91-2.06 (m, 2H) 2.26-2.36 (m, 1H) 2.43 (td, J=4.74, 2.65 Hz, 1H) 2.70 (dd, J=13.39, 7.33 Hz, 1H) 2.75-2.85 (m, 1H) 3.04 (d, J=10.36 Hz, 1H) 3.82 (d, J=15.41 Hz, 1H) 3.96-4.10 (m, 2H) 4.23 (br. s., 1H) 7.27 (d, J=8.34 Hz, 2H) 7.35 (t, J=7.33 Hz, 1H) 7.46 (t, J=7.58 Hz, 2H) 7.58 (d, J=8.08 Hz, 2H) 7.61-7.67 (m, 2H) 8.36 (d, J=8.59 Hz, 1H).

EXAMPLE 3-84

1H NMR (400 MHz, DMSO-$d_6$) δ ppm 1.07 (d, J=7.1 Hz, 3H), 1.33-1.44 (m, 1H), 1.78-1.87 (m, 1H), 2.39-2.47 (m, 1H), 2.73 (d, J=7.3 Hz, 2H), 3.84 (s, 2H), 3.91-4.01 (m, 1H), 7.23 (d, J=8.3 Hz, 2H), 7.30-7.38 (m, 1H), 7.45 (t, J=7.7 Hz, 2H), 7.54 (d, J=8.1 Hz, 2H), 7.64 (dd, J=8.2, 1.1 Hz, 2H), 8.24 (d, J=8.3 Hz, 1H), 12.02 (br. s., 1H).

EXAMPLE 3-85

1H NMR (400 MHz, DMSO-$d_6$) δ ppm 1.08 (d, J=7.1 Hz, 3H), 1.67-1.80 (m, 1H), 1.86-1.97 (m, 1H), 2.37-2.47 (m, 1H), 2.86 (dd, J=13.6, 6.1 Hz, 1H), 2.97 (dd, J=13.6, 7.8 Hz, 1H), 4.26-4.39 (m, 1H), 7.26-7.36 (m, 3H), 7.42 (t, J=7.6 Hz, 2H), 7.54 (d, J=8.1 Hz, 2H), 7.61 (d, J=7.3 Hz, 2H), 8.26 (s, 1H), 9.11 (d, J=9.3 Hz, 1H), 9.60 (s, 1H), 12.01 (br. s., 1H).

EXAMPLE 3-86

1H NMR (400 MHz, ACETONITRILE-$d_3$) δ ppm 1.04 (d, J=6.8 Hz, 3H), 1.56 (ddd, J=14.1, 10.7, 3.7 Hz, 1H), 2.38-2.54 (m, 1H), 2.68-2.87 (m, 3H), 4.18-4.35 (m, 1H), 6.88 (d, J=8.8 Hz, 1H), 7.23 (d, J=8.3 Hz, 2H), 7.26 (dt, J=7.4, 1.6 Hz, 1H), 7.30-7.39 (m, 2H), 7.46 (d, J=8.1 Hz, 2H), 7.49-7.55 (m, 2H), 7.97 (d, J=2.3 Hz, 1H), 8.08 (d, J=1.5 Hz, 1H).

EXAMPLE 3-87

1H NMR (400 MHz, DMSO-$d_6$) δ ppm 1.07 (d, J=7.3 Hz, 3H), 1.44 (ddd, J=13.9, 9.9, 4.6 Hz, 1H), 1.85 (ddd, J=13.6, 9.4, 4.0 Hz, 1H), 2.42 (ddd, J=9.3, 7.1, 4.6 Hz, 1H), 2.78 (d, J=6.6 Hz, 2H), 4.02-4.19 (m, 1H), 7.00 (t, J=2.2 Hz, 1H), 7.26 (s, 1H), 7.33 (t, J=7.3 Hz, 1H), 7.44 (t, J=7.7 Hz, 2H), 7.50-7.61 (m, 3H), 7.61-7.71 (m, 2H), 10.11 (s, 1H), 10.22 (br. s., 1H), 12.03 (br. s., 1H).

EXAMPLE 3-89

1H NMR (400 MHz, DMSO-$d_6$) δ ppm 1.08 (d, J=7.1 Hz, 3H), 1.48 (ddd, J=14.0, 10.0, 4.6 Hz, 1H), 1.87 (ddd, J=13.8, 9.6, 4.2 Hz, 1H), 2.43 (ddd, J=9.4, 7.0, 4.6 Hz, 1H), 2.72-2.87 (m, 2H), 3.98-4.22 (m, 1H), 7.27 (m, J=8.1 Hz, 2H), 7.34 (t, J=7.3 Hz, 1H), 7.39-7.50 (m, 2H), 7.58 (m, J=8.3 Hz, 2H), 7.61-7.71 (m, 3H), 8.06 (d, J=8.6 Hz, 1H), 11.12 (s, 1H), 12.04 (br. s., 1H).

EXAMPLE 3-90

1H NMR (400 MHz, CD$_3$OD) δ ppm 1.17 (d, J=7.3 Hz, 3H), 1.63 (ddd, J=14.2, 10.3, 4.0 Hz, 1H), 1.98 (ddd, J=13.9, 9.9, 3.8 Hz, 1H), 2.54 (ddd, J=9.7, 7.1, 4.2 Hz, 1H), 2.86 (d, J=6.8 Hz, 2H), 4.22-4.39 (m, 1H), 7.23-7.34 (m, 3H), 7.34-7.44 (m, 3H), 7.47-7.54 (m, 2H), 7.54-7.61 (m, 2H), 7.90 (d, J=8.6 Hz, 1H).

EXAMPLE 3-91

1H NMR (400 MHz, CD$_3$OD) δ ppm 1.18 (d, J=7.1 Hz, 3H), 1.68 (ddd, J=14.2, 10.4, 4.2 Hz, 1H), 1.99 (ddd, J=14.0, 10.0, 3.8 Hz, 1H), 2.46-2.61 (m, 1H), 2.88 (dd, 2H), 4.28-4.42 (m, 1H), 7.24-7.33 (m, 3H), 7.40 (t, J=7.7 Hz, 2H), 7.52 (d, J=8.3 Hz, 2H), 7.57 (dd, J=8.3, 1.3 Hz, 2H).

EXAMPLE 3-92

1H NMR (400 MHz, ACETONITRILE-$d_3$) δ ppm 1.06 (d, J=7.1 Hz, 3H) 1.55 (ddd, J=14.2, 10.5, 3.9 Hz, 1H) 1.86-1.92 (m, 1H) 2.57 (m, 1H) 2.73-2.90 (m, 2H) 4.21-4.37 (m, 1H) 6.84 (dd, J=8.5, 5.4 Hz, 1H) 6.91 (ddd, J=10.7, 8.5, 6.1 Hz, 1H) 7.21-7.26 (m, 2H) 7.31-7.38 (m, 2H) 7.47 (d, J=8.1 Hz, 2H) 7.52 (d, J=7.1 Hz, 2H)

EXAMPLE 3-93

1H NMR (400 MHz, CD$_3$OD) δ ppm 1.12 (d, J=7.1 Hz, 3H) 1.49 (ddd, J=14.0, 10.0, 4.0 Hz, 1H) 1.99 (ddd, J=13.9, 10.2, 3.7 Hz, 1H) 2.43 (ddd, J=10.6, 6.9, 4.0 Hz, 1H) 2.86 (dd, J=13.6, 5.8 Hz, 1H) 2.94 (dd, J=13.6, 5.8 Hz, 1H) 4.24-4.50 (m, 1H) 7.25-7.34 (m, 3H) 7.35-7.41 (m, 2H) 7.47 (d, J=8.3 Hz, 2H) 7.52-7.57 (m, 2H)

EXAMPLE 3-94

1H NMR (400 MHz, DMSO-$d_6$) δ ppm 1.08 (d, J=7.3 Hz, 3H) 1.53 (ddd, J=13.9, 9.9, 4.6 Hz, 1H) 1.87 (ddd, J=13.7, 9.3, 4.0 Hz, 1H) 2.42 (ddd, J=9.2, 7.1, 4.7 Hz, 1H) 2.75-2.90 (m, 2H) 4.13-4.23 (m, 1H) 5.95 (s, 1H) 7.27 (d, J=8.3 Hz, 2H) 7.29-7.36 (m, 1H) 7.38-7.47 (m, 2H) 7.56 (d, J=8.3 Hz, 2H) 7.61-7.69 (m, 2H) 7.94 (d, J=8.6 Hz, 1H).

EXAMPLE 3-95

1H NMR (400 MHz, CD$_3$OD) δ ppm 1.18 (d, J=7.1 Hz, 3H) 1.64-1.75 (m, 1H) 2.00 (ddd, J=14.0, 10.0, 3.8 Hz, 1H) 2.48-2.63 (m, 1H) 2.86-2.91 (m, 2H) 4.30-4.40 (m, 1H) 7.25-7.33 (m, 4H) 7.37-7.43 (m, 3H) 7.52 (d, J=8.3 Hz, 2H) 7.55-7.60 (m, 2H)

EXAMPLE 3-96

1H NMR (400 MHz, DMSO-$d_6$) δ ppm 1.07 (d, J=7.1 Hz, 3H) 1.47-1.61 (m, 1H) 1.75-1.88 (m, 1H) 2.31-2.45 (m, 1H) 2.75 (dd, J=13.4, 7.6 Hz, 1H) 2.83 (dd, J=13.4, 7.6 Hz, 1H) 4.06-4.24 (m, 1H) 7.26 (d, J=8.1 Hz, 2H) 7.30-7.37 (m, 1H)

7.44 (t, J=7.7 Hz, 2H) 7.51 (d, J=2.5 Hz, 1H) 7.57 (d, J=8.3 Hz, 2H) 7.61-7.71 (m, 2H) 8.09 (d, J=8.8 Hz, 1H) 11.24 (s, 1H) 12.03 (br. s., 1H).

EXAMPLE 4-1

Synthesis of (2R,4S)-5-biphenyl-4-yl-4-((2S,3S)-2,3-diacetoxy-3-carboxy-propionylamino)-2-methyl-pentanoic acid

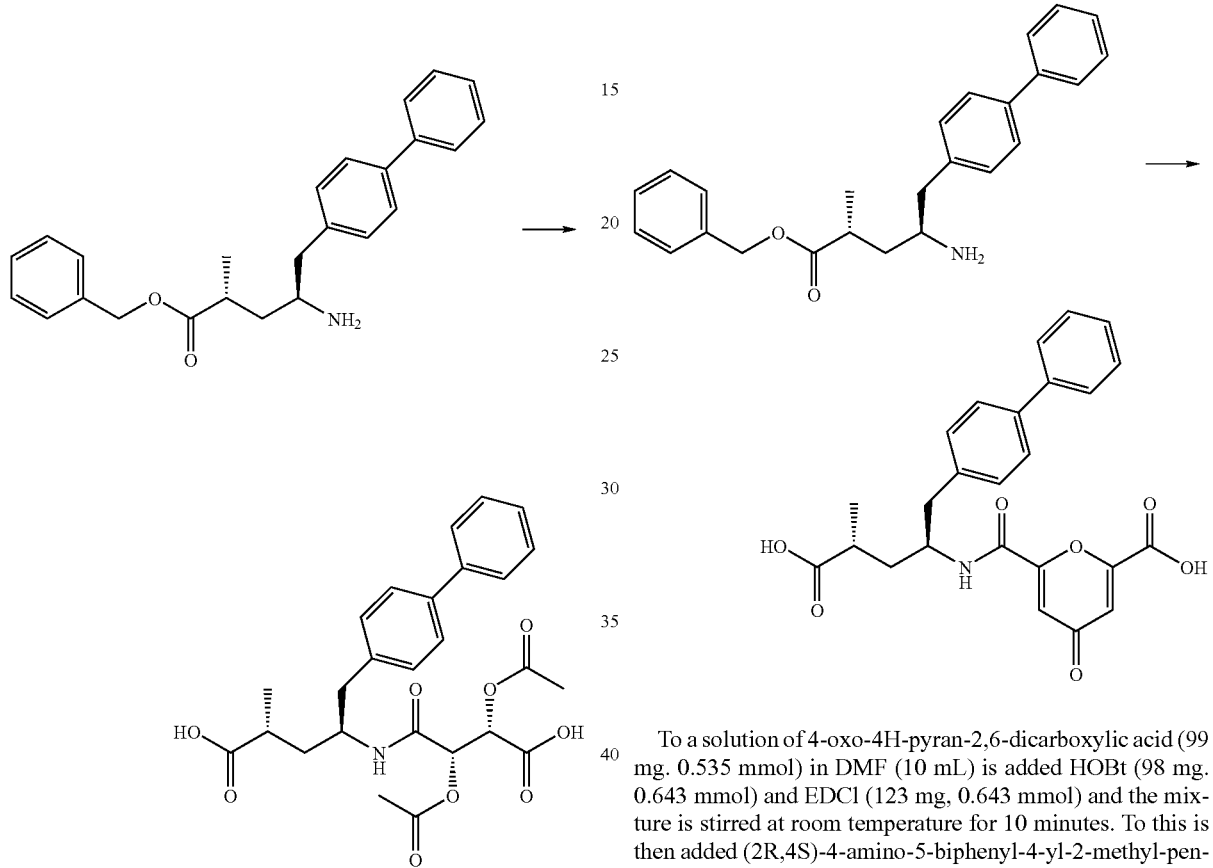

A solution of (2R,4S)-4-amino-5-biphenyl-4-yl-2-methyl-pentanoic acid benzyl ester hydrochloride (100 mg, 0.287 mmol) and acetic acid (3S,4S)-4-acetoxy-2,5-dioxo-tetrahydro-furan-3-yl ester (0.431 mmol) in 1:1 methylene chloride/pyridine (1.4 mL) is stirred at room temperature for 24 hours. The solvents are removed under reduced pressure and obtained residue is used directly in the subsequent hydrolysis reaction.

Next, a solution of the benzyl ester in ethyl acetate is hydrogenated at 1 atm over 10% Pd/C for 18 hours. Methanol is added and the catalyst is filtered through Celite. The Solvent is removed under reduced pressure and the residue is purified by preparative HPLC using a gradient of 10-100% MeCN/water (0.1% TFA). The proper fractions are lyophilized to furnish (2R,4S)-5-biphenyl-4-yl-4-((2S,3S)-2,3-diacetoxy-3-carboxy-propionylamino)-2-methyl-pentanoic acid. HPLC Retention time 0.95 minutes (condition A); MS 500.3 (M+1); 1H NMR (400 MHz, DMSO-d6) δ ppm 1.09 (d, J=7.20 Hz, 3H), 1.45 (m, 1H), 1.82 (m, 1H), 2.39 (m, 1H), 2.70 (d, J=6.82 Hz, 2H), 4.01 (m, 1H), 5.38 (m, 2H), 7.19 (d, J=8.21 Hz, 2H), 7.34 (t, 1H), 7.45 (t, 2H), 7.53 (d, J=8.21 Hz, 2H), 7.64 (d, J=7.20 Hz, 2H), 8.00 (d, J=8.72 Hz, 1H).

EXAMPLE 5-1

Synthesis of 6-((1S,3R)-1-biphenyl-4-ylmethyl-3-carboxy-butylcarbamoyl)-4-oxo-4H-pyran-2-carboxylic acid To a solution of 4-oxo-4H-pyran-2,6-dicarboxylic acid (99 mg, 0.535 mmol) in DMF (10 mL) is added HOBt (98 mg, 0.643 mmol) and EDCl (123 mg, 0.643 mmol) and the mixture is stirred at room temperature for 10 minutes. To this is then added (2R,4S)-4-amino-5-biphenyl-4-yl-2-methyl-pentanoic acid benzyl ester hydrochloride (200 mg, 0.535 mmol) and triethylamine (0.224 mL, 1.61 mmol) and the mixture is stirred at room temperature for 48 hours. Water is added and the mixture is extracted with ethyl acetate. The organic phase is washed with water and brine and is dried over magnesium sulfate. The solvent is removed under reduced pressure and the residue is purified by preparative HPLC using a gradient of 10-100% MeCN/water (0.1% TFA) to elute the product, 6-((1S,3R)-3-benzyloxycarbonyl-1-biphenyl-4-ylmethyl-butylcarbamoyl)-4-oxo-4H-pyran-2-carboxylic acid. MS 540.2 (M+1).

Next, to a solution of 6-((1S,3R)-3-benzyloxycarbonyl-1-biphenyl-4-ylmethyl-butylcarbamoyl)-4-oxo-4H-pyran-2-carboxylic acid (100 mg, 0.185 mmol) in methylene chloride (5 mL) is added BCl₃ (65.1 mg, 0.556 mmol) and the mixture is stirred at room temperature for 10 minutes. The mixture is acidified to pH 2-3 with aqueous 1M HCl and is extracted with ethyl acetate. The organic phase is washed with water and brine and is dried over magnesium sulfate. The solvent is removed under reduced pressure and the residue is purified by preparative HPLC using a gradient of 10-100% MeCN/water (0.1% TFA) to elute the product. The proper fractions are lyophilized to furnish 6-((1S,3R)-1-biphenyl-4-ylmethyl-3- carboxy-butylcarbamoyl)-4-oxo-4H-pyran-2-carboxylic acid. MS 450.1 (M+1); $^1$H-NMR (400 Hz, DMSO-d6); δ ppm 1.07 (d, J=7.07 Hz, 3H), 1.59 (m, 1H), 1.88 (m, 1H), 2.45 (m, 1H), 2.84 (d, J=6.69 Hz, 2H), 4.19 (m, 1H), 6.84 (s, 1H), 6.93 (s, 1H), 7.32 (dd, J=8.08 Hz, 6.57 Hz, 3H), 7.45 (t, J=7.83 Hz, 2H), 7.58 (d, J=8.21 Hz, 2H), 7.64 (d, J=7.33 Hz, 2H), 8.61 (d, J=8.72 Hz, 1H).

EXAMPLE 6-1

Synthesis of (S)-1-((1S,3R)-1-biphenyl-4-ylmethyl-3-carboxy-butylcarbamoyl)-pyrrolidine-2-carboxylic acid

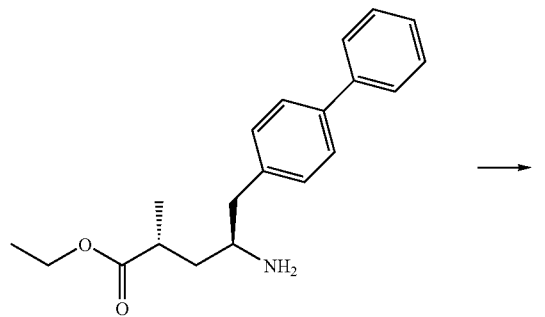

To a vigorously stirred 1:1 mixture of methylene chloride/ 8% aqueous NaHCO$_3$ (30 mL) at 0° C. is added triphosgene (114 mg, 0.384 mmol). After stirring the mixture at 0° C. for 5 minutes, (2R,4S)-4-amino-5-biphenyl-4-yl-2-methyl-pentanoic acid ethyl ester hydrochloride (400 mg, 1.15 mmol) is added and stirring is continued for 15 minutes. The organic phase is separated and dried over sodium sulfate. The solvent is removed under reduced pressure to furnish (2R,4S)-5-biphenyl-4-yl-4-isocyanato-2-methyl-pentanoic acid ethyl ester.

Next, to a solution of (2R,4S)-5-biphenyl-4-yl-4-isocyanato-2-methyl-pentanoic acid ethyl ester (1.15 mmol) in methylene chloride (10 mL) is added (S)-pyrrolidine-2-carboxylic acid methyl ester (1.15 mmol) and diisopropylethylamine (2.3 mmol). The mixture is stirred at room temperature for 18 hours. The mixture is washed with aqueous 1M HCl and the organic phase is dried over sodium sulfate and the solvent is removed under reduced pressure. The residue is purified by column chromatography using hexane/methylene chloride to elute the product.

Next, to a solution of the obtained residue (0.287 mmol) in ethanol (10 mL) is added aqueous 1M NaOH (2 mL, 6.97 mmol) and the mixture is stirred at room temperature for 18 hours. The mixture is poured into ethyl acetate and is washed with aqueous 1M HCl, the organic phase is dried over magnesium sulfate and the solvent is removed under reduced pressure. The residue is purified by preparative HPLC using a gradient of MeCN/water (0.1% TFA). The proper fractions are lyophilized to furnish (S)-1-((1S,3R)-1-biphenyl-4-ylmethyl-3-carboxy-butylcarbamoyl)-pyrrolidine-2-carboxylic acid. HPLC Retention time 0.97 minutes (condition A); MS 425.3 (M+1); 1H NMR (400 MHz, DMSO-d6) δ ppm 1.03 (d, J=7.07 Hz, 3H), 1.43 (m, 1H), 1.71 (m, 1H), 1.86 (m, 3H), 2.09 (m, 1H), 2.45 (m, 1H), 2.66-2.83 (m, 2H), 3.84 (m, 1H), 6.00 (d, J=8.21 Hz, 1H), 7.27 (d, J=8.08 Hz, 2H), 7.34 (t, 1H), 7.45 (t, 2H), 7.57 (d, J=8.21 Hz, 2H), 7.65 (d, J=7.20, 2H).

Following compounds are prepared using similar procedure as example 6-1 with appropriate reagents and conditions:

| Example # | Product | Reagent | Hydrolysis Condition | HPLC-RT (condition) | MS (M + 1) |
|---|---|---|---|---|---|
| Example 6-2 | 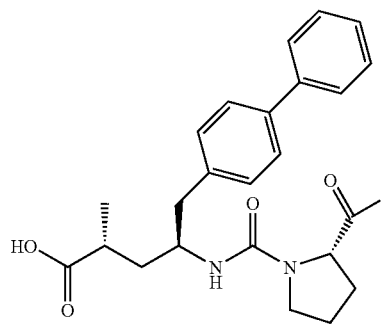<br>(2R,4S)-5-biphenyl-4-yl-4-(3-carboxymethyl-3-methyl-ureido)-2-methyl-pentanoic acid | Triethylamine instead of diisopropylethylamine | Aq. NaOH, EtOH, RT | 0.94 min. (A) | 399.3 |

-continued

| Example # | Product | Reagent | Hydrolysis Condition | HPLC-RT (condition) | MS (M + 1) |
|---|---|---|---|---|---|
| Example 6-3 | 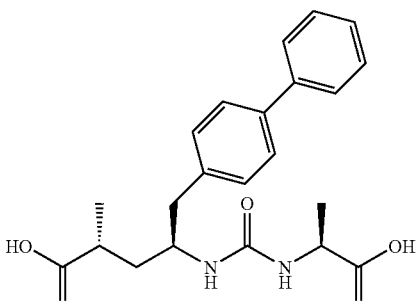<br>(2R,4S)-5-biphenyl-4-yl-4-[3-((S)-1-carboxy-ethyl)-ureido]-2-methyl-pentanoic acid | 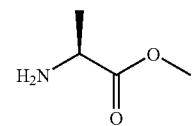 | Aq. NaOH, EtOH, RT | 0.98 min. (A) | 399.3 |
| Example 6-4 | 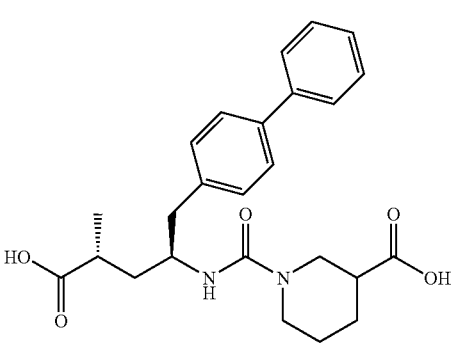<br>1-((1S,3R)-1-biphenyl-4-ylmethyl-3-carboxy-butylcarbamoyl)-piperidine-3-carboxylic acid | 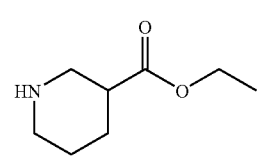 | Aq. NaOH, EtOH, RT | 1.15 min. (A) | 439.3 |
| Example 6-5 | 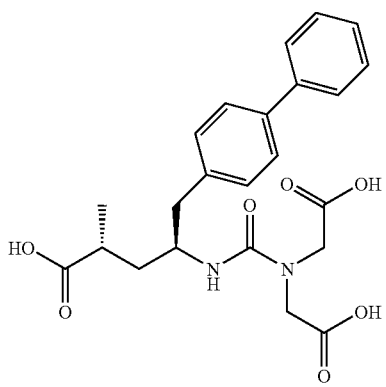<br>(2R,4S)-5-biphenyl-4-yl-4-(3,3-bis-carboxymethyl-ureido)-2-methyl-pentanoic acid | 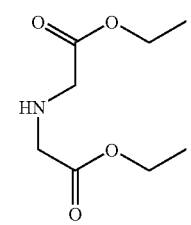 | Aq. NaOH, EtOH, RT | 0.90 min. (A) | 443.3 |

| Example # | Product | Reagent | Hydrolysis Condition | HPLC-RT (condition) | MS (M + 1) |
|---|---|---|---|---|---|
| Example 6-6 | 1-((1S,3R)-1-biphenyl-4-ylmethyl-3-carboxy-butylcarbamoyl)-pyrrolidine-3-carboxylic acid | | Aq. NaOH, EtOH, RT | 0.98 min. (A) | 425.3 |
| Example 6-7 | (R)-1-((1S,3R)-1-biphenyl-4-ylmethyl-3-carboxy-butylcarbamoyl)-pyrrolidine-3-carboxylic acid | | Aq. NaOH, EtOH, 50° C. | 1.16 min. (A) | 425.2 |
| Example 6-8 | (S)-1-((1S,3R)-1-biphenyl-4-ylmethyl-3-carboxy-butylcarbamoyl)-pyrrolidine-3-carboxylic acid | | Aq. NaOH, EtOH, 50° C. | 1.17 min. (A) | 425.2 |

EXAMPLE 6-2

1H NMR (400 MHz, DMSO-d6) δ ppm 1.02 (d, J=6.95 Hz, 3H), 1.43 (m, 1H), 1.70 (m, 1H), 2.45 (m, 1H), 2.66 (m, 1H), 2.78 (m, 2H), 2.79 (s, 2H), 3.81 (m, 3H), 7.26 (d, J=8.08 Hz, 2H), 7.34 (t, 1H), 7.45 (t, 2H), 7.56 (d, J=8.21 Hz, 2H), 7.65 (d, J=7.20 Hz, 2H).

EXAMPLE 6-3

1H NMR (400 MHz, DMSO-d6) δ ppm 1.06 (d, J=7.07 Hz, 3H), 1.20 (d, J=7.20, 3H), 1.27 (m, 1H), 1.76 (m, 1H), 2.45 (m, 1H), 2.71 (m, 2H), 3.77 (m, 1H), 4.06 (m, 1H), 5.99 (d, J=8.46 Hz, 1H), 6.07 (d, J=7.83 Hz, 1H), 7.25 (d, J=8.21 Hz, 2H), 7.34 (t, 1H), 7.45 (t, 2H), 7.57 (d, J=8.21 Hz, 2H), 7.65 (d, J=7.20, 2H).

EXAMPLE 6-4

1H NMR (400 MHz, DMSO-d6) δ ppm 1.05 (d, J=7.07 Hz, 3H), 1.22 (m, 1H), 1.39-1.58 (m, 3H), 1.74 (m, 1H), 1.89 (m, 1H), 2.18 (m, 1H), 2.43 (m, 1H), 2.62-2.77 (m, 4H), 3.79 (t, 1H), 3.89 (m, 1H), 4.01 (m, 1H), 6.28 (d, J=8.34 Hz, 1H), 7.25 (d, J=7.83 Hz, 2H), 7.34 (t, 1H), 7.44 (t, 2H), 7.56 (d, J=8.34 Hz, 2H), 7.64 (d, J=7.20 Hz, 2H).

EXAMPLE 6-5

1H NMR (400 MHz, DMSO-d6) δ ppm 1.03 (d, J=7.07 Hz, 3H), 1.36 (m, 1H), 1.71 (m, 1H), 2.41 (m, 1H), 2.63-2.78 (m, 2H), 3.83 (m, 1H), 3.96 (m, 4H), 6.33 (d, J=7.96 Hz, 1H), 7.25 (d, J=8.21 Hz, 2H), 7.34 (t, 1H), 7.45 (t, 2H), 7.55 (d, J=8.21 Hz, 2H), 7.65 (d, J=7.20 Hz, 2H).

EXAMPLE 6-6

1H NMR (400 MHz, DMSO-d6) δ ppm 1.04 (d, J=7.07 Hz, 3H), 1.44 (m, 1H), 1.73 (m, 1H), 1.91-2.08 (m, 2H), 2.45 (m, 1H), 2.64-2.81 (m, 2H), 3.03 (m, 1H), 3.20 (m, 1H), 3.26-3.46 (m, 3H), 3.84 (m, 1H), 5.94 (d, J=8.46 Hz, 1H), 7.25 (d, J=8.21 Hz, 2H), 7.34 (t, 1H), 7.45 (t, 2H), 7.57 (d, J=7.96 Hz, 2H), 7.65 (d, J=7.20 Hz, 2H).

EXAMPLE 6-7

1H NMR (400 MHz, DMSO-d6) δ ppm 1.04 (d, J=6.95 Hz, 3H), 1.44 (m, 1H), 1.73 (m, 1H), 1.91-2.08 (m, 2H), 2.45 (m, 1H), 2.64-2.81 (m, 2H), 3.02 (m, 1H), 3.20 (m, 1H), 3.26-3.44 (m, 4H), 3.84 (m, 1H), 5.94 (d, J=8.46 Hz, 1H), 7.25 (d, J=8.08 Hz, 2H), 7.34 (t, 1H), 7.45 (t, 2H), 7.57 (d, J=8.21 Hz, 2H), 7.65 (d, J=7.20 Hz, 2H).

EXAMPLE 6-8

1H NMR (400 MHz, DMSO-d6) δ ppm 1.04 (d, J=7.07 Hz, 3H), 1.45 (m, 1H), 1.73 (m, 1H), 1.91-2.06 (m, 2H), 2.45 (m, 1H), 2.64-2.81 (m, 2H), 3.02 (m, 1H), 3.20 (m, 1H), 3.27-3.46 (m, 4H), 3.84 (m, 1H), 5.94 (d, J=8.46 Hz, 1H), 7.25 (d, J=8.21 Hz, 2H), 7.34 (t, 1H), 7.45 (t, 2H), 7.57 (d, J=8.21 Hz, 2H), 7.65 (d, J=7.20 Hz, 2H).

EXAMPLE 7-1

Synthesis of (2R,4S)-5-biphenyl-4-yl-4-(3-carboxymethyl-ureido)-2-methyl-pentanoic acid

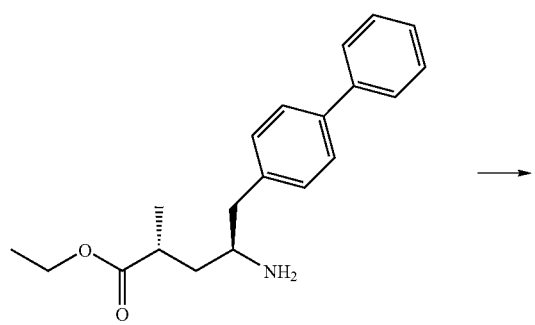

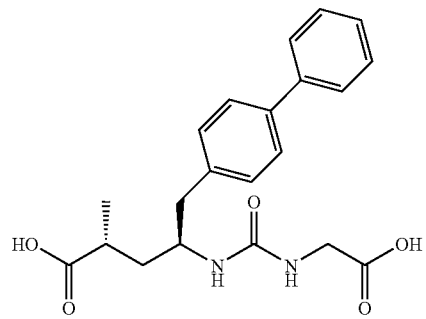

To a mixture of (2R,4S)-4-amino-5-biphenyl-4-yl-2-methyl-pentanoic acid ethyl ester hydrochloride (50 mg, 0.161 mmol) and Isocyanato-acetic acid ethyl ester (0.161 mmol) in DMF (8 mL) is added pyridine (0.161 mmol) and the mixture is stirred at room temperature for 18 hours. Water is added and the mixture is extracted with ethyl acetate (3×). The combined organic layers are washed with water and brine then is dried over magnesium sulfate. The solvent is removed under reduced pressure to afford the ester product. This is used in the subsequent hydrolysis reaction.

Next, to a solution of the obtained residue (0.287 mmol) in ethanol (10 mL) is added aqueous 1M NaOH (2 mL, 6.97 mmol) and the mixture is stirred at room temperature for 18 hours.

The mixture is poured into ethyl acetate and is washed with aqueous 1M HCl, the organic phase is dried over magnesium sulfate and the solvent is removed under reduced pressure. The residue is purified by preparative HPLC using a gradient of MeCN/water (0.1% TFA). The proper fractions are lyophilized to furnish (S)-1-((1S,3R)-1-biphenyl-4-ylmethyl-3-carboxy-butylcarbamoyl)-pyrrolidine-2-carboxylic acid. HPLC Retention time 0.91 minutes (condition A); MS 385.4 (M+1); 1H NMR (400 MHz, MeOD-d4) δ ppm 1.15 (d, J=7.20 Hz, 3H), 1.40 (m, 1H), 1.91 (m, 1H), 2.60 (m, 1H), 2.81 (d, J=6.32 Hz, 2H), 3.85 (d, J=1.89 Hz, 2H), 4.00 (m, 1H), 7.32 (m, 3H), 7.42 (m, 2H), 7.53 (m, 2H), 7.59 (m, 2H).

Following compounds are prepared using similar procedure as example 7-1 with appropriate reagents and conditions:

| Example # | Product | Reagent | Hydrolysis Condition | HPLC-RT (condition) | MS (M + 1) |
|---|---|---|---|---|---|
| Example 7-2 | 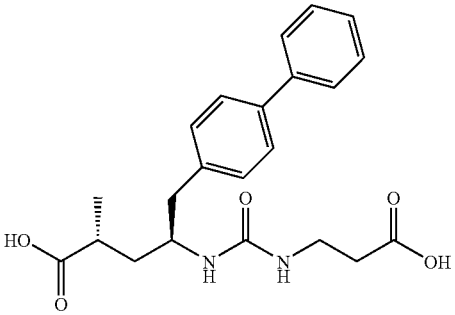<br>(2R,4S)-5-biphenyl-4-yl-4-[3-(2-carboxy-ethyl)-ureido]-2-methyl-pentanoic acid | 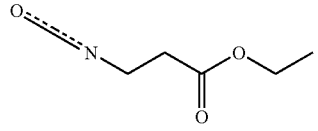 | Aq. NaOH, EtOH, RT | 0.98 min. (A) | 399.4 |

EXAMPLE 7-2

1H NMR (400 MHz, MeOD-d4) δ ppm 1.14 (d, J=7.07 Hz, 3H), 1.40 (m, 1H), 1.88 (m, 1H), 2.39 (t, J=6.44 Hz, 2H), 2.55 (m, 1H), 2.79 (m, 2H), 3.34 (m, 2H), 3.96 (m, 1H), 7.28 (m, 3H), 7.41 (m, 2H), 7.51 (m, 2H), 7.58 (m, 2H).

EXAMPLE 8-1

Synthesis of (2R,4S)-5-biphenyl-4-yl-4-[3-((R)-1-carboxy-ethyl)-ureido]-2-methyl-pentanoic acid

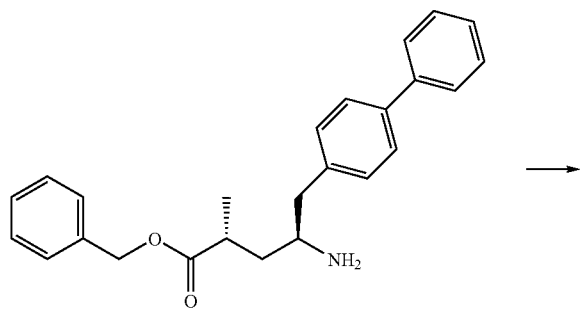

→

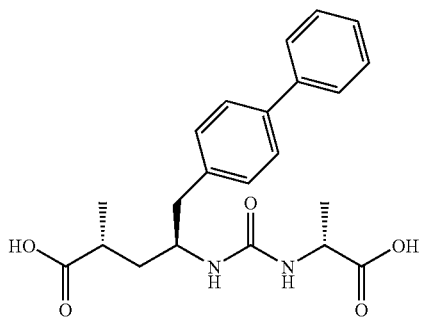

To a vigorously stirred 1:1 mixture of methylene chloride/8% aqueous NaHCO₃ (30 mL) at 0° C. is added triphosgene. After stirring the mixture at 0° C. for 5 minutes, (2R,4S)-4-amino-5-biphenyl-4-yl-2-methyl-pentanoic acid ethyl ester hydrochloride (400 mg, 1.15 mmol) is added and stirring is continued for 15 minutes. The organic phase is separated and dried over sodium sulfate. The solvent is removed under reduced pressure to furnish (2R,4S)-5-biphenyl-4-yl-4-isocyanato-2-methyl-pentanoic acid ethyl ester.

Next, to a solution of (2R,4S)-5-biphenyl-4-yl-4-isocyanato-2-methyl-pentanoic acid ethyl ester (1.15 mmol) in methylene chloride (10 mL) is added (R)-2-amino-propionic acid benzyl ester (1.15 mmol) and diisopropylethylamine (2.3 mmol). The mixture is stirred at room temperature for 18 hours. The mixture is washed with aqueous 1M HCl and the organic phase is dried over sodium sulfate and the solvent is removed under reduced pressure. The residue is purified by column chromatography using hexane/methylene chloride to elute the product.

Next, a solution of the benzyl ester in ethyl acetate is hydrogenated at 1 atm over 10% Pd/C for 18 hours. Methanol is added and the catalyst is filtered through Celite. The Solvent is removed under reduced pressure and the residue is purified by preparative HPLC using a gradient of 10-100% MeCN/water (0.1% TFA). The proper fractions are lyophilized to furnish (2R,4S)-5-biphenyl-4-yl-4-[3-((R)-1-carboxy-ethyl)-ureido]-2-methyl-pentanoic acid. HPLC Retention time 0.94 minutes (condition A); MS 399.3 (M+1); 1H NMR (400 MHz, DMSO-d6) δ ppm 1.03 (d, J=7.20 Hz, 3H), 1.23 (d, J=7.20, 3H), 1.26 (m, 1H), 1.74 (m, 1H), 2.43 (m, 1H), 2.71 (d, J=6.19 Hz, 2H), 3.78 (m, 1H), 4.08 (m, 1H), 5.98

(d, J=8.34 Hz, 1H), 6.07 (d, broad, J=6.44 Hz, 1H), 7.26 (d, J=8.21 Hz, 2H), 7.34 (t, 1H), 7.45 (t, 2H), 7.57 (d, J=8.21 Hz, 2H), 7.65 (d, J=7.20, 2H).

EXAMPLE 9-1

Synthesis of 1-((1S,3R)-1-biphenyl-4-ylmethyl-3-carboxy-butylcarbamoyl)-1H-pyrazole-3-carboxylic acid

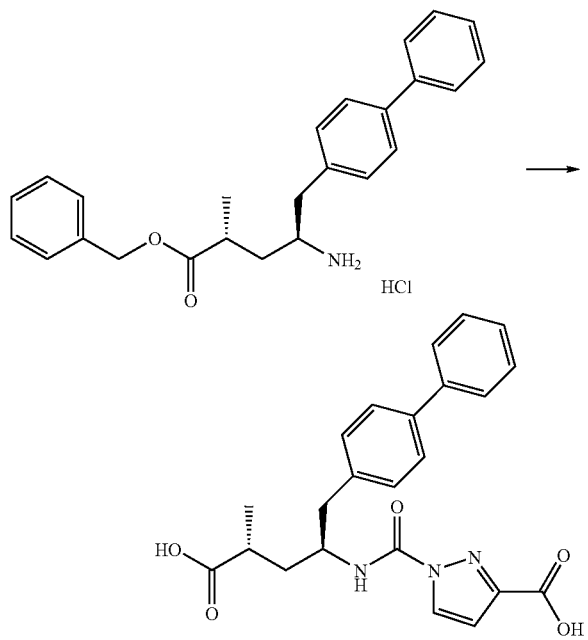

To a vigorously stirred 1:1 mixture of methylene chloride/8% aqueous NaHCO₃ (6 mL) at 0° C. is added triphosgene (18 mg, 0.061 mmol). After stirring the mixture at 0° C. for 5 minutes, (2R,4S)-4-amino-5-biphenyl-4-yl-2-methyl-pentanoic acid benzyl ester hydrochloride (75 mg, 0.183 mmol) is added and stirring is continued for 15 minutes. The organic phase is separated and dried over sodium sulfate. The solvent is removed under reduced pressure to furnish (2R,4S)-5-biphenyl-4-yl-4-isocyanato-2-methyl-pentanoic acid benzyl ester.

Next, to a solution of 1H-pyrazole-3-carboxylic acid (20.5 mg, 0.183 mmol) in DMF (1 mL) is added diisopropylethylamine (0.032 mL, 0.183 mmol). After 15 min a solution of the above (2R,4S)-5-biphenyl-4-yl-4-isocyanato-2-methyl-pentanoic acid benzyl ester in DMF (1 mL) is added dropwise and the mixture is stirred at room temperature for 18 hours. The mixture is purified by preparative HPLC using a gradient of 10% MeCN to 100% MeCN (0.1% TFA). Lyophilization of the appropriate fractions furnishes 1-((1S,3R)-3-benzyloxycarbonyl-1-biphenyl-4-ylmethyl-butylcarbamoyl)-1H-pyrazole-3-carboxylic acid.

Next, a solution of 1-((1S,3R)-3-benzyloxycarbonyl-1-biphenyl-4-ylmethyl-butylcarbamoyl)-1H-pyrazole-3-carboxylic acid (60 mg, 0.117 mmol) in EtOAc (10 mL) is hydrogenated over 10% Pd/C (40 mg) at 1 atm for 5 hours. The catalyst is filtered through Celite and the filtrate evaporated under reduced pressure. The residue is purified by preparative HPLC using a gradient of 10% MeCN to 100% MeCN (0.1% TFA). Lyophilization of the appropriate fractions furnishes 1-((1S,3R)-1-biphenyl-4-ylmethyl-3-carboxy-butylcarbamoyl)-1H-pyrazole-3-carboxylic acid.

HPLC Retention time 0.96 minutes (condition A); MS 422.0 (M+1); 1H NMR (400 MHz, DMSO-d6) δ ppm 1.09 (d, J=7.07 Hz, 3H), 1.78 (m, 1H), 1.88 (m, 1H), 2.45 (m, 1H), 2.86 (m, 1H), 2.98 (m, 1H), 4.14 (m, 1H), 6.84 (d, J=2.65 Hz, 1H), 7.28 (d, J=8.34 Hz, 2H), 7.33 (t, 1H), 7.43 (t, 2H), 7.56 (d, J=8.34 Hz, 2H), 7.63 (d, J=7.07 Hz, 2H), 8.29 (d, J=2.78 Hz, 1H), 8.58 (d, J=9.09 Hz, 1H).

Following compounds are prepared using similar procedure as example 9-1 with appropriate reagents and conditions:

| Example # | Product | Reagent | Hydrolysis Condition | HPLC-RT (condition) | MS (M + 1) |
|---|---|---|---|---|---|
| Example 9-2 | ![structure] 1-((1S,3R)-1-Biphenyl-4-ylmethyl-3-carboxy-butylcarbamoyl)-1H-pyrazole-4-carboxylic acid | 1H-pyrazole-4-carboxylic acid used in place of 1H-pyrazole-3-carboxylic acid | 10% Pd/C, 1 atm, H2, EtOAc | 1.32 min. (A) | 422.2 |

EXAMPLE 9-2

1H NMR (400 MHz, DMSO-d6) δ ppm 1.08 (d, J=7.07 Hz, 3H), 1.73 (m, 1H), 1.89 (m, 1H), 2.44 (m, 1H), 2.84 (m, 1H), 2.96 (m, 1H), 4.11 (m, 1H), 7.28 (d, J=8.34 Hz, 2H), 7.33 (t, 1H), 7.43 (t, 2H), 7.56 (d, J=8.08 Hz, 2H), 7.63 (d, J=7.07 Hz, 2H), 8.10 (s, 1H), 8.52 (s, 1H), 8.68 (d, J=9.09 Hz, 1H).

EXAMPLE 10-1

(2R,4S)-5-biphenyl-4-yl-4-[(5-carbamoyl-thiophene-2-carbonyl)-amino]-2-methyl-pentanoic acid

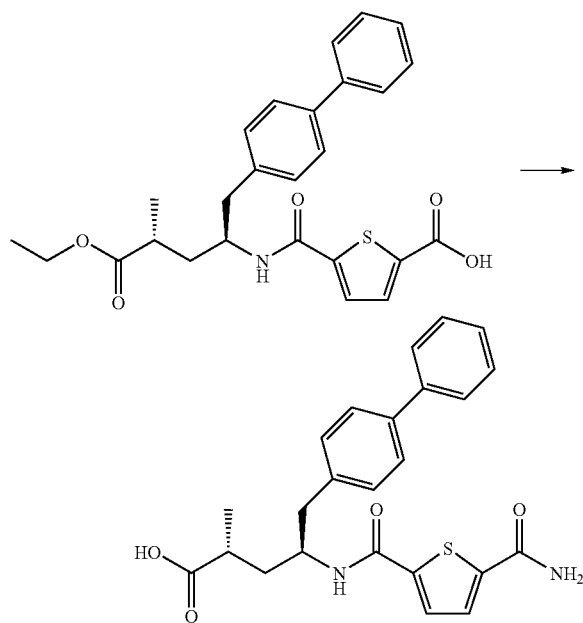

To a solution of 5-((1S,3R)-1-biphenyl-4-ylmethyl-3-ethoxycarbonyl-butylcarbamoyl)-thiophene-2-carboxylic acid (115 mg, 0.247 mmol) in THF (1 mL) at 0° C. is added diisopropylethylamine (63.8 mg, 0.494 mmol) followed by dropwise addition of a solution of isobutyl chloroformate (33.7 mg, 0.247 mmol) in THF (0.1 mL). The mixture is stirred at 0° C. for 30 minutes then ammonium hydroxide (0.3 mL of 14.8 M solution) is added. The mixture is allowed to warm to room temperature then aqueous 1M HCl (3 mL) is added. Most of the THF is removed under reduced pressure and the mixture is extracted with ethyl acetate. The organic phase is dried over sodium sulfate and the solvent is removed under reduced pressure to give (2R,4S)-5-biphenyl-4-yl-4-[(5-carbamoyl-thiophene-2-carbonyl)-amino]-2-methyl-pentanoic acid ethyl ester. MS 465.3 (M+1).

Next, to a solution of (2R,4S)-5-biphenyl-4-yl-4-[(5-carbamoyl-thiophene-2-carbonyl)-amino]-2-methyl-pentanoic acid ethyl ester (115 mg, 0.248 mmol) in ethanol (8 mL) is added aqueous 1M NaOH (0.866 mL, 0.866 mmol) and the mixture is stirred at 50° C. for 3.5 hours. The ethanol is removed under reduced pressure and water is added to the residue. The resulting solution is acidified with aqueous 1M HCl and the resulting precipitate is filtered and washed with water. The solid is purified by preparative HPLC using 50% MeCN/water to elute the product. The appropriate fractions are lyophilized to give (2R,4S)-5-biphenyl-4-yl-4-[(5-carbamoyl-thiophene-2-carbonyl)-amino]-2-methyl-pentanoic acid. MS 437.2 (M+1); $^1$H-NMR (400 MHz, DMSO-d6); δ ppm 1.09 (d, J=7.20 Hz, 3H), 1.57 (m, 1H), 1.88 (m, 1H), 2.46 (m, 1H), 2.84 (m, 2H), 4.18 (m, 1H), 7.28 (d, J=8.21 Hz, 1H), 7.33 (t, 1H), 7.44 (t, 1H), 7.57 (d, J=8.21 Hz, 2H), 7.64 (d, J=7.33, 2H), 7.69 (m, 2H), 8.06 (s, 1H), 8.38 (d, J=8.59 Hz, 1H), 12.07 (s, broad, 1H).

EXAMPLE 11-1

Synthesis of (2R,4S)-5-biphenyl-4-yl-2-methyl-4-(3-1H-tetrazol-5-yl-propionylamino)-pentanoic acid

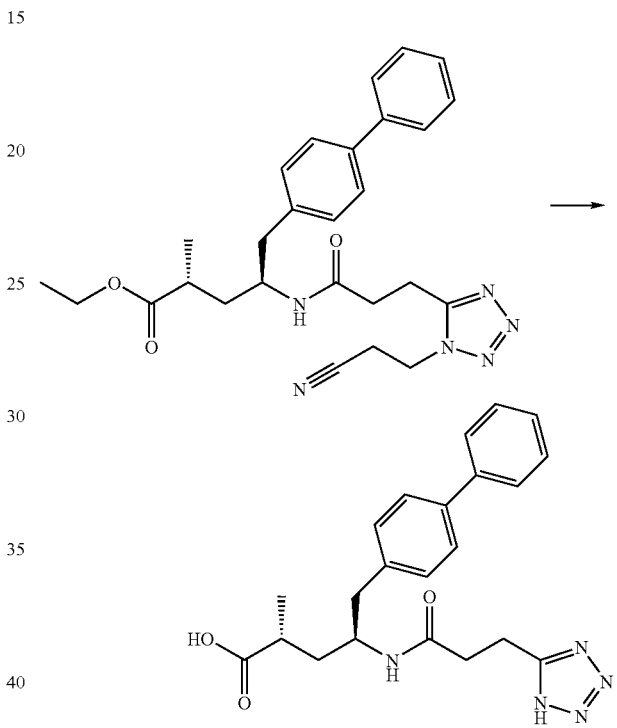

To a solution of (2R,4S)-5-Biphenyl-4-yl-4-{3-[1-(2-cyano-ethyl)-1H-tetrazol-5-yl]-propionylamino}-2-methyl-pentanoic acid ethyl ester (32 mg, 0.065 mmol) in dichloromethane (1 mL) is added DBU (24 mg, 0.164 mmol). After stirring for 3 hours, additional DBU (24 mg, 0.146 mmol) is added. After stirring for 2 hours, the reaction mixture is diluted with dichloromethane and washed with saturated aqueous NH$_4$Cl. The organic layer is dried over Na$_2$SO$_4$ and concentrated. The residue is dissolved in MeOH and treated with aqueous 2M NaOH. After stirring for 1 hours, the reaction mixture is diluted with ethyl acetate and acidified with aqueous 1M HCl. The mixture is extracted with ethyl acetate and washed with brine. The organic layer is dried over Na$_2$SO$_4$ and concentrated. The residue is purified by reverse phase HPLC (0.1% TFA-H2O/MeCN) to give (2R,4S)-5-biphenyl-4-yl-2-methyl-4-(3-1H-tetrazol-5-yl-propionylamino)-pentanoic acid (14 mg). HPLC Retention time 1.17 minutes (condition C); MS 408.0 (M+1); 1H NMR (400 MHz, DMSO-d6) δ ppm 1.03 (d, J=7.07 Hz, 3H), 1.34 (ddd, J=4.80, 10.11, 14.91 Hz, 1H), 1.78 (ddd, J=4.04, 9.60, 13.64 Hz, 1H), 2.31-2.42 (m, 1H), 2.52-2.59 (m, 2H), 2.68 (d, J=7.07 Hz, 2H), 3.03 (dd, J=7.58, 7.58 Hz, 2H), 3.90-4.01 (m, 1H), 7.20 (d, J=8.08 Hz, 2H), 7.34 (t, J=9.09 Hz, 1H), 7.45 (d, J=7.83 Hz, 2H), 7.55 (d, J=8.34 Hz, 2H), 7.64 (d, J=7.33 Hz, 2H), 7.84 (d, J=8.34 Hz, 1H), 11.99 (bs, 1H).

EXAMPLE 12-1

Synthesis of (2S,4S)-5-biphenyl-4-yl-4-((S)-3-carboxy-3-cyclohexyl-propionylamino)-2-methyl-pentanoic acid

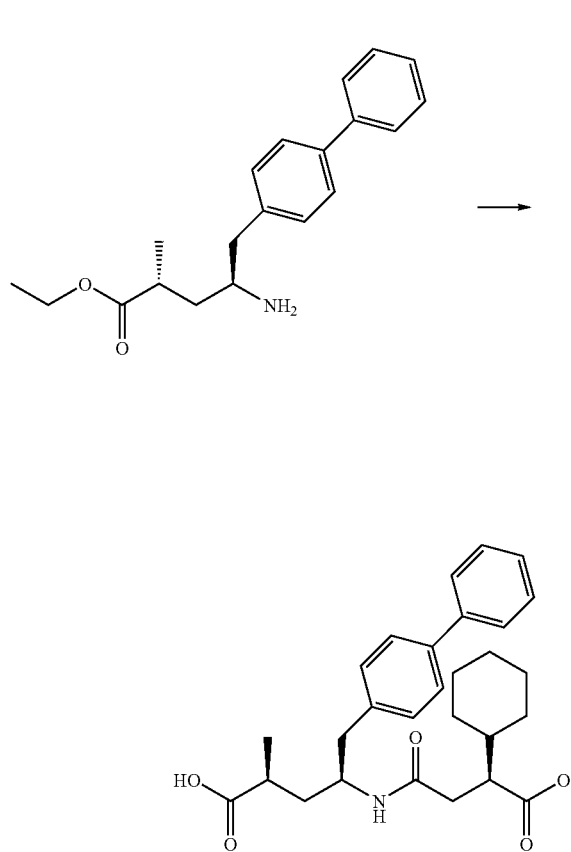

To a solution of (S)-2-cyclohexyl-succinic acid 1-methyl ester (0.144 mmol) in DMF (5 mL) is added HATU (0.216 mmol). After stirring the mixture at room temperature for 10 minutes, (2R,4S)-4-amino-5-biphenyl-4-yl-2-methyl-pentanoic acid ethyl ester hydrochloride (0.144 mmol) and triethylamine (0.359 mmol) is added and the mixture is stirred at room temperature for 18 hours. The mixture is poured into ethyl acetate and the mixture is washed with aqueous 1M HCl and brine. The organic phase is dried over magnesium sulfate and the solvent is removed under reduced pressure to give the ester product which is used directly in the subsequent hydrolysis reaction.

Next, to a solution of the obtained ester product (0.287 mmol) in ethanol (10 mL) is added aqueous 1M NaOH (2 mL, 6.97 mmol) and the mixture is stirred at room temperature for 18 hours. The mixture is poured into ethyl acetate and is washed with aqueous 1M HCl, the organic phase is dried over magnesium sulfate and the solvent is removed under reduced pressure. The residue is purified, and the diastereomers are separated, by preparative HPLC using a gradient of MeCN/water (0.1% TFA). The proper fractions are lyophilized to furnish (2S,4S)-5-biphenyl-4-yl-4-((S)-3-carboxy-3-cyclohexyl-propionylamino)-2-methyl-pentanoic acid. HPLC Retention time 1.21 minutes (condition A); MS 466.4 (M+1).

EXAMPLE 13-1

Synthesis of (2R,4S)-5-biphenyl-4-yl-2-methyl-4-[(1H-tetrazole-5-carbonyl)-amino]-pentanoic acid

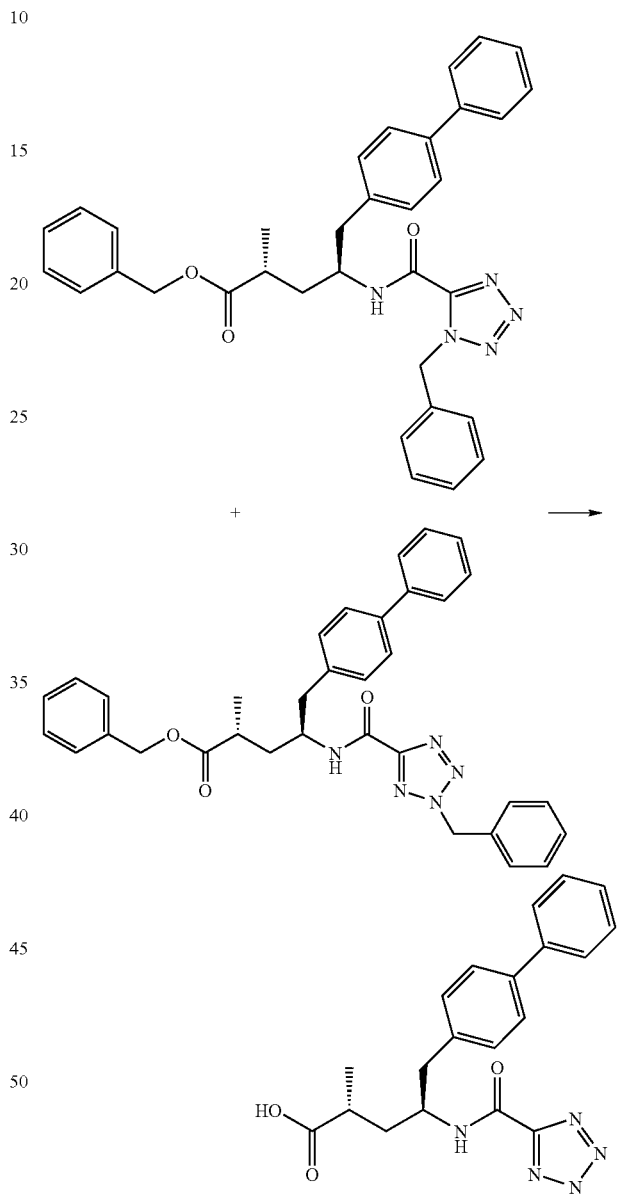

A mixture of (2R,4S)-4-[(1-benzyl-1H-tetrazole-5-carbonyl)-amino]-5-biphenyl-4-yl-2-methyl-pentanoic acid benzyl ester and (2R,4S)-4-[(2-benzyl-2H-tetrazole-5-carbonyl)-amino]-5-biphenyl-4-yl-2-methyl-pentanoic acid benzyl ester (126 mg, 0.225 mmol) in MeOH is hydrogenated with 10% Pd/C for 6 h. The reaction mixture is concentrated and purified by reverse phase HPLC to give (2R,4S)-5-biphenyl-4-yl-2-methyl-4-[(1H-tetrazole-5-carbonyl)-amino]-pentanoic acid. HPLC Retention time 1.16 minutes (condition D); MS 380.0 (M+1); $^1$H NMR (400 MHz, DMSO-d6) δ ppm 1.09 (d, J=7.20 Hz, 3H), 1.63-1.73 (m, 1H), 1.86-1.95

(m, 1H), 2.40-2.50 (m, 1H), 2.80-2.95 (m, 2H), 4.22-4.34 (m, 1H), 7.29-7.35 (m, 1H), 7.43 (dd, J=7.83, 7.83 Hz, 2H), 7.55 (d, J=10.23 Hz, 2H), 7.61-7.64 (2H, m), 9.16 (d, J=9.09 Hz, 1H), 12.03, (s, 1H).

EXAMPLE 14-1

Synthesis of (2R,4S)-5-biphenyl-4-yl-2-methyl-4-[(5-trifluoromethyl-[1,3,4]oxadiazole-2-carbonyl)-amino]-pentanoic acid

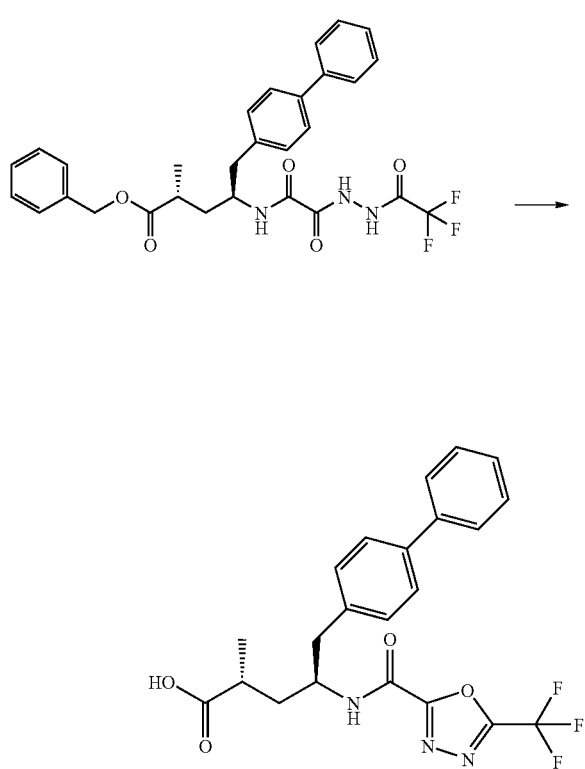

To a solution of (2R,4S)-5-biphenyl-4-yl-2-methyl-4-{2-oxo-2-[N'-(2,2,2-trifluoro-acetyl)-hydrazino]-acetylamino}-pentanoic acid benzyl ester (177 mg, 0.319 mmol) in THF (10 mL) at room temperature is added Burgess reagent (304 mg, 1.274 mmol). The reaction is carried out in a microwave at 130° C. for 30 minutes. The reaction is quenched by brine and is extracted with ethyl acetate. The combined organic layer is concentrated and purified by reverse phase HPLC [70% to 85% acetonitrile-H$_2$O (containing 0.1% TFA)] to give the benzyl ester of the title compound. The obtained benzyl ester intermediate is dissolved in MeOH (4 mL) and is hydrogenated with 10% Pd/C at room temperature for 20 minutes. The reaction mixture is purified by reverse phase HPLC [45% to 70% acetonitrile-H$_2$O (containing 0.1% TFA)] to give (2R,4S)-5-biphenyl-4-yl-2-methyl-4-[(5-trifluoromethyl-[1,3,4]oxadiazole-2-carbonyl)-amino]-pentanoic acid. HPLC Retention time 1.38 minutes (condition D); MS 448 (M+1); 1H NMR (400 MHz, DMSO-d$_6$) δ ppm 1.09 (d, J=7.3 Hz, 3H), 1.60-1.71 (m, 1H), 1.84-1.95 (m, 1H), 2.41-2.49 (m, 1H), 2.80-2.88 (m, J=13.9, 6.1 Hz, 1H), 2.92 (dd, J=13.6, 7.8 Hz, 1H), 4.21-4.34 (m, 1H), 7.27-7.37 (m, 3H), 7.44 (t, J=7.7 Hz, 2H), 7.58 (d, J=8.3 Hz, 2H), 7.61-7.66 (m, 2H), 9.50 (d, J=8.8 Hz, 1H), 12.05 (br. s., 1H).

EXAMPLE 15-1

Synthesis of (2R,4S)-5-biphenyl-4-yl-4-(3,5-difluoro-4-hydroxy-benzoylamino)-2-methyl-pentanoic acid

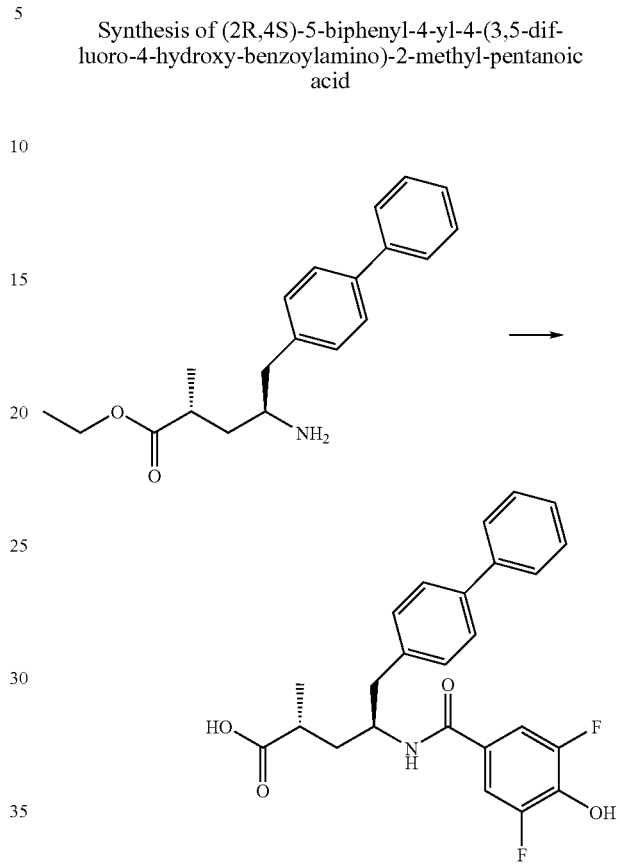

To a solution of (2R,4S)-4-amino-5-biphenyl-4-yl-2-methyl-pentanoic acid ethyl ester hydrochloride salt (200 mg, 0.58 mmol) in CH2Cl2 (2 mL) and DMF (2 mL) at rt is added 3,5difluoro-4-methoxy benzoic acid (108 mg, 0.58 mmol) followed by an addition of TEA (0.32 mL, 2.3 mmol) and HATU (262 mg, 0.69 mmol). The mixture is stirred at rt for 4 hours and quenched with saturated NaHCO$_3$ and diluted in ethyl acetate. The organic layer is washed with water, brine, dried over MgSO$_4$, filtered, and concentrated under reduced pressure. The obtained material is purified by preparative silica gel thin-layer chromatography plates (eluent:EtOAc/hepane=3/2) to give 265 mg of (2R,4S)-5-biphenyl-4-yl-4-(3,5-difluoro-4-methoxy-benzoylamino)-2-methyl-pentanoic acid ethyl ester.

Next, to a solution of (2R,4S)-5-biphenyl-4-yl-4-(3,5-difluoro-4-methoxy-benzoylamino)-2-methyl-pentanoic acid ethyl ester (125 mg, 0.260 mmol) in DCM (2.6 mL) is slowly added BBr3 (2.60 mL, 2.60 mmol) under nitrogen. The reaction is stirred for 18 hours at rt. The reaction is quenched with MeOH, diluted with EtOAc, washed with H$_2$O and brine, dried over MgSO$_4$, and concentrated under reduced pressure. The obtained material is purified by preparative silica gel thin-layer chromatography (7% MeOH in DCM) to give 100 mg (2R,4S)-5-biphenyl-4-yl-4-(3,5-difluoro-4-hydroxy-benzoylamino)-2-methyl-pentanoic acid ethyl ester.

Next, to a solution of (2R,4S)-5-biphenyl-4-yl-4-(3,5-difluoro-4-hydroxy-benzoylamino)-2-methyl-pentanoic acid ethyl ester (30 mg, 0.064 mmol) in MeOH (2 mL) at room temperature is added aqueous 1M NaOH (4 mL, 4.0 mmol).

After stirring for 1 hour the reaction is quenched with aqueous 1M HCl (4 mL, 4.0 mmol). The mixture is concentrated under reduced pressure and filtered to remove NaCl salt. The obtained residue is purified by preparative silica gel thin-layer chromatography (7% MeOH in DCM) to give 17.1 mg of (2R,4S)-5-biphenyl-4-yl-4-(3,5-difluoro-4-hydroxy-benzoylamino)-2-methyl-pentanoic acid. HPLC Retention time 1.56 minutes (condition B); MS 440 (M+1); 1H NMR (400 MHz, ACETONITRILE-d3) δ ppm 1.19 (d, J=7.07 Hz, 3H) 1.55 (ddd, J=14.27, 10.74, 3.79 Hz, 1H) 1.90-1.96 (m, 1H) 2.54-2.71 (m, 1H) 2.91 (dd, J=6.69, 3.16 Hz, 2H) 4.25-4.43 (m, 1H) 6.49 (d, J=9.60 Hz, 2H) 6.93 (d, J=8.84 Hz, 1H) 7.33-7.42 (m, 3H) 7.49 (t, J=7.71 Hz, 2H) 7.61 (d, J=8.34 Hz, 2H) 7.67 (dd, J=8.34, 1.26 Hz, 2H).

Following compounds are prepared and isolated after the coupling reaction and prior to the hydrolysis reaction described in the above example:

| Example # | Product | Coupling reaction described in | HPLC-RT (condition) | MS (M + 1) |
|---|---|---|---|---|
| Example 16-1 | 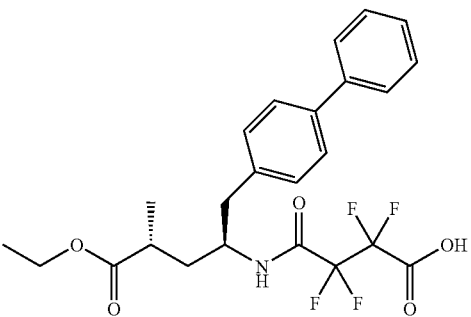 4-((2S,4R)-1-(biphenyl-4-yl)-5-ethoxy-4-methyl-5-oxopentan-2-ylamino)-2,2,3,3-tetrafluoro-4-oxobutanoic acid | Example 2-3 | 1.17 min. (A) | 484.3 |
| Example 17-1 | 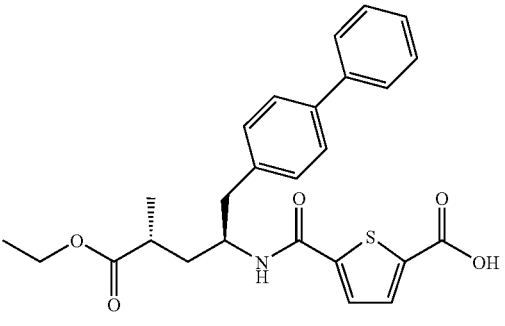 5-((1S,3R)-1-biphenyl-4-ylmethyl-3-ethoxycarbonyl-butylcarbamoyl)-thiophene-2-carboxylic acid | Example 3-14 | 1.23 min. (A) | 466.3 |
| Example 18-1 | 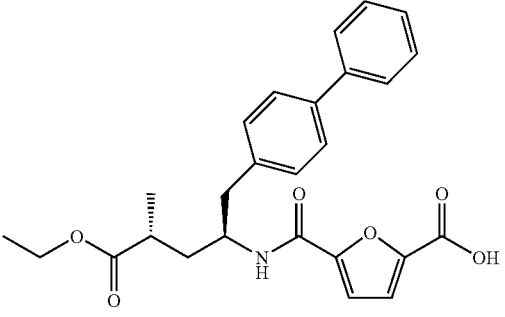 5-((1S,3R)-1-biphenyl-4-ylmethyl-3-ethoxycarbonyl-butylcarbamoyl)-furan-2-carboxylic acid | Example 3-13 | 1.11 min. (A) | 450.3 |

-continued

| Example # | Product | Coupling reaction described in | HPLC-RT (condition) | MS (M + 1) |
|---|---|---|---|---|
| Example 19-1 | 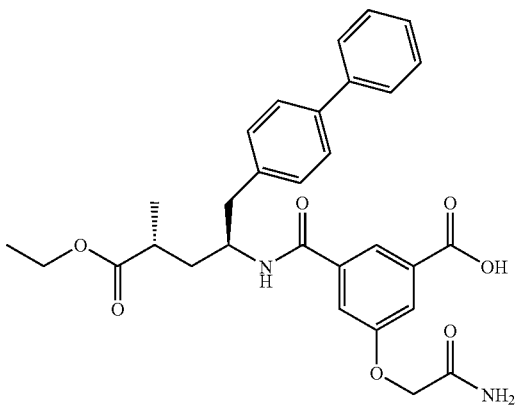

N-((1S,3R)-1-biphenyl-4-ylmethyl-3-ethoxycarbonyl-butyl)-5-carbamoylmethoxy-isophthalamic acid | Example 3-29 | 1.25 min. (A) | 533.3 |
| Example 20-1 | 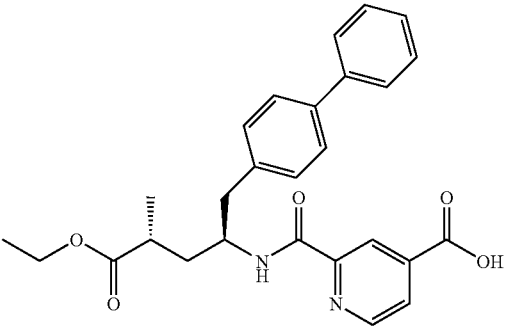

2-((1S,3R)-1-biphenyl-4-ylmethyl-3-ethoxycarbonyl-butylcarbamoyl)-isonicotinic acid | Example 3-27 | 1.56 min. (A) | 461.2 |
| Example 21-1 | 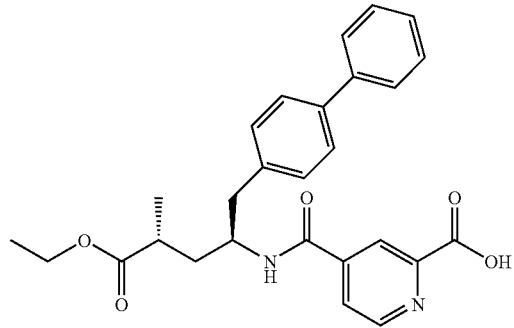

4-((1S,3R)-1-biphenyl-4-ylmethyl-3-ethoxycarbonyl-butylcarbamoyl)-pyridine-2-carboxylic acid | Example 3-26 | 1.47 min. (A) | 461.2 |

-continued

| Example # | Product | Coupling reaction described in | HPLC-RT (condition) | MS (M + 1) |
|---|---|---|---|---|
| Example 22-1 | 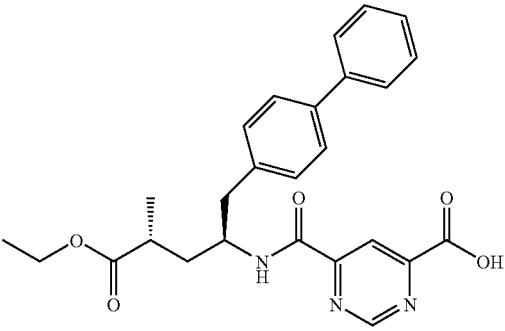 6-((2S,4R)-1-(biphenyl-4-yl)-5-ethoxy-4-methyl-5-oxopentan-2-ylcarbamoyl)pyrimidine-4-carboxylic acid | Example 3-32 | 1.36 min. (A) | 462.2 |
| Example 23-1 | 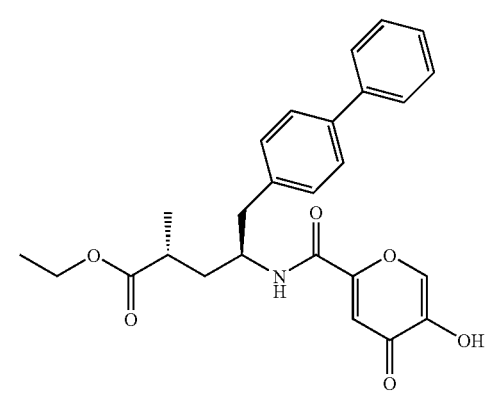 (2R,4S)-5-biphenyl-4-yl-4-[(5-hydroxy-4-oxo-4H-pyran-2-carbonyl)-amino]-2-methyl-pentanoic acid ethyl ester | Example 3-31 | 1.55 min. (A) | 450.2 |
| Example 24-1 | 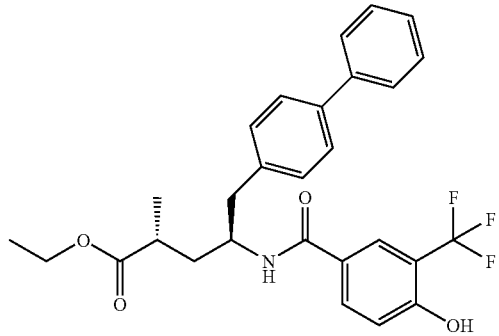 (2R,4S)-5-biphenyl-4-yl-4-(4-hydroxy-3-trifluoromethyl-benzoylamino)-2-methyl-pentanoic acid ethyl ester | Example 3-38 | 1.66 min. (A) | 500.3 |

| Example # | Product | Coupling reaction described in | HPLC-RT (condition) | MS (M + 1) |
|---|---|---|---|---|
| Example 25-1 | 5-((1S,3R)-1-Biphenyl-4-ylmethyl-3-ethoxycarbonyl-butylcarbamoyl)-1H-pyrazole-3-carboxylic acid | Example 3-47 | 1.53 min. (A) | 450.0 |

EXAMPLE 16-1

1H NMR (400 MHz, MeOD-d4) δ ppm 1.12 (d, J=7.07 Hz, 3H), 1.19 (t, J=7.20 Hz, 3H), 1.59 (m, 1H), 1.92 (m, 1H), 2.58 (m, 1H), 2.78 (dd, J=7.20 Hz, 7.20 Hz, 1H), 2.90 (dd, J=6.57 Hz, 6.69 Hz, 1H), 4.06 (d, J=7.20 Hz, 2H), 4.19 (m, 1H), 7.30 (m, 3H), 7.41 (t, J=6.69 Hz, 2H), 7.52 (d, J=8.21 Hz, 2H), 7.58 (dd, J=1.01 Hz, 1.26 Hz, 2H), 8.93 (d, J=8.72 Hz, 1H).

EXAMPLE 18-1

1H NMR (400 MHz, DMSO-d6) δ ppm 1.09 (m, 6H), 1.66 (m, 1H), 1.86 (m, 1H), 2.77-2.90 (m, 2H), 3.98 (q, 2H), 4.19 (m, 1H), 7.19 (d, J=3.54 Hz, 1H), 7.28 (m, 3H), 7.33 (t, 1H), 7.44 (t, 1H), 7.58 (d, J=8.34 Hz, 2H), 7.64 (d, J=7.07, 2H), 8.43 (d, J=8.84 Hz, 1H).

EXAMPLE 19-1

1H NMR (400 MHz, DMSO-d6) δ ppm 1.09 (m, 6H), 1.65 (m, 1H), 1.87 (m, 1H), 2.78-2.91 (m, 2H), 3.99 (q, 2H), 4.22 (m, 1H), 4.55 (s, 2H), 7.29 (d, J=8.08 Hz, 2H), 7.33 (t, 1H), 7.43 (m, 3H), 7.57-7.65 (m, 7H), 8.03 (s, 1H), 8.47 (d, J=8.46 Hz, 1H).

EXAMPLE 20-1

1H NMR (400 MHz, DMSO-d6) δ ppm 1.09 (m, 6H), 1.78 (m, 1H), 1.88 (m, 1H), 2.48 (m, 1H), 2.80-2.98 (m, 2H), 3.97 (q, 2H), 4.30 (m, 1H), 7.29 (d, J=8.21 Hz, 2H), 7.33 (t, 1H), 7.43 (t, 2H), 7.56 (d, J=8.21 Hz, 2H), 7.63 (d, J=7.20 Hz, 2H), 8.00 (m, 1H), 8.35 (s, 1H), 8.77 (d, J=9.35 Hz, 1H), 8.85 (d, J=4.29 Hz, 1H).

EXAMPLE 21-1

1H NMR (400 MHz, DMSO-d6) δ ppm 1.110 (1, 6H), 1.66 (m, 1H), 1.89 (m, 1H), 2.55 (m, 1H), 2.80-2.91 (m, 2H), 3.99 (q, 2H), 4.23 (m, 1H), 7.29 (d, J=8.21 Hz, 2H), 7.33 (t, 1H), 7.44 (t, 2H), 7.57 (d, J=8.21 Hz, 2H), 7.63 (d, J=7.20 Hz, 2H), 7.92 (m, 1H), 8.39 (s, 1H), 8.76 (d, J=8.46 Hz, 1H), 8.84 (d, J=4.93 Hz, 1H).

EXAMPLE 22-1

1H NMR (400 MHz, MeOD-d4) δ ppm 1.18 (m, 6H), 1.79 (m, 1H), 2.04 (m, 1H), 2.59 (m, 1H), 2.95 (m, 2H), 4.07 (q, J=7.07 Hz, 2H), 4.44 (m, 1H), 7.30 (m, 3H), 7.40 (m, 2H), 7.50 (m, 2H), 7.55 (m, 2H), 8.54 (s, 1H), 8.98 (d, J=9.47 Hz, 1H), 9.42 (s, 1H).

EXAMPLE 23-1

1H NMR (400 MHz, DMSO-d6) δ ppm 1.07 (d, J=7.07 Hz, 3H), 1.10 (t, 3H), 1.66 (m, 1H), 1.84 (m, 1H), 2.75-2.89 (m, 2H), 4.14 (m, 1H), 6.83 (s, 1H), 7.27 (d, J=8.21 Hz, 2H), 7.34 (t, 1H), 7.44 (t, 2H), 7.58 (d, J=8.21 Hz, 2H), 7.64 (d, J=7.20 Hz, 2H), 8.13 (s, 1H), 8.77 (d, J=8.84 Hz, 1H).

EXAMPLE 24-1

1H NMR (400 MHz, DMSO-d6) δ ppm 1.0.8 (d, J=7.07 Hz, 3H), 1.09 (t, 3H), 1.62 (m, 1H), 1.86 (m, 1H), 2.52 (m, 1H), 2.76-2.89 (m, 2H), 3.97 (q, 2H), 4.20 (m, 1H), 7.05 (d, J=8.59, 1H), 7.29 (d, J=8.21 Hz, 2H), 7.33 (t, 1H), 7.44 (t, 2H), 7.57 (d, J=8.21 Hz, 2H), 7.63 (d, J=7.33 Hz, 2H), 7.93 (m, 1H), 8.00 (s, 1H), 8.25 (d, J=8.46 Hz, 1H), 11.16 (s, 1H).

EXAMPLE 25-1

1H NMR (400 MHz, DMSO-d6) δ ppm 1.0.8 (d, J=7.07 Hz, 3H), 1.10 (t, 3H), 1.64 (m, 1H), 1.86 (m, 1H), 2.53 (m, 1H), 2.75-2.90 (m, 2H), 3.98 (q, 2H), 4.19 (m, 1H), 7.18 (s, broad, 1H), 7.28 (d, J=8.34, 2H), 7.33 (t, 1H), 7.44 (t, 2H), 7.57 (d, J=8.34 Hz, 2H), 7.63 (d, J=7.33 Hz, 2H), 8.25 (d, broad, J=8.34 Hz, 1H).

EXAMPLE 26-1

Synthesis of 1-((1S,3R)-1-Biphenyl-4-ylmethyl-3-ethoxycarbonyl-butylcarbamoyl)-1H-pyrazole-3-carboxylic acid

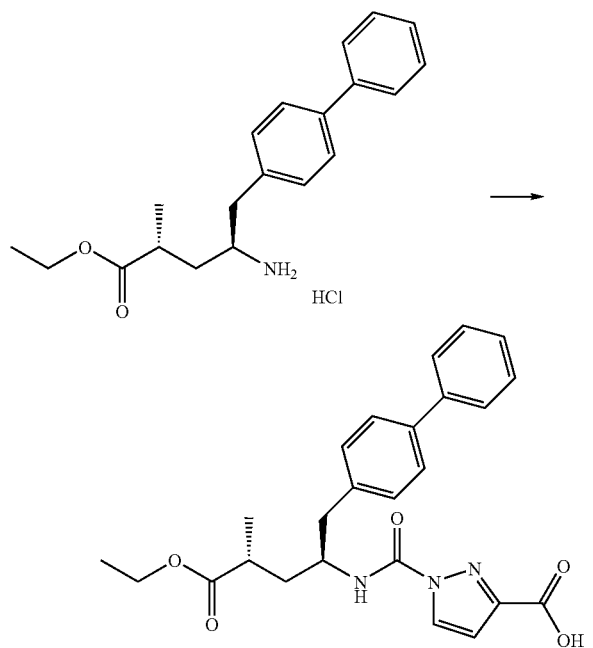

To a vigorously stirred 1:1 mixture of methylene chloride/8% aqueous $NaHCO_3$ (8 mL) at 0° C. is added triphosgene (28.4 mg, 0.096 mmol). After stirring the mixture at 0° C. for 5 minutes, (2R,4S)-4-amino-5-biphenyl-4-yl-2-methyl-pentanoic acid ethyl ester hydrochloride (100 mg, 0.287 mmol) is added and stirring is continued for 15 minutes. The organic phase is separated and dried over sodium sulfate. The solvent is removed under reduced pressure to furnish (2R,4S)-5-biphenyl-4-yl-4-isocyanate-2-methyl-pentanoic acid ethyl ester.

Next, to a solution of 1H-pyrazole-3-carboxylic acid (32.2 mg, 0.287 mmol) in DMF (1 mL) is added diisopropylethylamine (0.05 mL, 0.287 mmol). After 15 min a solution of the above (2R,4S)-5-biphenyl-4-yl-4-isocyanato-2-methyl-pentanoic acid ethyl ester in DMF (1 mL) is added dropwise and the mixture is stirred at room temperature for 18 hours. The mixture is purified by preparative HPLC using a gradient of 10% MeCN to 100% MeCN (0.1% TFA). Lyophilization of the appropriate fractions furnishes the title compound. HPLC Retention time 1.5 minutes (condition A); MS 450.3 (M+1); 1H NMR (400 MHz, DMSO-d6) δ ppm 1.08 (d, J=7.07 Hz, 3H), 1.10 (t, 3H), 1.86 (t, 2H), 2.52 (m, 1H), 2.85 (m, 1H), 2.98 (m, 1H), 3.98 (q, 2H), 4.11 (m, 1H), 6.85 (d, J=2.65 Hz, 1H), 7.28 (d, J=8.08 Hz, 2H), 7.33 (t, 1H), 7.44 (t, 2H), 7.57 (d, J=8.21 Hz, 2H), 7.63 (d, J=7.33 Hz, 2H), 8.29 (d, J=2.65 Hz, 1H), 8.58 (d, J=9.22 Hz, 1H), 13.33 (s, broad, 1H).

Following compounds are prepared and isolated after the coupling reaction and prior to the hydrolysis reaction described in example 15-1:

| Example # | Product | Coupling reaction described in | HPLC-RT (condition) | MS (M + 1) |
|---|---|---|---|---|
| Example 27-1 | 5-((1S,3R)-1-Biphenyl-4-ylmethyl-3-ethoxycarbonyl-butylcarbamoyl)-1H-pyrrole-2-carboxylic acid | Example 3-52 | 1.18 min. (C) | 449.4 |

| Example # | Product | Coupling reaction described in | HPLC-RT (condition) | MS (M + 1) |
|---|---|---|---|---|
| Example 28-1 | (2R,4S)-5-Biphenyl-4-yl-4-[(1H-imidazole-4-carbonyl)-amino]-2-methyl-pentanoic acid ethyl ester | Example 3-59 | 1.33 min. (C) | 406.4 |
| Example 29-1 | (2R,4S)-5-Biphenyl-4-yl-4-[(3-hydroxy-isoxazole-5-carbonyl)-amino]-2-methyl-pentanoic acid ethyl ester | Example 3-65 | 1.24 min. (C) | 423.3 |
| Example 30-1 | 2-((1S,3R)-1-Biphenyl-4-ylmethyl-3-ethoxycarbonyl-butylcarbamoyl)-pyrimidine-4-carboxylic acid | Example 3-73 | 1.22 min. (C) | 462.4 |

-continued

| Example # | Product | Coupling reaction described in | HPLC-RT (condition) | MS (M + 1) |
|---|---|---|---|---|
| Example 31-1 | 4-((1S,3R)-1-Biphenyl-4-ylmethyl-3-ethoxycarbonyl-butylcarbamoyl)-pyrimidine-2-carboxylic acid | Example 3-74 | 1.18 min. (C) | 462.4 |
| Example 32-1 | (2R,4S)-5-(3'-Chloro-biphenyl-4-yl)-4-[(3-hydroxy-isoxazole-5-carbonyl)-amino]-2-methyl-pentanoic acid ethyl ester | Example 49-1 | 1.33 min. (C) | 457.3 |
| Example 33-1 | 5-[(1S,3R)-1-(3'-Chloro-biphenyl-4-ylmethyl)-3-ethoxycarbonyl-butylcarbamoyl]-1H-pyrazole-3-carboxylic acid | Example 49-2 | 1.29 min. (C) | 484.3 |

-continued

| Example # | Product | Coupling reaction described in | HPLC-RT (condition) | MS (M + 1) |
|---|---|---|---|---|
| Example 34-1 | 5-[(1S,3R)-1-(3'-Chloro-biphenyl-4-ylmethyl)-3-ethoxycarbonyl-butylcarbamoyl]-furan-2-carboxylic acid | Example 49-3 | 1.23 min. (C) | 484.1 |
| Example 35-1 | (2R,4S)-4-(3-Carboxymethyl-ureido)-5-(3'-chloro-biphenyl-4-yl)-2-methyl-pentanoic acid ethyl ester | Example 49-4 | 1.71 min. (C) | 483.0 |
| Example 36-1 | (2R,4S)-4-(3-Carboxy-2,2,3,3-tetrafluoro-propionylamino)-5-(3'-chloro-biphenyl-4-yl)-2-methyl-pentanoic acid ethyl ester | Example 49-6 | 1.60 min. (C) | 518.2 |

EXAMPLE 27-1

1H NMR (400 MHz, DMSO-d6): δ ppm 1.05-1.10 (m, 6H), 1.49-1.56 (m, 1H), 1.84-1.91 (m, 1H), 2.52-2.56 (m, 1H), 2.77-2.86 (m, 2H), 3.91-3.99 (q, J=7.07 Hz, 2H), 4.11-4.20 (m, 1H), 6.73-6.74 (d, J=2.27 Hz, 2H), 7.27-7.29 (d, J=8.08 Hz, 2H), 7.31-7.35 (J=7.33 Hz, 1H), 7.42-7.45 (m, 2H), 7.57-7.59 (d, J=8.08 Hz, 2H), 7.63-7.65 (m, 2H), 8.08-8.10 (d, J=8.34 Hz, 1H), 11.90 (s, 1H), 12.75 (s, 1H).

EXAMPLE 28-1

1H NMR (400 MHz, DMSO-d6) δ ppm 1.08-1.12 (m, 6H), 1.60 (m, 1H), 1.90 (m, 1H), 2.52 (m, 1H), 2.79-2.88 (m, 2H), 3.95-4.03 (m, 3H), 4.20 (m, 1H), 7.29 (d, J=8.34 Hz, 2H), 7.34 (t, 1H), 7.44 (t, 2H), 7.57 (d, J=8.34 Hz, 2H), 7.63 (d, J=7.07 Hz, 2H), 7.99 (s, 1H), 8.39 (d, broad, J=8.34 Hz, 1H), 8.73 (s, broad, 1H).

EXAMPLE 29-1

1H NMR (400 MHz, DMSO-d6) δ ppm 1.07 (d, J=7.07 Hz, 3H), 1.11 (t, 3H), 1.64 (m, 1H), 1.85 (m, 1H), 2.75-2.87 (m, 2H), 3.98 (q, 2H), 4.14 (m, 1H), 6.51 (s, 1H), 7.27 (d, J=8.08 Hz, 2H), 7.34 (t, 1H), 7.44 (t, 2H), 7.58 (d, J=8.34 Hz, 2H), 7.64 (d, J=7.07 Hz, 2H), 8.67 (d, J=8.59 Hz, 1H), 11.67 (s, 1H).

EXAMPLE 30-1

1H NMR (400 MHz, DMSO-d6): 1H NMR (400 MHz, DMSO-d6): δ ppm 1.07-1.12 (m, 6H), 1.69-1.77 (m, 1H), 1.84-1.92 (m, 1H), 2.45-2.55 (m, 1H), 2.80-2.85 (m, 1H), 2.93-2.99 (m, 1H), 3.96-4.01 (q, J=7.33 Hz, 2H), 4.23-4.31 (m, 1H), 7.26 (s, br, 1H), 7.30-7.35 (m, 2H), 7.40-7.46 (m, 2H), 7.56-7.58 (m, 2H), 7.62-7.65 (m, 2H), 7.94-7.95 (d, J=4.80 Hz, 1H), 8.85-8.88 (d, J=9.09 Hz, 1H), 9.02-9.03 (d, J=4.80 Hz, 1H).

EXAMPLE 31-1

1H NMR (400 MHz, DMSO-d6): 1H NMR (400 MHz, DMSO-d6): δ ppm 1.06-1.11 (m, 6H), 1.73-1.81 (m, 1H), 1.85-1.92 (m, 1H), 2.43-2.54 (m, 1H), 2.82-2.87 (m, 1H), 2.92-2.97 (m, 1H), 3.95-4.00 (q, J=7.07 Hz, 2H), 4.24-4.32 (m, 1H), 7.28-7.35 (m, 3H), 7.42-7.45 (t, J=8.08 Hz, 2H), 7.56-7.58 (d, J=8.34 Hz, 2H), 7.62-7.64 (m, 2H), 7.84-7.88 (s, 1H), 8.77-8.79 (d, J=8.08 Hz, 1H), 9.00 (s, 1H).

EXAMPLE 32-1

1H NMR (600 MHz, DMSO-$d_6$) δ ppm 1.07 (d, J=7.06 Hz, 3H) 1.11 (t, J=7.11 Hz, 3H) 1.59-1.70 (m, 1H) 1.79-1.90 (m, 1H) 2.73-2.90 (m, 2H) 3.98 (d, J=6.79 Hz, 2H) 4.06-4.19 (m, 1H) 6.50 (s, 1H) 7.28 (d, J=8.07 Hz, 2H) 7.41 (s, 1H) 7.47 (s, 1H) 7.62 (d, J=8.07 Hz, 3H) 7.70 (s, 1H) 8.68 (d, J=8.80 Hz, 1H) 11.63-11.73 (m, 1H).

EXAMPLE 33-1

1H NMR (400 MHz, DMSO-d6) δ ppm 1.09 (q, 6H) 1.65 (br. s., 1H) 1.83 (d, J=9.60 Hz, 1H) 2.71-2.95 (m, 2H) 3.98 (q, J=7.07 Hz, 2H) 4.19 (dd, J=8.97, 6.19 Hz, 1H) 7.29 (d, J=8.34 Hz, 2H) 7.36-7.42 (m, 1H) 7.46 (t, J=7.96 Hz, 1H) 7.55-7.65 (m, 3H) 7.69 (t, J=1.89 Hz, 1H) 7.97-8.27 (m, 1H).

EXAMPLE 34-1

1H NMR (400 MHz, DMSO-d6) δ ppm 1.03-1.14 (m, 6H) 1.60-1.72 (m, 1H) 1.85 (ddd, J=13.77, 9.85, 3.92 Hz, 1H) 2.75-2.94 (m, 2H) 3.98 (q, J=7.07 Hz, 2H) 4.12-4.26 (m, 1H) 7.10-7.21 (m, 2H) 7.29 (d, J=8.08 Hz, 2H) 7.37-7.42 (m, 1H) 7.46 (t, J=7.83 Hz, 1H) 7.62 (d, J=8.08 Hz, 3H) 7.69 (t, J=1.89 Hz, 1H) 8.37 (d, J=8.59 Hz, 1H).

EXAMPLE 35-1

1H NMR (400 MHz, DMSO-d6): δ ppm 1.07-1.10 (m, 6H), 1.49-1.56 (m, 1H), 1.84-1.91 (m, 1H), 2.47-2.56 (m, 1H), 2.77-2.87 (m, 2H), 3.94-3.99 (q, J=7.07 Hz, 14.05 Hz, 2H), 4.11-4.20 (m, 1H), 6.72-6.73 (d, J=2.27 Hz, 2H), 7.28-7.30 (m, 2H), 7.38-7.41 (m, 1H), 7.44-7.48 (t, J=7.83 Hz, 1H), 7.61-7.64 (m, 3H), 7.69-7.70 (t, J=1.77 Hz, 1H), 8.07-8.10 (d, J=8.34 Hz, 1H), 11.89 (s, 1H), 12.74 (s, 1H).

EXAMPLE 36-1

1H NMR (400 MHz, DMSO-d6): δ ppm 1.05-1.13 (m, 6H), 1.53-1.60 (m, 1H), 1.75-1.83 (m, 1H), 2.43-2.50 (m, 1H), 2.71-2.83 (m, 2H), 3.96-4.00 (m, 3H), 7.26-7.28 (m, 2H), 7.39-7.42 (m, 1H), 7.46-7.50 (t, J=7.83 Hz, 1H), 7.61-7.65 (m, 3H), 7.70-7.71 (t, J=1.77 Hz, 1H), 9.60 (s, 1H).

EXAMPLE 37-1

Synthesis of (2R,4S)-5-Biphenyl-4-yl-4-(3-carboxymethyl-benzoylamino)-2-methyl-pentanoic acid and

EXAMPLE 38-1

Synthesis of 3-[((1S,3R)-1-Biphenyl-4-ylmethyl-3-carboxy-butylcarbamoyl)-methyl]-benzoic acid

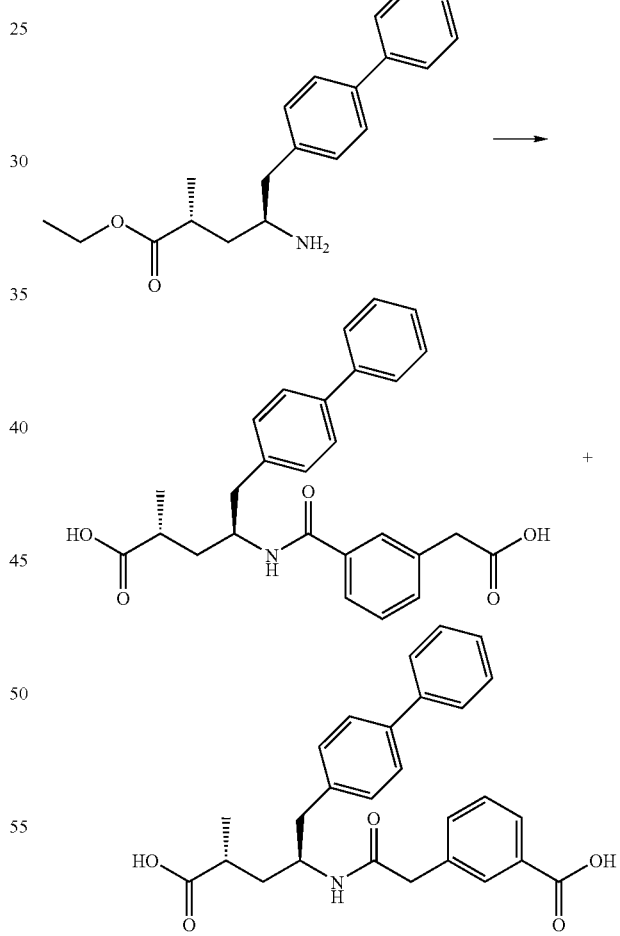

To a solution of Intermediate 1 (100 mg, 0.287 mmol), Intermediate 21 (57 mg, 0.316 mmol), EDCl (71.6 mg, 0.374 mmol) and HOBt (50.5 mg, 0.374 mmol) in DMF (3 mL) is added triethylamine (116 mg, 0.159 mL) and the mixture is stirred at room temperature for 18 hrs. Any insoluble material is removed by filtration and the solvent is removed under reduced pressure.

Next, the above residue is dissolved in EtOH (8 mL) and 1N NaOH (1.27 mL, 1.27 mmol) is added. The mixture is stirred at 50° C. for 5 hrs then the solvent is removed under reduced pressure. Water (5 mL) is added and the mixture is acidified with 1N HCl. The mixture is extracted with EtOAc and the organic phase is dried over sodium sulfate. The solvent is removed under reduced pressure and the residue is purified by preparative HPLC using a gradient of 10% MeCN/water to 100% MeCN (0.1% TFA) to elute the products (2R,4S)-5-biphenyl-4-yl-4-(3-carboxymethyl-benzoylamino)-2-methyl-pentanoic acid, HPLC Retention time 1.02 minutes (condition C); MS 446.3 (M+1); 1H NMR (400 MHz, DMSO-d6) δ ppm 1.08 (d, J=7.07 Hz, 3H), 1.58 (m, 1H), 1.88 (m, 1H), 2.46 (m, 1H), 2.79-2.90 (m, 2H), 3.62 (s, 2H), 4.25 (m, 1H), 7.29 (d, J=8.08 Hz, 2H), 7.34 (d, J=7.33 Hz, 1H), 7.40 (m, 2H), 7.43 (t, 2H), 7.57 (d, J=8.08 Hz, 2H), 7.63 (d, J=8.08 Hz, 2H), 7.68 (m, 2H), 8.22 (d, J=8.34 Hz, 1H) and 3-[((1S,3R)-1-biphenyl-4-ylmethyl-3-carboxy-butylcarbamoyl)-methyl]-benzoic acid, HPLC Retention time 1.03 minutes (condition C); MS 446.3 (M+1); 1H NMR (400 MHz, DMSO-d6) δ ppm 1.05 (d, J=7.07 Hz, 3H), 1.36 (m, 1H), 1.81 (m, 1H), 2.41 (m, 1H), 2.63-2.75 (m, 2H), 3.37-3.46 (m, 2H), 3.94 (m, 1H), 7.15 (d, J=8.08 Hz, 2H), 7.32-7.50 (m, 7H), 7.61 (d, J=7.33 Hz, 2H), 7.80 (m, 1H), 7.88 (s, 1H), 8.00 (d, J=8.59 Hz, 1H).

EXAMPLE 37-2

Synthesis of (2R,4S)-5-Biphenyl-4-yl-4-[(5-carboxymethyl-furan-2-carbonyl)-amino]-2-methyl-pentanoic acid and

EXAMPLE 38-2

Synthesis of 5-[((1S,3R)-1-Biphenyl-4-ylmethyl-3-carboxy-butylcarbamoyl)-methyl]-furan-2-carboxylic acid

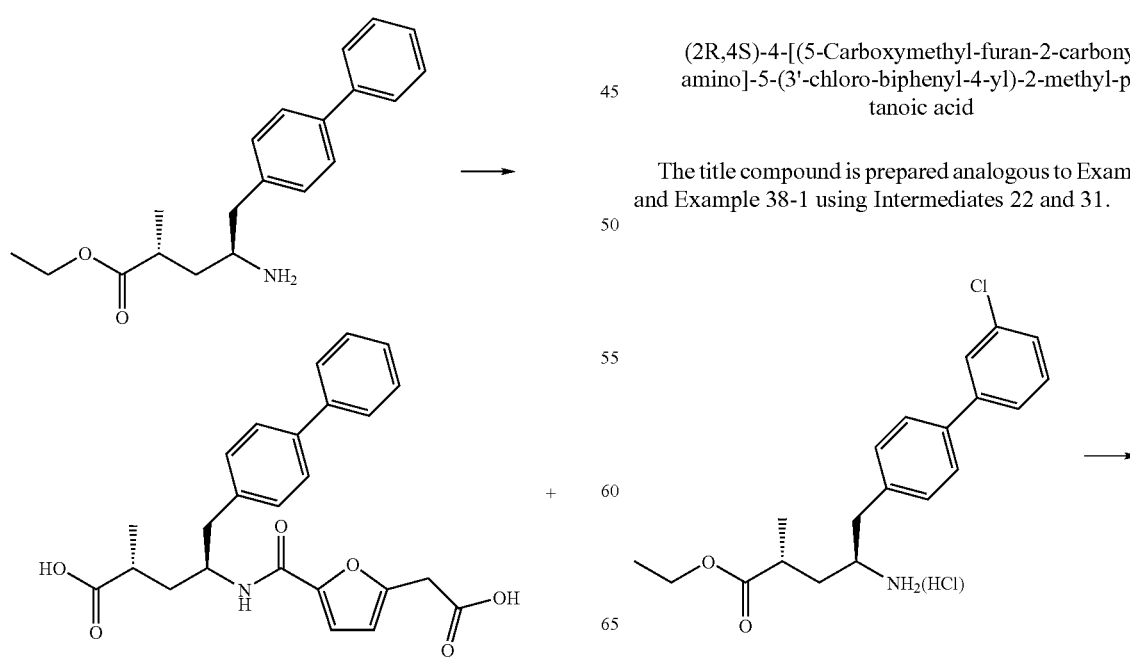

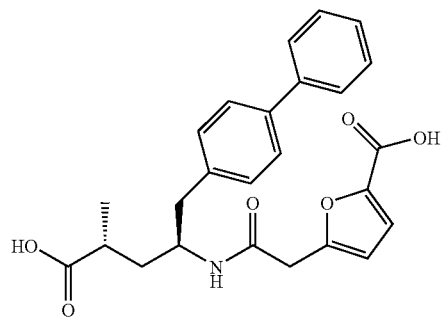

The title compounds are prepared analogous to Example 37-1 and Example 38-1 using Intermediates 1 and 22.

(2R,4S)-5-biphenyl-4-yl-4-[(5-carboxymethyl-furan-2-carbonyl)-amino]-2-methyl-pentanoic acid, HPLC Retention time 1.13 minutes (condition C); MS 436.3 (M+1); 1H NMR (400 MHz, DMSO-d6) δ ppm 1.07 (d, J=7.07 Hz, 3H), 1.55 (m, 1H), 1.85 (m, 1H), 2.41 (m, 1H), 2.75-2.88 (m, 2H), 3.74 (s, 2H), 4.19 (m, 1H), 6.39 (d, J=3.28 Hz, 1H), 7.01 (d, J=3.28 Hz, 1H), 7.27 (d, J=8.08 Hz, 2H), 7.33 (t, 1H), 7.44 (t, 2H), 7.56 (d, J=8.34 Hz, 2H), 7.64 (d, J=7.33 Hz, 2H), 8.08 (d, J=8.59 Hz, 1H).

5-[((1S,3R)-1-biphenyl-4-ylmethyl-3-carboxy-butylcarbamoyl)-methyl]-furan-2-carboxylic acid, HPLC Retention time 1.03 minutes (condition C); MS 436.3 (M+1); 1H NMR (400 MHz, DMSO-d6) δ ppm 1.06 (d, J=7.07 Hz, 3H), 1.36 (m, 1H), 1.81 (m, 1H), 2.42 (m, 1H), 2.67-2.78 (m, 2H), 3.54 (s, 2H), 3.97 (m, 1H), 6.30 (d, J=3.28 Hz, 1H), 7.12 (d, J=3.28 Hz, 1H), 7.23 (d, J=8.08 Hz, 2H), 7.34 (t, 1H), 7.45 (t, 2H), 7.56 (d, J=8.34 Hz, 2H), 7.64 (d, J=7.33 Hz, 2H), 8.05 (d, J=8.34 Hz, 1H).

EXAMPLE 38-3

(2R,4S)-4-[(5-Carboxymethyl-furan-2-carbonyl)-amino]-5-(3'-chloro-biphenyl-4-yl)-2-methyl-pentanoic acid The title compound is prepared analogous to Example 37-1 and Example 38-1 using Intermediates 22 and 31.

-continued

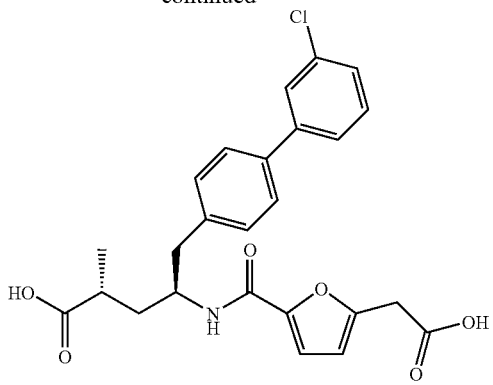

HPLC Retention time 1.37 minutes (condition C); MS (m+1)=470.0; 1H NMR (400 MHz, DMSO-d6) δ ppm 1.07 (d, J=7.07 Hz, 3H), 1.55 (m, 1H), 1.85 (m, 1H), 2.41 (m, 1H), 2.76-2.88 (m, 2H), 3.74 (s, 2H), 4.19 (m, 1H), 6.39 (d, J=3.28 Hz, 1H), 7.01 (d, J=3.28 Hz, 1H), 7.28 (d, J=8.08 Hz, 2H), 7.39 (m, 1H), 7.46 (t, 2H), 7.59-7.63 (m, 3H), 7.69 (m, 1H), 8.09 (d, J=8.84 Hz, 1H)

EXAMPLE 39-1

Synthesis of 6-Amino-2-((1S,3R)-1-biphenyl-4-ylmethyl-3-carboxy-butylcarbamoyl)-pyrimidine-4-carboxylic acid and

EXAMPLE 40-1

Synthesis of 4-Amino-6-((1S,3R)-1-biphenyl-4-ylmethyl-3-carboxy-butylcarbamoyl)-pyrimidine-2-carboxylic acid

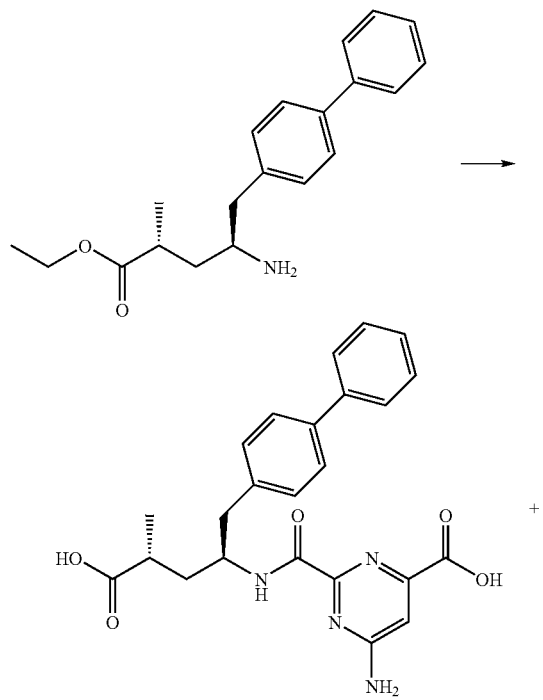

-continued

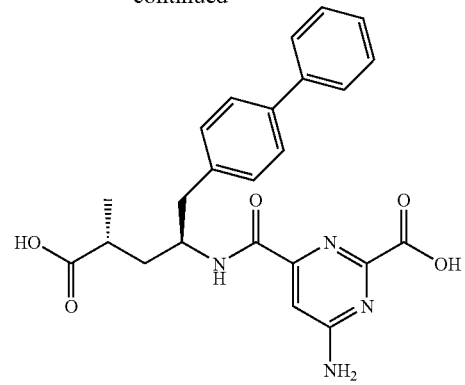

To a stirred solution of triethyl 1,3,5-triazine-2,4,6-tricarboxylate (J. Org. Chem. 59, 4950, 1994) (2.02 g, 6.80 mmol.) in DMF (15 mL) is added 1-aminoethaniminium chloride (1.29 g, 13.60 mmol). After the addition, the mixture is heated at 100° C. for 18 hours then the mixture is extracted three times with ethyl acetate. The combined organic layers are washed with water and brine then is dried over magnesium sulfate. The solvent is removed under reduced pressure and the residue is purified by flash chromatography (heptane/ethyl acetate=3:1) to give diethyl 6-aminopyrimidine-2,4-dicarboxylate; HPLC Retention time 0.89 minutes (condition C); MS 240.3 (M+1).

Next, to a stirred solution of diethyl 6-aminopyrimidine-2,4-dicarboxylate (120 mg, 0.50 mmol) in EtOH (3 mL) is added 1N NaOH (0.5 mL) and the mixture is stirred at room temperature for 18 hours. The solution is carefully acidified with 1N HCl and the solvent is removed under reduced pressure to give a mixture of 4-amino-6-(ethoxycarbonyl)pyrimidine-2-carboxylic acid and 6-amino-pyrimidine-2,4-dicarboxylic acid 2-ethyl ester.

Next, to a solution of Intermediate 1 (100 mg, 0.321 mmol) and the above monoester mixture in DMF (8 mL) is added HATU (122 mg, 0.321 mmol) and triethylamine (0.134 mL, 0.963 mmol) and the mixture is stirred at room temperature for 2 hours. The solvent is removed under reduced pressure and the residue is used directly in the next reaction.

Next, to a solution of the above residue in EtOH (5 mL) is added 1N NaOH (3 mL) and the mixture is stirred at room temperature for 2 hours. The mixture is acidified with 1N HCl and the solvent is removed under reduced pressure. The residue is purified by preparative HPLC using a gradient of 10% MeCN/water to 100% MeCN (0.1% TF) to elute the products 6-Amino-2-((1S,3R)-1-biphenyl-4-ylmethyl-3-carboxy-butylcarbamoyl)-pyrimidine-4-carboxylic acid; HPLC Retention time 1.03 minutes (condition C); MS 449.3 (M+1); 1H NMR (400 MHz, DMSO-d6) δ ppm 0.97-0.99 (d, J=6.82 Hz, 3H), 1.75-1.79 (m, 2H), 2.45-2.55 (m, 1H), 2.82-2.87 (m, 1H), 2.92-2.97 (m, 1H), 4.16-4.22 (m, 1H), 6.95 (s, 1H), 7.29-7.35 (m, 3H), 7.41-7.45 (m, 2H), 7.57-7.59 (m, 2H), 7.63-7.65 (m, 2H), 8.85-8.88 (d, J=8.84 Hz, 1H) and 4-Amino-6-((1S,3R)-1-biphenyl-4-ylmethyl-3-carboxy-butylcarbamoyl)-pyrimidine-2-carboxylic acid; HPLC Retention time 1.13 minutes (condition C); MS 449.3 (M+1); 1H NMR (400 MHz, DMSO-d6) δ ppm 1.07-1.09 (d, J=7.07 Hz, 3H), 1.57-1.65 (m, 1H), 1.89-1.96 (m, 1H), 2.38-2.44 (m, 1H), 2.86-2.89 (m, 2H), 4.21-4.30 (m, 1H), 7.06 (s, 1H), 7.27-7.35 (m, 3 H), 7.41-7.45 (m, 2H), 7.55-7.57 (m, 2H), 7.62-7.64 (m, 2H), 8.78-8.80 (d, J=9.35 Hz, 1H), 12.05 (s, 1H), 12.89 (s, 1H).

EXAMPLE 41-1

Synthesis of 6-((1S,3R)-1-Biphenyl-4-ylmethyl-3-ethoxycarbonyl-butylcarbamoyl)-2-hydroxy-pyrimidine-4-carboxylic acid

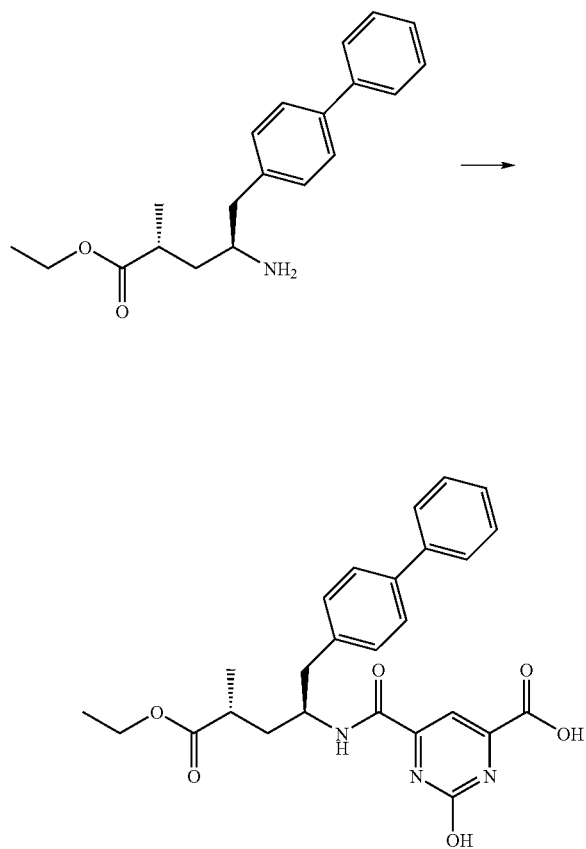

To a stirred solution of 2-hydroxypyrimidine-4,6-dicarboxylic acid (71 mg, 0.39 mmol) in DMF (10 mL) is added HOBT (59 mg, 0.39 mmol) and EDCl (74 mg, 0.39 mmol) and the mixture is stirred at room temperature for 10 minutes then (2R,4S)-4-amino-5-biphenyl-4-yl-2-methyl-pentanoic acid ethyl ester hydrochloride (Intermediate 1) (120 mg, 0.35 mmol) and triethylamine (0.15 ml, 1.16 mmol) are added. After stirring the mixture at room temperature for five hours, water is added and the mixture is extracted with ethyl acetate (3×). The combined organic layers are washed with water and brine then is dried over magnesium sulfate. The solvent is removed under reduced pressure and residue is purified by preparative HPLC using a gradient of 10% MeCN/water to 100% MeCN (0.1% TFA) to elute the title compound. HPLC retention time 1.32 minutes (condition C); MS 478.3 (M+H); 1H NMR (400 MHz, DMSO-d6): δ ppm 1.05-1.07 (d, J=7.07 Hz, 3H), 1.09-1.12 (t, J=7.07 Hz, 3H), 1.72-1.79 (m, 1H), 1.81-1.89 (m, 1H), 2.44-2.49 (m, 1H), 2.77-2.82 (m, 1H), 2.89-2.95 (m, 1H), 3.95-4.01 (q, J=7.07 Hz, 2H), 4.16-4.26 (m, 1H), 7.26-7.28 (m, 2H), 7.31-7.35 (m, 1H), 7.41-7.45 (m, 2H), 7.55-7.57 (m, 2H), 7.62-7.64 (m, 2H), 8.73-8.76 (d, J=9.35 Hz, 1H).

EXAMPLE 42-1

Synthesis of 6-((1S,3R)-1-Biphenyl-4-ylmethyl-3-carboxy-butylcarbamoyl)-2-ethoxy-pyrimidine-4-carboxylic acid

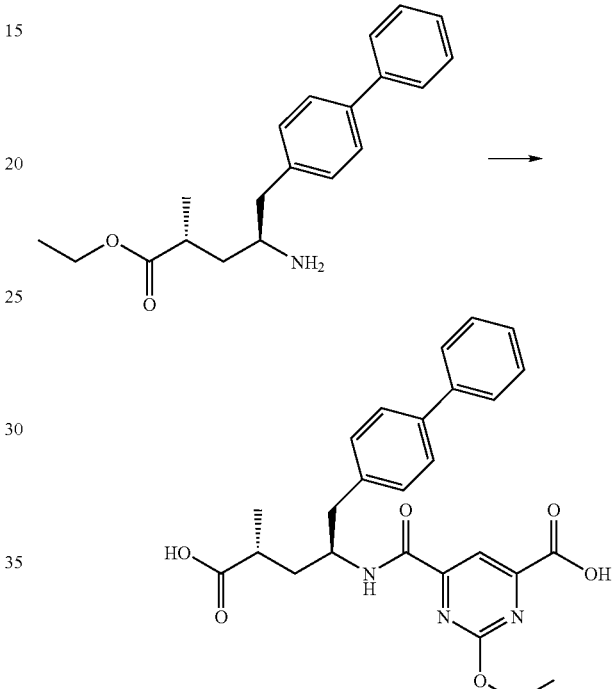

To a solution of Intermediate 1 (311 mg, 1 mmol) and Intermediate 24 (260 mg, 1.2 mmol) in DMF (10 mL) is added HATU (380 mg, 1 mmol) and triethylamine (0.418 mL, 3 mmol) and the mixture is stirred at room temperature for 1 hour. Water is added and the mixture is extracted with EtOAc. The organic phase is washed with brine and is dried over magnesium sulfate. The solvent is removed under reduced pressure to give 6-((1S,3R)-1-biphenyl-4-ylmethyl-3-ethoxycarbonyl-butylcarbamoyl)-2-chloro-pyrimidine-4-carboxylic acid methyl ester which is used directly in the next reaction.

Next, to a solution of the above product in EtOH (7 mL) is added 1N NaOH (10 mL) and the mixture is stirred at room temperature for 18 hours. The mixture is acidified with 1N HCl and extracted with EtOAc. The organic phase is washed with brine and dried over magnesium sulfate. The solvent is removed under reduced pressure and the residue is purified by preparative HPLC using a gradient of 10% MeCN/water to 100% MeCN to elute the title compound; HPLC retention time 1.15 minutes (condition C); MS 478.3 (M+H); 1H NMR (400 MHz, MeOD-d4): δ ppm 1.18-1.20 (d, J=7.07 Hz, 3H), 1.43-1.46 (t, J=7.07 Hz, 3H), 1.76-1.83 (m, 1H), 2.02-2.09 (m, 1H), 2.55-2.61 (m, 1H), 2.96-2.98 (d, J=6.82 Hz, 2H), 4.42-4.49 (m, 1H), 4.55-4.61 (q, J=7.07 Hz, 2H), 7.27-7.33

(m, 3 H), 7.37-7.41 (t, J=7.83 Hz, 2H), 7.50-7.52 (d, J=8.34 Hz, 2H), 7.55-7.57 (d, J=7.33 Hz, 2H), 8.11 (s, 1H), 8.58-8.61 (d, J=9.35, 1H).

EXAMPLE 43-1

Synthesis of 6-((1S,3R)-1-Biphenyl-4-ylmethyl-3-carboxy-butylcarbamoyl)-2-methoxy-pyrimidine-4-carboxylic acid

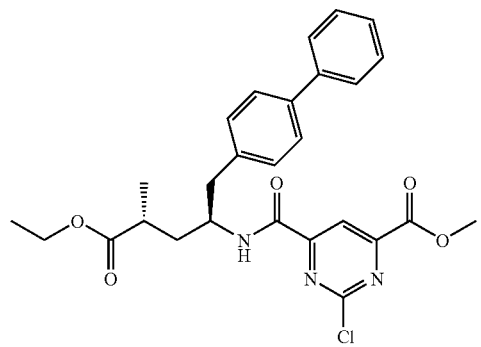

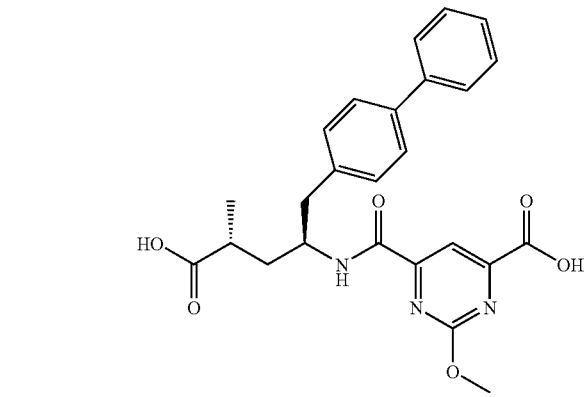

To a solution of 6-((1S,3R)-1-biphenyl-4-ylmethyl-3-ethoxycarbonyl-butylcarbamoyl)-2-chloro-pyrimidine-4-carboxylic acid methyl ester (74 mg, 0.145 mmol, from Example 42-1) in THF (5 mL) is added sodium methoxide (47 mg, 0.218 mmol) and the mixture is stirred at room temperature for 18 hours. Water is added and the mixture is extracted with EtOAc. The organic phase is washed with brine and dried over magnesium sulfate. The solvent is removed under reduced pressure to give 6-((1S,3R)-1-biphenyl-4-ylmethyl-3-ethoxycarbonyl-butylcarbamoyl)-2-methoxy-pyrimidine-4-carboxylic acid methyl ester.

Next, to a solution of the above diester in EtOH (3 mL) is added 1N NaOH (3 mL) and the mixture is stirred at room temperature for 18 hours. The mixture is acidified to pH3 and is extracted with EtOAc. The organic phase is washed with brine and dried over magnesium sulfate. The solvent is removed under reduced pressure to give the title compound; HPLC retention time 1.31 minutes (condition C); MS 464.3 (M+H); 1H NMR (400 MHz, MeOD-d4): δ ppm 1.18-1.20 (d, J=7.07 Hz, 3H), 1.77-1.84 (m, 1H), 2.02-2.09 (m, 1H), 2.55-2.61 (m, 1H), 2.96-2.98 (d, J=7.07 Hz, 2H), 4.15 (s, 3H), 4.43-4.49 (m, 1H), 7.27-7.34 (m, 3 H), 7.38-7.41 (m, 2H), 7.50-7.52 (m, 2H), 7.55-7.57 (m, 2H), 8.12 (s, 1H), 8.63-8.66 (d, J=9.35, 1H).

EXAMPLE 44-1

Synthesis of (2R,4S)-5-Biphenyl-4-yl-4-[(6-carbamoyl-2-hydroxy-pyrimidine-4-carbonyl)-amino]-2-methyl-pentanoic acid

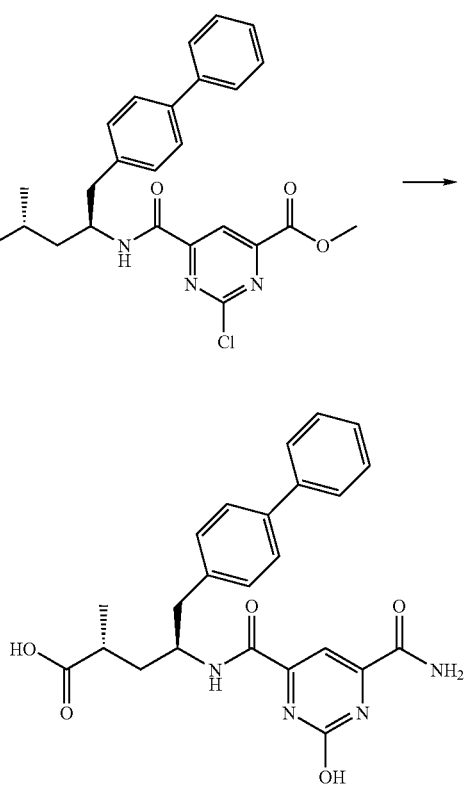

To a 7N solution of ammonia in MeOH (5 mL) is added 6-((1S,3R)-1-biphenyl-4-ylmethyl-3-ethoxycarbonyl-butylcarbamoyl)-2-chloro-pyrimidine-4-carboxylic acid methyl ester (120 mg, 0.235 mmol, from Example 42-1) and the mixture is stirred at room temperature for 20 minutes. The solvent is removed under reduced pressure to give (2R,4S)-5-biphenyl-4-yl-4-[(6-carbamoyl-2-chloro-pyrimidine-4-carbonyl)-amino]-2-methyl-pentanoic acid ethyl ester; HPLC retention time 1.50 minutes (condition C); MS 495.3 (M+H);

Next, to a solution of the above compound in EtOH (5 mL) is added 1N NaOH (5 mL) and the mixture is stirred at room temperature for 18 hours. The mixture is acidified to pH3 and is extracted with EtOAc. The organic phase is washed with brine and dried over magnesium sulfate. The solvent is removed under reduced pressure to give the title compound; HPLC retention time 1.08 minutes (condition C); MS 449.3 (M+H); 1H NMR (400 MHz, DMSO-d6): 1H NMR (400 MHz, DMSO-d6): δ ppm 1.06-1.07 (d, J=7.07 Hz, 3H), 1.57-1.64 (m, 1H), 1.85-1.92 (m, 1H), 2.39-2.45 (m, 1H), 2.81-2.92 (m, 2H), 4.21-4.30 (m, 1H), 7.27-7.29 (m, 2H), 7.31-

7.35 (m, 1H), 7.42-7.45 (m, 3H), 7.56-7.59 (m, 2H), 7.63-7.65 (m, 2H), 8.29-8.31 (d, J=9.35 Hz, 1H), 12.09 (s, 1H), 13.60 (s, 1H).

EXAMPLE 45-1

Synthesis of (2R,4S)-5-Biphenyl-4-yl-4-[(5-methoxy-4-oxo-4H-pyran-2-carbonyl)-amino]-2-methyl-pentanoic acid

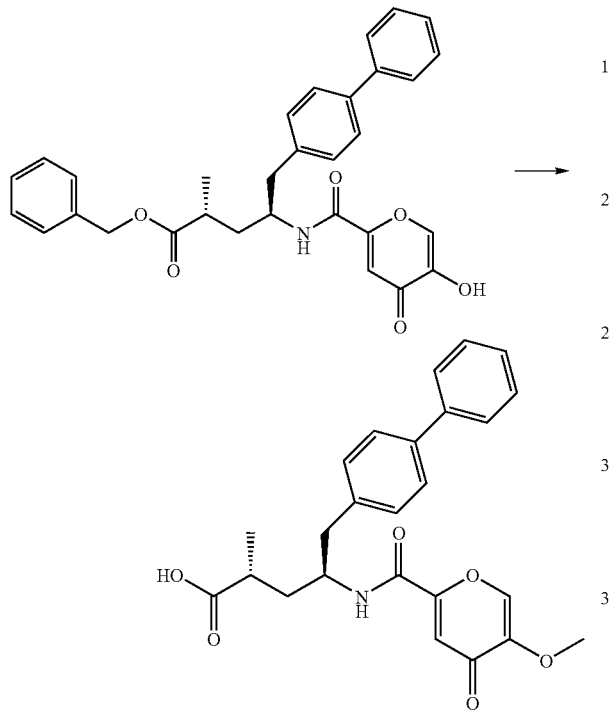

(2R,4S)-5-Biphenyl-4-yl-4-[(5-hydroxy-4-oxo-4H-pyran-2-carbonyl)-amino]-2-methyl-pentanoic acid benzyl ester is prepared from Intermediate 2 and 5-hydroxy-4-oxo-4H-pyran-2-carboxylic acid analogous to Example 41-1; HPLC Retention time 1.32 minutes (condition C): MS 510.3 (M−1).

Next, to a solution of (2R,4S)-5-biphenyl-4-yl-4-[(5-hydroxy-4-oxo-4H-pyran-2-carbonyl)-amino]-2-methyl-pentanoic acid benzyl ester (54 mg, 0.106 mmol) in DMF (1 mL) is added K₂CO₃ (29.2 mg, 0.211 mmol) and MeI (16.5 mg, 0.116 mmol), and the resulting mixture is stirred at room temperature overnight. Then ice/water is added and the mixture is extracted with EtOAc. The combined organic phases are washed with brine, dried over MgSO4, filtered and concentrated to give (2R,4S)-5-biphenyl-4-yl-4-[(5-methoxy-4-oxo-4H-pyran-2-carbonyl)-amino]-2-methyl-pentanoic acid benzyl ester which is used without further purification. HPLC Retention time 1.55 minutes (condition C): MS 526.3 (M+1).

Next, To a solution of (2R,4S)-5-biphenyl-4-yl-4-[(5-methoxy-4-oxo-4H-pyran-2-carbonyl)-amino]-2-methyl-pentanoic acid benzyl ester in methylene chloride (1 mL) is added BCl₃ (0.12 mL of a 1M solution in methylene chloride) and the mixture is stirred at room temperature for 18 hours. An additional 0.12 mL of the BCl₃ solution is added and stirring is continued for 5 hours. An additional 0.12 mL of the BCl₃ solution is added and stirring is continued for 18 hours. The mixture is quenched with water (2 drops) and DMF (1 mL) is added. The solution is purified by preparative HPLC using a gradient of 10% MeCN/water to 100% MeCN (0.1% TFA) to elute the title compound; HPLC Retention time 1.28 minutes (condition C): MS 436.1 (M+1)

1H NMR (400 MHz, DMSO-d₆) δ ppm 0.87-1.30 (m, 3H) 1.43-1.74 (m, 1H) 1.74-1.99 (m, 1H) 2.71-3.01 (m, 2H) 3.17 (s, 1H) 3.71 (s, 3H) 3.97-4.42 (m, 1H) 6.52-6.94 (m, 1H) 7.15-7.37 (m, 2H) 7.44 (t, J=7.71 Hz, 2H) 7.59-7.71 (m, 2H) 8.13 (s, 1H) 8.77 (d, J=8.84 Hz, 1H).

EXAMPLE 46-1

Synthesis of (2R,4S)-5-Biphenyl-4-yl-4-[(5-hydroxy-1-methyl-4-oxo-1,4-dihydro-pyridine-2-carbonyl)-amino]-2-methyl-pentanoic acid

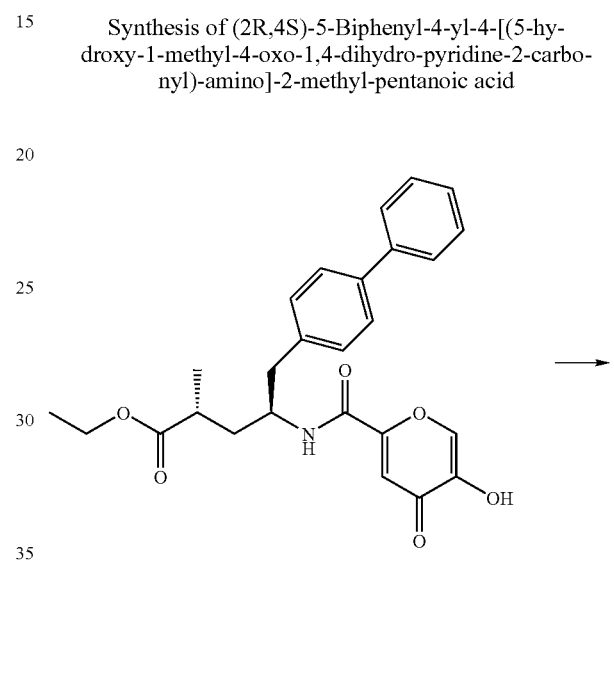

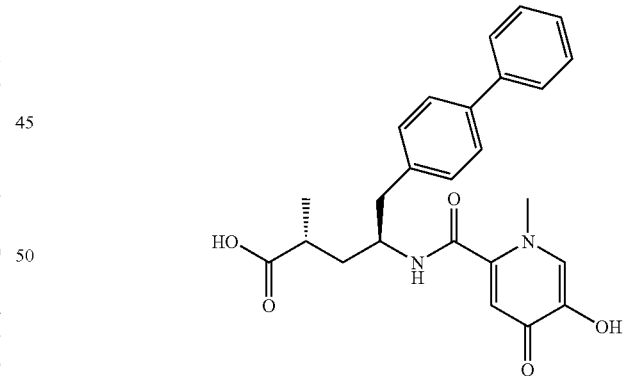

To a suspension of (2R,4S)-5-biphenyl-4-yl-4-[(5-hydroxy-4-oxo-4H-pyran-2-carbonyl)-amino]-2-methyl-pentanoic acid ethyl ester (Example 23-1) (50 mg) in water (1 mL) is added methylamine (1 mL of a 40% solution in water) and the resulting mixture is heated to reflux for 6 hours. The mixture is under reduced pressure and is purified by preparative HPLC using a gradient of 10% MeCN/water to 100% MeCN (0.1% TFA) to elute the title compound; HPLC Retention time 1.21 minutes (condition C): MS 435.1 (M+1); 1H NMR (400 MHz, DMSO-d₆) δ ppm 1.12 (d, J=7.07 Hz, 3H) 1.45-1.65 (m, 1H) 1.82-1.98 (m, 1H) 2.25-2.38 (m, 1H) 2.63-

2.78 (m, 1H) 2.79-2.97 (m, 1H) 4.14-4.32 (m, 1H) 6.45 (br. s., 1H) 7.26-7.39 (m, 2H) 7.45 (t, J=7.58 Hz, 2H) 7.55-7.68 (m, 4H) 8.79 (d, J=9.09 Hz, 1H).

EXAMPLE 47-1

Synthesis of (2R,4S)-5-Biphenyl-4-yl-2-methyl-4-[(pyridazine-4-carbonyl)-amino]-pentanoic acid

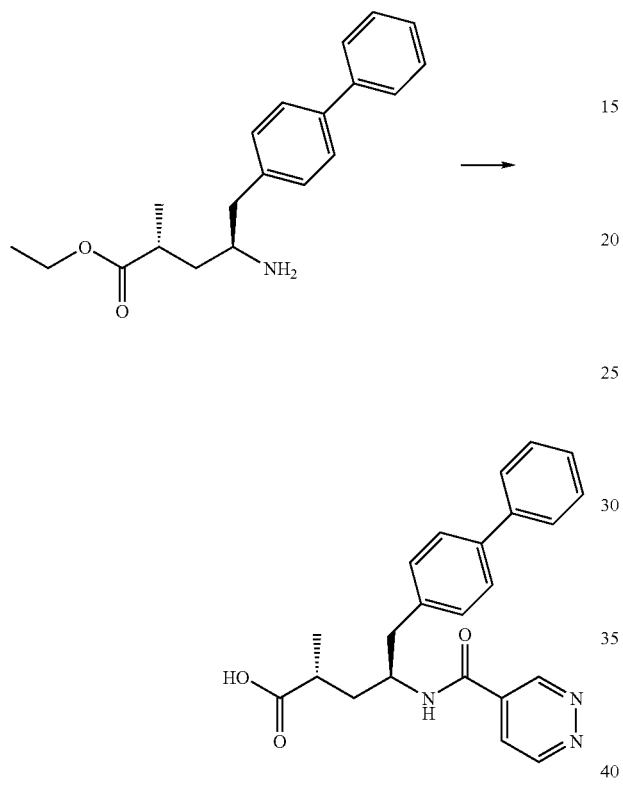

To a stirred solution of pyridazine-4-carboxylic acid (21 mg, 0.17 mmol) in DMF (6 mL) is added HOBT (26 mg, 0.17 mmol) and HBTU (65 mg, 0.17 mmol) and the mixture is stirred at room temperature for 10 minutes. (2R,4S)-4-Amino-5-biphenyl-4-yl-2-methyl-pentanoic acid ethyl ester hydrochloride (50 mg, 0.14 mmol) and DIEA (42 mg, 0.56 mmol) are added. After stirring the mixture at room temperature for 18 hours, water is added and the mixture is extracted three times with ethyl acetate. The combined organic layers are washed with water and brine then is dried over magnesium sulfate. The solvent is removed under reduced pressure to give the title compound; HPLC retention time 1.19 minutes (condition C); MS 390.3 (M+H); 1H NMR (400 MHz, DMSO-d6): δ ppm 1.08-1.10 (d, J=7.07 Hz, 3H), 1.59-1.66 (m, 1H), 1.88-1.95 (m, 1H), 2.46-2.53 (m, 1H), 2.85-2.87 (d, J=6.82 Hz, 2H), 4.22-4.30 (m, 1H), 7.29-7.32 (m, 2H), 7.33-7.36 (m, 1H), 7.42-7.46 (m, 2H), 7.57-7.59 (m, 2H), 7.62-7.65 (m, 2H), 7.91-7.93 (q, J=2.27 Hz, 1H), 8.76-8.78 (d, J=8.59 Hz, 1H), 9.41-9.43 (m, 1H), 9.45-9.46 (m, 1H), 12.09 (s, 1H).

Following compounds are prepared and isolated after the coupling reaction and prior to the hydrolysis reaction described in the above example:

| Example # | Product | Reagent | LCMS-RT (condition) | MS (M + 1) |
|---|---|---|---|---|
| Example 47-2 | (2R,4S)-ethyl 5-(biphenyl-4-yl)-4-(2-hydroxyisonicotinamido)-2-methylpentanoate | (2-hydroxyisonicotinic acid) EDCl and HOAt used instead of HATU | 1.63 min. (A) | 433.1 |

| Example # | Product | Reagent | LCMS-RT (condition) | MS (M + 1) |
|---|---|---|---|---|
| Example 47-3 | 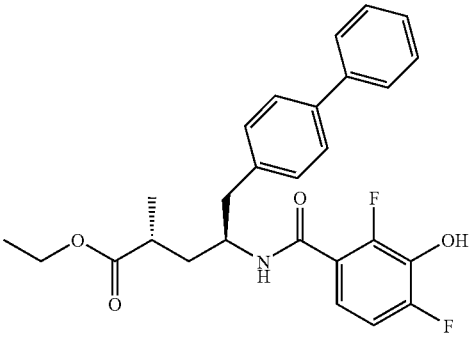<br>(2R,4S)-ethyl 5-(biphenyl-4-yl)-4-(2,4-difluoro-3-hydroxybenzamido)-2-methylpentanoate | 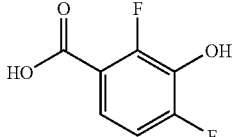<br>EDCl and HOAt used instead of HATU | 1.79 min. (A) | 468.2 |
| Example 47-4 | 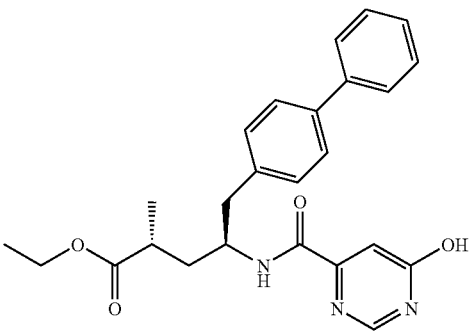<br>(2R,4S)-ethyl 5-(biphenyl-4-yl)-4-(6-hydroxypyrimidine-4-carboxamido)-2-methylpentanoate | 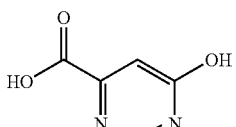<br>EDCl and HOAt used instead of HATU | 1.70 min. (A) | 434.2 |
| Example 47-5 | 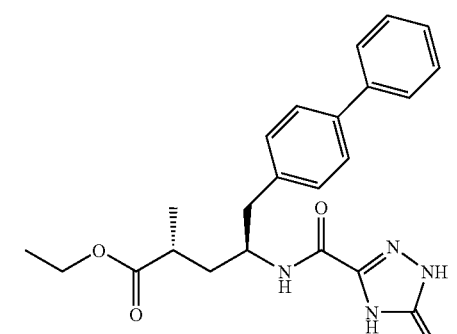<br>(2R,4S)-ethyl 5-(biphenyl-4-yl)-2-methyl-4-(5-oxo-4,5-dihydro-1H-1,2,4-triazole-3-carboxamido)pentanoate | 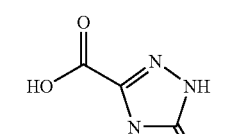<br>EDCl and HOAt used instead of HATU | 1.85 min. (B) | 423.2 |

-continued

| Example # | Product | Reagent | LCMS-RT (condition) | MS (M + 1) |
|---|---|---|---|---|
| Example 47-6 | (2R,4S)-ethyl 5-(biphenyl-4-yl)-2-methyl-4-(5-oxo-4,5-dihydro-1,2,4-oxadiazole-3-carboxamido)pentanoate | Intermediate 35 | 1.76 min. (B) | 424.3 |
| Example 47-7 | (2R,4S)-ethyl 5-(biphenyl-4-yl)-2-methyl-4-(5-oxo-2,5-dihydro-1H-pyrazole-3-carboxamido)pentanoate | EDCl and HOAt used instead of HATU | 1.61 min. (B) | 422.3 |
| Example 47-8 | (2R,4S)-ethyl 5-(biphenyl-4-yl)-4-(3,5-difluoro-4-methoxybenzamido)-2-methylpentanoate | | 1.78 min. (B) | 482.4 |

-continued

| Example # | Product | Reagent | LCMS-RT (condition) | MS (M + 1) |
|---|---|---|---|---|
| Example 47-9 | 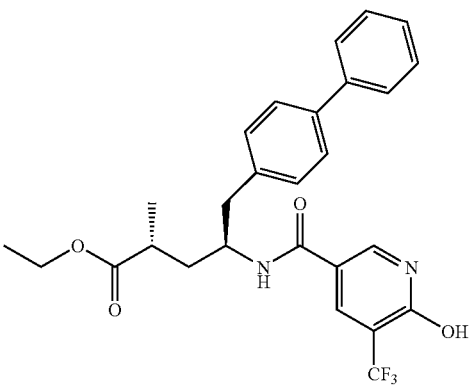<br>(2R,4S)-ethyl 5-(biphenyl-4-yl)-4-(6-hydroxy-5-(trifluoromethyl)nicotinamido)-2-methylpentanoate | 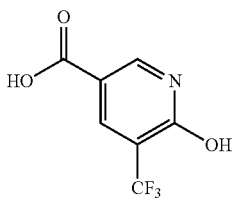<br>Intermediate 37 | 1.75 min. (B) | 501.2 |
| Example 47-10 | 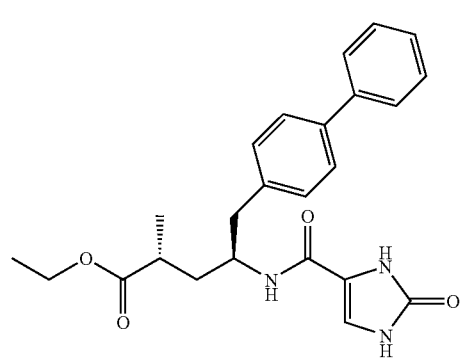<br>(2R,4S)-ethyl 5-(biphenyl-4-yl)-2-methyl-4-(2-oxo-2,3-dihydro-1H-imidazole-4-carboxamido)pentanoate | 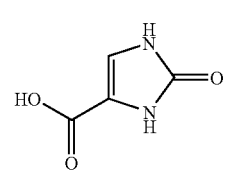<br>EDCl and HOAt used instead of HATU | 1.66 min. (B) | 422.3 |
| Example 47-11 | 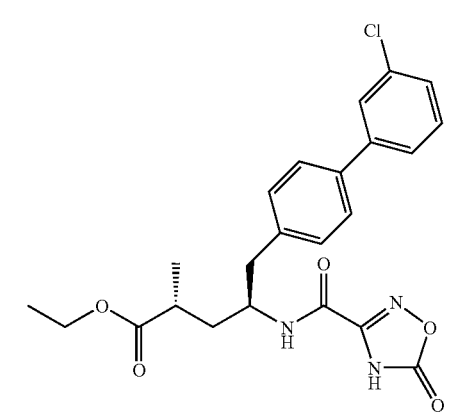<br>(2R,4S)-ethyl 5-(3'-chlorobiphenyl-4-yl)-2-methyl-4-(5-oxo-4,5-dihydro-1,2,4-oxadiazole-3-carboxamido)pentanoate | 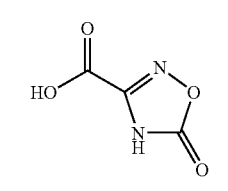<br>Intermediate 35 | 1.52 min. (A) | 458.3 |

EXAMPLE 47-2

1H NMR (400 MHz, CHLOROFORM-d) δ ppm 1.11 (d, J=7.3 Hz, 3H) 1.14 (t, J=7.2 Hz, 3H) 1.64 (ddd, J=14.2, 9.9, 4.2 Hz, 1H) 1.93 (ddd, J=14.0, 9.5, 4.0 Hz, 1H) 2.57 (m, 1H) 2.83 (dd, J=13.7, 6.3 Hz, 1H) 2.92 (dd, J=13.7, 6.3 Hz, 1H) 4.04 (q, J=7.2 Hz, 2H) 4.22-4.42 (m, 1H) 6.45 (d, J=6.6 Hz, 1H) 6.68 (d, J=8.6 Hz, 1H) 6.74 (s, 1H) 7.19 (d, J=8.1 Hz, 2H) 7.21-7.28 (m, 2H) 7.33 (t, J=7.6 Hz, 2H) 7.46 (dd, J=14.5, 7.7 Hz, 4H) 12.79 (br. s., 1H)

EXAMPLE 47-3

1H NMR (400 MHz, CHLOROFORM-d) δ ppm 1.14-1.30 (m, 6H) 1.55-1.76 (m, 1H) 1.99-2.17 (m, 1H) 2.55-2.75 (m, 1H) 2.88-3.07 (m, 2H) 4.02-4.22 (m, 2H) 4.45-4.66 (m, 1H) 6.49-6.69 (m, 1H) 6.77-6.94 (m, 1H) 7.24-7.36 (m, 3H) 7.36-7.47 (m, 2H) 7.48-7.65 (m, 5H) 8.88 (br. s., 1H)

EXAMPLE 47-4

1H NMR (400 MHz, CHLOROFORM-d) δ ppm 1.07-1.22 (m, 6H) 1.80-2.16 (m, 2H) 2.33-2.55 (m, 1H) 2.70 (dd, J=13.4, 7.4 Hz, 1H) 2.80 (dd, J=13.4, 7.4 Hz, 1H) 3.69-3.87 (m, 1H) 3.87-4.53 (m, 2H) 5.46-5.70 (m, 1H) 7.16 (s, 1H) 7.25-7.31 (m, 2H) 7.34-7.40 (m, 3H) 7.42-7.48 (m, 2H) 7.48-7.53 (m, 3H)

EXAMPLE 47-5

1H NMR (400 MHz, CD$_3$OD) δ ppm 1.15 (d, J=7.1 Hz, 3H) 1.19 (t, J=7.1 Hz, 3H) 1.62-1.75 (m, 1H) 1.89-2.03 (m, 1H) 2.50-2.64 (m, 1H) 2.75-2.95 (m, 2H) 3.98-4.14 (m, 2H) 4.20-4.36 (m, 1H) 7.29 (d, J=8.1 Hz, 3H) 7.36-7.44 (m, 2H) 7.52 (d, J=8.3 Hz, 2H) 7.54-7.59 (m, 2H)

EXAMPLE 47-6

1H NMR (400 MHz, DMSO-d$_6$) δ ppm 1.08 (d, J=7.1 Hz, 3H) 1.13 (t, J=7.1 Hz, 3H) 1.67 (ddd, J=14.1, 10.2, 4.3 Hz, 1H) 1.86 (ddd, J=13.8, 9.9, 3.8 Hz, 1H) 2.78 (dd, J=13.4, 7.5 Hz, 1H) 2.85 (dd, J=13.4, 7.5 Hz, 1H) 3.23-3.46 (m, 1H) 3.92-4.08 (m, 2H) 4.08-4.22 (m, 1H) 7.27 (d, J=8.1 Hz, 2H) 7.31-7.38 (m, 1H) 7.45 (t, J=7.7 Hz, 2H) 7.58 (d, J=8.3 Hz, 2H) 7.64 (d, J=7.3 Hz, 2H) 9.03 (d, J=8.8 Hz, 1H) 13.10 (br. s., 1H)

EXAMPLE 47-7

1H NMR (400 MHz, DMSO-d$_6$) δ ppm 0.97 (d, J=7.1 Hz, 3H) 1.11 (t, J=7.1 Hz, 3H) 1.85 (ddd, J=13.7, 9.7, 3.9 Hz, 1H) 1.99 (ddd, J=12.4, 8.8, 3.0 Hz, 1H) 2.09-2.25 (m, 1H) 2.74-2.86 (m, 2H) 3.91-4.05 (m, 2H) 4.08-4.24 (m, 1H) 5.95 (br s, 1H) 7.27 (d, J=8.1 Hz, 2H) 7.33 (t, J=7.6 Hz, 2H) 7.45 (q, J=7.4 Hz, 2H) 7.55-7.67 (m, 3H) 7.74 (s, 1H) 7.95 (d, J=8.6 Hz, 1H)

EXAMPLE 47-8

1H NMR (400 MHz, CHLOROFORM-d) δ ppm 1.12 (d, J=7.1 Hz, 3H), 1.16 (t, J=7.1 Hz, 3H), 1.54 (ddd, J=14.3, 10.0, 4.3 Hz, 1H), 1.93 (ddd, J=14.1, 9.6, 4.0 Hz, 1H), 2.47-2.64 (m, 1H), 2.76-2.99 (m, 2H), 3.65-3.76 (m, 3H), 4.04 (q, J=7.1 Hz, 2H), 4.24-4.44 (m, 1H), 5.81 (d, J=8.3 Hz, 1H), 6.30-6.43 (m, 2H), 7.20-7.28 (m, 3H), 7.34 (t, J=7.6 Hz, 2H), 7.45 (d, J=8.1 Hz, 2H), 7.47-7.54 (m, 2H).

EXAMPLE 47-9

1H NMR (400 MHz, CHLOROFORM-d) δ ppm 1.23 (d, J=7.3 Hz, 3H), 1.28 (t, J=7.2 Hz, 3H), 1.68-1.86 (m, 1H), 1.91-2.04 (m, 1H), 2.73 (ddd, J=9.1, 7.2, 3.4 Hz, 1H), 2.90 (dd, J=13.6, 7.3 Hz, 1H), 3.11 (dd, J=13.6, 5.6 Hz, 1H), 4.18 (q, 2H), 4.35-4.51 (m, 1H), 6.77 (d, J=7.8 Hz, 1H), 7.31 (d, J=8.1 Hz, 2H), 7.33-7.40 (m, 1H), 7.42-7.50 (m, 2H), 7.53-7.65 (m, 4H), 8.20 (d, J=2.3 Hz, 1H), 8.28 (s, 1H).

EXAMPLE 47-10

1H NMR (400 MHz, CD$_3$OD) δ ppm 1.15 (d, J=7.1 Hz, 3H), 1.18 (t, J=7.2 Hz, 3H), 1.58 (ddd, J=14.2, 10.6, 4.0 Hz, 1H), 1.97 (ddd, J=13.9, 10.2, 3.7 Hz, 1H), 2.56 (ddd, J=10.5, 7.0, 4.0 Hz, 1H), 2.84 (dd, J=6.7, 4.2 Hz, 2H), 3.96-4.15 (m, 2H), 4.19-4.37 (m, 1H), 7.03 (s, 1H), 7.20-7.34 (m, 3H), 7.40 (t, J=7.6 Hz, 2H), 7.52 (d, J=8.1 Hz, 2H), 7.57 (d, J=7.3 Hz, 2H), 7.72 (d, J=8.8 Hz, 1H).

EXAMPLE 47-11

1H NMR (400 MHz, DMSO-d$_6$) δ ppm 1.07 (d, J=7.1 Hz, 3H) 1.12 (t, J=7.1 Hz, 3H) 1.66 (ddd, J=14.1, 10.3, 4.4 Hz, 1H) 1.83 (ddd, J=13.7, 9.9, 3.7 Hz, 1H) 2.43-2.49 (m, 1H) 2.77 (dd, J=13.7, 7.9 Hz, 1H) 2.85 (dd, J=13.7, 7.9 Hz, 1H) 3.94-4.05 (m, 2H) 4.07-4.20 (m, 1H) 7.28 (d, J=8.3 Hz, 2H) 7.37-7.43 (m, 1H) 7.47 (t, J=7.8 Hz, 1H) 7.59-7.66 (m, 3H) 7.70 (t, J=1.9 Hz, 1H) 8.83 (br. s., 1H) 13.12 (br. s., 1H).

EXAMPLE 49-1

Synthesis of (2R,4S)-5-(3'-Chloro-biphenyl-4-yl)-4-[(3-hydroxy-isoxazole-5-carbonyl)-amino]-2-methyl-pentanoic acid and

EXAMPLE 50-1

Synthesis of (2S,4S)-5-(3'-Chloro-biphenyl-4-yl)-4-[(3-hydroxy-isoxazole-5-carbonyl)-amino]-2-methyl-pentanoic acid

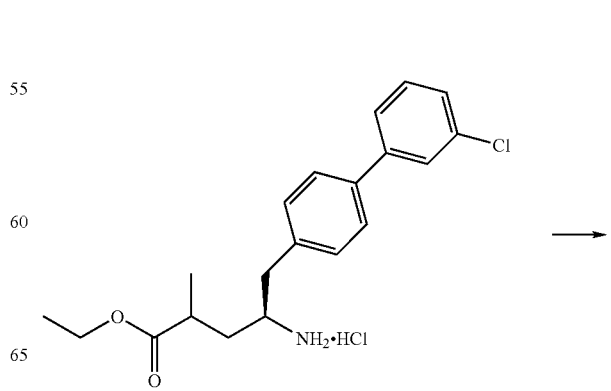

-continued

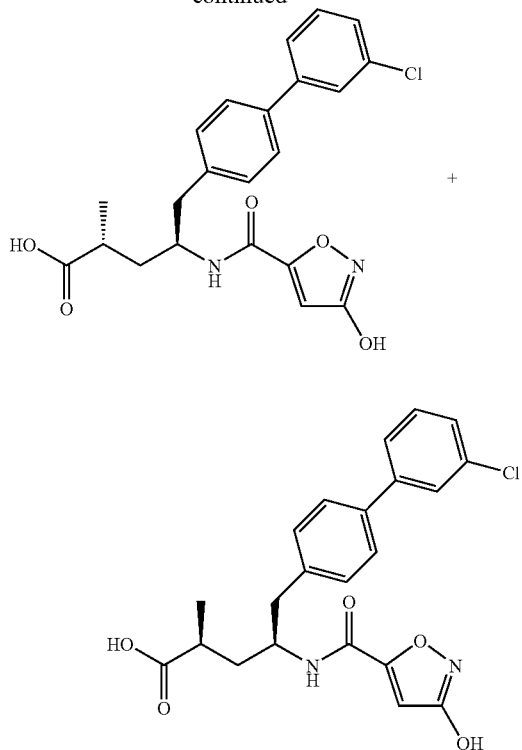

To a solution of 3-hydroxy-isoxazole-5-carboxylic acid (Intermediate 20) (74.6 mg, 0.578 mmol), HATU (264 mg, 0.694 mmol) in DMF (3 mL) is added pyridine (0.14 mL, 1.735 mmol) and the resulting mixture is stirred at room temperature for 15 minutes. Then (S)-4-amino-5-(3'-chloro-biphenyl-4-yl)-2-methyl-pentanoic acid ethyl ester hydrochloride (Intermediate 31) (200 mg, 0.578 mmol) is added and the mixture is stirred at room temperature for 2 hours. Any insoluble material is filtered and the filtrate purified by preparative HPLC using a gradient of 10% MeCN/water to 100% MeCN (0.1% TFA). The diastereomeric mixture is further purified by chiral HPLC on a Chirapak IA column using heptane/ethanol (80:20) (0.1% TFA) to elute each diastereomer, (2R,4S)-5-(3'-chloro-biphenyl-4-yl)-4-[(3-hydroxy-isoxazole-5-carbonyl)-amino]-2-methyl-pentanoic acid ethyl ester and (2S,4S)-5-(3'-chloro-biphenyl-4-yl)-4-[(3-hydroxy-isoxazole-5-carbonyl)-amino]-2-methyl-pentanoic acid ethyl ester.

Next, to a solution of (2R,4S)-5-(3'-chloro-biphenyl-4-yl)-4-[(3-hydroxy-isoxazole-5-carbonyl)-amino]-2-methyl-pentanoic acid ethyl ester (73 mg, 0.16 mmol) in ethanol (4 mL) is added 1N NaOH (2 mL) and the resulting mixture is stirred at room temperature for 2 hours. The mixture is acidified with 1N HCl and the solvent is removed under reduced pressure. The resulting residue is purified by preparative HPLC using a gradient of 10% MeCN/water to 100% MeCN (0.1% TFA) to give (2R,4S)-5-(3'-chloro-biphenyl-4-yl)-4-[(3-hydroxy-isoxazole-5-carbonyl)-amino]-2-methyl-pentanoic acid; HPLC Retention time 1.05 minutes (condition C): MS 429.1 (M+1); 1H NMR (400 MHz, DMSO-$d_6$) δ ppm 1.07 (d, 3H) 1.58 (ddd, J=13.89, 9.98, 4.42 Hz, 1H) 1.87 (ddd, J=13.71, 9.66, 3.92 Hz, 1H) 2.41 (ddd, J=9.54, 7.14, 4.55 Hz, 1H) 2.82 (dd, J=6.69, 3.41 Hz, 2H) 4.10-4.24 (m, 1H) 6.50 (s, 1H) 7.28 (d, J=8.34 Hz, 2H) 7.36-7.42 (m, 1H) 7.47 (t, J=7.83 Hz, 1H) 7.58-7.65 (m, 3H) 7.70 (t, J=1.89 Hz, 1H) 8.66 (d, J=8.59 Hz, 1H).

The second diastereomer, (2S,4S)-5-(3'-chloro-biphenyl-4-yl)-4-[(3-hydroxy-isoxazole-5-carbonyl)-amino]-2-methyl-pentanoic acid is prepared from the hydrolysis of (2R,4S)-5-(3'-chloro-biphenyl-4-yl)-4-[(3-hydroxy-isoxazole-5-carbonyl)-amino]-2-methyl-pentanoic acid ethyl ester analogous to the above example; HPLC Retention time 1.17 minutes (condition C): MS 429.3 (M+1); 1H NMR (400 MHz, DMSO-$d_6$) δ ppm 1.06 (d, J=7.07 Hz, 3H) 1.55 (ddd, J=13.64, 9.47, 3.92 Hz, 1H) 1.96 (ddd, J=13.83, 10.67, 4.80 Hz, 1H) 2.32 (ddd, J=9.09, 7.07, 5.05 Hz, 1H) 2.86 (d, J=7.07 Hz, 2H) 4.17-4.31 (m, 1H) 6.50 (s, 1H) 7.30 (d, J=8.34 Hz, 2H) 7.36-7.43 (m, 1H) 7.46 (t, J=7.83 Hz, 1H) 7.56-7.65 (m, 3H) 7.70 (t, J=1.89 Hz, 1H) 8.68 (d, J=9.09 Hz, 1H) 11.67 (s, 1H).

The following compounds are prepared using similar procedure as example 49-1 with appropriate reagents and conditions:

| Example # | Product | Reagents | Hydrolysis Condition | HPLC-RT (condition) | MS (M + 1) |
|---|---|---|---|---|---|
| Example 49-2 | 5-[(1S,3R)-3-Carboxy-1-(3'-chloro-biphenyl-4-ylmethyl)-butylcarbamoyl]-1H-pyrazole-3-carboxylic acid | | Aq. NaOH, EtOH, RT | 1.13 min. (C) | 456.3 |

-continued

| Example # | Product | Reagents | Hydrolysis Condition | HPLC-RT (condition) | MS (M + 1) |
|---|---|---|---|---|---|
| Example 49-3 | 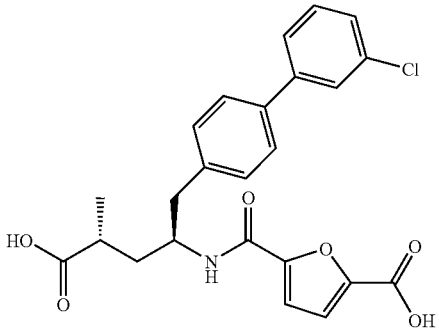<br>5-[(1S,3R)-3-Carboxy-1-(3′-chloro-biphenyl-4-ylmethyl)-butylcarbamoyl]-furan-2-carboxylic acid | 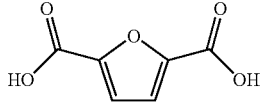 | Aq. NaOH, EtOH, RT | 1.00 min. (C) | 456.1 |
| Example 49-4 | 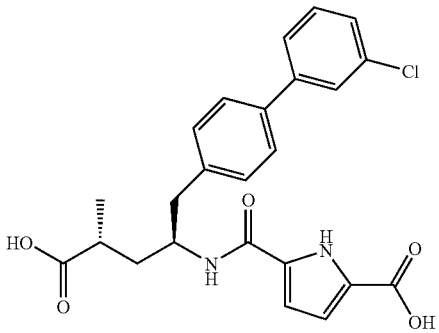<br>5-[(1S,3R)-3-Carboxy-1-(3′-chloro-biphenyl-4-ylmethyl)-butylcarbamoyl]-1H-pyrrole-2-carboxylic acid | 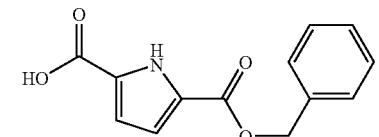 | Aq. NaOH, EtOH, RT | 1.19 min. (C) | 455.3 |
| Example 49-5 | 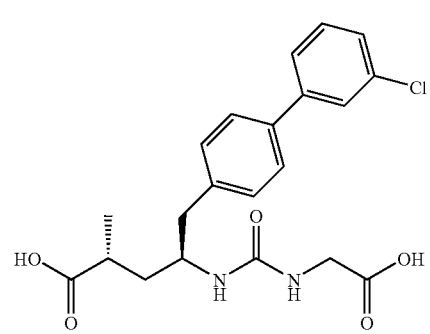<br>(2R,4S)-4-(3-Carboxymethyl-ureido)-5-(3′-chloro-biphenyl-4-yl)-2-methyl-pentanoic acid | from Example 51-1 | Aq. NaOH, EtOH, RT | 1.18 min. (C) | 419.3 |

-continued

| Example # | Product | Reagents | Hydrolysis Condition | HPLC-RT (condition) | MS (M + 1) |
|---|---|---|---|---|---|
| Example 49-6 | 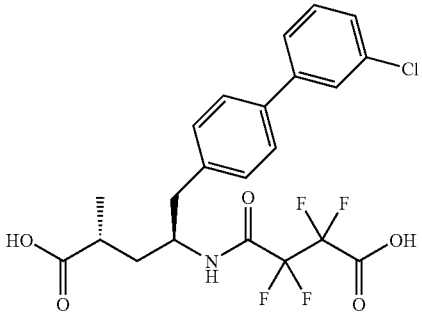<br>(2R,4S)-4-(3-Carboxy-2,2,3,3-tetrafluoro-propionylamino)-5-(3'-chloro-biphenyl-4-yl)-2-methyl-pentanoic acid | 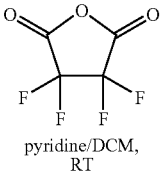<br>pyridine/DCM, RT | Aq. NaOH, EtOH, RT | 1.27 min. (C) | 490.1 |
| Example 49-7 | 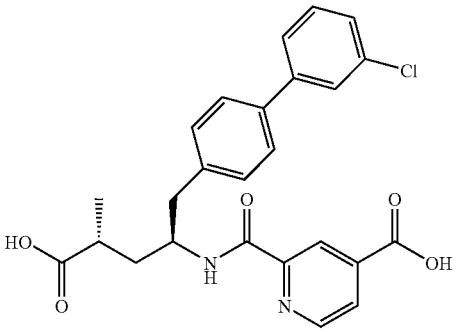<br>2-((2S,4R)-4-carboxy-1-(3'-chlorobiphenyl-4-yl)pentan-2-ylcarbamoyl)isonicotinic acid | from Example 77-1 | Aq. NaOH, EtOH, RT | 1.45 min. (C) | 467.2 |
| Example 49-8 | 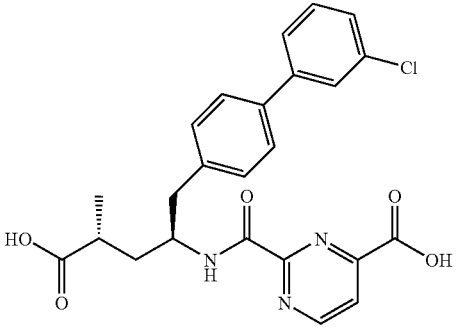<br>2-((2S,4R)-4-carboxy-1-(3'-chlorobiphenyl-4-yl)pentan-2-ylcarbamoyl)pyrimidine-4-carboxylic acid | from Example 76-1 | Aq. NaOH, EtOH, RT | 1.24 min. (C) | 468.2 |

| Example # | Product | Reagents | Hydrolysis Condition | HPLC-RT (condition) | MS (M + 1) |
|---|---|---|---|---|---|
| Example 49-9 | 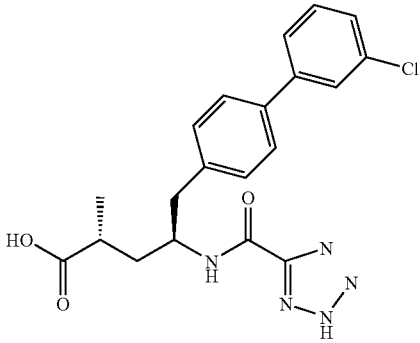<br>(2R,4S)-5-(3'-chlorobiphenyl-4-yl)-2-methyl-4-(2H-tetrazole-5-carboxamido)pentanoic acid | from Example 52-1 | Aq. NaOH, EtOH, RT | 1.26 min. (C) | 414.3 |
| Example 49-10 | 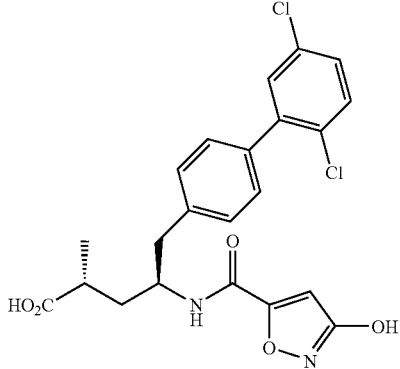<br>(2R,4S)-5-(2',5'-dichlorobiphenyl-4-yl)-4-(3-hydroxyisoxazole-5-carboxamido)-2-methylpentanoic acid | Example 77-1 | Aq. NaOH, EtOH, RT | 1.49 min (C) | 463.2 |

EXAMPLE 49-2

1H NMR (400 MHz, DMSO-d6) δ ppm 1.08 (d, J=7.07 Hz, 3H) 1.50-1.66 (m, 1H) 1.78-1.94 (m, 1H) 2.70-2.93 (m, 2H) 4.22 (br. s., 1H) 7.29 (d, J=8.34 Hz, 2H) 7.35-7.41 (m, 1H) 7.46 (t, J=7.83 Hz, 1H) 7.53-7.64 (m, 3H) 7.69 (t, J=1.89 Hz, 1H) 8.25 (br. s., 1H).

EXAMPLE 49-3

1H NMR (400 MHz, DMSO-d6) δ ppm 1.08 (d, J=7.07 Hz, 3H, 1.54-1.65 (m, 1H) 1.81-1.93 (m, 1H) 2.37-2.46 (m, 2H) 2.85 (dd, J=10.23, 6.95 Hz, 2H) 4.23 (br. s., 1H) 7.16 (d, J=3.54 Hz, 1H) 7.22 (br. s., 1H) 7.29 (d, J=8.34 Hz, 2H) 7.34-7.42 (m, 1H) 7.46 (t, J=7.83 Hz, 1H) 7.57-7.65 (m, 3H) 7.69 (t, J=1.89 Hz, 1H) 8.40 (d, J=8.84 Hz, 1H).

EXAMPLE 49-4

1H NMR (400 MHz, DMSO-d6) δ ppm 1.08 (d, J=7.07 Hz, 3H), 1.46 (m, 1H), 1.88 (m, 1H), 2.45 (m, 1H), 2.83 (d, J=6.57 Hz, 2H), 4.19 (m, 1H), 6.72 (d, J=2.53 Hz, 1H), 7.29 (d, J=8.34 Hz, 2H), 7.38-7.41 (m, 1H), 7.46 (t, 2H), 7.62 (d, J=8.08 Hz, 3H), 7.70 (m, 1H), 8.09 (d, J=8.34 Hz, 1H), 11.89 (s, broad, 1H).

EXAMPLE 49-5

1H NMR (400 MHz, DMSO-d6): δ ppm 1.03-1.05 (d, J=7.07 Hz, 3H), 1.21-1.35 (m, 2H), 1.69-1.77 (m, 1H), 2.62-2.67 (m, 1H), 2.70-2.71 (m, 2H), 3.67-3.68 (d, J=5.81 Hz, 2H), 3.73-3.80 (m, 1H), 5.97-6.01 (t, J=8.08 Hz, 1H), 6.12-6.14 (d, J=8.34 Hz, 1H), 7.26-7.28 (m, 2H), 7.38-7.41 (m, 1H), 7.45-7.49 (t, J=7.83 Hz, 1H), 7.59-7.64 (m, 3H), 7.69-7.70 (t, J=2.02 Hz, 1H), 12.09 (s, 1H), 12.43 (s, 1H).

EXAMPLE 49-6

1H NMR (400 MHz, DMSO-d$_6$): δ ppm 1.07-1.10 (m, 6H), 1.49-1.56 (m, 1H), 1.84-1.91 (m, 1H), 2.47-2.56 (m, 1H), 2.77-2.87 (m, 2H), 3.94-3.99 (q, J=7.07 Hz, 14.05 Hz, 2H), 4.11-4.20 (m, 1H), 6.72-6.73 (d, J=2.27 Hz, 2H), 7.28-7.30 (m, 2H), 7.38-7.41 (m, 1H), 7.44-7.48 (t, J=7.83 Hz, 1H), 7.61-7.64 (m, 3H), 7.69-7.70 (t, J=1.77 Hz, 1H), 8.07-8.10 (d, J=8.34 Hz, 1H), 11.89 (s, 1H), 12.74 (s, 1H).

EXAMPLE 49-7

1H NMR (400 MHz, DMSO-d$_6$) δ ppm 1.07 (d, 3H) 1.64-1.74 (m, 1H) 1.84-1.94 (m, 1H) 2.41 (ddd, J=9.35, 7.07, 4.55

Hz, 1H) 2.80-2.89 (m, 1H) 2.92-3.01 (m, 1H) 4.26-4.40 (m, 1H) 7.30 (d, J=8.08 Hz, 2H) 7.35-7.40 (m, 1H) 7.45 (t, J=7.83 Hz, 1H) 7.52-7.63 (m, 3H) 7.68 (t, J=1.77 Hz, 1H) 8.00 (dd, J=4.93, 1.64 Hz, 1H) 8.33 (s, 1H) 8.78 (d, J=9.35 Hz, 1H) 8.85 (d, J=4.80 Hz, 1H).

EXAMPLE 49-8

1H NMR (400 MHz, DMSO-d$_6$): δ ppm 1.08-1.10 (d, J=7.07 Hz, 3H), 1.62-1.69 (m, 1H), 1.89-1.96 (m, 1H), 2.41-2.50 (m, 1H), 2.85-2.98 (m, 2H), 4.26-36 (m, 1H), 7.33-7.35 (m, 2H), 7.38-7.41 (m, 1H), 7.45-7.49 (t, J=7.83 Hz, 1H), 7.60-7.63 (m, 3H), 7.69-7.70 (t, J=2.02 Hz, 1H), 8.12-8.13 (d, J=5.05 Hz, 1H), 8.87-8.89 (d, J=9.09 Hz, 1H), 9.19-9.21 (d, J=5.05 Hz, 1H), 12.06 (s, 1H), 13.99 (s, 1H).

EXAMPLE 49-9

1H NMR (400 MHz, DMSO-d$_6$) δ ppm 1.09 (d, J=7.07 Hz, 3H) 1.68 (ddd, J=13.96, 10.04, 4.29 Hz, 1H) 1.90 (ddd, J=13.71, 9.79, 4.04 Hz, 1H) 2.79-2.96 (m, 2H) 4.27 (br. s., 1H) 7.30 (d, J=8.34 Hz, 2H) 7.37-7.42 (m, 1H) 7.46 (t, J=7.83 Hz, 1H) 7.56-7.64 (m, 3H) 7.68 (t, J=1.77 Hz, 1H) 9.24 (br. s., 1H) 11.59-12.34 (m, 1H)

EXAMPLE 49-10

1H NMR (400 MHz, DMSO-d$_6$) δ ppm 1.02-1.13 (m, 3H) 1.59 (ddd, J=13.89, 9.85, 4.55 Hz, 1H) 1.88 (ddd, J=13.71, 9.54, 4.04 Hz, 1H) 2.42 (ddd, J=9.35, 7.07, 4.55 Hz, 1H) 2.78-2.92 (m, 2H) 4.13-4.29 (m, 1H) 6.50 (s, 1H) 7.24-7.32 (m, 2H) 7.33-7.39 (m, 2H) 7.41-7.49 (m, 2H) 7.55-7.62 (m, 1H) 8.68 (d, J=8.84 Hz, 1H) 11.66 (br. s., 1H)

The following (2S,4S)-compounds are prepared using similar procedure as example 50-1 with appropriate reagents and conditions:

| Example # | Product | Reagents | Hydrolysis Condition | HPLC-RT (condition) | MS (M + 1) |
|---|---|---|---|---|---|
| Example 50-2 | 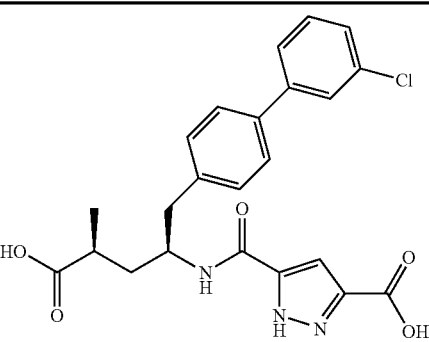<br>5-[(1S,3S)-3-Carboxy-1-(3'-chloro-biphenyl-4-ylmethyl)-butylcarbamoyl]-1H-pyrazole-3-carboxylic acid | 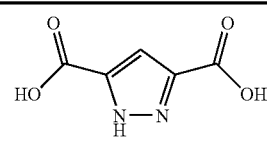 | Aq. NaOH, EtOH, RT | 1.14 min. (C) | 456.3 |
| Example 50-3 | 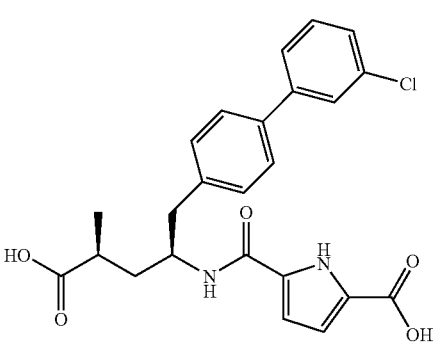<br>5-[(1S,3S)-3-Carboxy-1-(3'-chloro-biphenyl-4-ylmethyl)-butylcarbamoyl]-1H-pyrrole-2-carboxylic acid | 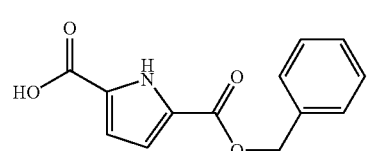 | Aq. NaOH, EtOH, RT | 1.15 min. (C) | 455.3 |

| Example # | Product | Reagents | Hydrolysis Condition | HPLC-RT (condition) | MS (M + 1) |
|---|---|---|---|---|---|
| Example 50-4 | 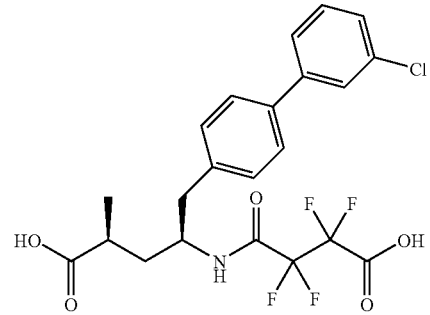<br>(2S,4S)-4-(3-Carboxy-2,2,3,3-tetrafluoro-propionylamino)-5-(3'-chloro-biphenyl-4-yl)-2-methyl-pentanoic acid | 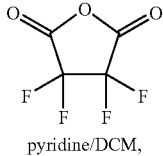<br>pyridine/DCM, RT | Aq. NaOH, EtOH, RT | 1.25 min. (C) | 490.2 |
| Example 50-5 | 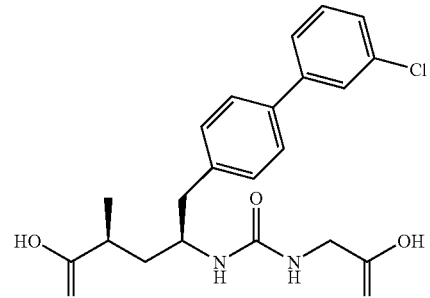<br>(2S,4S)-4-(3-Carboxymethyl-ureido)-5-(3'-chloro-biphenyl-4-yl)-2-methyl-pentanoic acid | from Example 51-1 | Aq. NaOH, EtOH, RT | 1.15 min. (C) | 419.3 |
| Example 50-6 | 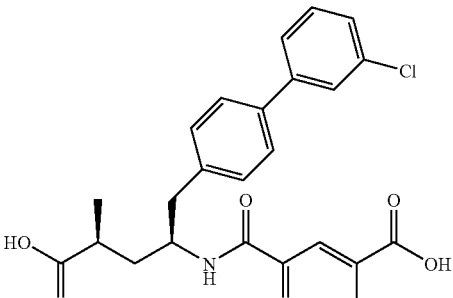<br>2-((2S,4S)-4-carboxy-1-(3'-chlorobiphenyl-4-yl)pentan-2-ylcarbamoyl)isonicotinic acid | 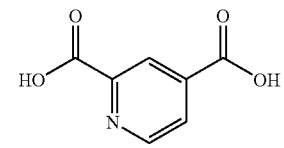 | Aq. NaOH, EtOH, RT | 1.31 min. (C) | 467.2 |

| Example # | Product | Reagents | Hydrolysis Condition | HPLC-RT (condition) | MS (M + 1) |
|---|---|---|---|---|---|
| Example 50-7 | 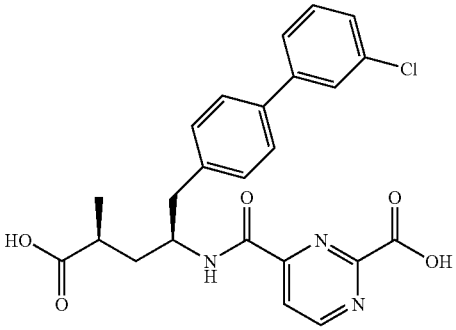<br>4-((2S,4S)-4-carboxy-1-(3'-chlorobiphenyl-4-yl)pentan-2-ylcarbamoyl)pyrimidine-2-carboxylic acid | 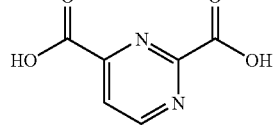 | Aq. NaOH, EtOH, RT | 1.25 min. (C) | 468.3 |
| Example 50-8 | 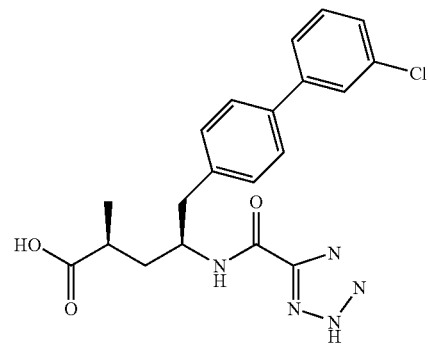<br>(2S,4S)-5-(3'-chlorobiphenyl-4-yl)-2-methyl-4-(2H-tetrazole-5-carboxamido)pentanoic acid | From Intermediate 32 | Aq. NaOH, EtOH, RT | 1.30 min. (C) | 414.3 |

EXAMPLE 50-2

1H NMR (400 MHz, DMSO-d6) δ ppm 0.99-1.13 (m, J=7.07, Hz 3H) 1.42-1.65 (m, 1H) 1.86-2.10 (m, 1H) 2.73-2.96 (m, 2H) 4.17-4.37 (m, 1H) 7.28-7.34 (m, 2H) 7.35-7.42 (m, 1H) 7.45 (t, J=7.96 Hz, 1H) 7.55-7.64 (m, 3H) 7.66-7.72 (m, 1H) 8.10-8.49 (m, 1H) 12.12 (br. s., 1H) 13.98-14.30 (m, 1H).

EXAMPLE 50-3

1H NMR (400 MHz, DMSO-d6): δ ppm 1.04-1.05 (d, J=6.82 Hz, 3H), 1.50-1.58 (m, 1H), 1.83-1.90 (m, 1H), 2.32-2.39 (m, 1H), 2.80-2.89 (m, 2H), 4.22-4.31 (m, 1H), 6.72 (d, J=1.77 Hz, 2H), 7.28-7.32 (m, 2H), 7.38-7.40 (m, 1H), 7.44-7.48 (t, J=7.83 Hz, 1H), 7.61-7.63 (m, 3H), 7.70 (s, 1H), 8.10-8.12 (d, J=8.84 Hz, 1H), 11.91 (s, 1H).

EXAMPLE 50-4

1H NMR (400 MHz, DMSO-d6): δ ppm 1.10-1.12 (d, J=6.82 Hz, 3H), 1.48-1.55 (m, 1H), 1.90-1.97 (m, 1H), 2.32-2.39 (m, 1H), 2.82-2.89 (m, 2H), 4.06-4.13 (m, 1H), 7.27-7.29 (d, J=8.34 Hz, 2H), 7.39-7.42 (m, 1H), 7.46-7.50 (t, J=7.83 Hz, 1H), 7.61-7.65 (m, 3H), 7.70-7.71 (t, J=1.77 Hz, 1H), 9.25-9.28 (d, J=9.09 Hz, 1H).

EXAMPLE 50-5

1H NMR (400 MHz, DMSO-d6): δ ppm 0.99-1.01 (d, J=6.82 Hz, 3H), 1.35-1.42 (m, 1H), 1.62-1.69 (m, 1H), 2.35-2.41 (m, 1H), 2.71-2.74 (m, 2H), 3.68-3.69 (d, J=7.33 Hz, 2H), 3.84-3.91 (m, 1H), 5.98-6.01 (m, 1H), 6.07-6.13 (m, 1H), 7.27-7.29 (m, 2H), 7.38-7.41 (m, 1H), 7.45-7.49 (t, J=7.71 Hz, 1H), 7.60-7.65 (m, 3H), 7.69-7.71 (m, 1H).

EXAMPLE 50-6

1H NMR (400 MHz, DMSO-$d_6$) δ ppm 1.08 (d, 3H) 1.51-1.62 (m, 1H) 2.01-2.11 (m, 1H) 2.28-2.36 (m, 1H) 2.86-2.95 (m, 1H) 2.95-3.04 (m, 1H) 4.38 (br. s., 1H) 7.31 (d, J=8.34 Hz, 2H) 7.35-7.41 (m, 1H) 7.45 (t, J=7.96 Hz, 1H) 7.55-7.62 (m, 3H) 7.68 (t, J=1.77 Hz, 1H) 8.00 (dd, J=4.93, 1.64 Hz, 1H) 8.33 (s, 1H) 8.78 (d, J=9.60 Hz, 1H) 8.85 (d, J=5.05 Hz, 1H).

EXAMPLE 50-7

1H NMR (400 MHz, DMSO-$d_6$): δ ppm 1.06-1.08 (d, J=6.82 Hz, 3H), 1.54-1.61 (m, 1H), 1.98-2.06 (m, 1H), 2.31-2.37 (m, 1H), 2.91-2.99 (m, 2H), 4.31-40 (m, 1H), 7.32-7.34 (m, 2H), 7.36-7.39 (m, 1H), 7.42-7.46 (t, J=7.58 Hz, 1H), 7.58-7.61 (m, 3H), 7.67-7.68 (t, J=1.77 Hz, 1H), 8.10-8.11 (d, J=4.80 Hz, 1H), 8.88-8.90 (d, J=9.85 Hz, 1H), 9.17-9.18 (d, J=5.05 Hz, 1H), 12.11 (s, 1H)

EXAMPLE 50-8

1H NMR (400 MHz, DMSO-d$_6$) δ ppm 1.08 (d, 3H) 1.59 (ddd, J=13.64, 9.60, 3.79 Hz, 1H) 1.93-2.15 (m, 1H) 2.28-2.44 (m, 1H) 2.77-3.00 (m, 2H) 4.32 (br. s., 1H) 7.32 (d, J=8.08 Hz, 2H) 7.36-7.41 (m, 1H) 7.46 (t, J=7.83 Hz, 1H) 7.55-7.63 (m, 3H) 7.68 (t, J=1.77 Hz, 1H) 9.19 (d, J=9.09 Hz, 1H) 12.13 (br. s., 1H)

EXAMPLE 51-1

Synthesis of (2R,4S)-4-(3-Carboxymethyl-ureido)-5-(3'-chloro-biphenyl-4-yl)-2-methyl-pentanoic acid ethyl ester

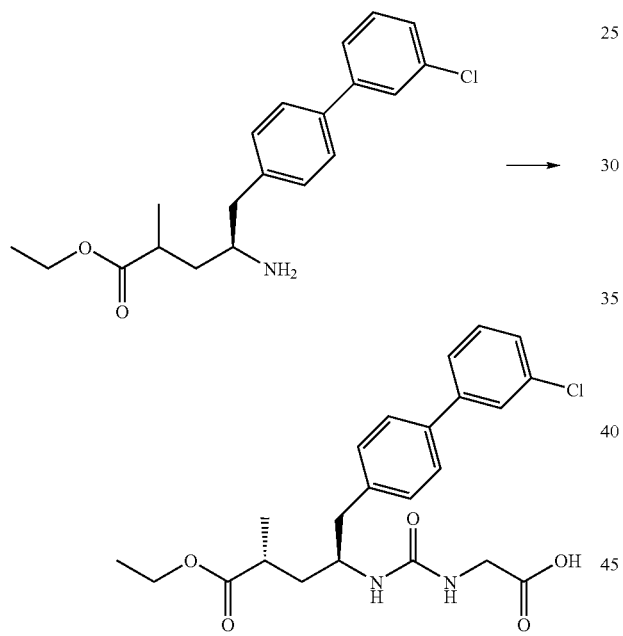

(S)-5-(3'-Chloro-biphenyl-4-yl)-4-isocyanato-2-methyl-pentanoic acid ethyl ester is prepared from (S)-4-amino-5-(3'-chloro-biphenyl-4-yl)-2-methyl-pentanoic acid ethyl ester hydrochloride (Intermediate 31) and triphosgene analogous to the procedure described for Example 6-1.

Next, to a solution of tert-butyl 2-aminoacetate (140 mg, 1.065 mmol) in DMF (5 mL) is added DIEA (344 mg, 2.66 mmol). The solution is stirred at room temperature for 5 minutes then (S)-5-(3'-chloro-biphenyl-4-yl)-4-isocyanato-2-methyl-pentanoic acid ethyl ester (330 mg, 0.887 mmol) is added. The mixture is stirred at room temperature for 2 hours then the solvent is removed under reduced pressure to give (S)-4-(3-tert-butoxycarbonylmethyl-ureido)-5-(3'-chloro-biphenyl-4-yl)-2-methyl-pentanoic acid ethyl ester which is used directly in the following reaction.

Next, a solution of (S)-4-(3-tert-butoxycarbonylmethyl-ureido)-5-(3'-chloro-biphenyl-4-yl)-2-methyl-pentanoic acid ethyl ester (261 mg, 59.1 mmol) in 8 mL of methylene chloride/TFA (1:1) is stirred at room temperature for 1 hour. The solvent is removed under reduced pressure and the residue is purified by preparative HPLC using a gradient of 10% MeCN/water to 100% MeCN (0.1% TFA) and the product is further purified by chiral HPLC on a Chirapak OD-H column using heptane/ethanol (90:10) (0.1% TFA) to elute the title compound; HPLC Retention time 1.48 minutes (condition C): MS 447.3 (M+1); 1H NMR (400 MHz, DMSO-d6): δ ppm 1.03-1.05 (d, J=7.07 Hz, 3H), 1.08-1.12 (t, J=7.33 Hz, 3H), 1.27-1.34 (m, 1H), 1.70-1.76 (m, 1H), 2.62-2.67 (m, 1H), 2.71-2.76 (m, 2H), 3.66-3.68 (d, J=5.81 Hz, 2H), 3.71-3.78 (m, 1H), 3.95-4.00 (q, J=7.07 Hz, 14.40 Hz, 2H), 5.94-5.97 (t, J=5.56 Hz, 1H), 6.07-6.09 (d, J=8.34 Hz, 1H), 7.25-7.28 (m, 2H), 7.38-7.41 (m, 1H), 7.45-7.49 (t, J=7.83 Hz, 1H), 7.60-7.63 (m, 3H), 7.69-7.70 (t, J=1.77 Hz, 1H), 12.42 (s, 1H).

EXAMPLE 52-1

Synthesis of (2R,4S)-5-(3'-Chloro-biphenyl-4-yl)-2-methyl-4-[(2H-tetrazole-5-carbonyl)-amino]-pentanoic acid ethyl ester

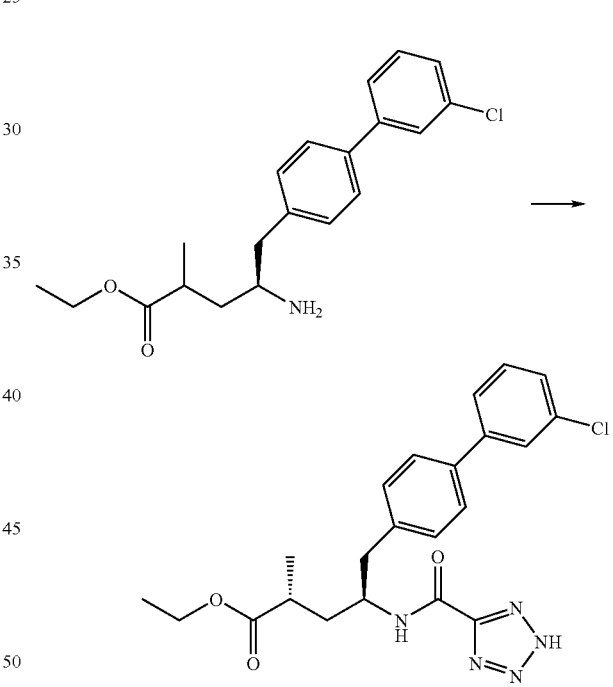

To a solution of 2-(4-methoxy-benzyl)-2H-tetrazole-5-carboxylic acid (Intermediate 32) (149 mg, 0.636 mmol) in DMF (2 mL) is added HATU. The mixture is stirred at room temperature for 15 minutes then (S)-4-amino-5-(3'-chloro-biphenyl-4-yl)-2-methyl-pentanoic acid ethyl ester hydrochloride (Intermediate 31) (200 mg, 0.578 mmol) is added and the mixture is stirred at room temperature for 2 hours. Any insoluble material is filtered and the filtrate is purified by preparative HPLC using a gradient of 10% MeCN/water to 100% MeCN (0.1% TFA) to give (S)-5-(3'-chloro-biphenyl-4-yl)-4-{[2-(4-methoxy-benzyl)-2H-tetrazole-5-carbonyl]-amino}-2-methyl-pentanoic acid ethyl ester; HPLC Retention time 1.79 minutes (condition C): MS 562.4 (M+1).

Next, a solution of (S)-5-(3'-chloro-biphenyl-4-yl)-4-{[2-(4-methoxy-benzyl)-2H-tetrazole-5-carbonyl]-amino}-2- methyl-pentanoic acid ethyl ester (212 mg, 0.377 mmol) in TFA (5 mL) is stirred at room temperature for 18 hours. The solvent is removed under reduced pressure and the residue is purified by chiral HPLC on a Chirapak IA column using heptane/ethanol (80:20) (0.1% TFA) to elute the title compound; HPLC Retention time 1.59 minutes (condition C): MS 442.2 (M+1); 1H NMR (400 MHz, DMSO-d6) δ ppm 1.05-1.10 (m, 3H) 1.10-1.16 (m, 3H) 1.69-1.79 (m, 1H) 1.88 (ddd, J=13.89, 9.98, 3.92 Hz, 1H) 2.77-2.87 (m, 1H) 2.87-2.96 (m, 1H) 3.91-4.05 (m, J=10.72, 7.14, 7.14, 3.66, 3.66 Hz, 2H) 4.24 (br. s., 1H) 6.85-6.85 (m, 0H) 7.30 (d, J=8.34 Hz, 2H) 7.37-7.42 (m, 1H) 7.46 (t, J=7.83 Hz, 1H) 7.56-7.64 (m, 3H) 7.68 (t, J=1.77 Hz, 1H) 9.18 (br. s., 1H).

EXAMPLE 53-1

Synthesis of (2R,4S)-5-Biphenyl-4-yl-2-methyl-4-(1H-tetrazol-5-ylcarbamoyl)-pentanoic acid ethyl ester

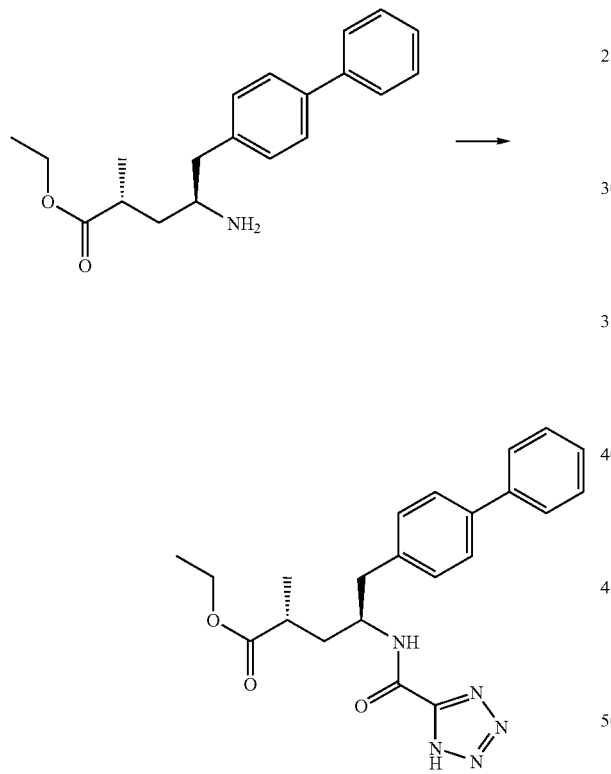

Prepared using similar procedure described in Example 52-1 with appropriate intermediates and conditions. Intermediate 1 and benzyl-H-tetrazole-5-carbonyl chloride (prepared according to *J. Med. Chem.* 1986, 29, 538-549) are used instead of intermediates 31 and 32. For coupling reaction, Et3N and DCM are used instead of HATU and DMF. For deprotection, hydrogeneation with Pd on carbon is used instead of TFA.

HPLC Retention time 1.36 minutes (condition C): MS 408 (M+1); $^1$H NMR (400 MHz, DMSO-d6) δ 1.08 (d, 3H, J=7.1 Hz), 1.10 (t, 3H, J=7.3 Hz), 1.75 (ddd, 1H, J=4.2, 10.4, 13.9 Hz), 1.89 (ddd, 1H, J=4.1, 9.9, 13.9 Hz), 2.50-2.56 (m, 2H), 2.82 (dd, 1H, J=6.1, 13.6 Hz), 2.91 (dd, 1H, J=8.1, 13.6 Hz), 3.93-4.03 (m, 2H), 4.19-4.31 (m, 1H), 7.28 (d, 2H, J=8.3 Hz), 7.30-7.36 (m, 1H), 7.43 (dd, 2H, J=7.8, 7.8 Hz), 7.56 (d, 2H, J=8.1 Hz), 7.62 (d, 2H, J=7.1 Hz).

EXAMPLE 54-1

Synthesis of (2R,4S)-5-(3'-chlorobiphenyl-4-yl)-2-methyl-4-(5-oxo-4,5-dihydro-1,2,4-oxadiazole-3-carboxamido)pentanoic acid

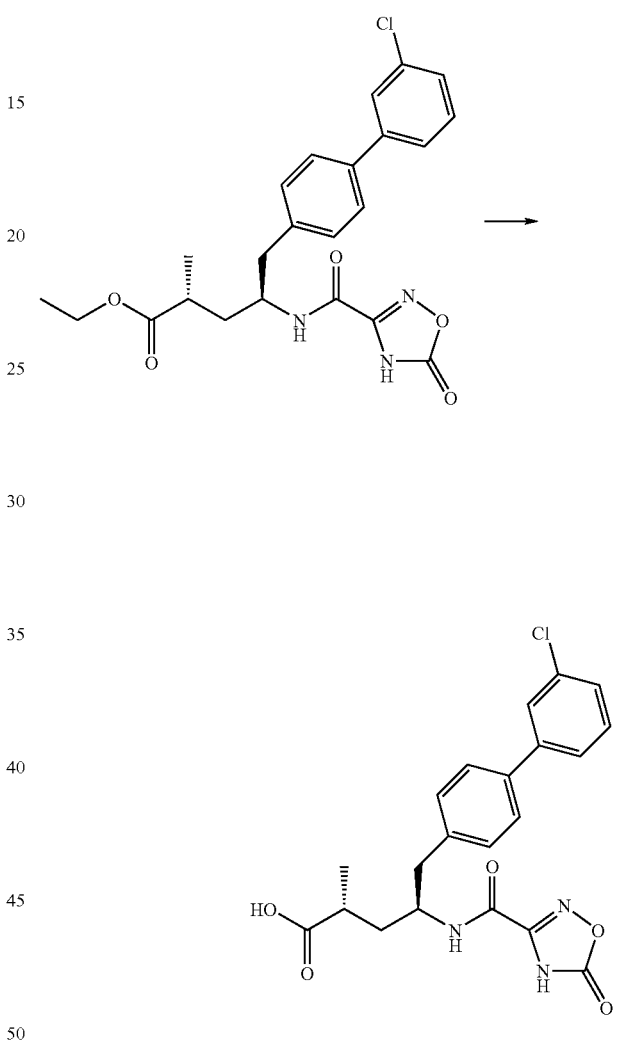

To a solution of (2R,4S)-ethyl 5-(3'-chlorobiphenyl-4-yl)-2-methyl-4-(5-oxo-4,5-dihydro-1,2,4-oxadiazole-3-carboxamido)pentanoate (25 mg, 0.055 mmol) in MeOH (2 mL) is added aqueous 1 N NaOH (4 mL). After stirring at room temperature for 2 hours, the crude is quenched with 1N HCl and concentrated under reduced pressure to remove MeOH. The crude is diluted with EtOAc. The organic layer is washed with brine, dried over Na$_2$SO$_4$, filtered and concentrated under reduced pressure. The obtained residue is purified by RP-HPLC (SunFire C18, H$_2$O(0.1% TFA)/CH$_3$CN), and then lyophilized to give (2R,4S)-5-(3'-chlorobiphenyl-4-yl)-2-methyl-4-(5-oxo-4,5-dihydro-1,2,4-oxadiazole-3-carboxamido)pentanoic acid (22 mg). HPLC retention time=1.64 minutes (condition B); MS (m+1)=430.2; 1H NMR (400 MHz, CD$_3$OD) δ ppm 1.18 (d, J=7.1 Hz, 3 H) 1.68 (ddd, J=14.3, 10.5, 4.0 Hz, 1H) 1.99-2.05 (m, 1H) 2.55 (ddd, J=10.2, 6.8, 3.9 Hz, 1H) 2.80-2.97 (m, 2H) 4.27-4.44 (m, 1H) 7.28-7.35 (m, 3H) 7.39 (t, J=7.8 Hz, 1H) 7.49-7.55 (m, 3H) 7.58 (t, J=1.9 Hz, 1H)

EXAMPLE 55-1

Synthesis of (2R,4S)-5-(3'-chlorobiphenyl-4-yl)-2-methyl-4-(5-oxo-4,5-dihydro-1,3,4-oxadiazole-2-carboxamido)pentanoic acid

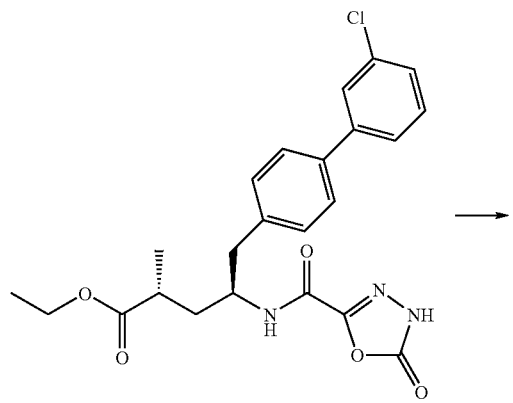

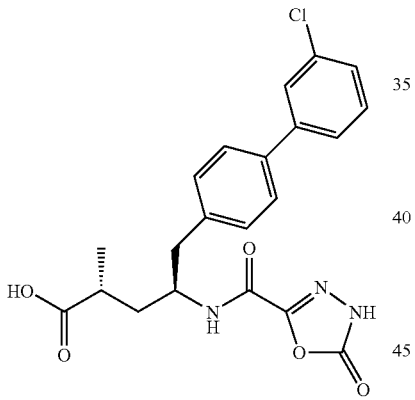

To a solution of (2R,4S)-ethyl 5-(3'-chlorobiphenyl-4-yl)-2-methyl-4-(5-oxo-4,5-dihydro-1,3,4-oxadiazole-2-carboxamido)pentanoate (91 mg, 0.198 mmol) in MeOH (2 mL) is added aqueous 1N NaOH (4 mL, 4 mmol). After stirring at room temperature for 2 hours, the crude is quenched with 1N HCl and concentrated under reduced pressure to remove MeOH and is diluted with EtOAc, the organic layer is washed with brine, dried over $Na_2SO_4$, filtered and concentrated under reduced pressure. The obtained residue is purified by RP-HPLC (SunFire C18, $H_2O$(0.1% TFA)/$CH_3CN$), and then lyophilized to give (2R,4S)-5-(3'-chlorobiphenyl-4-yl)-2-methyl-4-(5-oxo-4,5-dihydro-1,3,4-oxadiazole-2-carboxamido)pentanoic acid (62 mg). HPLC retention time=1.60 minutes (condition B); MS (m+1)=430.1; 1H NMR (400 MHz, DMSO-$d_6$) δ ppm 1.01-1.12 (d, J=7.1 Hz, 3H) 1.60 (ddd, J=13.8, 9.9, 4.3 Hz, 1H) 1.85 (ddd, J=13.6, 9.6, 4.0 Hz, 1H) 2.35-2.47 (m, 1H) 2.79 (dd, J=13.7, 7.8 Hz, 1H) 2.86 (dd, J=13.7, 7.8 Hz, 1H) 4.11-4.28 (m, 1H) 7.28 (d, J=8.3 Hz, 2H) 7.35-7.43 (m, 1H) 7.47 (t, J=7.8 Hz, 1H) 7.57-7.65 (m, 3H) 7.70 (t, J=1.8 Hz, 1H) 8.84 (d, J=8.8 Hz, 1H) 12.05 (br. s., 1H) 12.92 (s, 1H).

EXAMPLE 56-1

Synthesis of (2R,4S)-ethyl 5-(biphenyl-4-yl)-2-methyl-4-(2-oxo-2,3-dihydrothiazole-5-carboxamido)pentanoate

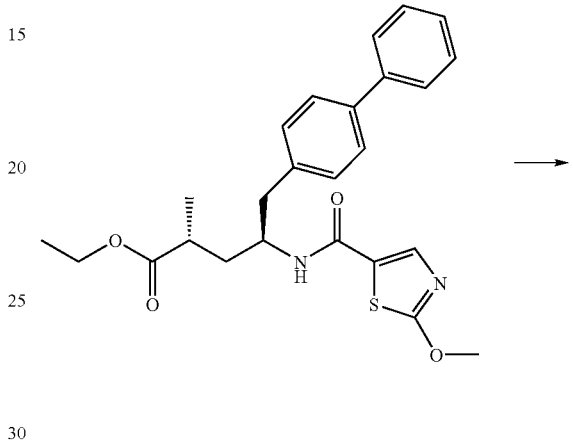

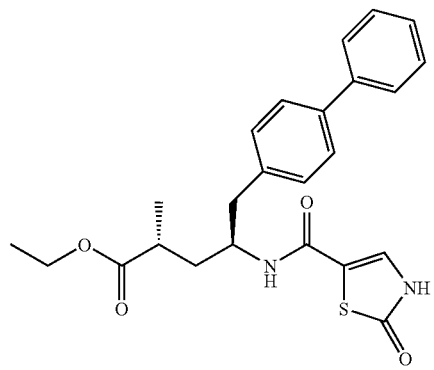

To a solution of (2R,4S)-ethyl 5-(biphenyl-4-yl)-4-(2-methoxythiazole-5-carboxamido)-2-methylpentanoate, intermediate 19, (171 mg, 0.38 mmol) in dioxane (6 mL) is added 4 M HCl in dioxane (0.25 mL, 1.00 mmol). The crude is stirred at room temperature for 5 hrs. The residue is purified by preparative HPLC using a gradient of MeCN/water (0.1% TFA). The proper fractions are lyophilized to furnish (2R,4S)-ethyl 5-(biphenyl-4-yl)-2-methyl-4-(2-oxo-2,3-dihydrothiazole-5-carboxamido)pentanoate (57 mg). HPLC retention time=1.80 minutes (condition A), MS 439.3 (M+1). 1H NMR (400 MHz, CHLOROFORM-d) δ ppm 1.17 (d, J=7.1 Hz, 3H), 1.23 (t, J=7.2 Hz, 3H), 1.67 (ddd, J=14.0, 10.0, 3.5 Hz, 1H), 1.85-2.03 (m, 1H), 2.51-2.69 (m, 1H), 2.77-2.91 (m, 1H), 2.93-3.05 (m, 1H), 4.13 (q, J=7.1 Hz, 2H), 4.26-4.42 (m, 1H), 5.97 (d, J=8.1 Hz, 1H), 7.17-7.29 (m, 2H) 7.29-7.37

(m, 1H) 7.42 (t, J=7.6 Hz, 2H) 7.53 (d, J=7.8 Hz, 2H) 7.57 (d, J=8.1 Hz, 2H) 9.46 (br. s., 1H).

EXAMPLE 57-1

(2R,4S)-ethyl 5-(biphenyl-4-yl)-2-methyl-4-(5-oxo-4,5-dihydro-1,3,4-oxadiazole-2-carboxamido)pentanoate

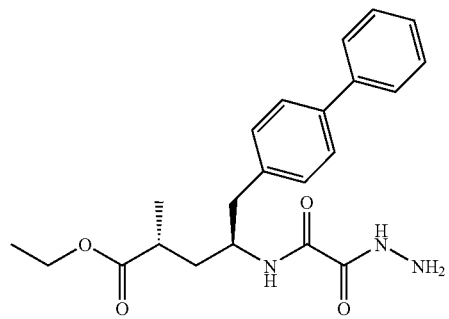

To a solution of (2R,4S)-ethyl 5-(biphenyl-4-yl)-4-(2-hydrazinyl-2-oxoacetamido)-2-methylpentanoate, intermediate 24, (200 mg, 0.50 mmol) in THF (10 mL) is added CDI (86 mg, 0.53 mmol). The crude is stirred at room temperature for 4 hrs. The crude is heated to 60 deg C. for 30 mins. This reaction is quenched with water and diluted in EtOAc. The organic layer is washed with brine, dried over MgSO$_4$, filtered and concentrated. The crude residue is purified via HPLC MeCN/water (0.1% TFA) to give (2R,4S)-ethyl 5-(biphenyl-4-yl)-2-methyl-4-(5-oxo-4,5-dihydro-1,3,4-oxadiazole-2-carboxamido)pentanoate (69 mg). HPLC retention time=1.79 minutes (condition A), MS 424.2 (M+1). 1H NMR (400 MHz, CHLOROFORM-d) δ ppm 1.17 (d, J=7.1 Hz, 3H), 1.22 (t, J=7.1 Hz, 3H), 1.66 (ddd, J=14.3, 10.2, 3.8 Hz, 1H), 2.02 (ddd, J=14.2, 10.0, 3.8 Hz, 1H), 2.59 (m, 1H), 2.89 (dd, 1H), 2.96 (dd, 1H), 4.03-4.19 (q, 2H), 4.37-4.47 (m, 1H), 6.91 (d, J=8.8 Hz, 1H), 7.25 (d, 1H), 7.28-7.35 (m, 1H), 7.40 (t, J=7.6 Hz, 2H), 7.49-7.60 (m, 4H), 10.51 (br. s., 1H).

EXAMPLE 58-1

Synthesis of (2R,4S)-ethyl 5-(biphenyl-4-yl)-2-methyl-4-(2-oxo-2,3-dihydrooxazole-5-carboxamido)pentanoate

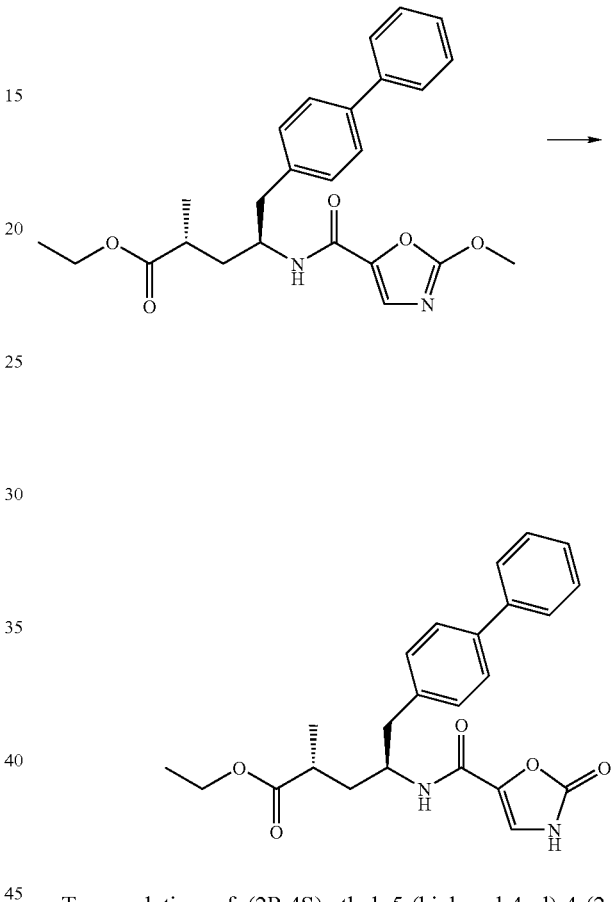

To a solution of (2R,4S)-ethyl 5-(biphenyl-4-yl)-4-(2-methoxyoxazole-5-carboxamido)-2-methylpentanoate, intermediate 20, (175 mg, 0.40 mmol) in dioxane (5 mL) is added a solution of 4M HCl in dioxane (501 µL, 2.01 mmol) at room temperature. After stirring at room temperature for 1 hour, the reaction mixture is concentrated under reduced pressure. The obtained residue is purified by RP-HPLC (SunFire C18, H$_2$O(0.1% TFA)/CH$_3$CN), and then lyophilized to give (2R,4S)-ethyl 5-(biphenyl-4-yl)-2-methyl-4-(2-oxo-2,3-dihydrooxazole-5-carboxamido)pentanoate (154 mg). HPLC retention time=1.89 minutes (condition B); MS 423.3 (M+1). 1HNMR (400 MHz, DMSO-d$_6$) δ ppm 1.07 (d, J=7.1 Hz, 3H) 1.11 (t, J=7.1 Hz, 3H) 1.61 (ddd, J=14.0, 10.2, 4.3 Hz, 1H) 1.81 (ddd, J=13.8, 9.9, 3.9 Hz, 1H) 2.41-2.50 (m, 1H) 2.73 (dd, J=13.3, 7.3 Hz, 1H) 2.83 (dd, J=13.3, 7.3 Hz, 1H) 3.99 (q, J=7.1, 2H) 4.05-4.22 (m, 1 H) 7.26 (d, J=8.1 Hz, 2H) 7.30-7.39 (m, 1H) 7.44 (t, J=7.7 Hz, 2H) 7.53 (s, 1H) 7.58 (d, J=8.3 Hz, 2H) 7.64 (d, J=7.1 Hz, 2H) 8.10 (d, J=8.8 Hz, 1H) 11.25 (s, 1H)

EXAMPLE 59-1

Synthesis of (2R,4S)-ethyl 5-(3'-chlorobiphenyl-4-yl)-2-methyl-4-(5-oxo-4,5-dihydro-1,3,4-oxadiazole-2-carboxamido)pentanoate

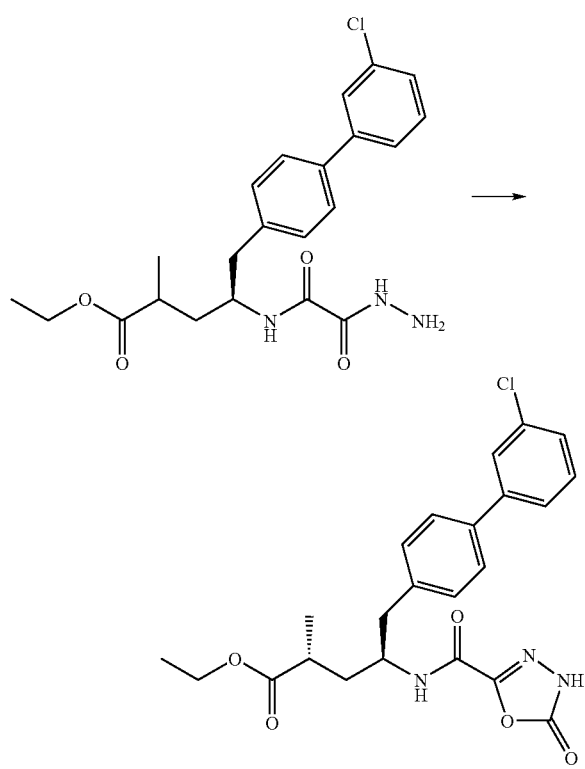

To a solution of (4S)-ethyl 5-(3'-chlorobiphenyl-4-yl)-4-(2-hydrazinyl-2-oxoacetamido)-2-methylpentanoate, intermediate 26, (542 mg, 1.25 mmol) in THF (16 mL) is added CDI (244 mg, 1.50 mmol) at room temperature. After stirring for 18 hour at room temperature, the reaction is quenched with H₂O and 1M HCl and diluted in EtOAc. The organic layer is washed with brine, dried over Na₂SO₄, filtered, and concentrated under reduced pressure. The obtained residue is purified by RP-HPLC (SunFire C18, H₂O(0.1% TFA)/CH₃CN) and by Chiral-HPLC (OJ-H 21×250 mm, EtOH (0.1% TFA)/Heptane=30/70) to give (2R,4S)-ethyl 5-(3'-chlorobiphenyl-4-yl)-2-methyl-4-(5-oxo-4,5-dihydro-1,3,4-oxadiazole-2-carboxamido)pentanoate (333 mg). HPLC retention time=1.74 minutes (condition A); MS 458.2 (M+1); 1H NMR (400 MHz, DMSO-d₆) δ ppm 1.07 (d, J=7.1 Hz, 3H) 1.12 (t, J=7.1 Hz, 3H) 1.58-1.74 (m, 1H) 1.76-1.91 (m, 1H) 2.45-2.50 (m, 1H) 2.77 (dd, J=13.7, 7.9 Hz, 1H) 2.86 (dd, J=13.7, 7.9 Hz, 1H) 4.00 (q, J=7.1 Hz, 2H) 4.06-4.22 (m, 1H) 7.28 (d, J=8.1 Hz, 2H) 7.37-7.42 (m, 1H) 7.47 (t, J=7.8 Hz, 1H) 7.58-7.66 (m, 3H) 7.67-7.73 (m, 1H) 8.86 (d, J=8.8 Hz, 1H) 12.95 (s, 1H).

EXAMPLE 60-1

Synthesis of (2S,4S)-5-(3'-chlorobiphenyl-4-yl)-4-(2-ethyloxazole-5-carboxamido)-2-methylpentanoic acid

EXAMPLE 61-1

(2R,4S)-5-(3'-chlorobiphenyl-4-yl)-4-(2-ethyloxazole-5-carboxamido)-2-methylpentanoic acid

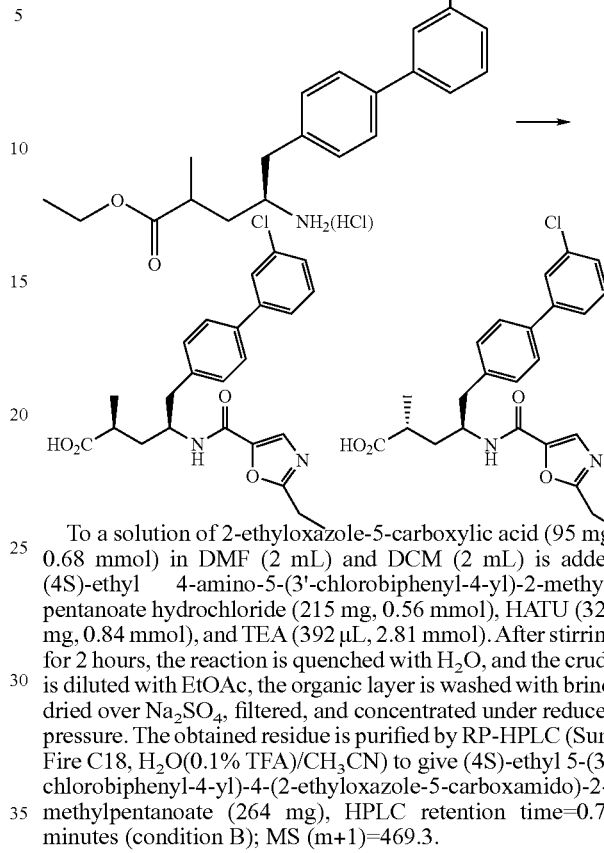

To a solution of 2-ethyloxazole-5-carboxylic acid (95 mg, 0.68 mmol) in DMF (2 mL) and DCM (2 mL) is added (4S)-ethyl 4-amino-5-(3'-chlorobiphenyl-4-yl)-2-methylpentanoate hydrochloride (215 mg, 0.56 mmol), HATU (321 mg, 0.84 mmol), and TEA (392 µL, 2.81 mmol). After stirring for 2 hours, the reaction is quenched with H₂O, and the crude is diluted with EtOAc, the organic layer is washed with brine, dried over Na₂SO₄, filtered, and concentrated under reduced pressure. The obtained residue is purified by RP-HPLC (SunFire C18, H₂O(0.1% TFA)/CH₃CN) to give (4S)-ethyl 5-(3'-chlorobiphenyl-4-yl)-4-(2-ethyloxazole-5-carboxamido)-2-methylpentanoate (264 mg), HPLC retention time=0.71 minutes (condition B); MS (m+1)=469.3.

Next, to a solution of (4S)-ethyl 5-(3'-chlorobiphenyl-4-yl)-4-(2-ethyloxazole-5-carboxamido)-2-methylpentanoate (264 mg, 0.56 mmol) in MeOH (2 mL) is added aqueous 1N NaOH (4 mL) After stirring at room temperature for 2 hours, the crude is concentrated under reduced pressure to remove MeOH and is diluted with EtOAc, the organic layer is washed with brine, dried over Na₂SO₄, filtered and concentrated under reduced pressure.

The obtained residue is purified by RP-HPLC (SunFire C18, H₂O(0.1% TFA)/CH₃CN) and then is purified by chiral-HPLC (OJ-H, 15% EtOH(0.1% TFA)/Heptane), and then lyophilized to give (2S,4S)-5-(3'-chlorobiphenyl-4-yl)-4-(2-ethyloxazole-5-carboxamido)-2-methylpentanoic acid (43 mg), HPLC retention time=1.63 minutes (condition B); MS (m+1)=441.2; 1H NMR (400 MHz, CD₃OD) δ ppm 1H NMR (400 MHz, CD₃OD) δ ppm 1.17 (d, J=7.1 Hz, 3H) 1.35 (t, J=7.7 Hz, 3H) 1.69 (ddd, J=14.0, 8.3, 3.9 Hz, 1H) 2.06 (ddd, J=14.1, 10.8, 5.9 Hz, 1H) 2.39-2.55 (m, 1H) 2.85 (q, J=7.6 Hz, 2H) 2.90 (dd, J=13.4, 7.6 Hz, 1H) 2.95 (dd, J=13.1, 5.8 Hz, 1H) 4.31-4.52 (m, 1H) 7.26-7.35 (m, 3H) 7.38 (t, J=7.8 Hz, 1H) 7.46-7.55 (m, 4H) 7.57 (t, J=1.9 Hz, 1H) and (2R,4S)-5-(3'-chlorobiphenyl-4-yl)-4-(2-ethyloxazole-5-carboxamido)-2-methylpentanoic acid (60 mg). HPLC retention time=1.62 minutes (condition B); MS (m+1)=441.2; 1H NMR (400 MHz, CD₃OD) δ ppm 1.18 (d, J=7.1 Hz, 3H) 1.35 (t, J=7.6 Hz, 3H) 1.69 (ddd, J=14.1, 10.4, 4.3 Hz, 1H) 2.01 (ddd, J=14.0, 10.0, 3.8 Hz, 1H) 2.46-2.63 (m, 1H) 2.85 (q, J=7.6 Hz, 2H) 2.91 (d, J=7.1 Hz, 2H) 4.30-4.49 (m, 1H) 7.26-7.34 (m, 3H) 7.38 (t, J=7.8 Hz, 1H) 7.46-7.52 (m, 3H) 7.52 (s, 1H) 7.56 (t, J=1.9 Hz, 1H) 8.31 (d, J=9.1 Hz, 1H).

The following examples are prepared using a similar procedure described examples 60-1 and examples 61-1 via amide bond coupling reactions of various amine hydrochloride intermediates with various carboxylic acids with HATU. The ethyl ester hydrolysis proceeds under aq. NaOH conditions in methanol at rt.

| Example # | Product | Amine hydrochloride | Carboxylic acid | HPLC-RT (condition) | MS (M + 1) |
|---|---|---|---|---|---|
| Example 62-1 | (2S,4S)-5-(2',5'-dichlorobiphenyl-4-yl)-4-(2-ethyloxazole-5-carboxamido)-2-methylpentanoic acid | | | 1.71 min (B) | 476.2 |

| Example # | Product | Amine hydrochloride | Carboxylic acid | HPLC-RT (condition) | MS (M + 1) |
|---|---|---|---|---|---|
| Example 63-1 | (2R,4S)-5-(2',5'-dichlorobiphenyl-4-yl)-4-(2-ethyloxazole-5-carboxamido)-2-methylpentanoic acid | | | 1.69 min (B) | 476.2 |

| Example # | Product | Amine hydrochloride | Carboxylic acid | HPLC-RT (condition) | MS (M + 1) |
|---|---|---|---|---|---|
| Example 64-1 | 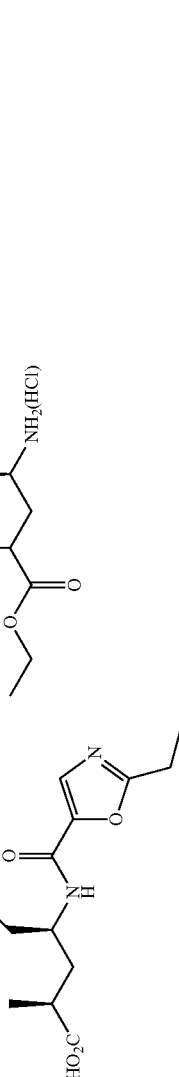 (2S,4S)-4-(2-ethyloxazole-5-carboxamido)-5-(5'-fluoro-2'-methoxybiphenyl-4-yl)-2-methylpentanoic acid | 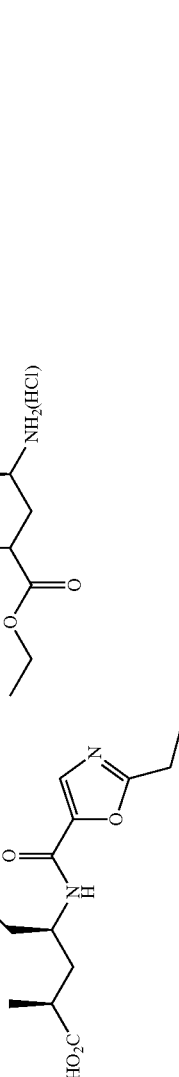 | 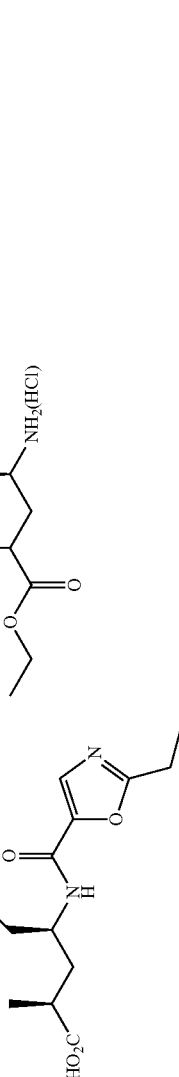 | 1.66 min (B) | 455.2 |

-continued

| Example # | Product | Amine hydrochloride | Carboxylic acid | HPLC-RT (condition) | MS (M + 1) |
|---|---|---|---|---|---|
| Example 65-1 | (2R,4S)-4-(2-ethyloxazole-5-carboxamido)-5-(5'-fluoro-2'-methoxybiphenyl-4-yl)-2-methylpentanoic acid | | 2-ethyloxazole-5-carboxylic acid | 1.66 min (B) | 455.2 |
| Example 66-1 | (2R,4S)-5-(2',5'-dichlorobiphenyl-4-yl)-2-methyl-4-(oxazole-5-carboxamido)pentanoic acid | | oxazole-5-carboxylic acid | 1.77 min (B) | 448.0 |

| Example # | Product | Amine hydrochloride | Carboxylic acid | HPLC-RT (condition) | MS (M + 1) |
|---|---|---|---|---|---|
| Example 67-1 | (2S,4S)-5-(2',5'-dichlorobiphenyl-4-yl)-2-methyl-4-(oxazole-5-carboxamido)pentanoic acid | | | 1.76 min (B) | 448.0 |
| Example 68-1 | (2R,4S)-5-(5'-chloro-2'-fluorobiphenyl-4-yl)-2-methyl-4-(oxazole-5-carboxamido)pentanoic acid | | | 1.71 min (B) | 431.1 |

| Example # | Product | Amine hydrochloride | Carboxylic acid | HPLC-RT (condition) | MS (M + 1) |
|---|---|---|---|---|---|
| Example 69-1 | (2S,4S)-5-(5'-chloro-2'-fluorobiphenyl-4-yl)-2-methyl-4-(oxazole-5-carboxamido)pentanoic acid | | | 1.73 min (B) | 431.1 |

| Example # | Amine hydrochloride | Carboxylic acid | Product | HPLC-RT (condition) | MS (M + 1) |
|---|---|---|---|---|---|
| Example 70-1 | | | (2S,4S)-5-(5'-chloro-2'-fluorobiphenyl-4-yl)-4-(2-ethyloxazole-5-carboxamido)-2-methylpentanoic acid | 1.81 min (B) | 459.1 |

-continued

| Example # | Product | Amine hydrochloride | Carboxylic acid | HPLC-RT (condition) | MS (M + 1) |
|---|---|---|---|---|---|
| Example 71-1 | (2R,4S)-5-(5'-chloro-2'-fluorobiphenyl-4-yl)-4-(2-ethyloxazole-5-carboxamido)-2-methylpentanoic acid | | | 1.80 min (B) | 459.1 |

| Example # | Product | Amine hydrochloride | Carboxylic acid | HPLC-RT (condition) | MS (M + 1) |
|---|---|---|---|---|---|
| Example 72-1 | (2S,4S)-5-(2',5'-dichlorobiphenyl-4-yl)-4-(3-hydroxyisoxazole-5-carboxamido)-2-methylpentanoic acid | | | 1.45 min (C) | 463.2 |

EXAMPLE 62-1

1H NMR (400 MHz, CD$_3$OD) δ ppm 1.18 (d, J=6.8 Hz, 3H) 1.34 (t, J=7.6 Hz, 3H) 1.71 (ddd, J=14.0, 8.4, 3.9 Hz, 1H) 2.07 (ddd, J=14.0, 10.7, 5.8 Hz, 1H) 2.41-2.56 (m, 1H) 2.85 (q, J=7.6 Hz, 2H) 2.92 (dd, J=13.6, 8.3 Hz, 1H) 2.97 (dd, J=13.6, 6.3 Hz, 1H) 4.37-4.52 (m, 1H) 7.26-7.35 (m, 6H) 7.44 (d, J=8.8 Hz, 1H) 7.52 (s, 1H) 8.30 (d, J=9.3 Hz, 1H).

EXAMPLE 63-1

1H NMR (400 MHz, DMSO-d$_6$) δ ppm 1.08 (d, J=7.1 Hz, 3H) 1.26 (t, J=7.6 Hz, 3H) 1.57 (ddd, J=13.9, 9.7, 4.2 Hz, 1H) 1.89 (ddd, J=13.9, 9.5, 4.2 Hz, 1H) 2.35-2.47 (m, 1H) 2.80 (q, J=7.6 Hz, 2H) 2.84 (d, J=4.0 Hz, 1H) 2.87 (dd, J=13.9, 7.8 Hz, 1H) 4.15-4.30 (m, 1H) 7.29 (d, J=8.3 Hz, 2H) 7.36 (d, J=8.3 Hz, 2H) 7.42-7.48 (m, 2H) 7.55-7.61 (m, 2H) 8.30 (d, J=8.6 Hz, 1H) 12.00 (br. s., 1H).

EXAMPLE 64-1

1H NMR (400 MHz, CD$_3$OD) δ ppm 1.17 (d, J=7.1 Hz, 3H) 1.35 (t, J=7.6 Hz, 3H) 1.70 (ddd, J=14.1, 8.4, 4.0 Hz, 1H) 2.05 (ddd, J=14.1, 10.8, 5.7 Hz, 1H) 2.41-2.52 (m, 1H) 2.86 (q, J=7.6 Hz, 2H) 2.90 (dd, J=5.8, 2.8 Hz, 1H) 2.93 (dd, J=13.9, 6.6 Hz, 1H) 3.72 (s, 3H) 4.33-4.49 (m, 1H) 6.94-7.06 (m, 3H) 7.26 (d, J=8.1 Hz, 2H) 7.39 (d, J=8.1 Hz, 2H) 7.53 (s, 1H) 8.29 (d, J=9.1 Hz, 1H).

EXAMPLE 65-1

1H NMR (400 MHz, CD$_3$OD) δ ppm 1.19 (d, J=7.1 Hz, 3H) 1.35 (t, J=7.7 Hz, 3H) 1.69 (ddd, J=14.2, 10.3, 4.0 Hz, 1H) 2.02 (ddd, J=14.0, 10.0, 3.8 Hz, 1H) 2.49-2.61 (m, 1H) 2.86 (q, J=7.7 Hz, 2H) 2.90 (d, J=7.1 Hz, 2H) 3.72 (s, 3H) 4.34-4.46 (m, 1H) 6.95-7.04 (m, 3H) 7.25 (d, J=8.3 Hz, 2H) 7.38 (d, J=8.1 Hz, 2H) 7.52 (s, 1H) 8.29 (d, J=8.8 Hz, 1H).

EXAMPLE 66-1

1H NMR (400 MHz, CD$_3$OD) δ ppm 1.19 (d, J=7.1 Hz, 3H) 1.70 (ddd, J=14.2, 10.3, 4.0 Hz, 1H) 2.04 (ddd, J=13.9, 9.9, 3.8 Hz, 1H) 2.47-2.64 (m, 1H) 2.87-2.93 (m, J=13.6, 7.8 Hz, 1H) 2.97 (dd, J=13.6, 6.3 Hz, 1H) 4.29-4.56 (m, 1H) 7.28-7.34 (m, 6H) 7.44 (d, J=8.6 Hz, 1H) 7.64 (s, 1H) 8.28 (s, 1H).

EXAMPLE 67-1

1H NMR (400 MHz, CD$_3$OD) δ ppm 1.18 (d, J=6.8 Hz, 3H) 1.68-1.74 (m, 1H) 2.07 (ddd, J=14.0, 10.7, 5.9 Hz, 1H) 2.42-2.55 (m, 1H) 2.91 (dd, J=13.6, 8.1 Hz, 1H) 2.98 (dd, J=13.6, 6.1 Hz, 1H) 4.37-4.51 (m, 1H) 7.29-7.35 (m, 6H) 7.45 (d, J=8.8 Hz, 1H) 7.64 (s, 1H) 8.28 (s, 1H).

EXAMPLE 68-1

1H NMR (400 MHz, CD$_3$OD) δ ppm 1.19 (d, J=7.3 Hz, 3H) 1.70 (ddd, J=14.1, 10.4, 4.0 Hz, 1H) 2.03 (ddd, J=14.0, 10.0, 3.8 Hz, 1H) 2.47-2.66 (m, 1H) 2.89 (dd, J=13.6, 7.6 Hz, 1H) 2.95 (dd, J=13.9, 6.6 Hz, 1H) 4.33-4.51 (m, 1H) 7.10-7.20 (m, 1H) 7.27-7.36 (m, 3H) 7.38-7.47 (m, 3H) 7.65 (s, 1H) 8.28 (s, 1H).

EXAMPLE 69-1

1H NMR (400 MHz, CD$_3$OD) δ ppm 1.18 (d, J=7.1 Hz, 3H) 1.71 (ddd, J=14.0, 8.2, 4.0 Hz, 1H) 2.07 (ddd, J=14.0, 10.7, 6.1 Hz, 1H) 2.40-2.59 (m, 1H) 2.91 (dd, J=13.4, 8.1 Hz, 1H) 2.97 (dd, J=13.6, 6.3 Hz, 1H) 4.36-4.53 (m, 1H) 7.09-7.20 (m, 1H) 7.27-7.36 (m, 3H) 7.39-7.47 (m, 3H) 7.65 (s, 1H) 8.28 (s, 1H).

EXAMPLE 70-1

1H NMR (400 MHz, CD$_3$OD) δ ppm 1.17 (d, J=6.8 Hz, 3H) 1.35 (t, J=7.7 Hz, 3H) 1.70 (ddd, J=14.1, 8.3, 3.9 Hz, 1H) 2.06 (ddd, J=14.0, 10.7, 5.8 Hz, 1H) 2.40-2.55 (m, 1H) 2.85 (q, J=7.6 Hz, 2H) 2.91 (dd, J=13.9, 8.1 Hz, 1H) 2.96 (dd, J=13.6, 6.3 Hz, 1H) 4.35-4.55 (m, 1H) 7.16 (dd, J=10.1, 8.8 Hz, 1H) 7.27-7.37 (m, 3H) 7.39-7.47 (m, 3H) 7.53 (s, 1H).

EXAMPLE 71-1

1H NMR (400 MHz, CD$_3$OD) δ ppm 1.19 (d, J=7.3 Hz, 3H) 1.34 (t, J=7.7 Hz, 3H) 1.70 (ddd, J=14.1, 10.4, 4.0 Hz, 1H) 2.02 (ddd, J=14.0, 10.0, 3.8 Hz, 1H) 2.46-2.65 (m, 1H) 2.85 (q, J=7.6 Hz, 2H) 2.90 (dd, J=8.3, 2.0 Hz, 1H) 2.95 (dd, J=14.1, 6.6 Hz, 1H) 4.27-4.52 (m, 1H) 7.15 (dd, J=10.1, 8.8 Hz, 1H) 7.26-7.37 (m, 3H) 7.42 (d, J=9.3 Hz, 3H) 7.53 (s, 1H).

EXAMPLE 72-1

1H NMR (400 MHz, DMSO-d$_6$) δ ppm 1.06 (d, 3H) 1.56 (ddd, J=13.64, 9.47, 3.92 Hz, 1H) 1.88-2.03 (m, 1H) 2.33 (ddd, J=9.16, 6.76, 5.05 Hz, 1H) 2.88 (d, J=6.82 Hz, 2H) 4.25 (dd, J=9.09, 6.57 Hz, 1H) 6.50 (s, 1H) 7.26-7.33 (m, 2H) 7.33-7.39 (m, 2H) 7.42-7.49 (m, 2H) 7.52-7.63 (m, 1H) 8.62-8.77 (m, 1H) 11.66 (br. s., 1H) 11.97-12.31 (m, 1H)

EXAMPLE 73-1

Synthesis of (2R,4S)-ethyl 5-(5'-fluoro-2'-methoxy-biphenyl-4-yl)-4-(3-hydroxyisoxazole-5-carboxamido)-2-methylpentanoate

EXAMPLE 74-1

Synthesis of (2S,4S)-ethyl 5-(5'-fluoro-2'-methoxy-biphenyl-4-yl)-4-(3-hydroxyisoxazole-5-carboxamido)-2-methylpentanoate

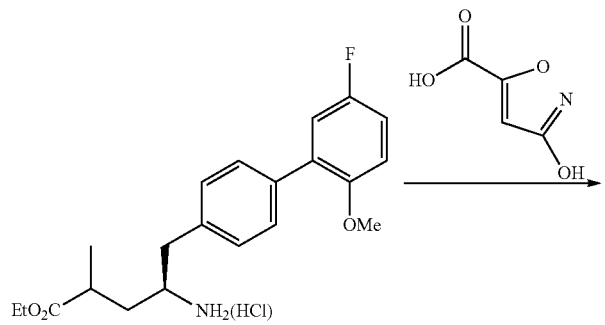

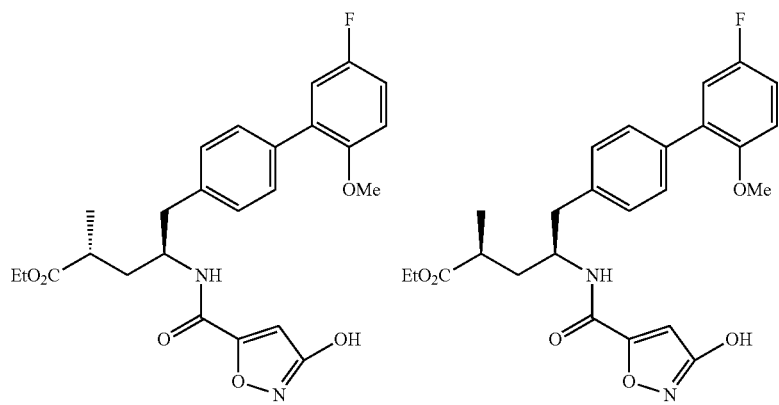

To a solution of 3-hydroxyisoxazole-5-carboxylic acid (137 mg, 1.06 mmol) in DMF (3 mL) and DCM (3 mL) is added (4S)-ethyl 4-amino-5-(5'-fluoro-2'-methoxybiphenyl-4-yl)-2-methylpentanoate hydrochloride (350 mg, 0.88 mmol), HATU (504 mg, 1.33 mmol), and TEA (616 μL, 4.42 mmol). After stirring for 2 hours, the reaction is quenched with $H_2O$, and the crude is diluted with EtOAc, the organic layer is washed with brine, dried over $Na_2SO_4$, filtered, and concentrated under reduced pressure.

The obtained residue is purified by RP-HPLC (SunFire C18, $H_2O$(0.1% TFA)/$CH_3CN$) and then is purified by chiral-HPLC (OJ-H, 15% EtOH(0.1% TFA)/Heptane), and then lyophilized to give (2R,4S)-ethyl 5-(5'-fluoro-2'-methoxybiphenyl-4-yl)-4-(3-hydroxyisoxazole-5-carboxamido)-2-methylpentanoate (110 mg), HPLC retention time=1.46 minutes (condition A); MS (m+1)=471.2; 1H NMR (400 MHz, $CD_3OD$) δ ppm 1.16 (d, J=7.1 Hz, 3H) 1.19 (t, J=7.1 Hz, 3H) 1.70 (ddd, J=14.2, 10.7, 3.9 Hz, 1H) 1.98 (ddd, J=14.0, 10.4, 3.7 Hz, 1H) 2.49-2.63 (m, 1H) 2.85 (dd, J=13.6, 6.8 Hz, 1H) 2.89 (dd, J=13.6, 7.3 Hz, 1H) 3.72 (s, 3H) 4.02-4.12 (m, 2H) 4.23-4.42 (m, 1H) 6.42 (s, 1H) 7.00 (d, J=7.8 Hz, 3H) 7.24 (d, J=8.1 Hz, 2H) 7.39 (d, J=8.3 Hz, 2H) 8.58 (d, J=8.8 Hz, 1H), and (2S,4S)-ethyl 5-(5'-fluoro-2'-methoxybiphenyl-4-yl)-4-(3-hydroxyisoxazole-5-carboxamido)-2-methylpentanoate (66 mg). HPLC retention time=1.60 minutes (condition A); MS (m+1)=471.2; 1H NMR (400 MHz, $CD_3OD$) δ ppm 1.15 (d, J=7.1 Hz, 3H) 1.19 (t, J=7.1 Hz, 3H) 1.70 (ddd, J=14.1, 7.5, 3.9 Hz, 1H) 2.05 (ddd, J=14.0, 10.6, 6.7 Hz, 1H) 2.43-2.55 (m, 1H) 2.86 (dd, J=13.6, 7.8 Hz, 1H) 2.92 (dd, J=13.6, 6.6 Hz, 1H) 3.72 (s, 3H) 3.97-4.10 (m, 2H) 4.32-4.43 (m, 1H) 6.41 (s, 1H) 6.97-7.04 (m, 3H) 7.25 (d, J=8.3 Hz, 2H) 7.39 (d, J=8.1 Hz, 2H).

The title compound is prepared analogous to Example 73-1 and Example 74-1 using Intermediate 31 or 31-3.

| Example # | Product | Reagent/Conditions | HPLC-RT (condition) | MS (M + 1) |
|---|---|---|---|---|
| Example 75-1 | 2-((2S,4R)-1-(3'-chlorobiphenyl-4-yl)-5-ethoxy-4-methyl-5-oxopentan-2-ylcarbamoyl)pyrimidine-4-carboxylic acid | Intermediate 26 HATU | 1.51 min. (C) | 496.3 |
| Example 76-1 | 2-((2S,4R)-1-(3'-chlorobiphenyl-4-yl)-5-ethoxy-4-methyl-5-oxopentan-2-ylcarbamoyl)isonicotinic acid | EDCl and HOBt used instead of HATU | 1.65 min. (C) | 495.3 |
| Example 77-1 | (2R,4S)-ethyl 5-(2',5'-dichlorobiphenyl-4-yl)-4-(3-hydroxyisoxazole-5-carboxamido)-2-methylpentanoate | Intermediate 20 HATU | 1.63 min. (C) | 491.2 |

283 -continued

| Example # | Product | Reagent/Conditions | HPLC-RT (condition) | MS (M + 1) |
|---|---|---|---|---|
| Example 78-1 | 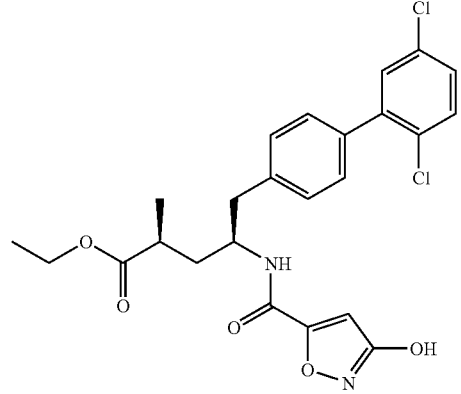(2S,4S)-ethyl 5-(2',5'-dichlorobiphenyl-4-yl)-4-(3-hydroxyisoxazole-5-carboxamido)-2-methylpentanoate | Intermediate 20 HATU | 1.66 min. (C) | 491.2 |

EXAMPLE 75-1

1H NMR (400 MHz, DMSO-d$_6$) δ ppm 1.08-1.15 (m, 6H), 1.69-1.77 (m, 1H), 1.87-1.95 (m, 1H), 2.83-2.88 (m, 1H), 2.94-2.99 (m, 2H), 3.97-4.02 (q, J=6.95 Hz, 14.02 Hz, 2H), 4.24-4.33 (m, 1H), 7.33-7.35 (m, 2H), 7.38-7.41 (m, 1H), 7.45-7.49 (t, J=7.83 Hz, 1H), 7.61-7.63 (m, 3H), 7.68-7.69 (1, J=1.77 Hz, 1H), 8.08-8.10 (d, J=5.18 Hz, 1H), 8.83-8.85 (d, J=7.33 Hz, 1H), 9.17-9.18 (d, J=4.80 Hz, 1H).

EXAMPLE 76-1

1H NMR (400 MHz, DMSO-d$_6$) δ ppm 1.03-1.20 (m, 6H) 1.70-1.82 (m, 1H) 1.82-1.91 (m, 1H) 2.79-2.87 (m, 1H) 2.90-2.98 (m, 1H) 3.92-4.01 (m, 2H) 4.19-4.33 (m, 1H) 7.30 (d, J=8.34 Hz, 2H) 7.36-7.42 (m, 1H) 7.46 (t, J=7.83 Hz, 1H) 7.56-7.63 (m, 3H) 7.68 (t, J=1.77 Hz, 1H) 7.96 (dd, J=4.80, 1.52 Hz, 1H) 8.32 (s, 1H) 8.73 (d, J=9.35 Hz, 1H) 8.78 (d, J=5.05 Hz, 1H)

Example 77-1

1H NMR (400 MHz, DMSO-d$_6$) δ ppm 1.03-1.16 (m, 6H) 1.65 (ddd, J=14.02, 10.11, 4.42 Hz, 1H) 1.86 (ddd, J=13.77, 9.85, 3.92 Hz, 1H) 2.75-2.93 (m, 2H) 3.93-4.03 (m, 2H) 4.09-4.23 (m, 1H) 6.50 (s, 1H) 7.25-7.32 (m, 2H) 7.33-7.40 (m, 2H) 7.41-7.49 (m, 2H) 7.54-7.63 (m, 1H) 8.69 (d, J=8.84 Hz, 1H) 11.71 (br. s., 1H)

EXAMPLE 79-1

Synthesis of 2H-Tetrazole-5-carboxylic acid ((1S, 3R)-1-biphenyl-4-ylmethyl-4-methanesulfonylamino-3-methyl-4-oxo-butyl)-amide

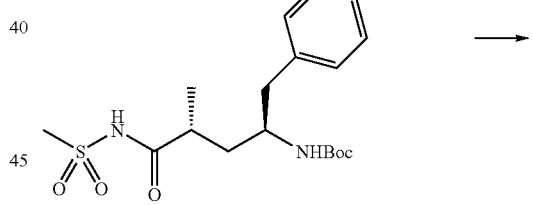

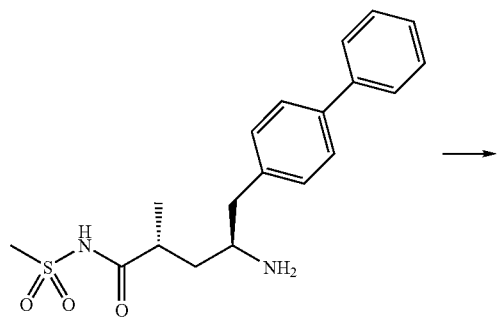

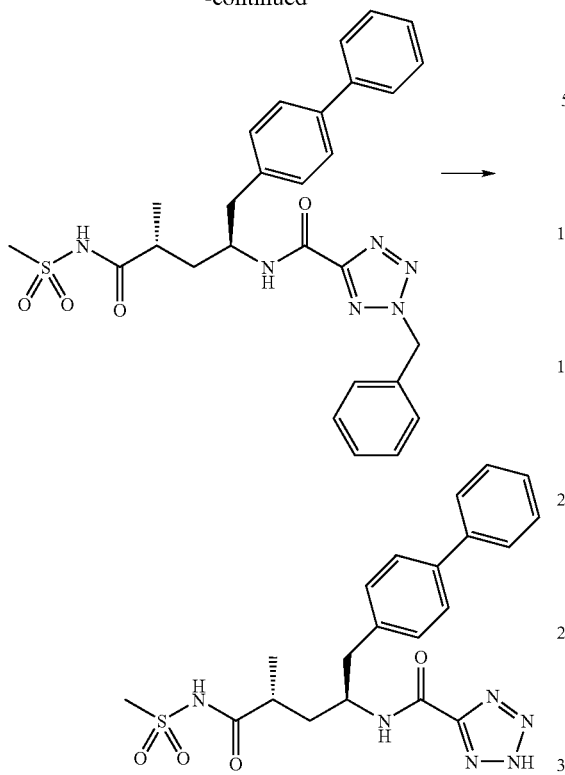

To a solution of ((1S,3R)-1-biphenyl-4-ylmethyl-4-methanesulfonylamino-3-methyl-4-oxo-butyl)-carbamic acid tert-butyl ester (90 mg, 0.195 mmol) in DCM (3 ml) at room temperature is added TFA (1 ml, 12.98 mmol). The reaction is stirred at room temperature. The mixture is concentrated to give N-((2R,4S)-4-Amino-5-biphenyl-4-yl-2-methyl-pentanoyl)-methanesulfonamide. Next, this crude is added a half solution of 2-benzyl-2H-tetrazole-5-carbonyl chloride (131 mg, 0.588 mmol) in DCM at 0° C. and is followed by half of TEA (0.109 mL, 0.782 mmol). And then after half hour, the other half reagents are added into the reaction. The reaction is warmed up slowly to room temperature. The reaction is quenched by brine and is extracted with DCM. The combined organic layer i washed with brine and dried over anhydrous sodium sulfate, filtered and concentrated. Reverse phase HPLC [15 to 50% ACN—H2O (0.1% NH4OH) over 10 min by X-bridge phenyl column] provides 2-Benzyl-2H-tetrazole-5-carboxylic acid ((1S,3R)-1-biphenyl-4-ylmethyl-4-methanesulfonylamino-3-methyl-4-oxo-butyl)-amide.
HPLC retention time=1.50 minutes (condition C), MS (M−1) =545.3.

Next, A solution of 2-benzyl-2H-tetrazole-5-carboxylic acid ((1S,3R)-1-biphenyl-4-ylmethyl-4-methanesulfonylamino-3-methyl-4-oxo-butyl)-amide in MeOH/EtOAc is hydrogenated under H$_2$ baloon by catalyst 10% Pd/C wet for 2 hours. The reaction is filtered off the catalyst and is concentrated. Reverse phase HPLC [35 to 80% ACN—H2O (0.1% TFA) over 10 min by Sunfire C18 column] provides 2H-Tetrazole-5-carboxylic acid ((1S,3R)-1-biphenyl-4-ylmethyl-4-methanesulfonylamino-3-methyl-4-oxo-butyl)-amide. 1H NMR (400 MHz, DMSO-d$_6$) δ ppm 1.06 (d, J=7.1 Hz, 2H), 1.66 (ddd, J=13.8, 10.9, 3.5 Hz, 1H), 1.91 (ddd, J=13.7, 10.7, 3.4 Hz, 1H), 2.54-2.63 (m, 1H), 2.79-2.86 (m, 1H), 2.86-2.93 (m, 1H), 3.24 (s, 3H), 4.15-4.28 (m, 1H), 7.27 (d, J=8.3 Hz, 2H), 7.30-7.36 (m, 1H), 7.43 (t, J=7.6 Hz, 2H), 7.55 (d, J=8.3 Hz, 2H), 7.59-7.65 (m, 2H), 9.19 (br. s., 1H), 11.54 (br. s., 1H). HPLC retention time=1.24 min (method C): MS (m+1) =457.1.

Starting materials or intermediates are prepared in following manner:

Intermediate 1: (2R,4S)-4-amino-5-biphenyl-4-yl-2-methyl-pentanoic acid ethyl ester

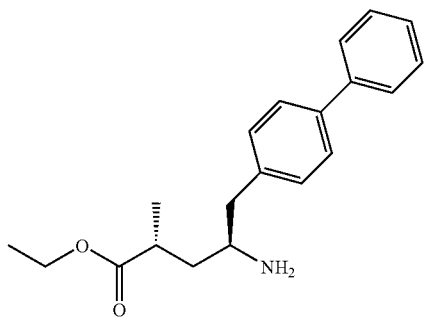

Using the same procedure described in WO2008083967 or US005217996.

Intermediate 2: (2R,4S)-4-amino-5-biphenyl-4-yl-2-methyl-pentanoic acid benzyl ester hydrochloride

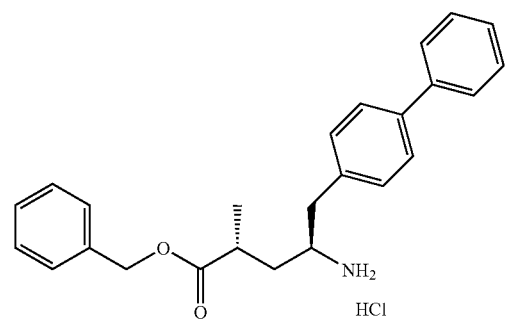

To a solution of (2R,4S)-5-biphenyl-4-yl-4-tert-butoxycarbonylamino-2-methyl-pentanoic acid (prepared using the procedure described in WO 2008083967) (1.0 g, 2.61 mmol) and benzyl bromide (468 mg, 2.74 mmol) in DMF (15 mL) is added potassium carbonate (541 mg, 3.91 mmol) and the mixture is stirred at room temperature for 2 hours. Water is added and the mixture is extracted with ethyl acetate. The combined organic layers are washed with water and dried over magnesium sulfate. The solvent is removed under reduced pressure and the residual oil is purified by column chromatography using heptane/EtOAc (4:1) to furnish (2R, 4S)-5-biphenyl-4-yl-4-tert-butoxycarbonylamino-2-methyl-pentanoic acid benzyl ester.

Next, to a solution of (2R,4S)-5-biphenyl-4-yl-4-tert-butoxycarbonylamino-2-methyl-pentanoic acid benzyl ester in THF (5 mL) is added 4M HCl in dioxane (3 mL) and the solution is stirred at room temperature for 1 hour. The solvent is removed under reduced pressure to give the title compound. MS 374.4 (M+1).

Intermediate 3: (2R,4S)-4-[(1-Benzyl-1H-tetrazole-5-carbonyl)-amino]-5-biphenyl-4-yl-2-methyl-pentanoic acid benzyl ester and (2R,4S)-4-[(2-benzyl-2H-tetrazole-5-carbonyl)-amino]-5-biphenyl-4-yl-2-methyl-pentanoic acid benzyl ester

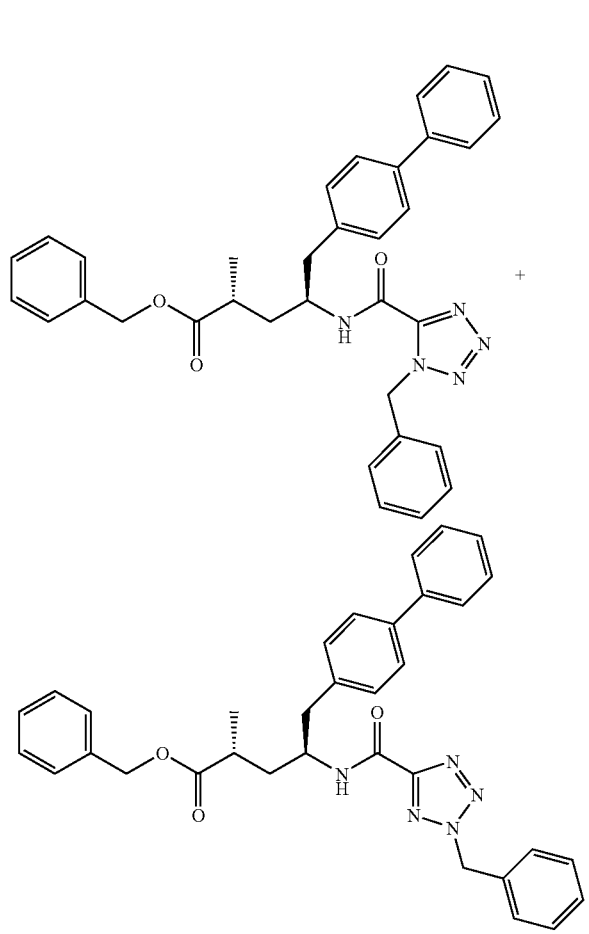

To a solution of (2R,4S)-benzyl 4-amino-5-(biphenyl-4-yl)-2-methylpentanoate (92 mg, 0.224 mmol) and Et₃N (0.078 mL, 0.561 mmol)) in DCM (2 mL) are added benzyl-H-tetrazole-5-carbonyl chloride (mixture of 1 and 2-benzyl isomers, 60 mg, 0.269 mmol, prepared according to *J. Med. Chem.* 1986, 29, 538-549). After stirring for 0.5 hour, Et₃N (0.078 mL, 0.561 mmol) and the acid chloride (60 mg, 0.269 mmol) are added. After stirring for 0.5 hour, the reaction mixture is diluted with ethyl acetate, washed with H₂O and brine, dried over Na₂SO₄, and concentrated. The residue is purified by silica gel column chromatography to give a mixture of (2R,4S)-4-[(1-benzyl-1H-tetrazole-5-carbonyl)-amino]-5-biphenyl-4-yl-2-methyl-pentanoic acid benzyl ester and (2R,4S)-4-[(2-benzyl-2H-tetrazole-5-carbonyl)-amino]-5-biphenyl-4-yl-2-methyl-pentanoic acid benzyl ester. HPLC Retention time 1.71 minutes (condition D); MS 560.0 (M+1); ¹H NMR (400 MHz, CDCl₃) δ ppm 1.19 (d, J=7.07 Hz, 3H), 1.62-1.71 (m, 1H), 2.03-2.11 (m, 1H), 2.62-2.71 (m, 1H), 2.89-3.00 (m, 2H), 4.45-4.56 (m, 1H), 5.05 (d, J=12.38 Hz, 1H), 5.13 (d, J=12.38 Hz, 1H), 5.79 (s, 2H), 6.97 (d, J=9.09 Hz, 1H), 7.21 (d, J=8.08 Hz, 2H), 7.27-7.50 (m, 15H), 7.55 (d, J=7.07 Hz, 2H).

Intermediate 4: (2R,4S)-5-Biphenyl-4-yl-2-methyl-4-{2-oxo-2-[N'-(2,2,2-trifluoro-acetyl)-hydrazino]-acetylamino}-pentanoic acid benzyl ester

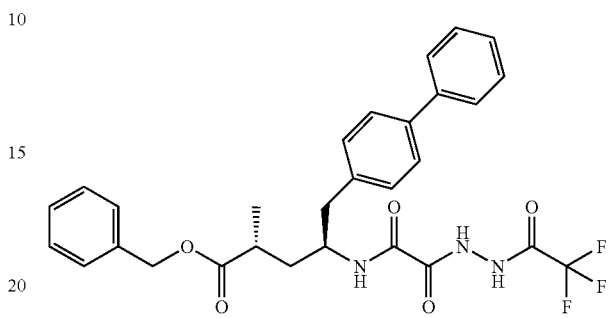

To a suspension of (2R,4S)-4-amino-5-biphenyl-4-yl-2-methyl-pentanoic acid benzyl ester HCl salt (800 mg, 2.142 mmol) in dichloromethane (30 mL) at ice bath is added ethyl oxalyl chloride (0.288 mL, 2.57 mmol) and followed by triethylamine (0.657 mL, 4.71 mmol). The mixture is stirred at ice bath for 5 minutes, and the reaction is quenched by brine and added dichloromethane. The combined organic layer is washed with brine and dried over anhydrous sodium sulfate, filtered and concentrated under reduced pressure. The obtained residue is purified by flash chromatography (silica gel, 20% to 40% ethyl acetate/heptane) to give (2R,4S)-5-biphenyl-4-yl-4-(ethoxyoxalyl-amino)-2-methyl-pentanoic acid benzyl ester (830 mg, 82% yield). HPLC Retention time 1.61 minutes (condition D); MS 474.0 (M+1).

Next, to a solution of (2R,4S)-5-biphenyl-4-yl-4-(ethoxyoxalyl-amino)-2-methyl-pentanoic acid benzyl ester (645 mg, 1.362 mmol) in EtOH (25 mL) at −20° C. is added a solution of hydrazine hydrate (0.066 mL, 1.362 mmol) in EtOH (10 mL) and the mixture is stirred at −20° C. to −5° C. After 3 hours, more hydrazine hydrate is added and the reaction is continued to stir at −20° C. to −5° C. The suspension mixture is filtered to collect (2R,4S)-5-bipheyl-4-yl-4-(hydrazinooxalyl-amino)-2-methyl-pentanoic acid benzyl ester (555 mg, 89% yield). HPLC Retention time 1.44 minutes (condition D); MS 460.0 (M+1).

Next, to a solution of (2R,4S)-5-bipheyl-4-yl-4-(hydrazinooxalyl-amino)-2-methyl-pentanoic acid benzyl ester (200 mg, 0.435 mmol) in THF (6 mL) cooled in ice bath is added DIPEA (0.099 mL, 0.566 mmol) followed by trifluoroacetic anhydride (0.080 mL, 0.566 mmol). The reaction is stirred at room temperature. The reaction is quenched by brine and is extracted with ethyl acetate. The combined organic layer is washed with brine and dried over anhydrous sodium sulfate, filtered and concentrated under reduced pressure. The obtained residue is purified by flash chromatography (silica gel, 1% to 5% MeOH/DCM) to give (2R,4S)-5-biphenyl-4-yl-2-methyl-4-{2-oxo-2-[N'-(2,2,2-trifluoro-acetyl)-hydrazino]-acetylamino}-pentanoic acid benzyl ester (177 mg).

HPLC Retention time 1.01 minutes (condition E); MS 554.0 (M−1).

Intermediate 5: trans-1,2-cyclopropanedicarboxylic acid monoethyl ester

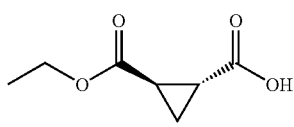

To a solution of diethyl trans-1,2-cyclopropanedicarboxylate (110 mg, 0.59 mmol) in ethanol (3 mL) is added aqueous 1M NaOH (0.65 mL, 0.65 mmol) and the mixture is stirred at room temperature for 48 hours. To this mixture is added 0.65 mL of aqueous 1M HCl and the solvent is removed under reduced pressure to afford the title compound.

Intermediate 6: 5-chloroisophthalic acid monomethyl ester

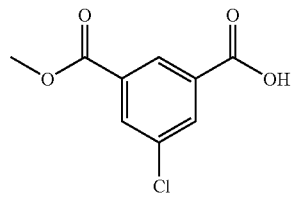

To a solution of 5-chloroisophthalic acid dimethyl ester (457 mg, 2 mmol) in methanol (10 mL) is added aqueous 1M NaOH (1.0 mL, 0.65 mmol) and the mixture is stirred at room temperature for 18 hours. The solvent is removed under reduced pressure and water is added to the residue. The solution is washed with ethyl acetate and the aqueous phase is acidified with aqueous 1M HCl. The mixture is extracted with ethyl acetate and the organic phase is washed with brine and dried over sodium sulfate. The solvent is removed under reduced pressure to give the title compound. MS 213.2 (M−1); $^1$H-NMR (400 MHz, DMSO-d6); δ ppm 3.91 (s, 3H), 8.15 (s, 2H), 8.38 (s, 1H), 13.71 (s, 1H).

Intermediate 7: 5-carbamoylmethoxyisophthalic acid monomethyl ester

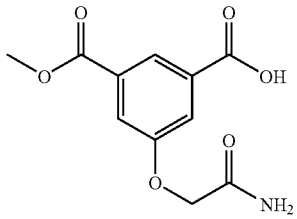

To a mixture of 5-hydroxyisophthalic acid dimethyl ester (500 mg, 2.38 mmol) and chloroacetamide (245 mg, 2.62 mmol) in DMF (7 mL) is added potassium carbonate (986 mg, 7.14 mmol) and the mixture is stirred at room temperature for 2 days. Water is added to the mixture and then it is extracted with ethyl acetate. The organic phase is washed with water and brine and is dried over sodium sulfate. The organic solution is concentrated to one fourth volume to give a precipitate. The solid is filtered, washed with ethyl acetate and dried under reduced pressure to give 5-carbamoylmethoxyisophthalic acid dimethyl ester. MS 268.2 (M+1); $^1$H-NMR (400 MHz, CDCl$_3$); δ ppm 3.96 (s, 6H), 4.59 (s, 2H), 5.87 (s, broad, 1H), 6.55 (s, broad, 1H), 7.79 (s, 2H), 8.37 (s, 1H).

Next, to a solution of 5-carbamoylmethoxyisophthalic acid dimethyl ester (371 mg, 1.39 mmol) in MeOH (10 mL) is added aqueous 1M NaOH (1.39 mL, 1.39 mmol) and the mixture is stirred at 50° C. for 18 hours. The solvent is removed under reduced pressure and water is added to the residue. The aqueous solution is acidified with aqueous 1M HCl and the resulting precipitate is filtered, washed with water and dried under reduced pressure to give 5-carbamoylmethoxyisophthalic acid monomethyl ester. MS 254.3 (M+1); $^1$H-NMR (400 MHz, DMSO-d6); δ ppm 3.89 (s, 3H), 4.59 (s, 2H), 7.43 (s, 1H), 7.70 (m 3H), 8.10 (s, 1), 13.38 (s, 1H).

Intermediate 8: pyrimidine-4,6-dicarboxylic acid

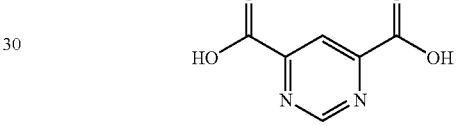

Prepared by the KMnO$_4$ oxidation of 2,6-dimethylpyrimidine according to the procedure described in *J. Chem. Soc.* 525 (1959).

Intermediate 9: (5-ethyl-[1,3,4]thiadiazol-2-yl)-acetic acid

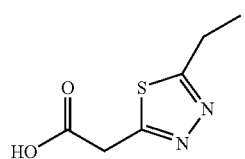

To a mixture of hydrazinocarbonylacetic acid ethyl ester (1.0 g, 6.84 mmol) and diisopropypethylamine (1.77 g, 13.69 mmol) in THF (7 mL) is added a solution of propionyl chloride (633 mg, 6.84 mmol) in THF (2 mL) dropwise and the mixture is stirred at room temperature for 18 hours. The mixture is poured into ethyl acetate and is washed with aqueous 1M HCl and brine. The organic phase is dried over magnesium sulfate and the solvent is removed under reduced pressure to furnish 3-oxo-3-(N'-propionylhydrazino)-propionic acid ethyl ester. $^1$H-NMR (400 MHz, CDCl$_3$); δ ppm 1.21 (t, 3H), 1.30 (t, 3H), 2.31 (q, 2H), 3.43 (s, 2H), 4.23 (q, 2H), 8.27 (s, 1H), 9.63 (s, 1H).

Next, a mixture of 3-oxo-3-(N'-propionylhydrazino)-propionic acid ethyl ester (600 mg, 2.97 mmol) and Lawesson's reagent (3.6 g, 8.90 mmol) in THF (30 mL) is stirred at 50° C. for 18 hours. The solvent is removed under reduced pressure and the residue is purified by column chromatography using a gradient of 20-50% heptane/EtOAc to elute the product, (5-ethyl-[1,3,4]thiadiazol-2-yl)-acetic acid ethyl ester. MS 201.2 (M+1); $^1$H-NMR (400 MHz, CDCl$_3$); δ ppm 1.31 (t, 3H), 1.43 (t, 3H), 3.14 (q, 2H), 4.17 (s, 2H), 4.24 (q, 2H).

Next, to a solution of (5-ethyl-[1,3,4]thiadiazol-2-yl)-acetic acid ethyl ester (230 mg, 1.15 mmol) in ethanol (5 mL) is added aqueous 1M NaOH (2 mL, 2.0 mmol) and the mixture is stirred at room temperature for 18 hours. The mixture is acidified with aqueous 1M HCl and the ethanol is removed under reduced pressure. The remaining aqueous solution is lyophilized to give (5-ethyl-[1,3,4]thiadiazol-2-yl)-acetic acid.

Intermediate 10: 3-benzenesulfonylaminopropionic acid

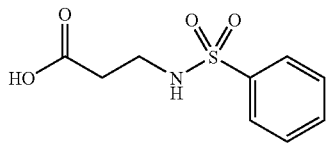

To a solution of benzenesulfonyl chloride (500 mg, 2.83 mmol) in pyridine (10 mL) is added 3-amino-propionic acid ethyl ester (672 mg, 8.49 mmol) and the mixture is stirred at room temperature for 18 hours. The mixture is poured into ethyl acetate and is washed with aqueous 1M HCl and brine. The organic phase is dried over magnesium sulfate and the solvent is removed under reduced pressure. The residue is purified by column chromatography using a gradient of 10-50% heptane/EtOAc to afford 3-benzenesulfonylaminopropionic acid ethyl ester. MS 258.3 (M+1); $^1$H-NMR (400 MHz, CDCl$_3$); δ ppm 1.24 (t, 3H), 2.53 (t, 2H), 3.21 (q, 2H), 5.22 (m, 1H), 7.51-7.61 (m, 3H), 7.87 (d, J=7.20 Hz, 2H).

Next, to a solution of 3-benzenesulfonylaminopropionic acid ethyl ester (340 mg, 1.32 mmol) in ethanol (15 mL) is added aqueous 1M NaOH (4 mL, 4.0 mmol) and the mixture is stirred at room temperature for 4 hours. The mixture is poured into water and is extracted with ether. The aqueous phase is acidified with aqueous 1M HCl and the solution is lyophilized to give 3-benzenesulfonylaminopropionic acid.

Intermediate 11: 3-(2-methyl-benzothiazol-6-yl)-propionic acid

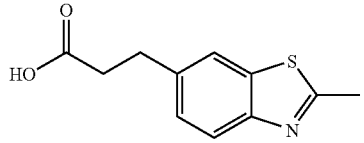

A mixture of 6-iodo-2-methylbenzo[d]thiazole (275 mg, 1 mmol), methyl acrylate (103 mg, 1.2 mmol), diacetoxypalladium (22 mg, 0.1 mmol) and triethylamine (304 mg, 3 mmol) MeCN (8 mL) is heated in a microwave apparatus at 100° C. for 10 min. The solvent is removed under reduce pressure and the residue is purified by flash chromatography (heptane:EtOAc, 2:1) to give (E)-3-(2-methyl-benzothiazol-6-yl)-acrylic acid methyl ester. MS 234.3 (M+1).

Next, a solution of (E)-3-(2-methyl-benzothiazol-6-yl)-acrylic acid methyl ester in ethyl acetate (10 mL) is hydrogenated over 10% Pd/C (22 mg, 10% w) at 1 atm for 18 hours. The catalyst is filtered through Celite and the solvent is removed under reduced pressure. The residue is purified by flash chromatography (heptane:EtOAc, 2:1) to give 3-(2-methyl-benzothiazol-6-yl)-propionic acid methyl ester. MS 236.3 (M+1).

Next, to a solution of 3-(2-methyl-benzothiazol-6-yl)-propionic acid methyl ester (150 mg, 1.67 mmol) in EtOH (5 mL) is added aqueous 1M NaOH (5 mL) and the mixture is stirred at room temperature for 2 hours. The solution is acidified to pH 3 with aqueous 1M HCl and is extracted with ethyl acetate. The organic layer is washed with water, brine, dried over magnesium sulfate and filtered. The solvent is removed under reduced pressure and the residue is purified by preparative HPLC using a gradient of 10-100% MeCN/water (0.1% TFA) to give 3-(2-methyl-benzothiazol-6-yl)-propionic acid.

Intermediate 12: 4-(2-methyl-benzothiazol-6-yl)-butyric acid

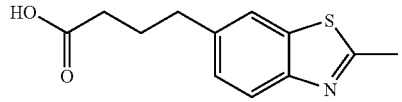

A mixture of 6-iodo-2-methylbenzo[d]thiazole (275 mg, 1 mmol), but-3-enoic acid methyl ester (100 mg, 1.2 mmol), diacetoxypalladium (22 mg, 0.1 mmol) and triethylamine (304 mg, 3 mmol) MeCN (8 mL) is heated in a microwave apparatus at 130° C. for 30 minutes. The solvent is removed under reduce pressure and the residue is purified by flash chromatography (heptane:EtOAc, 2:1) to give (E)-4-(2-methyl-benzothiazol-6-yl)-but-3-enoic acid methyl ester. MS 248.3 (M+1).

Next, a solution of (E)-4-(2-methyl-benzothiazol-6-yl)-but-3-enoic acid methyl ester in THF (10 mL) is hydrogenated over 10% Pd/C (22 mg, 10% wet) at 1 atm for 48 hours. The catalyst is filtered through Celite and the solvent is removed under reduced pressure. The residue is purified by flash chromatography (heptane:EtOAc, 2:1) to give 4-(2-methyl-benzothiazol-6-yl)-butyric acid methyl ester. MS 250.4 (M+1).

Next, to a solution of 4-(2-methyl-benzothiazol-6-yl)-butyric acid methyl ester in EtOH (4 mL) is added aqueous 1M NaOH (4 mL) and the mixture is stirred at room temperature for 2 hours. The solution is acidified to pH 2 with aqueous 1M HCl and is extracted with ethyl acetate. The organic layer is washed with water, brine, dried over magnesium sulfate and filtered. The solvent is removed under reduced pressure to give 4-(2-methyl-benzothiazol-6-yl)-butyric acid. MS 236.3 (M+1).

Intermediate 13: 2-methyl-succinic acid 1-tert-butyl ester

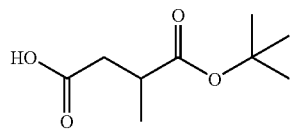

Succinic acid mono-tert-butyl ester is prepared according to the procedure described in J. Org. Chem. 59, 4862 (1994).

To a stirred solution of LDA (6.3 mmol, 2M in hexane) in THF (5 mL) at −78° C. is added a solution of succinic acid mono-tert-butyl ester (523 mg, 3 mmol) in THF (2 mL) dropwise. After the addition, the mixture is warmed to −20° C. slowly and stirred at −20° C. for 30 minutes. The solution is re-cooled to −78° C. and MeI (511 mg, 3.6 mmol) is added dropwise. The mixture is warmed to room temperature and stirred for 18 hours. The mixture is quenched with water and extracted with ethyl acetate. The organic layer is washed with water, brine, dried over MgSO$_4$ and filtered. The solvent is removed under reduced pressure to give 2-methyl-succinic acid 1-tert-butyl ester.

Intermediate 14:
1-carboxymethyl-cyclopentanecarboxylic acid benzyl ester

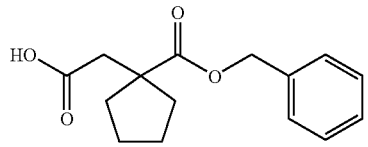

To a stirred solution of cyclopentanecarboxylic acid (1.14 g, 10 mmol) in DMF (15 mL) is added K$_2$CO$_3$ (2.07 g, 15 mmol) and benzyl bromide (1.71 g, 10 mmol). The suspension is stirred at room temperature for 18 hours. The mixture is quenched with water and extracted with ethyl acetate. The organic layer is washed with water, brine, dried over MgSO$_4$ and filtered. The solvent is removed under reduced pressure and the residue is purified by flash chromatography (heptane:EtOAc, 10:1) to give cyclopentanecarboxylic acid benzyl ester.

Next, to a stirred solution of LDA (4 mmol, 2M in Hexane) in THF (8 mL) at −78° C. is added a solution of cyclopentanecarboxylic acid benzyl ester (817 mg, 4 mmol) in THF (3 mL) dropwise. After the addition, the mixture is stirred at −78° C. for 5 hours then allyl bromide (726 mg, 6 mmol) is added dropwise. The mixture is warmed to room temperature during 4 hours then the reaction mixture is quenched with saturated NaHCO$_3$. Magnesium sulfate (2 g) is added and stirred until all the MgSO$_4$ is dissolved. The mixture is extracted with ethyl acetate and the organic layer is washed with water, brine, dried over MgSO$_4$ and filtered. The solvent is removed under reduced pressure and the residue is purified by flash chromatography (hep:EtOAc, 10:1) to give 1-allyl-cyclopentanecarboxylic acid benzyl ester.

Next, Ozone is bubbled through a solution of 1-allyl-cyclopentanecarboxylic acid benzyl ester in methylene chloride (15 mL) for 30 min then PS-triphenolphosphine (300 mg) is added and the mixture is stirred at room temperature for 5 hours. The resin is filtered and solvent is removed under reduced pressure. The residue is purified by flash chromatography (heptane:EtOAc, 10:1) to give 1-(2-oxo-ethyl)-cyclopentanecarboxylic acid benzyl ester MS 247.3 (M+1).

Next, to a solution of 1-(2-oxo-ethyl)-cyclopentanecarboxylic acid benzyl ester (200 mg, 0.81 mmol) in THF (5 mL) is added silver(II) oxide (201 mg, 1.62 mmol) and aqueous 1M NaOH (0.81 mL of 1.0 N, 0.81 mmol) and the suspension is stirred at room temperature for 18 hours. The mixture is acidified to pH 3 with aqueous 1M HCl and is extracted with ethyl acetate. The organic layer is washed with water, brine, dried over MgSO$_4$ and filtered. The solvent is removed under reduced pressure to furnish 1-carboxymethyl-cyclopentanecarboxylic acid benzyl ester MS 263.3 (M+1).

Intermediate 15: (2R,4S)-5-biphenyl-4-yl-4-[3-(2-cyano-ethylcarbamoyl)-propionylamino]-2-methyl pentanoic acid ethyl ester

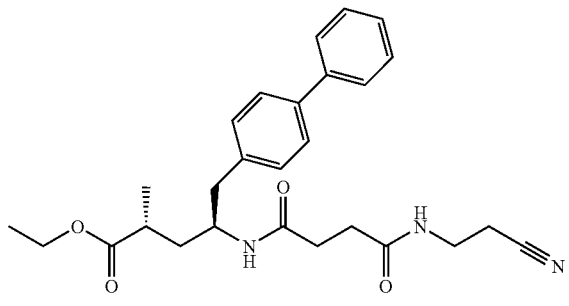

To a solution of (2R,4S)-5-biphenyl-4-yl-4-(3-carboxy-propionylamino)-2-methyl-pentanoic acid ethyl ester (prepared by using the procedure described in US005217996) (200 mg, 0.486 mmol) in DMF (3 mL) are added EDC-HCl (112 mg, 0.583 mmol) and HOAt (79 mg, 0.583 mmol) at room temperature. After stirring for 10 minutes, 3-aminopropionitrile (41 mg, 0.583 mmol) and triethylamine (0.081 mL, 0.583 mmol) is added and stirred overnight. Additional EDC-HCl (66 mg, 0.292 mmol), HOAt (40 mg, 0.292 mmol), aminopropionitrile (21 mg, 0.292 mmol), and triethylamine (0.081 mL, 0.583 mmol) are added. After stirring for 1 hour, the reaction mixture is heated to 50° C. and stirred for 5 hours. The reaction mixture is diluted with ethyl acetate and washed with H$_2$O and brine. The organic layer is dried over Na$_2$SO$_4$ and concentrated. The residue is purified by silica gel column chromatography to give (2R,4S)-5-biphenyl-4-yl-4-[3-(2-cyano-ethylcarbamoyl)-propionylamino]-2-methyl pentanoic acid ethyl ester. HPLC Retention time 1.37 minutes (condition B); MS 464 (M+1); 1H NMR (400 MHz, CDCl3) δ ppm 1.17 (d, J=7.33 Hz, 3H), 1.25 (t, J=7.07 Hz, 3H), 1.51 (ddd, J=4.29, 0.85, 14.14 Hz, 1H), 1.95 (ddd, J=4.29, 9.60, 13.89 Hz, 1H), 2.41-2.59 (m, 5H), 2.58 (t, J=6.57 Hz, 2H), 2.83 (d, J=6.57 Hz, 2H), 3.45 (ddd, J=2.53, 8.00, 12.0 Hz, 2H), 4.14 (ddd, J=2.53, 8.00, 14.01 Hz, 2H), 4.21-4.31 (m, 1H), 5.64 (d, J=9.09 Hz, 1H), 6.60-6.67 (m, 1H), 7.24 (d, J=8.34 Hz, 2H), 7.34 (t, J=7.33 Hz, 1H), 7.43 (t, J=7.83 Hz, 2H), 7.53 (d, J=8.34 Hz, 2H), 7.58 (d, J=7.07 Hz, 2H).

Intermediate 16: (2R,4S)-5-biphenyl-4-yl-4-{3-[1-(2-cyano-ethyl)-1H-tetrazol-5-yl]-propionylamino}-2-methyl-pentanoic acid ethyl ester

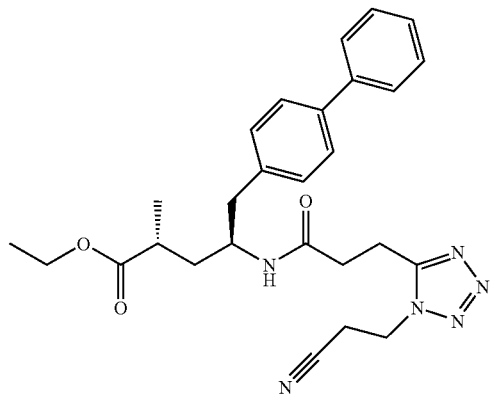

To a solution of (2R,4S)-5-biphenyl-4-yl-4-[3-(2-cyano-ethylcarbamoyl)-propionylamino]-2-methyl pentanoic acid ethyl ester (150 mg, 0.324 mmol) in THF (2 mL) is added triphenylphosphine (85 mg, 0.324 mmol). After stirring for 10 minutes, diisopropyl azodicarboxylate (0.063 mL, 0.324 mmol) and trimethylsilyl azide (0.043 mL, 0.324 mmol) are added. The mixture is stirred for 8 hours and additional triphenylphosphine, diisopropyl azocarboxylate, and trimethylsilyl azide (each 0.324 mmol) are added. After stirring overnight, the mixture is concentrated and purified by silica gel column chromatography to give (2R,4S)-5-biphenyl-4-yl-4-{3-[1-(2-cyano-ethyl)-1H-tetrazol-5-yl]-propionylamino}-2-methyl-pentanoic acid ethyl ester. HPLC Retention time 1.42 minutes (condition B); MS 489 (M+1); 1H NMR (400 MHz, CDCl3) δ ppm 1.11 (d, J=7.07 Hz, 3H), 1.23 (t, J=7.07 Hz, 3H), 1.47 (ddd, J=4.29, 10.10, 14.39 Hz, 1H), 1.91 (ddd, J=4.04, 9.60, 13.64 Hz, 1H), 2.31-2.41 (m, 1H), 2.67-2.81 (m, 4H), 3.00 (t, J=6.82 Hz, 2H), 3.05-3.17 (m, 2H), 4.03-4.22 (m, 3H), 4.50-4.68 (m, 2H), 5.69 (d, J=9.09 Hz, 1H), 7.14 (d, J=8.08 Hz, 2H), 7.34 (t, J=7.33 Hz, 1H), 7.44 (t, J=7.83 Hz, 2H), 7.50 (d, J=8.34 Hz, 2H), 7.59 (d, J=7.07 Hz, 2H).

Intermediate 17: 1H-Pyrrole-2,5-dicarboxylic acid monomethyl ester

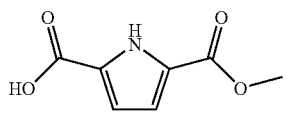

Prepared from methyl 2-pyrrolecarboxylate according to the procedure described in *Eur. J. Org. Chem.* 2397 (1999).

Intermediate 18: 1H-Pyrrole-2,5-dicarboxylic acid monobenzyl ester

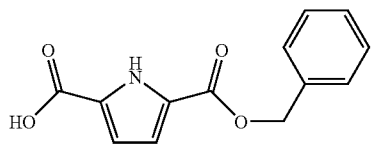

To a stirred solution of 1H-pyrrole-2-carboxylic acid (1.11 g, 10 mmol) in DMF (15 mL) is added potassium carbonate (2.07 g, 15 mmol) and (bromomethyl)benzene (1.80 g, 10.50 mmol). After stirring the mixture at room temperature for 18 hours, water is added and the mixture is extracted three times with ethyl acetate. The combined organic layers are washed with water and brine then is dried over magnesium sulfate. The solvent is removed under reduced pressure and the residue is purified by flash chromatography (heptane/ethyl acetate=5:1) to give 1H-pyrrole-2-carboxylic acid benzylester.

Next, To a stirred solution of 1H-pyrrole-2-carboxylic acid benzylester (2.0 g, 9.94 mmol) in 1,2-dichloroethane (15 mL) at 5° C. is sequentially added DMF (1.12 g, 15.31 mmol) and phosphoryl trichloride (2.35 g, 15.31 mmol). After the addition, the mixture is heated to 50° C. and stirred for an hour. Water is added and the mixture is extracted with ethyl acetate (3×). The combined organic layers are washed with water and brine then is dried over magnesium sulfate. The solvent is removed under reduced pressure and the residue is purified by flash chromatography (heptane/ethyl acetate=3:1) to give 5-formyl-1H-pyrrole-2-carboxylic acid benzyl ester; HPLC Retention time 1.64 minutes (condition C): MS 230.3 (M+1).

Next, to a stirred solution of 5-formyl-1H-pyrrole-2-carboxylic acid benzyl ester (1.10 g, 4.80 mmol) in acetone (100 mL) is added a solution of potassium permanganate (1.52 g, 9.60 mmol) in 150 mL acetone/water (1:1) dropwise and the mixture is stirred for three hours. The mixture is poured into a solution of 200 mL of 10% NaHSO₃ in 1N HCl and the mixture is extracted three times with ethyl acetate. The combined organic layers are washed with water and brine then is dried over magnesium sulfate. The solvent is removed under reduced pressure to give the title compound; HPLC Retention time 0.88 minutes (condition C): MS 244.3 (M−1).

Intermediate 19: 1-Methyl-1H-pyrrole-2,5-dicarboxylic acid monobenzyl ester

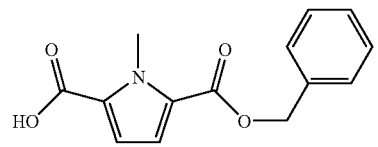

To a stirred solution of 5-formyl-1H-pyrrole-2-carboxylic acid benzyl ester (from the preparation of Intermediate 18) (400 mg, 1.75 mmol) in DMF (10 mL) is added cesium carbonate (853 mg, 2.62 mmol) and MeI (297 mg, 2.09 mmol). The mixture is stirred at room temperature for 2 hours then water is added and the mixture is extracted with ethyl acetate (3×). The combined organic layers are washed with water and brine then is dried over magnesium sulfate. The solvent is removed under reduced pressure to give benzyl 5-formyl-1-methyl-1H-pyrrole-2-carboxylate; HPLC Retention time 1.26 minutes (condition C): MS 244.3 (M+1).

Next, to a stirred solution of benzyl 5-formyl-1-methyl-1H-pyrrole-2-carboxylate (400 mg, 1.64 mmol) in acetone (25 mL) is added a solution of potassium permanganate (520 mg, 3.29 mmol) in 40 mL acetone/water (1:1) dropwise and the mixture is stirred for 3 hours. The mixture is poured into a solution of 60 mL 10% NaHSO₃ in 1N HCl and the mixture is extracted with ethyl acetate (3×). The combined organic layers are washed with water and brine then is dried over magnesium sulfate. The solvent is removed under reduced pressure to give the title compound. HPLC retention time 1.10 minutes (condition C); MS 260.3 (M+H).

Intermediate 20: 3-Hydroxy-isoxazole-5-carboxylic acid

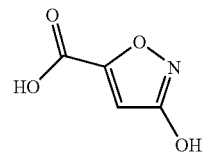

To a solution of 3-hydroxy-isoxazole-5-carboxylic acid methyl ester (286 mg, 2.0 mmol) in methanol (7 mL) is added 1N NaOH (4.0 mL, 4.0 mmol) and the mixture is stirred at room temperature for 18 hrs. The solvent is removed under reduced pressure and 4.0 mL of 1N HCl is added to the residue. The resulting solution is lyophilized to give the product which is used as is in subsequent reactions.

Intermediate 21: 3-Carboxymethylbenzoic acid

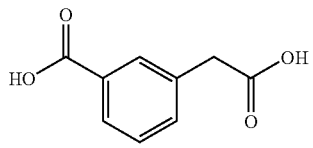

To a solution of 3-bromomethylbenzoic acid (2.29 g, 10 mmol) in methanol (30 mL) is added sodium cyanide (0.49 g, 10 mmol) and the mixture is stirred at 70° C. for 2 hrs. The solvent is removed under reduced pressure and water is added to the residue. The mixture is extracted with ether and the organic phase is dried over sodium sulfate. The solvent is removed under reduced pressure and the residue purified by column chromatography using $CH_2Cl_2$ as eluent to give 3-cyanomethylbenzoic acid.

Next, a mixture of the 3-cyanomethylbenzoic acid (950 mg, 5.42 mmol) in water (2.5 mL) and sulfuric acid (2.5 mL, d 1.84) is heated at 115° C. for 18 hrs. The mixture is cooled to room temperature and the resulting precipitate is filtered, washed with water and dried under reduced pressure to give 3-carboxymethylbenzoic acid.

Intermediate 22: 5-Carboxymethyl-furan-2-carboxylic acid

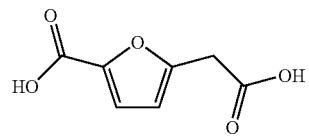

To a solution of 5-methoxycarbonylmethyl-furan-2-carboxylic acid methyl ester (250 mg, 1.26 mmol) in methanol (5 mL) is added 1N NaOH (2.78 mL, 2.78 mmol) and the mixture is stirred at room temperature for 18 hrs. The solvent is removed under reduced pressure and 2.78 mL of 1N HCl is added to the residue. The resulting solution is lyophilized to give the product which is used as is in subsequent reactions.

Intermediate 23: 5-Methoxycarbonylmethyl-furan-2-carboxylic acid

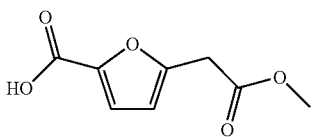

To a solution of Intermediate 22 (220 mg, 1.29 mmol) in methanol (8 mL) is added Amberlyst-15 resin (50 mg) and the mixture is stirred at room temperature for 18 hrs. The resin is filtered and the solvent is removed under reduced pressure to give the product which is used as is in subsequent reactions.

1H NMR (400 MHz, CHLOROFORM-d) δ ppm 3.75 (s, 3H), 3.82 (s, 2H), 6.45 (d, J=3.54 Hz, 1H), 7.29 (d, J=3.54 Hz, 1H), 10.17 (s, broad, 1H).

Intermediate 24: 2-chloro-pyrimidine-4,6-dicarboxylic acid monomethyl ester

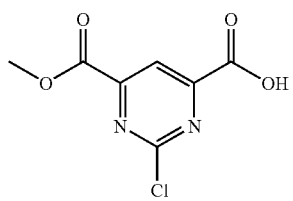

To a stirred solution of methyl 2-chloro-6-methylpyrimidine-4-carboxylate (3.73 g, 20 mmol.) in dioxane (20 mL) is added selenium dioxide (3.55 g, 32 mmol) and the mixture is heated at 105° C. for 12 hours. The suspension is filtered through Celite and washed well with dioxane. The solvent is removed under reduced pressure to give 2-chloro-pyrimidine-4,6-dicarboxylic acid monomethyl ester; HPLC Retention time 0.65 minutes (condition C); MS 217.2 (M+1).

Intermediate 25: 2-Hydroxy-pyrimidine-4,6-dicarboxylic acid

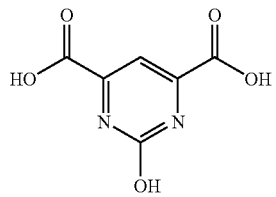

Next, to a stirred solution of 2-chloro-pyrimidine-4,6-dicarboxylic acid monomethyl ester (120 mg, 0.55 mmol) in THF (3 mL) is added 1N NaOH (1.10 mL) and the mixture is stirred at room temperature for 18 hours. The solution is carefully acidified with 1N HCl and the solvent is removed under reduced pressure to give 2-hydroxypyrimidine-4,6-dicarboxylic acid. This is used as is in subsequent reactions.

Intermediate 26: Pyrimidine-2,4-dicarboxylic acid

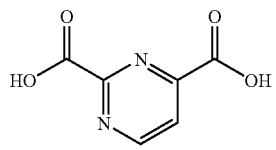

To a stirred solution of triethyl 1,3,5-triazine-2,4,6-tricarboxylate (J. Org. Chem. 59, 4950, 1994) (2.02 g, 6.80 mmol.) in DMF (15 mL) is added 1-aminoethaniminium chloride (1.29 g, 13.60 mmol). After the addition, the mixture is heated at 100° C. for 18 hours then the mixture is extracted three times with ethyl acetate. The combined organic layers are washed with water and brine then is dried over magnesium sulfate. The solvent is removed under reduced pressure and the residue is purified by flash chromatography (heptane/ethyl acetate=3:1) to give diethyl 6-aminopyrimidine-2,4-dicarboxylate; HPLC Retention time 0.89 minutes (condition C); MS 240.3 (M+1).

Next, To a stirred solution of tert-butyl nitrite (268 mg, 2.34 mmol.) in DMF (5 mL) at 60° C. is added a solution of diethyl 6-aminopyrimidine-2,4-dicarboxylate (280 mg, 1.17 mmol) in DMF (0.5 mL) dropwise and mixture is heated at 60° C. for 18 hours. The mixture is cooled to room temperature and poured into 1N HCl (10 mL). The mixture is extracted three times with ethyl acetate and the combined organic layers are washed with water and brine then is dried over magnesium sulfate. The solvent is removed under reduced pressure and the residue is purified by flash chromatography (heptane/ethyl acetate=4:1) to give diethyl pyrimidine-2,4-dicarboxylate.

Next, to a stirred solution of diethyl pyrimidine-2,4-dicarboxylate (130 mg, 0.58 mmol) in MeOH (3 mL) is added 1N NaOH (2 mL) and the mixture is stirred at room temperature for 3 hours. The solution is carefully acidified with 1N HCl and the solvent is removed under reduced pressure to give pyrimidine-2,4-dicarboxylic acid. This is used as is in subsequent reactions.

Intermediate 27: 1H-Imidazole-2,4-dicarboxylic acid 2-methyl ester

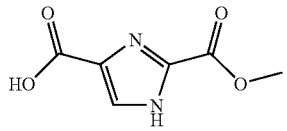

This intermediate is prepared according to the procedure described in patent application WO2005/040345.

Intermediate 28:
2-Chloromethyl-oxazole-5-carboxylic acid

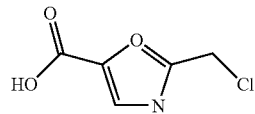

A mixture of 2-chloromethyl-oxazole-5-carboxylic acid ethyl ester (J. Chromatography B, 674, 167, 1995) (190 mg, 1 mmol) and 1N NaOH (2 mL, 2 mmol) is stirred at room temperature for 3 hours then 1N HCl (2 mL, 2 mmol) is added and the solvent is removed under reduced pressure to give the title compound which is used as is in subsequent reactions.

Intermediate 29:
5-Hydroxy-6-oxo-6H-pyran-2-carboxylic acid

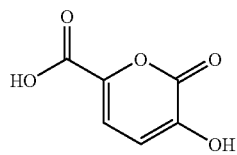

This intermediate is prepared according to the procedure described in Nippon Kagaku Zasshi, 82, 932 (1961).

Intermediate 30: (E)-(R)-5-(4-Bromo-phenyl)-4-tert-butoxycarbonylamino-2-methyl-pent-2-enoic acid ethyl ester

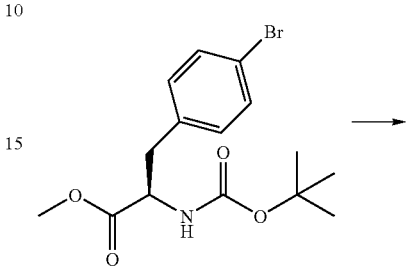

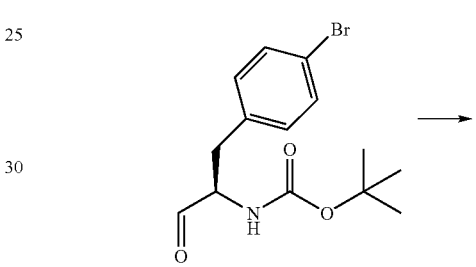

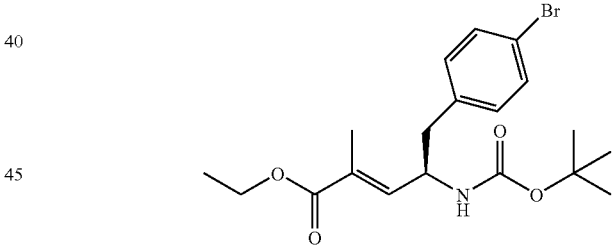

To a solution of (R)-3-(4-Bromo-phenyl)-2-tert-butoxycarbonylamino-propionic acid (1.0 g, 2.91 mmol) in DMF (5 mL) is added $Cs_2CO_3$ (1.041 g, 3.2 mmol) and the mixture is stirred at room temperature for 30 minutes. Then iodomethane (1.031 g, 7.26 mmol) is added and the mixture is stirred at room temperature about 72 hours. The pH is adjusted to 5~6 by adding 1N HCl then the mixture is extracted with EtOAc. The combined organic layers were washed with water and brine, dried over $MgSO_4$, filtered and concentrated to give (R)-3-(4-bromo-phenyl)-2-tert-butoxycarbonylamino-propionic acid methyl ester. HPLC Retention time 1.49 minutes (condition C): MS 358.3 (M−1).

Next, to a solution of (R)-3-(4-bromo-phenyl)-2-tert-butoxycarbonylamino-propionic acid methyl ester (1.0 g, 2.79 mmol) in DCM (20 mL) is added DIBAL-H (4.85 mL, 1.0M in DCM) slowly by using syringe pump at −78° C. After the addition is complete the reaction is quenched by adding EtOAc and the mixture is warmed to room temperature. Then a saturated sodium potassium tartaric acid is added and the mixture is and stirred at room temperature for 1 hour. The organic phase is separated and the aqueous layer is extracted with EtOAc. The combined organic layers were washed with brine, dried over MgSO4, filtered and concentrated to give [(R)-1-(4-bromo-benzyl)-2-oxo-ethyl]-carbamic acid tert-butyl ester which is used directly in the next reaction.

Next, to a solution of [(R)-1-(4-bromo-benzyl)-2-oxo-ethyl]-carbamic acid tert-butyl ester (800 mg, 2.438 mmol) in DCM (20 mL) is added (carbethoxylidene)triphenylphosphorane (1.767 g, 4.88 mmol) and the mixture is stirred at room temperature overnight. The solvent is removed under reduced pressure and the residue is purified by column chromatography to afford the title compound.

Intermediate 31: (S)-4-Amino-5-(3'-chloro-biphenyl-4-yl)-2-methyl-pentanoic acid ethyl ester hydrochloride

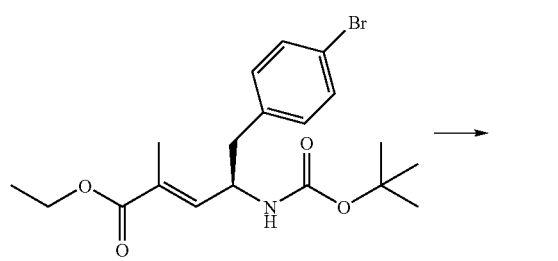

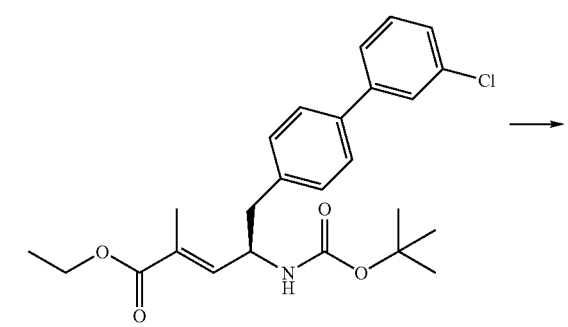

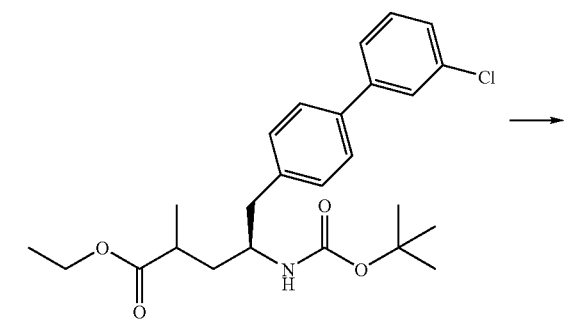

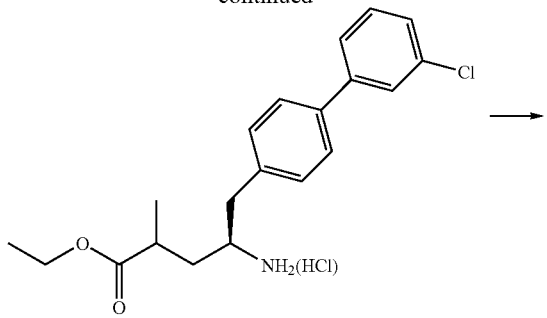

To a mixture of (R)-5-(4-bromo-phenyl)-4-tert-butoxycarbonylamino-2-methyl-pent-2-enoic acid ethyl ester (Intermediate 30) (2.6 g, 6.31 mmol), 3-chlorophenyl boronic acid (1.085 g, 6.94 mmol), PdCl$_2$(dppf).CH$_2$Cl$_2$ (0.257 g, 0.315 mmol) in DMF (30 mL) is bubbled nitrogen for 10 minutes then Na$_2$CO$_3$ (6.3 mL of a 2N aqueous solution) is added. The resulting mixture is heated to 100° C. for 2 hours then is cooled to room temperature. A mixture of ice and water is added and the mixture is extracted with EtOAc. The combined organic phases were washed with water and brine, dried over MgSO$_4$, filtered and concentrated to give (E)-(R)-4-tenbutoxycarbonylamino-5-(3'-chloro-biphenyl-4-yl)-2-methyl-pent-2-enoic acid ethyl ester.

Next, to a solution of (E)-(R)-4-tert-butoxycarbonylamino-5-(3'-chloro-biphenyl-4-yl)-2-methyl-pent-2-enoic acid ethyl ester (2.5 g, 5.63 mmol) in ethanol (20 mL) is added Pt/C (250 mg) and the mixture is stirred overnight under an atmosphere of hydrogen (H$_2$ balloon). The catalyst is filtered through a Celite pad and, the filtrate is concentrated to give (S)-4-tert-butoxycarbonylamino-5-(3'-chloro-biphenyl-4-yl)-2-methyl-pentanoic acid ethyl ester.

Next, to a solution of (S)-4-tert-butoxycarbonylamino-5-(3'-chloro-biphenyl-4-yl)-2-methyl-pentanoic acid ethyl ester (2.47 g, 5.54 mmol) in DCM (15 mL) is added 5 mL of HCl (4N in dioxane) and the mixture is stirred at room temperature for 2 hours. The solvent is removed under reduced pressure to afford the title compound; HPLC Retention time 1.48 minutes (condition C): MS 346.2 (M+1).

The following intermediates are synthesized according to the procedures described above using a suzuki reaction of (E)-(R)-5-(4-Bromo-phenyl)-4-tert-butoxycarbonylamino-2-methyl-pent-2-enoic acid ethyl ester with the relavant boronic acids, hydrogenation reaction, and HCl mediated deprotection of the Boc group to give the corresponding amine hydrochloride salt.

| Intermediate # | Product | Boronic Acid | LCMS-RT (condition) | MS (M + 1) |
|---|---|---|---|---|
| Intermediate 31-2 | (4S)-ethyl 4-amino-5-(5'-fluoro-2'-methoxybiphenyl-4-yl)-2-methylpentanoate hydrochloride | 5-fluoro-2-methoxyphenylboronic acid | 1.50 min. (A) | 360.3 |
| Intermediate 31-3 | (4S)-ethyl 4-amino-5-(5'-chloro-2'-methoxybiphenyl-4-yl)-2-methylpentanoate hydrochloride | 2,5-dichlorophenylboronic acid | 1.62 min. (A) | 380.2 |
| Intermediate 31-4 | (4S)-ethyl 4-amino-5-(2',5'-dichlorobiphenyl-4-yl)-2-methylpentanoate hydrochloride | 5-chloro-2-fluorophenylboronic acid | 0.91 min. (B) | 364.2 |

Intermediate 32: 2-(4-Methoxy-benzyl)-2H-tetrazole-5-carboxylic acid

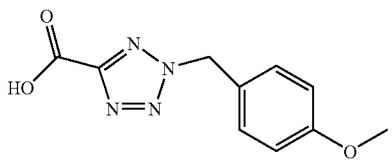

To a solution of sodium tetrazole-5-carboxylic acid ethyl ester (2 g, 12.19 mmol) in DMF (8 mL) is added 4-methoxybenzyl bromide (3.68 g, 18.28 mmol) followed by the addition of triethylamine (5.10 mL). The resulting mixture is stirred at room temperature overnight then ice/water is added. The mixture is extracted with EtOAc and the combined organic phases were washed with water and brine, dried over MgSO$_4$, filtered and concentrated. The residue is purified by column chromatography to afford 2-(4-methoxy-benzyl)-2H-tetrazole-5-carboxylic acid ethyl ester; HPLC Retention time 1.37 minutes (condition C): MS 263.2 (M+1).

Next, to a solution of 2-(4-methoxy-benzyl)-2H-tetrazole-5-carboxylic acid ethyl ester (1.5 g, 5.72 mmol) in ethanol (10 mL) is added 1N NaOH (10 mL, 10 mmol) and the mixture is stirred at room temperature for 2 hours. The solvent is removed under reduced pressure and the mixture acidified with 1N HCl. The mixture is extracted with EtOAc and the organic phase is washed with brine and dried over MgSO$_4$. The solvent is removed under reduced pressure to give the title compound; HPLC Retention time 0.73 minutes (condition C): MS 233.2 (M−1).

Intermediate 33: (S)-1-Carboxymethyl-pyrrolidine-2-carboxylic acid methyl ester

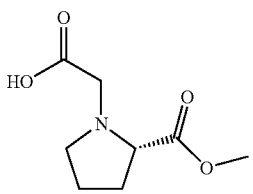

To a solution of chloroacetic benzyl ester (1.8 g, 9.75 mmol) in DCM (50 mL) is added (S)-pyrrolidine-2-carboxylic acid methyl ester hydrochloride (1.51 g, 11.70 mmol), diisopropylethylamine (4.09 mL, 23.40 mmol) and tetrabutylammonium iodide (3.60 g, 9.75 mmol) and the resulting mixture is stirred at room temperature overnight. The solvent is removed under reduced pressure and the residue purified by column chromatography using a gradient of 2-45% EtOAc/heptane to give (S)-1-benzyloxycarbonylmethyl-pyrrolidine-2-carboxylic acid methyl ester; 1H NMR (400 MHz, CHLOROFORM-d) δ ppm 1.81-2.05 (m, 3H), 2.13-2.24 (m, 1H), 2.78-2.84 (m, 1H), 3.15-3.20 (m, 1H), 3.57-3.69 (m, 3H), 3.70 (s, 3H), 5.15 (s, 2H), 7.36 (m, 5H).

Next, to the solution of (S)-1-benzyloxycarbonylmethyl-pyrrolidine-2-carboxylic acid methyl ester (2.50 g, 9.01 mmol) in methanol (30 mL)/ethyl acetate (30 mL) is added Pd/C (300 mg) and the mixture is stirred under an atmosphere of hydrogen (H$_2$ balloon) for 18 hours. The catalyst is filtered through a Celite pad and the filtrate is evaporated under reduced pressure to give the title compound; HPLC Retention time 0.94 minutes (condition C): MS188.4 (M+1).

Intermediate 34: ethyl 5-oxo-4,5-dihydro-1,2,4-oxadiazole-3-carboxylate

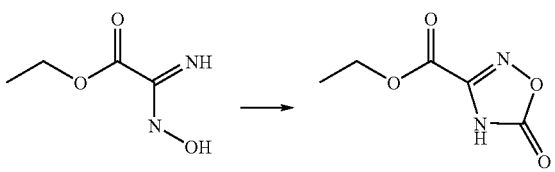

To a solution of ethyl 2-(hydroxyamino)-2-iminoacetate (2 g, 15.14 mmol) in dioxane (15.00 mL) is added CDI (2.7 g, 16.65 mmol) and DBU (2.5 ml, 16.65 mmol) at room temperature. After stirring for 1 hour at 80° C., the reaction is quenched with 1N HCl, and the crude is diluted with EtOAc. The organic layer is washed with brine, dried over Na$_2$SO$_4$, filtered and concentrated under reduced pressure to give ethyl 5-oxo-4,5-dihydro-1,2,4-oxadiazole-3-carboxylate (2.4 g). HPLC retention time=0.72 minutes (condition B); MS 159.1 (M+1).

Intermediate 35: 5-oxo-4,5-dihydro-1,2,4-oxadiazole-3-carboxylic acid

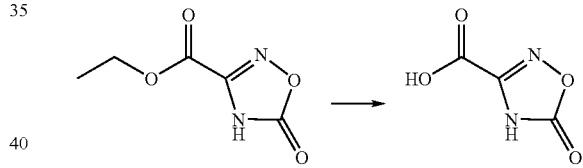

To a solution of crude ethyl 5-oxo-4,5-dihydro-1,2,4-oxadiazole-3-carboxylate (2.4 g, 15.14 mmol) in MeOH (2 mL) is added aqueous 1M NaOH (4 mL, 4 mmol) at room temperature. After stirring for 5 hours at room temperature the reaction was quenched with 1N HCl (5 mL, 5 mmol), the crude is concentrated under reduced pressure to remove MeOH. The crude is diluted with EtOAc, the organic layer is washed with brine, dried over Na$_2$SO$_4$, filtered and concentrated under reduced pressure to give 5-oxo-4,5-dihydro-1,2,4-oxadiazole-3-carboxylic acid (1.9 g).

Intermediate 36: 6-methoxy-5-(trifluoromethyl)nicotinic acid

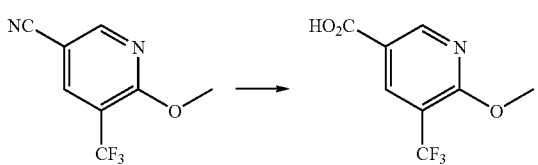

To a solution of 6-methoxy-5-(trifluoromethyl)nicotinonitrile (2 g, 9.89 mmol) in EtOH (12 mL) at room temperature is added 5 M NaOH (11.9 mL, 59.4 mmol). The crude is refluxed for 1.5 hrs. The crude is concentrated to remove EtOH. The crude is diluted in ether and water. The aq. layer is extracted with ether. The aq. layer is acidified with 1 N HCl at which time white precipitate forms. This crude is redissolved in ether. The ether layer is washed with brine, dried over MgSO₄, filtered and concentrated to give 6-methoxy-5-(trifluoromethyl)nicotinic acid (1.7 g).

Intermediate 37: Synthesis of
6-hydroxy-5-(trifluoromethyl)nicotinic acid

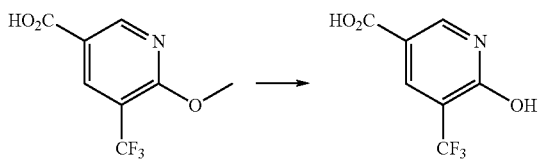

To a solution of TMSCl (0.75 mL, 5.88 mmol) in dry MeCN is added potassium iodide (0.98 g, 5.88 mmol). The crude is stirred at room temperature for 10 mins. To this crude is added a solution of 6-methoxy-5-(trifluoromethyl)nicotinic acid (1.3 g, 5.88 mmol) in MeCN (2 mL). The crude is stirred at 80 deg C. for 4 hrs and room temperature for overnight. The crude is concentrated and diluted in ether and 1 N HCl. The organic layer is washed with water, brine, dried over MgSO₄, filtered and concentrated. The crude is purified via RP-HPLC (SunFire C18, H₂O(0.1% TFA)/CH₃CN) to give 6-hydroxy-5-(trifluoromethyl)nicotinic acid (377 mg). HPLC retention time=0.85 minutes (condition B); MS 208.0 (M+1). 1H NMR (400 MHz, CD₃OD) δ ppm 8.34 (s, 2H).

Intermediate 38: (2R,4S)-ethyl 5-(biphenyl-4-yl)-4-
(2-methoxythiazole-5-carboxamido)-2-methylpentanoate

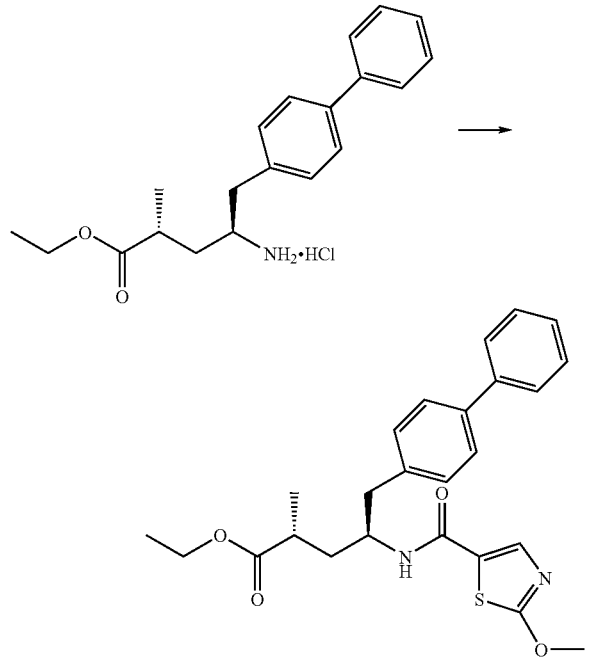

To a solution of 2-methoxythiazole-5-carboxylic acid (101 mg, 0.64 mmol) in DMF (6 mL) is added HOAt (107 mg, 0.58 mmol), EDCl (133 mg, 0.69 mmol), and TEA (0.48 mL, 3.47 mmol). The crude is stirred at room temperature for 15 mins. To this crude is added (2R,4S)-ethyl 4-amino-5-(biphenyl-4-yl)-2-methylpentanoate hydrochloride salt. The crude is stirred at room temperature for overnight. The crude is quenched with 1 N HCl and water, diluted in EtOAc. The organic layer is washed with brine, dried over MgSO₄, filtered, and concentrated. The residue is purified via flash column chromatography using 30% EtOAc/heptane to 70% EtOAc/heptane to give (2R,4S)-ethyl 5-(biphenyl-4-yl)-4-(2-methoxythiazole-5-carboxamido)-2-methylpentanoate (170 mg). HPLC retention time 1.94 minutes (condition A); MS 453.3 (M+1); 1H NMR (400 MHz, CHLOROFORM-d) δ ppm 1.18 (d, J=7.1 Hz, 3H), 1.23 (t, J=7.1 Hz, 3H), 1.71 (ddd, J=14.0, 9.9, 3.9 Hz, 1H), 1.88-2.04 (m, 1H), 2.56-2.73 (m, 1H), 2.78-2.96 (m, 1H), 2.96-3.09 (m, 1H), 4.09 (s, 3H), 4.09-4.18 (m, 2H), 4.30-4.47 (m, 1H), 6.15 (d, J=8.1 Hz, 1H), 7.27 (d, J=6.8 Hz, 2H), 7.29-7.36 (m, 1H), 7.42 (t, J=7.6 Hz, 2H), 7.49 (s, 1H), 7.53 (d, J=8.1 Hz, 2H), 7.57 (d, J=7.3 Hz, 2H).

Intermediate 39: (2R,4S)-ethyl 5-(biphenyl-4-yl)-4-
(2-methoxyoxazole-5-carboxamido)-2-methylpentanoate

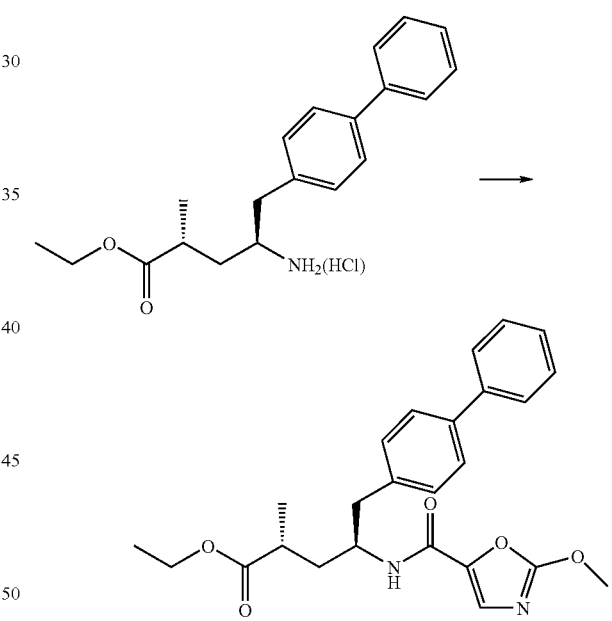

To a solution of 2-methoxyoxazole-5-carboxylic acid, intermediate 22, (68 mg, 0.47 mmol) in DMF (2 mL) and DCM (2 mL) is added (2R,4S)-ethyl 4-amino-5-(biphenyl-4-yl)-2-methylpentanoate hydrochloride (150 mg, 0.43 mmol), HATU (246 mg, 0.65 mmol), and triethylamine (180 µL, 1.29 mmol). After stirring the reaction for 2 hours at room temperature, the reaction is quenched with H₂O, and the crude is diluted in EtOAc. The organic layer is washed with brine, dried over Na₂SO₄, filtered, and concentrated under reduced pressure. The obtained residue is purified by RP-HPLC (SunFire C18, H₂O(0.1% TFA)/CH₃CN), and then lyophilized to give (2R,4S)-ethyl 5-(biphenyl-4-yl)-4-(2-methoxyoxazole-5-carboxamido)-2-methylpentanoate (175 mg). HPLC retention time=1.71 minutes (condition A); MS 437.5 (M+1); 1H NMR (400 MHz, CHLOROFORM-d) δ ppm 1.20 (d, J=7.1

Hz, 3H) 1.25 (t, J=7.1 Hz, 3H) 1.65 (ddd, J=14.3, 10.0, 4.3 Hz, 1H) 1.96-2.10 (m, 1H) 2.63 (ddd, J=9.4, 7.1, 4.2 Hz, 1H) 2.92 (dd, J=13.9, 6.3 Hz, 1H) 2.99 (dd, J=13.9, 6.3 Hz, 1H) 4.11 (s, 3H) 4.12-4.18 (m, 2H) 4.34-4.54 (m, 1H) 6.15 (d, J=8.8 Hz, 1H) 7.28 (d, J=8.3 Hz, 2H) 7.31-7.37 (m, 1H) 7.40-7.47 (m, 3H) 7.54 (d, J=8.3 Hz, 2H) 7.59 (dd, J=8.3, 1.26 Hz, 2H)

Intermediate 40: 2-oxo-2,3-dihydrooxazole-4-carboxylic acid

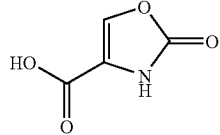

This intermediate is prepared according to: Okonya, J. F.; Hoffman, R. V.; Johnson, M. C.; *J. Org. Chem.* 2002, 67, 1102-1108.

Intermediate 41: 2-methoxyoxazole-5-carboxylic acid

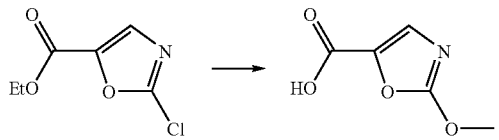

To a solution of ethyl 2-chlorooxazole-5-carboxylate (510 mg, 2.90 mmol) in anhdryous MeCN (10 mL) and anhydrous MeOH (10 mL) is added NaOMe (628 mg, 11.62 mmol). The crude is stirred at reflux for 2 hrs. To this crude is added additional MeOH. The crude is refluxed for another 4 hrs. The crude is cooled and then concentrated and is redissolved in MeOH (10 mL). To this crude is added 1 N NaOH (10 ml, 10 mmol). The crude is stirred at room temperature for 3 hrs. The crude is quenched with concentrated HCl, PH adjusted to 7 via pH paper indicator. The crude is concentrated to remove MeOH. The crude is diluted in water. The aq. layer is acidified with concentrated HCl and diluted in EtOAc. The organic layer is washed with water, brine, dried over MgSO₄, filtered, and concentrated to give 2-methoxyoxazole-5-carboxylic acid (290 mg). This acid is used without further purification. HPLC retention time=0.58 minutes (condition B); MS 144.0 (M+1).

Intermediate 42: (2R,4S)-ethyl 5-(biphenyl-4-yl)-4-(2-ethoxy-2-oxoacetamido)-2-methylpentanoate

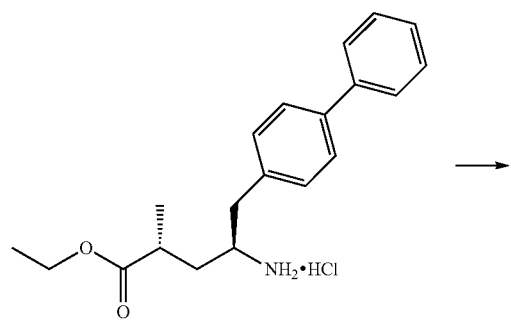

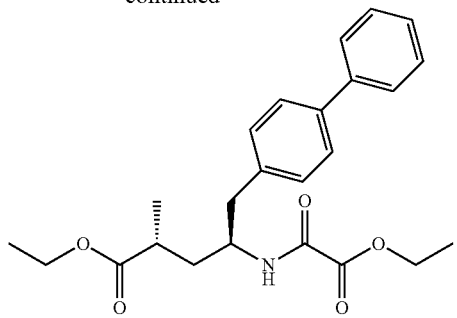

To a solution of (2R,4S)-ethyl 4-amino-5-(biphenyl-4-yl)-2-methylpentanoate hydrochloride salt (1 g, 2.87 mmol) in DMF (10 mL) is added TEA (0.42 mL, 3.02 mmol) followed by ethyl 2-chloro-2-oxoacetate (392 mg, 2.87 mmol). The crude is stirred at it for 1 hr. To the crude is added an additional 0.2 ml of ethyl 2-chloro-2-oxoacetate followed by triethylamine (1.26 mL, 9.06 mmol). The crude is quenched with water and diluted in EtOAc. The organic layer is washed with brine, dried over MgSO₄, filtered, and concentrated. The crude is purified via flash chromatography using 30% EtOAc/heptane to 50% EtOAc/heptane to give (2R,4S)-ethyl 5-(biphenyl-4-yl)-4-(2-ethoxy-2-oxoacetamido)-2-methylpentanoate (970 mg).

Intermediate 43: (2R,4S)-ethyl 5-(biphenyl-4-yl)-4-(2-hydrazinyl-2-oxoacetamido)-2-methylpentanoate

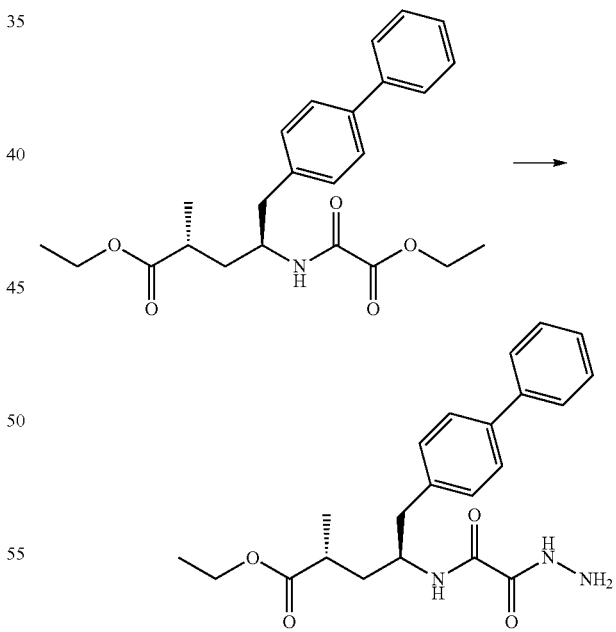

To a stirred solution of (2R,4S)-ethyl 5-(biphenyl-4-yl)-4-(2-ethoxy-2-oxoacetamido)-2-methylpentanoate (970 mg, 2.34 mmol) in anhydrous MeOH (20 mL) cooled to −20 deg C. is added a solution of 50% wt hydrazine hydrate (0.15 mL, 2.36 mmol) in MeOH (10 mL) dropwise. The crude is allowed to warm to rt in 2 hrs and is stirred overnight. The crude white precipitate is filtered to give (2R,4S)-ethyl 5-(biphenyl-4-yl)-4-(2-hydrazinyl-2-oxoacetamido)-2-methylpentanoate (870 mg). HPLC retention time=1.70 minutes (condition A); MS 398.2 (M+1).

Intermediate 44: (4S)-ethyl 5-(3'-chlorobiphenyl-4-yl)-4-(2-ethoxy-2-oxoacetamido)-2-methylpentanoate

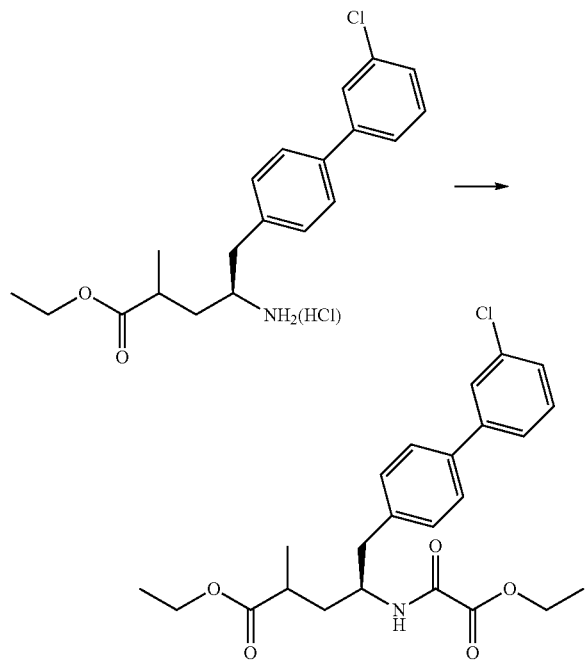

To a solution of (4S)-ethyl 4-amino-5-(3'-chlorobiphenyl-4-yl)-2-methylpentanoate hydrochloride salt (600 mg, 1.74 mmol) in DMF (13.1 mL) is added TEA (0.25 mL, 1.82 mmol) and ethyl 2-chloro-2-oxoacetate (0.19 mL, 1.74 mmol) at room temperature. After stirring this reaction for 1 hour at room temperature, the reaction is quenched with H$_2$O, and diluted in EtOAc. The organic layer is washed with brine, dried over Na$_2$SO$_4$, filtered, and concentrated under reduced pressure. The obtained residue is purified by flash column chromatography (eluent: heptane/EtOAc=70:30 to 50:50) to give (4S)-ethyl 5-(3'-chlorobiphenyl-4-yl)-4-(2-ethoxy-2-oxoacetamido)-2-methylpentanoate (637 mg). HPLC retention time=1.66 minutes (condition A); MS 446.5 (M+1).

Intermediate 45: (4S)-ethyl 5-(3'-chlorobiphenyl-4-yl)-4-(2-hydrazinyl-2-oxoacetamido)-2-methylpentanoate

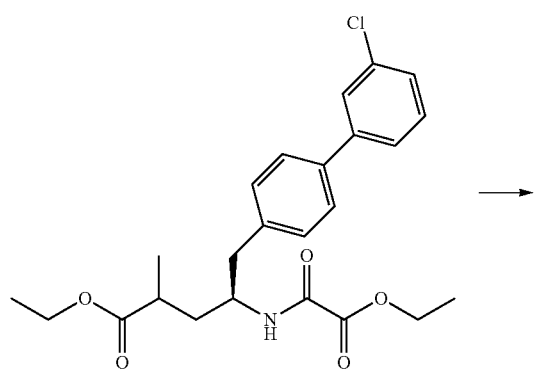

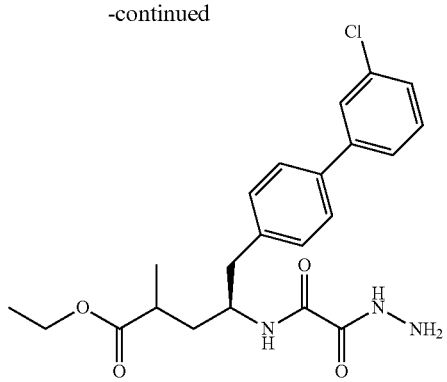

To a solution of (4S)-ethyl 5-(3'-chlorobiphenyl-4-yl)-4-(2-ethoxy-2-oxoacetamido)-2-methylpentanoate (637 mg, 1.43 mmol) in MeOH (40 mL) is added a solution of 50% wt hydrazine (0.09 mL, 1.43 mmol) in MeOH (10 mL) at −20° C. After stirring for 18 hour at room temperature, the reaction mixture is concentrated under reduced pressure to give (4S)-ethyl 5-(3'-chlorobiphenyl-4-yl)-4-(2-hydrazinyl-2-oxoacetamido)-2-methylpentanoate (542 mg). HPLC retention time=1.54 minutes (condition A); MS 432.3 (M+1).

Intermediate 46: ethyl 2-vinyloxazole-5-carboxylate

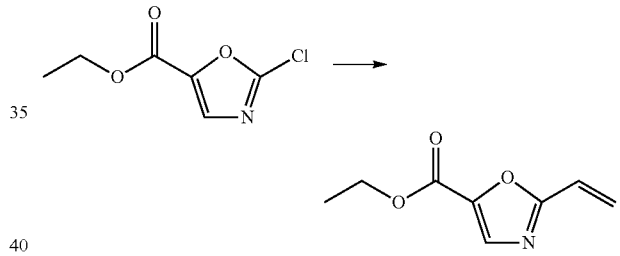

To a solution of tributyl(vinyl)stannane (1.1 mL, 3.83 mmol) and ethyl 2-chlorooxazole-5-carboxylate (546 mg, 3.11 mmol) in dioxane (37 mL) is added Pd(PPh$_3$)$_2$Cl$_2$ (222 mg, 0.32 mmol) at room temperature. After stirring at 100° C. under nitrogen for 4 hours, the solution is cooled to ambient temperature and then quenched with H$_2$O. The crude is diluted with EtOAc, the organic layer is washed with brine, dried over Na$_2$SO$_4$, filtered and concentrated under reduced pressure. The obtained residue is purified by flash column chromatography (eluent: heptane/EtOAc=90:10 to 80:20) to give ethyl 2-vinyloxazole-5-carboxylate (470 mg). HPLC retention time=0.39 minutes (condition B); MS (m+1)= 168.2; 1H NMR (400 MHz, CD$_3$OD) δ ppm 1.38 (t, J=7.1 Hz, 3H) 4.38 (q, J=7.2 Hz, 2H) 5.88 (d, J=11.4 Hz, 1H) 6.39 (d, J=17.7 Hz, 1H) 6.69 (dd, J=17.6, 11.2 Hz, 1H) 7.83 (s, 1H)

Intermediate 47: 2-ethyloxazole-5-carboxylic acid

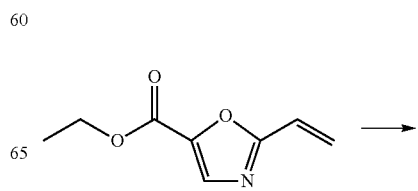

-continued

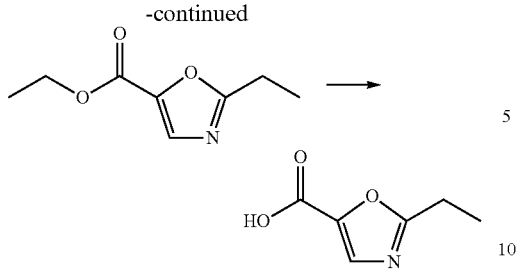

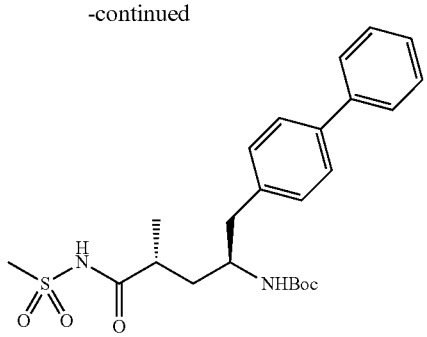

To a solution of ethyl 2-vinyloxazole-5-carboxylate (470 mg, 2.81 mmol) in MeOH (7 mL) is added 10% wt. Pd/C (100 mg, 0.094 mmol) at room temperature. After stirring at room temperature under a balloon of hydrogen for 1 hour, the crude is filtered to remove Pd/C. The filtrate is collected and concentrated to give ethyl 2-ethyloxazole-5-carboxylate (470 mg). HPLC retention time=1.09 minutes (condition A); MS (m+1)=170.3; 1H NMR (400 MHz, $CD_3OD$) δ ppm 1.35 (t, J=7.6 Hz, 3H) 1.36 (t, J=7.2 Hz, 3H) 2.87 (q, J=7.7 Hz, 2H) 4.35 (q, J=7.2 Hz, 2H) 7.71 (s, 1H)

Next, to a solution of 2-ethyloxazole-5-carboxylate (470 mg, 2.81 mmol) in MeOH (10 mL) is added 1N NaOH (6 mL, 6 mmol). After stirring at room temperature for 18 hours, the crude is concentrated under reduced pressure to remove MeOH and is diluted with EtOAc. The organic layer is washed with brine, dried over $Na_2SO_4$, filtered and concentrated under reduced pressure to give 2-ethyloxazole-5-carboxylic acid (244 mg). 1H NMR (400 MHz, $CD_3OD$) δ ppm 1.36 (t, J=7.7 Hz, 3H) 2.89 (q, J=7.6 Hz, 2H) 5.15 (br. s., 1H) 7.69 (s, 1H)

Intermediate 48: ((2R,4S)-5-(biphenyl-4-yl)-4-(tert-butoxycarbonylamino)-2-methylpentanoic acid

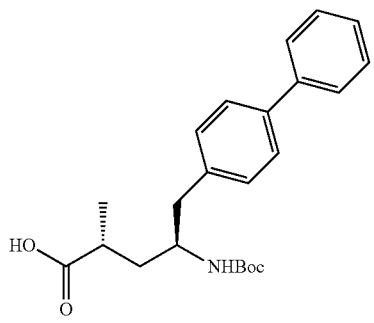

Using the same procedure described in WO2008083967.

Intermediate 49: ((1S,3R)-1-Biphenyl-4-ylmethyl-4-methanesulfonylamino-3-methyl-4-oxo-butyl)-carbamic acid tert-butyl ester

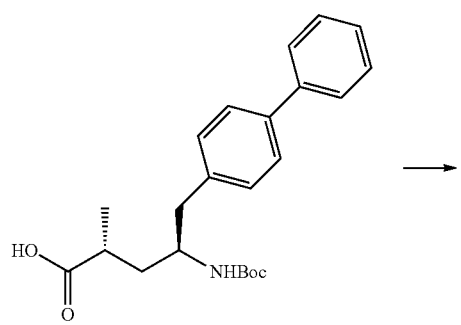

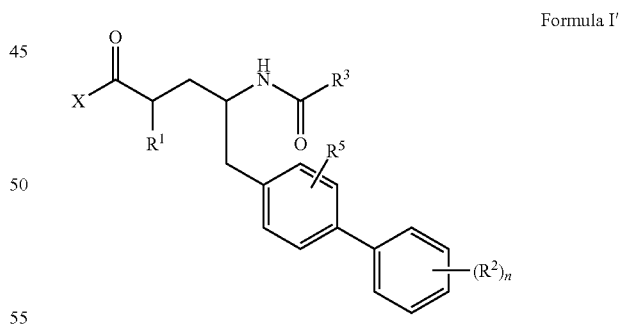

To a solution of (2R,4S)-5-biphenyl-4-yl-4-tert-butoxycarbonylamino-2-methyl-pentanoic acid (500 mg, 1.304 mmol) in DMF (10 ml) at room temperature is added methyl sulfonamide (223 mg, 2.347 mmol), EDC.HCl (450 mg, 2.347 mmol), 1-hydroxy-7-azabenzotriazole (284 mg, 2.086 mmol) and DIPEA (0.501 ml, 2.87 mmol). The reaction mixture is stirred at room temperature over night. The reaction is quenched by brine and is extracted with EtOAc. The combined organic layer is washed with brine and is dried over anhydrous sodium sulfate, filtered and concentrated. Reverse phase HPLC [15 to 60% ACN—H2O (0.1% NH4OH) over 10 min by X-bridge phenyl column] provides ((1S,3R)-1-Biphenyl-4-ylmethyl-4-methanesulfonylamino-3-methyl-4-oxo-butyl)-carbamic acid tert-butyl ester (333 mg, 55%). HPLC retention time=1.03 minutes (condition D), MS (m−1) =495.5, MS (m−55)=405.3, MS (m−99)=361.3.

It can be seen that the compounds of the invention are useful as inhibitors of Neutral endopeptidase (EC 3.4.24.11) activity and therefore useful in the treatment of diseases and conditions associated with Neutral endopeptidase (EC 3.4.24.11) activity such as the diseases disclosed herein.

It will be understood that the invention has been described by way of example only and modifications may be made whilst remaining within the scope and spirit of the invention.

What is claimed is:
1. A compound of the formula (I'):

Formula I' or a pharmaceutically acceptable salt or tautomer thereof, wherein:
$R^1$ is $C_{1-7}$alkyl;
for each occurrence, $R^2$ is independently $C_{1-7}$alkyl, $NO_2$, CN, halo, $C_{3-7}$cycloalkyl, hydroxy, $C_{1-7}$alkoxy, halo-$C_{1-7}$ alkyl, $NR^bR^c$, $C_{6-10}$aryl, heteroaryl or heterocyclyl; wherein $R^b$ and $R^c$ for each occurrence, are independently H or $C_{1-7}$alkyl;
$R^3$ is $A^2$-$R^4$;
$R^4$ is $C_{6-10}$aryl or a heteroaryl, which can be monocyclic or bicyclic and which can be optionally substituted with one or more substituents independently selected from hydroxy, hydroxy-$C_{1-7}$alkyl, $NR^bR^c$, nitro, $C_{1-7}$alkoxy, halo, $C_{1-7}$alkyl, halo-$C_{1-7}$alkyl, $C_{2-7}$alkenyl, $C_{6-10}$aryl, heteroaryl, —C(O)$C_{1-7}$alkyl, —NHS(O)$_2$-$C_{1-7}$alkyl, —SO$_2$C$_{1-7}$alkyl and benzyl;

$R^5$ is H, halo, hydroxy, $C_{1-7}$alkoxy, halo, $C_{1-7}$alkyl or halo-$C_{1-7}$alkyl; and X is OH, —O—$C_{1-7}$alkyl, —NR$^b$R$^c$, —NHS(O)$_2$—$C_{1-7}$alkyl, —NHS(O)$_2$-benzyl or —O—$C_{6-10}$aryl; wherein alkyl is optionally substituted with one or more substituents independently selected from the group consisting of aryl, heteroaryl, heterocyclyl, —C(O)NH$_2$, —C(O)NH—$C_{1-6}$alkyl, and —C(O)N(C$_{1-6}$alkyl)$_2$;

$A^2$ is a bond or a linear or branched $C_{1-7}$alkylene which is optionally substituted with one or more substituents independently selected from the group consisting of halo, $C_{1-7}$alkoxy, hydroxy, O-Acetate and $C_{3-7}$cycloalkyl;

n is 0, 1, 2, 3, 4 or 5;

wherein each heteroaryl is a monocyclic or bicyclic aromatic ring comprising 5-10 ring atoms selected from carbon atoms and 1 to 5 heteroatoms, and each heterocyclyl is a monocyclic saturated or partially saturated but non-aromatic moiety comprising 4-7 ring atoms selected from carbon atoms and 1-5 heteroatoms, wherein each heteroatom of a heteroaryl or a heterocyclyl is independently selected from O, N and S.

2. The compound of claim 1 wherein:

$R^1$ is $C_{1-7}$alkyl;

for each occurrence, $R^2$ is independently $C_{1-7}$alkyl, halo, $C_{3-7}$cycloalkyl, hydroxy, $C_{1-7}$alkoxy, halo-$C_{1-7}$alkyl, NR$^b$R$^c$, $C_{6-10}$aryl, heteroaryl or heterocyclyl; wherein R$^b$ and R$^c$, for each occurrence, are independently H or $C_{1-7}$alkyl;

$R^3$ is $A^2$-$R^4$;

$R^4$ is aryl or a heteroaryl, which can be monocyclic or bicyclic and which can be optionally substituted with one or more substituents independently selected from the group consisting of hydroxy, $C_{1-7}$alkoxy, halo, $C_{1-7}$alkyl, halo-$C_{1-7}$alkyl, $C_{6-10}$aryl, heteroaryl, —NHS(O)$_2$-$C_{1-7}$alkyl, —SO$_2$C$_{1-7}$alkyl and benzyl;

$R^5$ is H; and

X is OH, —O—$C_{1-7}$alkyl or NR$^b$R$^c$;

$A^2$ is a bond or a linear or branched $C_{1-7}$alkylene; optionally substituted with one or more substituents independently selected from the group consisting of halo, $C_{1-7}$alkoxy, hydroxy, O-Acetate and $C_{3-7}$cycloalkyl;

n is 0, 1, 2, 3, 4 or 5;

wherein each heteroaryl is a monocyclic or bicyclic aromatic ring comprising 5-10 ring atoms selected from carbon atoms and 1 to 5 heteroatoms, and each heterocyclyl is a monocyclic saturated or partially saturated but non-aromatic moiety comprising 4-7 ring atoms selected from carbon atoms and 1-5 heteroatoms, wherein each heteroatom of a heteroaryl or heterocyclyl is independently selected from O, N and S;

or a pharmaceutically acceptable salt or tautomer thereof.

3. The compound according to claim 1 having Formulae VI or VIA:

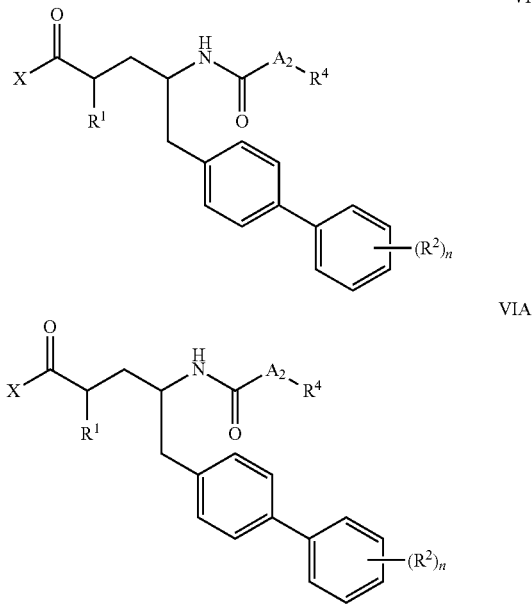

wherein $A^2$ is (CH$_2$)$_p$ and p is 0, 1, 2 or 3, or a pharmaceutically acceptable salt or tautomer thereof.

4. The compound according to claim 3 wherein $A^2$ is a bond, $R^4$ is a 5-membered ring heteroaryl selected from the group consisting of oxazole, pyrrole, pyrazole, isooxazole, triazole, tetrazole, oxadiazole, oxadiazolone, thiazole, isothiazole, thiophene, imidazole and thiadiazole, wherein the heteroaryl is optionally substituted with one or more substituents independently selected from hydroxy, $C_{1-7}$alkyl, $C_{1-7}$alkoxy, halo, halo-$C_{1-7}$alkyl and benzyl; or a pharmaceutically acceptable salt or tautomer thereof.

5. The compound of claim 1 wherein $R^1$ is methyl, $R^2$ is independently halo, $C_{1-7}$alkyl, halo-$C_{1-7}$alkyl, hydroxy and $C_{1-7}$alkoxy, n is 0, 1 or 2 and X is OH or —O—$C_{1-7}$alkyl; or a pharmaceutically acceptable salt or tautomer thereof.

6. The compound of claim 1 wherein n is 1 or 2; $R^2$ is meta-chloro and the other optional $R^2$ group is halo, $C_{1-7}$alkyl, halo-$C_{1-7}$alkyl, hydroxy and $C_{1-7}$alkoxy; or a pharmaceutically acceptable salt or tautomer thereof.

7. A pharmaceutical composition comprising a compound according to claim 1 or 4, or a pharmaceutically acceptable salt or tautomer thereof, and one or more pharmaceutically acceptable carriers.

8. A combination comprising: a compound according to claim 1 or a pharmaceutically acceptable salt or tautomer thereof, and one or more therapeutically active agents selected from HMG-Co-A reductase inhibitor, an anigiotensin receptor blocker, angiotensin converting enzyme Inhibitor, a calcium channel blocker, an endothelin antagonist, a renin inhibitor, a diuretic, an ApoA-I mimic, an antidiabetic agent, an obesity-reducing agent, an aldosterone receptor blocker, an endothelin receptor blocker, an aldosterone synthase inhibitors, a CETP inhibitor and a phosphodiesterase of type 5 (PDE5) inhibitor.

9. A method of inhibiting neutral endopeptidase EC. 3.4.24.11. activity in a subject in need thereof, comprising: administering to the subject a therapeutically effective amount of the compound according to claim 1 or a pharmaceutically acceptable salt or tautomer thereof.

10. A method of treating a disorder or a disease associated with neutral endopeptidase EC. 3.4.24.11. activity in a subject having a disorder or a disease associated with neutral endopeptidase EC.3.4.24.11. activity, comprising:
administering to the subject a therapeutically effective amount of the compound according to claim 1, or 4, or a pharmaceutically acceptable salt or tautomer thereof, wherein the disorder or disease is selected from hypertension, pulmonary hypertension, isolated systolic hypertension, resistant hypertension, peripheral vascular disease, congestive heart failure or pulmonary arterial hypertension.

11. The compound of claim 4 wherein n is 1 or 2; $R^2$ is meta-chloro and the other optional $R^2$ group is halo, $C_{1-7}$alkyl, halo-$C_{1-7}$alkyl, hydroxy and $C_{1-7}$alkoxy; or a pharmaceutically acceptable salt or tautomer thereof.

12. A pharmaceutical composition comprising a compound according to claim 11 or a pharmaceutically acceptable salt or tautomer thereof, and one or more pharmaceutically acceptable carriers.

13. A method of treating a disorder or a disease associated with neutral endopeptidase EC.3.4.24.11. activity in a subject having a disorder or a disease associated with neutral endopeptidase EC.3.4.24.11. activity, comprising: administering to the subject a therapeutically effective amount of the compound according to claim 11, or a pharmaceutically acceptable salt or tautomer thereof, wherein the disorder or disease is selected from hypertension, pulmonary hypertension, isolated systolic hypertension, resistant hypertension, peripheral vascular disease, congestive heart failure or pulmonary arterial hypertension.

14. A compound according to claim 1 selected from the group consisting of:
- (2R,4S)-5-(3'-Chloro-biphenyl-4-yl)-4-[(3-hydroxy-isoxazole-5-carbonyl)-amino]-2-methyl-pentanoic acid ethyl ester;
- (2R,4S)-5-(3'-Chloro-biphenyl-4-yl)-4-[(3-hydroxy-isoxazole-5-carbonyl)-amino]-2-methyl-pentanoic acid;
- (2S,4S)-5-(3'-Chloro-biphenyl-4-yl)-4-[(3-hydroxy-isoxazole-5-carbonyl)-amino]-2-methyl-pentanoic acid;
- (2R,4S)-5-(3'-chlorobiphenyl-4-yl)-2-methyl-4-(2H-tetrazole-5-carboxamido)pentanoic acid;
- (2R,4S)-5-(2',5'-dichlorobiphenyl-4-yl)-4-(3-hydroxyisoxazole-5-carboxamido)-2-methylpentanoic acid;
- (2R,4S)-5-(3'-Chloro-biphenyl-4-yl)-2-methyl-4-[(2H-tetrazole-5-carbonyl)-amino]-pentanoic acid ethyl ester;
- (2R,4S)-5-(3'-chlorobiphenyl-4-yl)-2-methyl-4-(5-oxo-4,5-dihydro-1,2,4-oxadiazole-3-carboxamido)pentanoic acid;
- (2R,4S)-5-(3'-chlorobiphenyl-4-yl)-2-methyl-4-(5-oxo-4,5-dihydro-1,3,4-oxadiazole-2-carboxamido)pentanoic acid;
- (2R,4S)-ethyl 5-(3'-chlorobiphenyl-4-yl)-2-methyl-4-(5-oxo-4,5-dihydro-1,3,4-oxadiazole-2-carboxamido) pentanoate;
- (2R,4S)-5-(3'-chlorobiphenyl-4-yl)-4-(2-ethyloxazole-5-carboxamido)-2-methylpentanoic acid;
- (2S,4S)-4-(2-ethyloxazole-5-carboxamido)-5-(5'-fluoro-2'-methoxybiphenyl-4-yl)-2-methylpentanoic acid;
- (2R,4S)-5-(2',5'-dichlorobiphenyl-4-yl)-4-(2-ethyloxazole-5-carboxamido)-2-methylpentanoic acid;
- (2R,4S)-5-(2',5'-dichlorobiphenyl-4-yl)-2-methyl-4-(oxazole-5-carboxamido)pentanoic acid;
- (2S,4S)-5-(5'-chloro-2'-fluorobiphenyl-4-yl)-2-methyl-4-(oxazole-5-carboxannido)pentanoic acid;
- (2R,4S)-5-(5'-chloro-2'-fluorobiphenyl-4-yl)-4-(2-ethyloxazole-5-carboxamido)-2-methylpentanoic acid;
- (2S,4S)-5-(2',5'-dichlorobiphenyl-4-yl)-4-(3-hydroxyisoxazole-5-carboxamido)-2-methylpentanoic acid;
- (2R,4S)-ethyl 5-(5'-fluoro-2'-methoxybiphenyl-4-yl)-4-(3-hydroxyisoxazole-5-carboxamido)-2-methylpentanoate;
- (2R,4S)-ethyl 5-(2',5'-dichlorobiphenyl-4-yl)-4-(3-hydroxyisoxazole-5-carboxamido)-2-methylpentanoate; and
- (2R,4S)-5-(5'-chloro-2'-fluorobiphenyl-4-yl)-2-methyl-4-(oxazole-5-carboxamido)pentanoic acid; or a pharmaceutically acceptable salt or tautomer thereof.

15. A compound according to claim 1 selected from the group consisting of:
- (2R,4S)-5-(3'-Chloro-biphenyl-4-yl)-4-[(3-hydroxy-isoxazole-5-carbonyl)-amino]-2-methyl-pentanoic acid;
- (2R,4S)-5-(5'-chloro-2'-fluorobiphenyl-4-yl)-2-methyl-4-(oxazole-5-carboxamido)pentanoic acid;
- (2R,4S)-5-(3'-chlorobiphenyl-4-yl)-2-methyl-4-(5-oxo-4,5-dihydro-1,3,4-oxadiazole-2-carboxamido)pentanoic acid;
- (2S,4S)-5-(3'-Chloro-biphenyl-4-yl)-4-[(3-hydroxy-isoxazole-5-carbonyl)-amino]-2-methyl-pentanoic acid;
- (2R,4S)-5-(3'-chlorobiphenyl-4-yl)-2-methyl-4-(5-oxo-4,5-dihydro-1,2,4-oxadiazole-3-carboxamido)pentanoic acid; and
- (2R,4S)-5-(2',5'-dichlorobiphenyl-4-yl)-4-(3-hydroxyisoxazole-5-carboxamido)-2-methylpentanoic acid; or a pharmaceutically acceptable salt or tautomer thereof.

* * * * *